(12) United States Patent
Park et al.

(10) Patent No.: US 12,305,203 B2
(45) Date of Patent: May 20, 2025

(54) PSICOSE-6-PHOSPHATE PHOSPHATASE, COMPOSITION FOR PRODUCING PSICOSE COMPRISING THE SAME, AND METHOD FOR PRODUCING PSICOSE USING THE SAME

(71) Applicant: CJ CHEILJEDANG CORPORATION, Seoul (KR)

(72) Inventors: Hyun June Park, Seoul (KR); Sang Young Yoon, Seoul (KR); Hyun Kug Cho, Seoul (KR); Sung Jae Yang, Seoul (KR); So-hyeong Kim, Seoul (KR); Seung Hwan Kim, Seoul (KR); Il Hyang Park, Seoul (KR); Byung-sam Son, Seoul (KR); Seong Bo Kim, Seoul (KR); Seung Won Park, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 783 days.

(21) Appl. No.: 17/312,697

(22) PCT Filed: Dec. 5, 2019

(86) PCT No.: PCT/KR2019/017114
§ 371 (c)(1),
(2) Date: Jun. 10, 2021

(87) PCT Pub. No.: WO2020/122504
PCT Pub. Date: Jun. 18, 2020

(65) Prior Publication Data
US 2022/0056426 A1  Feb. 24, 2022

(30) Foreign Application Priority Data
Dec. 11, 2018 (KR) .......... 10-2018-0159351

(51) Int. Cl.
*C12N 9/16* (2006.01)
*C12P 19/02* (2006.01)

(52) U.S. Cl.
CPC ............. *C12N 9/16* (2013.01); *C12P 19/02* (2013.01); *C12Y 501/03* (2013.01)

(58) Field of Classification Search
None
See application file for complete search history.

(56) References Cited

U.S. PATENT DOCUMENTS

| | | | |
|---|---|---|---|
| 10,745,683 B2 * | 8/2020 | Wichelecki .... | C12Y 503/01008 |
| 11,345,909 B2 * | 5/2022 | Wichelecki ......... | C12Y 501/03 |
| 12,006,526 B2 * | 6/2024 | Koch ......... | C12P 7/18 |

FOREIGN PATENT DOCUMENTS

| | | |
|---|---|---|
| CN | 111819278 A | 10/2020 |
| JP | 2007-525209 A | 9/2007 |
| JP | 6973898 B2 | 12/2021 |
| KR | 10-2018-0004023 A | 1/2018 |
| WO | 2005/066339 A2 | 7/2005 |
| WO | 2017/002978 A1 | 1/2017 |
| WO | 2017/059278 A1 | 4/2017 |
| WO | 2018/112139 A1 | 6/2018 |
| WO | 2018/129275 A1 | 7/2018 |
| WO | 2018/169957 A1 | 9/2018 |
| WO | 2019/027173 A2 | 2/2019 |

OTHER PUBLICATIONS

Partial Supplemental European Search Report issued in corresponding European Patent Application No. 19895174.1 dated Jan. 5, 2022.
Database UniProt [Online] Nov. 3, 2009, SubName: Full=Inositol monophosphatase {ECO: 0000313 EMBL: ACV59297.1} XP55871459, UniProt C8WRN6.
Bilal et al., "Metabolic engineering pathways for rare sugars biosynthesis, physiological functionalities, and applications—a review," Critical Reviews in Food Science and Nutrition, 58 (16): 2768-2778 (2018).
Office Action issued on Japanese Patent Application No. 2022-172294, dated Sep. 19, 2023.
Database: NCBI Reference Sequence, Accession No. WP_084001059, acylneuraminate cytidylyltransferase [Anaerolinea thermolimosa], Aug. 5, 2018 uploaded, Internet, www.ncbi.nih.gov (retrieved on Sep. 11, 2023).
Office Action dated Mar. 31, 2023, issued in corresponding Chinese Patent Application No. 201980089137.X.
NCBI Genbank Accession No. BAM00874.1,'putative phosphatase [Caldilinea aerophila DSM 14535 = NBRC 104270]'Oct. 7, 2016.
NCBI Genbank Accession No. APF18744.1,'3-deoxy-D-manno-octulosonate 8-phosphate phosphatase (KDO 8-Pphosphatase) [Caldithrixabyssi DSM 13497]', Nov. 28, 2016.
NCBI Genbank Accession No. KEF35131.1,'hydrolase [*Deinococcus* sp. RL]', Jun. 16, 2014.
NCBI Genbank Accession No. ADV64381.1,'phosphoglycolate phosphatase [Desulfurococcus mucosus DSM 2162]', Jun. 25, 2015.
Chan et al., "Structural Basis for Substrate Specificity in Phosphate Binding (beta/alpha)8-Barrels: D-Allulose 6-Phosphate 3-Epimerase from *Escherichia coli* K-12," Biochemistry, 47: 9608-9617 (2008).
Huang et al., "Panoramic view of a superfamily of phosphatases through substrate profiling," PNAS (2015).
Uhlman and Peyman, "Antisense Oligonucleotides," Chemical Reviews, 90 (4): 543-584(1990).

(Continued)

*Primary Examiner* — Blaine Lankford
(74) *Attorney, Agent, or Firm* — Morgan, Lewis & Bockius LLP

(57) ABSTRACT

The present application relates to a psicose-6-phosphate phosphatase, a microorganism comprising the same, and a method for producing psicose using the same.

20 Claims, No Drawings
Specification includes a Sequence Listing.

(56) References Cited

OTHER PUBLICATIONS

International Search Report issued in corresponding International Patent Application No. PCT/KR2019/017114 dated Apr. 2, 2020.
Database GenBank, ACV59297.1, "Inositol monophosphatase [Alicyclobacillus acidocaldarius subsp. acidocaldarius DSM 446]," (2013).
Database GenBank, KRW92667.1, "Haloacid dehalogenase [Alicyclobacillus tengchongensis]," (2015).
Database NCBI Reference Sequence, WP_058093972.1, "Hypothetical protein [Alicyclobacillus tengchongensis]," (2015).

* cited by examiner

SEQUENCE LISTING

<160> NUMBER OF SEQ ID NOS: 222

<210> SEQ ID NO 1
<211> LENGTH: 265
<212> TYPE: PRT
<213> ORGANISM: Alicyclobacillus acidocaldarius

<400> SEQUENCE: 1

Met Asp Lys Ala Trp Leu Asp Gly Leu Ala Glu Val Val Arg Glu Ala
1               5                   10                  15

Gly Arg Leu Val Glu Glu Ile Ala Arg Gln Gly Phe Asp Thr Gln Phe
            20                  25                  30

Lys His Pro Glu Glu Arg Arg Asp Pro Val Thr Thr Ala Asp Leu Ala
        35                  40                  45

Cys Asp Ala Phe Leu Lys Glu Arg Leu Leu Thr Leu Leu Pro Glu Ala
    50                  55                  60

Gly Trp Leu Ser Glu Glu Thr Lys Asp Arg Pro Asp Arg Leu Glu Lys
65                  70                  75                  80

Arg Trp Val Trp Ile Val Asp Pro Ile Asp Gly Thr Arg Glu Phe Val
                85                  90                  95

Arg Arg Ile Pro Glu Tyr Ala Ile Ser Val Ala Leu Ala Arg Asp Gly
            100                 105                 110

Glu Pro Val Ala Gly Ala Val Val Asn Pro Ala Thr Gly Asp Leu Phe
        115                 120                 125

Leu Gly Ala Val Gly Val Gly Ala Trp Arg Asn Gly Thr Pro Met Val
    130                 135                 140

Cys Ser Arg Ile Arg Gly Glu Arg Leu Thr Ile Leu Gly Ser Arg Ser
145                 150                 155                 160

Glu Met Asn Arg Gly Glu Phe Glu Pro Phe Ala Gly Ile Leu Glu Val
                165                 170                 175

Arg Ala Val Gly Ser Ile Ala Tyr Lys Leu Ala Leu Val Ala Ala Gly
            180                 185                 190

Glu Ala Asp Gly Thr Phe Ser Leu Gly Pro Lys His Glu Trp Asp Ile
        195                 200                 205

Ala Ala Gly Val Ala Leu Val Leu Ala Ala Gly Gly Arg Val His Asp
    210                 215                 220

Gly Ala Gly Arg Pro Phe Arg Phe Asn Gln Pro His Thr Leu Thr Arg
225                 230                 235                 240

Gly Ile Val Ala Ala Thr Arg Glu Ala Tyr Gly Asp Leu Ala Leu Leu
                245                 250                 255

Ile Glu Arg His Ala Pro Arg Arg Ala
            260                 265

<210> SEQ ID NO 2
<211> LENGTH: 262
<212> TYPE: PRT
<213> ORGANISM: Alicyclobacillus tengchongensis

<400> SEQUENCE: 2

Met Asn Gln Asp Val Tyr Thr Arg Leu Ala Asn Cys Asn Leu Phe Ile
1               5                   10                  15

Phe Asp Leu Asp Gly Thr Val Tyr Ala Glu Thr Asp His Phe Glu His
            20                  25                  30

Tyr Leu Gln Gln Leu Ala Arg Phe Val Gly Asp Glu Ala Arg Glu Ala
        35                  40                  45

Phe Leu Arg Glu Ala Gln Glu Ser Leu Ala Glu Gln Gly Gly Arg Phe

```
Tyr Gly Gln Ala Phe Thr Arg Leu Thr Gly Glu Pro Val Ala Val Glu
65                  70                  75                  80

Asp Glu Pro Ser Glu Gln His Leu His Val Asp Pro Trp Gly Val
                85                  90                  95

Leu Gln Ala Val Ala Ala Arg His Gly Val Ser Val Thr Asp Arg Asp
                100                 105                 110

Lys Ala Phe Leu Arg Thr Arg Asp Phe Met Ala Gly Pro Phe Pro Met
                115                 120                 125

Thr Pro Leu Ala Gly Leu Arg Asp Ala Met Leu Ala Leu Arg Ser Glu
                130                 135                 140

Gly Arg His Val Val Leu Ala Thr Asn Ser Pro Glu Pro Asp Ser Arg
145                 150                 155                 160

Ala Ile Leu Arg Lys Leu Glu Leu Glu Asp Val Leu Glu Asp Tyr Val
                165                 170                 175

Phe Gln Ala Arg Lys Pro Tyr Arg Thr Ala Glu His Phe Thr Arg Trp
                180                 185                 190

Leu Ala His Tyr Asp Ile Pro Pro Glu Gln Ala Val Ser Val Gly Asp
                195                 200                 205

His Tyr Arg Asn Glu Met Arg Pro Ala Ile Arg Leu Gly Met Asn Thr
210                 215                 220

Ile Tyr Ile Asp Arg Tyr Ile Gly Gln Pro Arg Ala Asp Val Thr Val
225                 230                 235                 240

Gln Leu Arg His Pro Gly Glu Leu Ala Asp Val Leu Arg Arg Ser Leu
                245                 250                 255

Arg Ser Ala Ala Ala Glu
                260
```

<210> SEQ ID NO 3
<211> LENGTH: 218
<212> TYPE: PRT
<213> ORGANISM: Alicyclobacillus tengchongensis

<400> SEQUENCE: 3

```
Met Arg Gly Ile Val Phe Asp Phe Asp Gly Thr Leu Ile Asp Thr Glu
1               5                   10                  15

Ser Ala Trp Tyr Thr Ala Phe Cys Asp Leu Tyr Gln Gln His Arg Val
                20                  25                  30

Glu Leu Pro Leu Ser Leu Tyr Ala Gln Cys Ile Gly Thr Thr His Asp
            35                  40                  45

Ala Phe Asp Pro Val Ala His Leu Ile Ala Ser Ala Glu Met Pro Ile
    50                  55                  60

Thr Glu Ser Glu Ile Glu Gln Phe Ile Gln Arg Arg His His Glu Leu
65                  70                  75                  80

Met Arg Glu Lys Ser Leu Arg Pro Gly Val Lys Lys Thr Ile Glu Thr
                85                  90                  95

Ala Arg Thr Leu Gly Leu Arg Ile Gly Leu Ala Thr Ser Ser His Arg
                100                 105                 110

Ala Trp Ile Asp Pro Phe Leu Glu Arg Leu Gly Ile Ala Asp Ala Phe
                115                 120                 125

His Cys Ile Arg Thr Ala Asp Asp Val Lys Arg Val Lys Pro Asp Pro
                130                 135                 140

Ala Leu Tyr Glu Leu Thr Leu Ala Cys Leu Gly Leu Lys Pro Asp Glu
145                 150                 155                 160
```

```
Ala Val Ala Ile Glu Asp Ser Pro Asn Gly Ala Leu Ala Val Arg
                165                 170                 175

Ala Gly Met His Val Leu Cys Thr Pro Asn Asp Val Thr Arg Gln Leu
            180                 185                 190

Pro Phe Pro Glu Asn Cys Asn His Val Ser Ser Leu Asp Glu Ile Asp
        195                 200                 205

Trp Pro Thr Trp Leu Gln Glu Arg Asn Arg
    210                 215
```

<210> SEQ ID NO 4
<211> LENGTH: 271
<212> TYPE: PRT
<213> ORGANISM: Amycolatopsis thermoflava

<400> SEQUENCE: 4

```
Met Glu Lys Pro Leu Leu Ile Ala Ser Asp Val Asp Gly Thr Leu Leu
1               5                   10                  15

Asp Pro Met Glu Arg Met Ser Pro Arg Thr Ala Ala Val Leu Arg Arg
            20                  25                  30

Ala Thr Asp Ala Gly Ile Pro Val Val Leu Ala Thr Gly Arg Pro Pro
        35                  40                  45

Arg Trp Ile Pro Ser Val Ala Gln Ala Gly Gly Leu Thr Gly Tyr Ala
    50                  55                  60

Val Cys Ala Asn Gly Ala Val Leu Tyr Asp Ile Gly Ala Asp Glu Val
65                  70                  75                  80

Val Gly Val His Gly Ala Leu Glu Pro Met Met Leu Asn Asp Ala Val
                85                  90                  95

His Glu Leu Thr Lys Ala Leu Pro Gly Ala Gly Phe Ala Ala Glu Arg
            100                 105                 110

Val Gly Arg Arg Ala Leu Asp Pro Asp Val Glu His Leu Val Val Glu
        115                 120                 125

His Gly Tyr His Asn Pro Trp Gly Asp Gly Glu Gly Val Pro Val Ser
    130                 135                 140

Arg Ala Glu Ile Val Gly Arg Pro Ala Val Lys Leu Leu Val Ser His
145                 150                 155                 160

Pro Asp Met Thr Ser Asp Glu Met Ala Arg Ala Arg Ala Val Leu
                165                 170                 175

Asp Glu Ser Val Asp Ile Thr Phe Ser Ala Ser Gly Gly Leu Ile Glu
            180                 185                 190

Ile Ala Ala His Gly Ile Thr Lys Ala Thr Gly Leu Ala Glu Val Ala
        195                 200                 205

Glu Arg Phe Gly Val Pro Val Glu Arg Ile Ile Ala Phe Gly Asp Met
    210                 215                 220

Pro Asn Asp Leu Glu Met Leu Lys Trp Ala Gly His Gly Val Ala Met
225                 230                 235                 240

Ala Asn Ala His Pro Asp Val Leu Ala Ile Ala Asp Glu Val Thr Ser
                245                 250                 255

Pro Asn Ser Glu Asp Gly Val Ala Gln Val Leu Glu Arg Trp Phe
            260                 265                 270
```

<210> SEQ ID NO 5
<211> LENGTH: 220
<212> TYPE: PRT
<213> ORGANISM: Amycolatopsis thermoflava

<400> SEQUENCE: 5

```
Met Ala Lys Val Leu Val Leu Asp Val Asp Gly Thr Leu Val Asp Thr
1               5                   10                  15

Asn Tyr His His Ala Leu Ala Trp Phe Arg Ala Phe Arg Gly His Gly
                20                  25                  30

Val Thr Val Pro Val Trp Arg Leu His Arg Ala Ile Gly Met Gly Gly
            35                  40                  45

Asp Gln Leu Val Pro Glu Val Ala Gly Gln Glu Val Glu Asp Ser Cys
        50                  55                  60

Gly Asp Asp Val Arg Ala Lys Trp Lys Glu Leu Val Asp Gly Met Leu
65                  70                  75                  80

Pro Glu Val Cys Ala Leu Asp Gly Ala His Glu Leu Leu Gln Ala Ala
                85                  90                  95

Asp Asp Ala Gly Tyr Arg Val Val Leu Ala Ser Ser Gly Lys Pro Asp
            100                 105                 110

His Val Asp His Tyr Leu Asp Leu Ile Asp Gly Arg Glu Leu Ala Ala
        115                 120                 125

Asp Trp Thr Ser Ser Lys Asp Val Glu Ala Thr Lys Pro Glu Pro Asp
    130                 135                 140

Leu Leu Glu Val Ala Leu Glu Lys Val Arg Gly Glu Glu Ala Val Val
145                 150                 155                 160

Ile Gly Asp Ser Val Trp Asp Cys Val Ala Ala Arg Ile Gly Leu
                165                 170                 175

Pro Cys Val Gly Leu Leu Thr Gly Gly Phe Ser Ala Ala Glu Leu Thr
                180                 185                 190

Asp Ala Gly Ala Ala Arg Thr Phe Thr Asp Leu Arg Glu Leu Arg Ala
            195                 200                 205

Ser Leu Asp Glu Leu Pro Phe Gly Ala Ser Pro Arg
    210                 215                 220

<210> SEQ ID NO 6
<211> LENGTH: 406
<212> TYPE: PRT
<213> ORGANISM: Anaerolinea thermolimosa

<400> SEQUENCE: 6

Met Val Lys Arg Glu Val Leu Ala Ile Ile Pro Ala Arg Gly Gly Ser
1               5                   10                  15

Lys Gly Ile Pro Arg Lys Asn Val Arg Leu Phe Ala Gly His Pro Leu
                20                  25                  30

Ile Ala Tyr Ser Ile Ala Ala Arg Gln Ser Glu Leu Val Thr Arg
            35                  40                  45

Val Ile Val Ser Thr Asp Asp Glu Ile Ala Arg Val Ala Arg Asp
        50                  55                  60

Tyr Gly Ala Glu Thr Pro Phe Leu Arg Pro Ala Glu Leu Ala Gln Asp
65                  70                  75                  80

Gln Thr Leu Asp Leu Pro Val Phe Gln His Ala Leu Arg Trp Leu Glu
                85                  90                  95

Glu Gln Glu Gly Tyr Gln Pro Glu Leu Val Val Gln Leu Arg Pro Thr
            100                 105                 110

Ser Pro Val Arg Pro Ala Leu Val Asp Glu Ala Val Gln Ile Leu
        115                 120                 125

Leu Ala His Pro Glu Ala His Ser Val Arg Gly Val Val Pro Ala Gly
    130                 135                 140

Gln Asn Pro His Lys Met Trp Arg Ile Asp Pro Gln Asn Gly Gln Met
145                 150                 155                 160
```

-continued

```
Ile Pro Leu Leu Gln Val Pro Gly Leu Glu Glu Pro Tyr Asn Ala Pro
            165                 170                 175

Arg Gln Val Leu Pro Val Tyr Trp Gln Thr Gly His Ile Asp Val
        180                 185                 190

Ile Arg Pro Glu Val Ile Arg Lys Gly Ser Met Ser Gly Gln Val Ile
        195                 200                 205

Leu Pro Val Met Val Asp Pro Ala Tyr Thr Val Asp Ile Asp Thr Pro
    210                 215                 220

Arg Asp Trp Ala Arg Ser Glu Trp Leu Val Trp Tyr Ser Glu Leu Glu
225                 230                 235                 240

Ile Val Tyr Pro Gly His Arg Arg Pro Leu Pro Glu Lys Val Asp
                245                 250                 255

Leu Val Val Phe Asp Phe Asp Gly Val Leu Thr Asp Asn Arg Val Trp
                260                 265                 270

Val Asp Glu Glu Gly His Glu Met Val Ala Ala Asn Arg Ser Asp Ser
            275                 280                 285

Leu Gly Val Ala Tyr Leu Arg Arg Ser Gly Leu Lys Met Val Val Leu
    290                 295                 300

Ser Thr Glu Thr Asn Pro Val Ala Ala Arg Cys Arg Lys Met Gln
305                 310                 315                 320

Ile Pro Val Val Gln Gly Val Trp Asp Lys Ala Gly Glu Leu Pro Arg
                325                 330                 335

Ile Met Ala Glu Phe Asn Ala Ala Pro Glu Arg Thr Ile Tyr Val Gly
            340                 345                 350

Asn Asp Val Asn Asp Val Pro Cys Phe Ser Leu Val Gly Cys Ala Val
        355                 360                 365

Ala Val Ala Asp Ala Gln Pro Ala Ala Arg Arg Ala Ala Asp Ile Val
    370                 375                 380

Leu Ser Arg Asn Gly Gly His Gly Ala Val Arg Glu Leu Leu Asp Ile
385                 390                 395                 400

Leu Met Gln Arg Met Lys
                405
```

<210> SEQ ID NO 7
<211> LENGTH: 226
<212> TYPE: PRT
<213> ORGANISM: Anaerolinea thermolimosa
<400> SEQUENCE: 7

```
Met Gly Ile Asp Arg Gln Arg Val Cys Gly Ile Cys Phe Asp Val Asp
1               5                   10                  15

Gly Thr Leu Ser Asp Thr Asp Asp Leu Trp Val Ala Arg Leu Ser Gly
            20                  25                  30

Trp Leu Lys Pro Val Ser Trp Ile Phe Pro Gln Arg Asn Pro Ser Arg
        35                  40                  45

Phe Ala Arg Trp Ala Ile Met Ala Ala Glu Ser Pro Gly Asn Leu Val
    50                  55                  60

Tyr Ser Leu Phe Asp Arg Phe Gly Leu Asp Asp Glu Ile Gly Arg Leu
65                  70                  75                  80

Phe His Trp Leu Asn Arg Gln Arg Gly Val Leu Arg Ser Gln Arg Phe
                85                  90                  95

Leu Leu Ile Pro Gly Val Gln Glu Ala Leu His Arg Leu His Lys His
            100                 105                 110

Phe Pro Leu Ala Val Val Ser Ala Arg Asp His Ala Gly Thr Leu Ala
```

```
            115                 120                 125
Phe Leu Gln His Phe Glu Leu Glu Pro Phe Phe Arg Cys Val Ala Thr
    130                 135                 140

Ser Gln Thr Cys Glu Phe Thr Lys Pro Phe Pro His Pro Ile Arg Trp
145                 150                 155                 160

Ala Ala Ala Gln Met Gly Val Lys Pro Glu Glu Leu Leu Met Val Gly
                165                 170                 175

Asp Thr Val Val Asp Ile Arg Ala Gly Lys Ala Ala Gly Ala Gln Thr
            180                 185                 190

Val Gly Val Leu Cys Gly Phe Gly Gln Glu Glu Leu Arg Arg Ala
        195                 200                 205

Gly Ala Asp Leu Ile Leu Pro His Thr Ala Gln Leu Ala Asp Val Leu
    210                 215                 220

Leu Asp
225

<210> SEQ ID NO 8
<211> LENGTH: 222
<212> TYPE: PRT
<213> ORGANISM: Anaerolinea thermolimosa

<400> SEQUENCE: 8

Met His Phe Ser Ala Tyr Ile Phe Asp Met Asp Gly Thr Leu Ile Asp
1               5                   10                  15

Asn Met Gly Phe His Gly Ala Ile Trp Ser Glu Phe Leu Ala Ser Leu
                20                  25                  30

Gly Ala Pro Val Asp Arg Glu Thr Phe Phe Arg Arg Thr Val Gly Lys
            35                  40                  45

Val Asn Ala Glu Ile Leu Arg Asp Leu Tyr Arg Ala Asp Leu Ser Asp
    50                  55                  60

Ala Glu Ile Glu Glu Leu Ser Arg Arg Lys Glu Gln Leu Tyr Arg Gln
65                  70                  75                  80

Arg Phe Ala Pro Leu Ile Thr Gln Lys Ala Val Pro Gly Val Arg Glu
                85                  90                  95

Phe Leu Gln Lys Ala His Gln Arg Gly Ile Ser Met Ala Val Ala Thr
                100                 105                 110

Ser Ala Gly Leu Glu Asn Thr Arg Phe Ile Leu Asp Gly Leu Gly Ile
            115                 120                 125

Thr Ala Tyr Phe Ser Ala Leu Val Thr Ser Glu Asp Val His Arg Gly
    130                 135                 140

Lys Pro Asp Pro Glu Ile Phe Leu Ile Ala Ala Gln Lys Leu Gly Val
145                 150                 155                 160

Pro Pro Glu Ala Cys Leu Val Phe Glu Asp Ser Pro Ala Gly Leu Glu
                165                 170                 175

Ala Ala His Arg Ala Gly Met Val Ser Val Ala Leu Ala Thr Thr Phe
            180                 185                 190

Pro Ala Glu Gln Leu Ala Gly Arg Pro Gly Val Leu Val Thr Gly
        195                 200                 205

Asp Tyr Ser Ala Ile Asp Leu Thr Arg Leu Ile Val Gly Thr
    210                 215                 220

<210> SEQ ID NO 9
<211> LENGTH: 259
<212> TYPE: PRT
<213> ORGANISM: Anaerolinea thermophila
```

-continued

```
<400> SEQUENCE: 9

Met Thr Thr Ser Leu Arg Asp Leu Leu Asp Phe Ala Val Glu Thr Ala
1               5                   10                  15

Tyr Leu Ala Gly Arg Thr Thr Leu Ala Tyr Phe Gln Thr Gly Val Gln
            20                  25                  30

Ala Glu Phe Lys Ala Asp Ser Ser Pro Val Thr Leu Ala Asp Arg Ala
        35                  40                  45

Ala Glu Gln Leu Ile Arg Gln Arg Ile Glu Lys Arg Phe Pro His His
    50                  55                  60

Ala Ile Val Gly Glu Glu Phe Gly Val Gln Gly Ser Ala Asp Ala Thr
65                  70                  75                  80

His Arg Trp Phe Ile Asp Pro Ile Asp Gly Thr Lys Ser Phe Leu Arg
                85                  90                  95

Gly Ile Pro Leu Tyr Ala Val Leu Leu Gly Leu Glu Ile Glu Gly Arg
            100                 105                 110

Val Gln Val Gly Val Ala Tyr Tyr Pro Ala Met Asp Glu Met Leu Ser
        115                 120                 125

Ala Ala Asp Gly Glu Gly Cys Trp Trp Asn Gly Arg Arg Ala Arg Val
    130                 135                 140

Ser Thr Ala Ser Arg Leu Ala Glu Ala Trp Val Thr Ser Thr Asp Pro
145                 150                 155                 160

Tyr Asn Phe Gln Lys Thr Gly Lys Asp Ala Ala Trp Gln Arg Ile Gln
                165                 170                 175

Ala Val Ser Tyr His Arg Gly Gly Trp Gly Asp Ala Tyr Gly Tyr Leu
            180                 185                 190

Leu Val Ala Thr Gly Arg Ala Glu Val Met Leu Asp Pro Ile Met Asn
        195                 200                 205

Glu Trp Asp Cys Ala Pro Phe Pro Pro Ile Phe Arg Glu Ala Gly Gly
    210                 215                 220

Phe Phe Gly Asp Trp Gln Gly Asn Glu Thr Ile Tyr Gly Gly Glu Ala
225                 230                 235                 240

Leu Ala Thr Thr Gln Val Leu Leu Pro Glu Val Leu Glu Cys Leu His
                245                 250                 255

Ser Ser Leu

<210> SEQ ID NO 10
<211> LENGTH: 223
<212> TYPE: PRT
<213> ORGANISM: Anaerolinea thermophila

<400> SEQUENCE: 10

Met Thr Lys Thr Asn Ile Lys Gly Ile Ile Phe Asp Phe Asp Gly Leu
1               5                   10                  15

Ile Leu Asp Thr Glu Thr Pro Glu Met Leu Ala Trp Glu Lys Ala Phe
            20                  25                  30

Thr Glu His Ser Leu Ser Phe Pro Ile Glu Arg Tyr Leu Asn Ser Ile
        35                  40                  45

Gly Thr Val Ser Asp Asn His Phe Val Gln Gly Phe Met Gln Glu Met
    50                  55                  60

Gly Leu Ser Glu Gly Glu Ile Gln Gln Thr Val Leu Ala Tyr Gln Ser
65                  70                  75                  80

His Ile Ala Thr Phe Glu His Met Asn His Pro Arg Glu Gly Val Leu
                85                  90                  95

Asp Leu Ile His Asp Ala Glu Lys Ile Gly Leu Arg Leu Ala Val Ala
```

```
                100             105             110
Ser Asn Ser Tyr Arg Thr Trp Val Val Asp Asn Leu Gln Arg Leu Ala
            115                 120                 125
Leu Asp Ser His Phe Asp Pro Ile Cys Thr Arg Asp Val Thr Asn
        130                 135                 140
Ser Lys Pro Asp Pro Glu Leu Tyr Asn Leu Val Leu Ala Lys Trp Gly
145                 150                 155                 160
Phe Thr Ser Asn Glu Val Leu Ala Leu Glu Asp Ser Pro Asn Gly Ile
                165                 170                 175
Lys Ala Ala Lys Asn Ala Gly Ile Phe Cys Val Ala Val Pro Asn Pro
            180                 185                 190
Ile Thr Ile Arg Met Asp Val Thr Leu Ala Asp Leu Ile Phe Ser Ser
        195                 200                 205
Phe Ser Asp Phe Ser Leu Gln Glu Ile Leu Phe Gln Leu Glu Lys
        210                 215                 220

<210> SEQ ID NO 11
<211> LENGTH: 232
<212> TYPE: PRT
<213> ORGANISM: Anaerolinea thermophila

<400> SEQUENCE: 11

Met Pro Leu Asp Val Ser Arg Ile Gln Ala Ile Cys Phe Asp Ile Asp
1               5                   10                  15
Gly Thr Leu Ser Asp Thr Asp Asp Glu Trp Ala Glu Arg Val Leu Lys
            20                  25                  30
Gly Ile Ser Phe Leu Lys Gly Trp Val Gly Glu Gln Arg Leu Arg Asn
        35                  40                  45
Leu Ala Arg Trp Val Val Met Glu Ile Glu Ser Pro Gly Asn Leu Leu
    50                  55                  60
Tyr Asn Leu Leu Asp Arg Leu His Leu Asp Asp Glu Ala Ser Arg Leu
65                  70                  75                  80
Phe Asn Phe Phe Val Arg Lys Phe His Pro Arg Pro Ser Arg Phe Arg
                85                  90                  95
Leu Ile Ser Gly Met Asp Lys Thr Leu Gln Thr Leu Ala Gln Tyr Tyr
            100                 105                 110
Pro Leu Ala Ile Val Ser Ala Arg Asp Glu Glu Ala Thr Leu Ala Phe
        115                 120                 125
Leu Gln Gln Phe Asp Leu Thr Ser Leu Phe Gln Val Ile Val Ser Ala
    130                 135                 140
His Thr Cys Lys Phe Thr Lys Pro Phe Pro Asp Pro Ile Leu Trp Ala
145                 150                 155                 160
Ala Glu Lys Leu Asn Val Pro Pro Ser Ala Cys Leu Met Val Gly Asp
                165                 170                 175
Thr Thr Val Asp Ile His Ala Gly Lys Lys Ala Gly Ala Gln Thr Val
            180                 185                 190
Gly Val Leu Cys Gly Phe Gly Thr His Lys Glu Leu Val Cys Ala Gly
        195                 200                 205
Ala Asp Leu Ile Leu Glu Thr Thr Ser Glu Leu Ala Glu Ile Leu Leu
    210                 215                 220
Lys Glu Lys Asn Ser Met Pro Asn
225                 230

<210> SEQ ID NO 12
<211> LENGTH: 252
```

```
<212> TYPE: PRT
<213> ORGANISM: Archaeoglobus fugidus

<400> SEQUENCE: 12

Met Asp Glu Arg Asp Ala Leu Arg Ile Ser Arg Glu Ile Ala Gly Glu
1               5                   10                  15

Val Arg Lys Ala Ile Ala Ser Met Pro Leu Arg Glu Arg Val Lys Asp
                20                  25                  30

Val Gly Met Gly Lys Asp Gly Thr Pro Thr Lys Ala Ala Asp Arg Val
            35                  40                  45

Ala Glu Asp Ala Ala Leu Glu Ile Leu Arg Lys Glu Arg Val Thr Val
        50                  55                  60

Val Thr Glu Glu Ser Gly Val Leu Gly Glu Gly Asp Val Phe Val Ala
65                  70                  75                  80

Leu Asp Pro Leu Asp Gly Thr Phe Asn Ala Thr Arg Gly Ile Pro Val
                85                  90                  95

Tyr Ser Val Ser Leu Cys Phe Ser Tyr Ser Asp Lys Leu Lys Asp Ala
            100                 105                 110

Phe Phe Gly Tyr Val Tyr Asn Leu Ala Thr Gly Asp Glu Tyr Tyr Ala
        115                 120                 125

Asp Ser Ser Gly Ala Tyr Arg Asn Gly Glu Arg Ile Glu Val Ser Asp
    130                 135                 140

Ala Glu Glu Leu Tyr Cys Asn Ala Ile Ile Tyr Tyr Pro Asp Arg Lys
145                 150                 155                 160

Phe Pro Phe Lys Arg Met Arg Ile Phe Gly Ser Ala Ala Thr Glu Leu
                165                 170                 175

Cys Phe Phe Ala Asp Gly Ser Phe Asp Cys Phe Leu Asp Ile Arg Pro
            180                 185                 190

Gly Lys Met Leu Arg Ile Tyr Asp Ala Ala Ala Gly Val Phe Ile Ala
        195                 200                 205

Glu Lys Ala Gly Gly Lys Val Thr Glu Leu Asp Gly Glu Ser Leu Gly
    210                 215                 220

Asn Lys Lys Phe Asp Met Gln Glu Arg Leu Asn Ile Val Ala Ala Asn
225                 230                 235                 240

Glu Lys Leu His Pro Lys Leu Leu Glu Leu Ile Lys
                245                 250

<210> SEQ ID NO 13
<211> LENGTH: 344
<212> TYPE: PRT
<213> ORGANISM: Archaeoglobus fugidus

<400> SEQUENCE: 13

Met Phe Val Met Phe Ile Val Ala Glu Val Asp Asp Glu Val Cys Val
1               5                   10                  15

Lys Arg Glu Val Glu Arg Ala Ala Gly Glu Val Gly Val His Val Ser
                20                  25                  30

Leu Thr Pro Phe Gln Arg Arg Glu Lys Ala Glu Lys Asn Leu Tyr Val
            35                  40                  45

Val Thr Ile Leu Gly Lys Asp Arg Val Gly Ile Val Arg Asp Ile Thr
        50                  55                  60

Arg Ala Phe Leu Asp Phe Gly Ile Asn Ile Glu Arg Thr Ser Leu Thr
65                  70                  75                  80

Ala Arg Glu Glu Leu Ile Ser Ile Glu Phe Leu Val Asp Leu Gly Gln
                85                  90                  95
```

Arg Asp Ala Ala Glu Val Arg Lys Arg Leu Arg Arg Glu Ala Glu Arg
            100                 105                 110

Leu Gly Leu Asp Ile Val Met Gln Pro Tyr Ser Thr Phe Asn Arg Glu
        115                 120                 125

Lys Arg Leu Ile Val Phe Asp Met Asp Ser Thr Leu Val Glu Ala Glu
    130                 135                 140

Ile Ile Asp Glu Leu Ala Lys Glu Ala Gly Val Gly Asp Glu Val Ser
145                 150                 155                 160

Lys Leu Thr Glu Arg Ala Met Arg Gly Glu Ile Gly Phe Lys Glu Ala
                165                 170                 175

Leu Glu Glu Arg Val Arg Leu Leu Lys Gly Leu Pro Val Glu Val Leu
            180                 185                 190

Glu Arg Ile Tyr Ser Arg Ile Lys Leu Thr Glu Gly Ala Lys Glu Leu
        195                 200                 205

Val Arg Ser Leu Lys Glu Ala Gly Tyr Lys Val Ala Val Val Ser Gly
    210                 215                 220

Gly Phe Ser Tyr Phe Thr Asp Arg Leu Lys Glu Glu Leu Gly Leu Asp
225                 230                 235                 240

Tyr Ala Phe Gly Asn Glu Leu Glu Ile Glu Asn Gly Arg Leu Thr Gly
                245                 250                 255

Arg Ile Lys Gly Arg Ile Ile Asp Ala Ser Glu Lys Ala Arg Ile Val
            260                 265                 270

Glu Glu Ile Ala Arg Lys Glu Gly Ile Ser Pro Glu Asn Val Val Ala
        275                 280                 285

Val Gly Asp Gly Ala Asn Asp Arg Leu Met Ile Glu Arg Ala Gly Leu
    290                 295                 300

Gly Ile Ala Phe Asn Ala Lys Glu Val Leu Lys Asp Val Ala Asp Gly
305                 310                 315                 320

Ser Ile Ser Lys Glu Asn Leu Val Gly Leu Ala Ser Val Leu Lys Leu
                325                 330                 335

Pro Ala Glu Phe Arg Lys Lys Val
            340

<210> SEQ ID NO 14
<211> LENGTH: 277
<212> TYPE: PRT
<213> ORGANISM: Archaeoglobus fugidus

<400> SEQUENCE: 14

Met Leu Lys Thr Pro Ser Asp Ala Ala Val Ala Gly Cys Leu Ser Leu
1               5                   10                  15

Leu Leu Glu Val Ser Gly Asn Pro Lys Ala Gly Asn Val Asp Arg Glu
            20                  25                  30

His Asp Phe Asp Asp Leu Lys Phe Glu His Phe Leu Ala Ser Ala Ala
        35                  40                  45

Gly Ala Phe Pro Ala Phe Leu Glu Val Ala Glu Lys Arg Ile Ile Gly
    50                  55                  60

Glu Gly Val Leu Arg Ala Val Lys Glu Ser Met Arg Trp His Arg Ala
65                  70                  75                  80

Glu Asn Val His Phe Gly Ala Phe Leu Leu Val Pro Leu Ile Ser
                85                  90                  95

Ser Trp Asp Ala Gly Gly Met Val Asp Ile Ala Glu Ala Ala Arg Asn
            100                 105                 110

Arg Leu Arg Arg Thr Asp Phe Arg Asp Ser Leu Ser Val Leu Glu Ala
        115                 120                 125

```
Phe Arg Leu Ser Asn Ala Arg Val Val Glu Ala Gly Glu Leu Asn Leu
        130                 135                 140

Lys Asp Arg Lys Thr Glu Glu Ile Ala Gln Lys Lys Ile Asn Leu
145                 150                 155                 160

Tyr Glu Trp Met Lys Met Ala Pro Glu Asn Leu Ile Ala Arg Glu
                165                 170                 175

Leu Val Asp Gly Phe Lys Ile Ser Ile Glu Gly Ala Lys Phe Leu Leu
                180                 185                 190

Ser Phe Gly Asn Ser Gly Lys Ala Val Val Glu Leu Tyr Tyr His Leu
        195                 200                 205

Leu Ser Lys Phe Pro Asp Pro Leu Val Ile Ala Lys Met Gly Arg Glu
    210                 215                 220

Tyr Ala Glu Lys Ile Thr Glu Trp Ala Glu Lys Ala Arg Thr Glu Glu
225                 230                 235                 240

Glu Arg Lys Glu Leu Asp Glu Lys Leu Leu Lys Asp Gly Ala Asn Pro
                245                 250                 255

Gly Thr Ile Ala Asp Leu Thr Ala Ser Ser Ile Phe Leu Ala Leu Ala
            260                 265                 270

Glu Gly Trp Arg Ile
            275

<210> SEQ ID NO 15
<211> LENGTH: 219
<212> TYPE: PRT
<213> ORGANISM: Archaeoglobus profundus

<400> SEQUENCE: 15

Met Phe Lys Ala Leu Val Val Asp Ile Asp Gly Thr Leu Thr Asp Lys
1               5                   10                  15

Lys Arg Ala Ile Asn Cys Arg Ala Val Glu Ala Leu Arg Lys Leu Lys
            20                  25                  30

Ile Pro Val Val Leu Ala Thr Gly Asn Ile Ser Cys Phe Ala Arg Ala
        35                  40                  45

Val Ala Lys Ile Ile Gly Val Ser Asp Ile Val Ile Ala Glu Asn Gly
50                  55                  60

Gly Val Val Arg Phe Ser Tyr Asp Gly Glu Asp Ile Val Leu Gly Asp
65                  70                  75                  80

Arg Ser Lys Cys Leu Arg Ala Leu Glu Thr Leu Arg Lys Arg Phe Lys
                85                  90                  95

Val Glu Leu Leu Asp Asn Glu Tyr Arg Lys Ser Glu Val Cys Met Arg
            100                 105                 110

Arg Asn Phe Pro Ile Glu Glu Ala Arg Lys Ile Leu Pro Lys Asp Val
        115                 120                 125

Arg Ile Val Asp Thr Gly Phe Ala Tyr His Ile Ile Asp Ala Asn Val
    130                 135                 140

Ser Lys Gly Lys Ala Leu Met Phe Ile Ala Asp Lys Leu Gly Leu Asp
145                 150                 155                 160

Val Lys Asp Phe Ile Ala Ile Gly Asp Ser Glu Asn Asp Ile Glu Met
                165                 170                 175

Leu Glu Val Ala Gly Phe Gly Val Ala Val Ala Asn Ala Asp Glu Lys
            180                 185                 190

Leu Lys Glu Val Ala Asp Leu Val Thr Ser Lys Pro Asn Gly Asp Gly
        195                 200                 205

Val Val Glu Ala Leu Glu Phe Leu Gly Leu Ile
                                        210                 215
```

<210> SEQ ID NO 16
<211> LENGTH: 224
<212> TYPE: PRT
<213> ORGANISM: Archaeoglobus veneficus

<400> SEQUENCE: 16

Met Leu Arg Pro Lys Gly Leu Ala Ile Asp Ile Asp Gly Thr Ile Thr
1               5                   10                  15

Tyr Arg Asn Arg Ser Leu Asn Cys Lys Ala Val Glu Ala Leu Arg Lys
                20                  25                  30

Val Lys Ile Pro Val Val Leu Ala Thr Gly Asn Ile Ser Cys Phe Ala
            35                  40                  45

Arg Thr Ala Ala Lys Leu Ile Gly Val Ser Asp Ile Val Ile Cys Glu
        50                  55                  60

Asn Gly Gly Ile Val Arg Phe Ser Tyr Asp Gly Asp Asp Ile Val Leu
65                  70                  75                  80

Gly Asp Ile Ser Lys Cys Leu Lys Ala Ala Glu Ile Leu Lys Glu Tyr
                85                  90                  95

Phe Glu Ile Glu Phe Leu Asp Ala Glu Tyr Arg Lys Ser Glu Val Cys
            100                 105                 110

Leu Arg Arg Asn Phe Pro Ile Glu Glu Ala Arg Lys Ile Leu His Asp
        115                 120                 125

Ala Lys Leu Asp Val Lys Ile Val Asp Ser Gly Phe Ala Tyr His Ile
    130                 135                 140

Met Asp Ala Lys Val Ser Lys Gly Arg Ala Leu Glu Tyr Ile Ala Asp
145                 150                 155                 160

Glu Leu Gly Ile Ser Pro Lys Glu Phe Ala Ala Ile Gly Asp Ser Glu
                165                 170                 175

Asn Asp Ile Asp Leu Ile Lys Ala Ala Gly Leu Gly Ile Ala Val Gly
            180                 185                 190

Asp Ala Asp Leu Lys Leu Lys Met Glu Ala Asp Val Val Ser Lys
        195                 200                 205

Lys Asn Gly Asp Gly Val Val Glu Ala Leu Glu Leu Leu Gly Leu Ile
    210                 215                 220

<210> SEQ ID NO 17
<211> LENGTH: 194
<212> TYPE: PRT
<213> ORGANISM: Bacillus licheniformis

<400> SEQUENCE: 17

Met Leu His Leu Gly Ile Asp Ile Asp Gly Thr Ile Thr Ala Gln Asp
1               5                   10                  15

Thr Phe Val Pro Tyr Leu Asn Glu Ser Phe Ser Leu Ser Ile Thr Leu
                20                  25                  30

Glu Asp Ile Lys Glu Tyr Asp Leu Thr Lys Leu Leu Asn Ile Ser Gln
            35                  40                  45

Glu Asp Phe Trp Lys Trp Met Asn Glu Asn Glu Pro Arg Ile Tyr Gln
        50                  55                  60

Glu Ala Leu Leu Ala Gln Tyr Ala Lys Gln Thr Leu Asp Glu Leu Lys
65                  70                  75                  80

Lys Gln His Lys Leu Ile Tyr Ile Thr Ala Arg Arg His His Leu Glu
                85                  90                  95

Asp Ile Thr Tyr Asp Trp Phe Glu Lys Arg Asp Ile His Tyr Asp His

```
            100                 105                 110
Ile Glu Leu Val Gly Gly His Asp Lys Leu Glu Ala Val Phe Arg His
            115                 120                 125
Glu Ile Asp Val Phe Phe Glu Asp His His Gly Asn Ala Thr Met Ile
        130                 135                 140
Ala Lys Glu Ala Gly Ile Pro Val Leu Leu Phe Asn Thr Pro Tyr Asn
145                 150                 155                 160
Gln Leu Pro Thr Asp Ser Asn Ile Val Arg Val Asp Ser Trp Leu Glu
                165                 170                 175
Ala Ala Glu Trp Leu Lys Lys Asn Glu Lys Thr Leu Lys Ala Ala Lys
                180                 185                 190
Ser Met

<210> SEQ ID NO 18
<211> LENGTH: 226
<212> TYPE: PRT
<213> ORGANISM: Bacillus licheniformis

<400> SEQUENCE: 18

Met Lys Ala Val Ile Phe Asp Leu Asp Gly Val Ile Thr Asp Thr Ala
1               5                   10                  15
Glu Tyr His Tyr Leu Ala Trp Lys His Thr Ala Glu Gln Ile Gly Ile
                20                  25                  30
Glu Ile Asp Arg Ser Phe Asn Glu Arg Leu Lys Gly Ile Asn Arg Glu
            35                  40                  45
Gln Ser Leu Asp Lys Ile Leu Ile His Gly Ala Ala Gly Lys Phe
50                  55                  60
Gln Glu Ala Glu Lys Gln Glu Ile Met Arg Arg Lys Asn Gln Tyr Tyr
65                  70                  75                  80
Gln Gln Leu Ile Gln Asn Leu Thr Pro His Asp Leu Leu Pro Gly Ile
                85                  90                  95
Ser Val Leu Phe Ala Glu Leu Lys Arg Glu His Ile Ser Ile Ala Leu
                100                 105                 110
Ala Ser Ser Ser Arg Asn Ala Pro Ala Ile Leu Gln Arg Leu Gly Val
                115                 120                 125
Met Asp Glu Phe Gln Gly Val Val Asp Pro Ala Ala Leu Ala His Gly
        130                 135                 140
Lys Pro Asp Pro Glu Ile Phe Leu Thr Ala Ala Ala Leu Leu Gly Val
145                 150                 155                 160
Pro Pro Ser Glu Cys Ala Ala Ile Glu Asp Ala Glu Ala Gly Ile Ala
                165                 170                 175
Ala Ile Lys Ser Ala Gly Met Phe Ala Val Gly Val Gly Asp Glu Thr
                180                 185                 190
Ser Leu Arg Gly Ala Asp Leu Ile Val His Asn Thr Asn Glu Leu Thr
                195                 200                 205
Phe Glu Leu Leu Asn Glu Gly Trp Gln Arg Tyr Cys Cys Ile Arg Glu
        210                 215                 220
Gly Lys
225

<210> SEQ ID NO 19
<211> LENGTH: 216
<212> TYPE: PRT
<213> ORGANISM: Bacillus licheniformis

<400> SEQUENCE: 19
```

```
Met Lys Lys Trp Ala Phe Val Ser Asp Phe Asp Gly Thr Ile Ser Lys
1               5                   10                  15

Gln Asp Phe Tyr Trp Met Val Ile Asp Lys Tyr Phe Pro Glu Gly Arg
            20                  25                  30

Glu Leu Phe Lys Lys Trp Lys Ser Gly Glu Leu Lys Asp Ile Glu Phe
        35                  40                  45

Leu Gly Thr Val Phe Ala Ser Ile Asn Gln Ser Glu Gln Lys Ile Ile
    50                  55                  60

Asp Asp Ile His Ser Ile Pro Ile Asp Glu Tyr Val Pro Asp Phe Ile
65                  70                  75                  80

Gln His Val Gln Lys Ser Gly Gly Asp Phe Tyr Ile Leu Ser Ala Gly
                85                  90                  95

Thr Asp Tyr Tyr Ile His Tyr Ile Leu Lys Lys Tyr Gly Ile Thr Asp
            100                 105                 110

Val Glu Val Tyr Ser Asn Lys Gly Phe Phe Lys Glu Asp Asn Val His
        115                 120                 125

Met Asp Ile Asp Glu Asn His Trp His Tyr Ser Glu Arg Tyr Gly Ile
    130                 135                 140

Asp Lys Ser Lys Val Ile Gln Lys Leu Lys Glu Glu Tyr Glu Thr Val
145                 150                 155                 160

Tyr Phe Ala Gly Asp Ser Glu Pro Asp Ser His Pro Ala Lys Phe Ala
                165                 170                 175

Asp Val Thr Phe Ala Lys Asp Ala Leu Gln Asp Leu Leu Arg Gln Gln
            180                 185                 190

Gly Val Pro Phe Val Ala Val Glu Thr Phe Glu Asp Ile Glu Gln Tyr
        195                 200                 205

Leu Lys Glu Lys Gly Arg Ile Val
    210                 215

<210> SEQ ID NO 20
<211> LENGTH: 223
<212> TYPE: PRT
<213> ORGANISM: Caldicellulosiruptor bescii

<400> SEQUENCE: 20

Met Gly Lys Ile Lys Ala Ala Ile Phe Asp Met Asp Gly Val Leu Thr
1               5                   10                  15

Asp Thr Val Lys Leu His Phe Lys Ala Trp Lys Lys Met Phe Glu Ser
            20                  25                  30

His Gly Tyr Lys Phe Glu Tyr Glu Asp Tyr Lys Trp Lys Val Asp Gly
        35                  40                  45

Lys Pro Arg Ile Asp Gly Ile Arg Ser Ile Ala Tyr Asp Met Pro Glu
    50                  55                  60

Asp Lys Leu Ile Glu Met Ala Glu Glu Lys Gln Lys Ile Phe Leu Glu
65                  70                  75                  80

Phe Val Glu Gln Glu Asn Leu Glu Ala Phe Glu Asp Ser Ile Trp Leu
                85                  90                  95

Leu Asn His Leu Lys Gln Asn Asp Ile Lys Leu Ala Val Ala Ser Ser
            100                 105                 110

Ser Lys Asn Thr Thr Lys Ile Leu Thr Lys Ile Gly Ile Tyr Asn Met
        115                 120                 125

Phe Asp Thr Ile Val Thr Gly Tyr Asp Phe Lys Lys Gly Lys Pro Asp
    130                 135                 140

Pro Glu Ile Phe Leu Thr Ala Ala Gln Arg Leu Asn Val Asn Pro Lys
```

```
            145                 150                 155                 160
Glu Cys Val Val Phe Glu Asp Ala Ile Asp Gly Val Lys Ala Gly Ile
                    165                 170                 175

Arg Ala Gly Met Leu Thr Ile Gly Val Cys Arg Asp Gly Gln Phe Asp
                180                 185                 190

Arg Leu Lys Glu Ala His Tyr Val Asp Arg Leu Asp Lys Ile Ser
            195                 200                 205

Leu Glu Leu Leu Glu Asn Leu His Glu Lys Leu Phe Lys Lys Val
        210                 215                 220

<210> SEQ ID NO 21
<211> LENGTH: 275
<212> TYPE: PRT
<213> ORGANISM: Caldicellulosiruptor bescii

<400> SEQUENCE: 21

Met Lys Asn Ser Ser Ile Leu Lys Asn Ile Asp Leu Phe Leu Leu Asp
1               5                   10                  15

Leu Asp Gly Thr Val Tyr Leu Gly Glu Lys Val Phe Glu Gly Ala Arg
                20                  25                  30

Glu Phe Ile Lys Leu Leu Asn Lys Asn Gln Lys Glu Phe Leu Phe Leu
            35                  40                  45

Thr Asn Asn Ser Ser Lys Ser Ser Glu Glu Tyr Tyr Ser Lys Leu Leu
50                  55                  60

Asn Met Gly Phe Glu Ile Thr Lys Glu Asn Val Phe Thr Ser Gly Gln
65                  70                  75                  80

Ala Met Gly Ile Tyr Ile Lys Thr Ile His Lys Lys Glu Lys Pro Pro
                85                  90                  95

Arg Val Tyr Val Val Gly Thr Thr Ser Leu Lys Arg Glu Leu Lys Ser
            100                 105                 110

Met Gly Ile Val Val Asp Ser Pro Asn Tyr Asn Ile Asp Tyr Leu
        115                 120                 125

Val Ile Gly Phe Asp Thr Thr Leu Thr Tyr Lys Lys Leu Leu Asp Ala
    130                 135                 140

Cys Glu Leu Ile Arg Arg Gly Val Pro Phe Leu Ala Thr Asn Pro Asp
145                 150                 155                 160

Leu Val Cys Pro Leu Asp Gly Arg Tyr Ile Pro Asp Cys Gly Ser
                165                 170                 175

Ile Cys Ile Met Leu Glu Asn Ala Thr Lys Lys Pro Val Phe Val
            180                 185                 190

Gly Lys Pro Ser Ser Ile Met Val Asp Ile Ile Ser Asn Leu Lys Lys
        195                 200                 205

Val Glu Lys Ser Arg Ile Ala Met Ile Gly Asp Arg Leu Tyr Thr Asp
    210                 215                 220

Met Lys Met Ala Lys Asp Ser Gly Met Val Ala Ala Leu Val Leu Ser
225                 230                 235                 240

Gly Glu Thr Lys Met Lys Asp Val Glu Ala Ser Thr Leu Lys Pro Asp
                245                 250                 255

Leu Ile Tyr Gly Ser Ile Lys Asp Met Tyr Glu Glu Leu Lys Leu Val
            260                 265                 270

Phe Gly Gly
        275

<210> SEQ ID NO 22
<211> LENGTH: 266
```

```
<212> TYPE: PRT
<213> ORGANISM: Caldicellulosiruptor bescii

<400> SEQUENCE: 22

Met Ile Lys Leu Val Ala Thr Asp Leu Asp Asp Thr Leu Leu Ser Lys
1               5                   10                  15

Asp Leu Thr Ile Thr Glu Lys Asn Leu Asn Ala Ile Glu Phe Leu Lys
            20                  25                  30

Lys Asn Asn Ile Ile Phe Ile Leu Ala Ser Gly Arg Pro Tyr Pro Ser
        35                  40                  45

Ile Lys Asn Val Ala Tyr Asp Leu Gln Asn Phe Tyr Pro Met Ile Thr
    50                  55                  60

Tyr Gln Gly Ala Leu Val Tyr Asp Pro Lys Asn Asp Lys Lys Leu Tyr
65                  70                  75                  80

Gly Cys Glu Ile Lys Pro Glu Asp Ala Lys Glu Leu Val Arg Leu Ala
                85                  90                  95

Lys Asp Glu Gly Ile His Val His Ile Tyr Ile Asp Asn Val Trp Tyr
            100                 105                 110

Val Glu Ala Met Asn Glu Lys Thr Glu Tyr Tyr Arg Asn Leu Thr Lys
        115                 120                 125

Leu Glu Pro His Ile Val Lys Asn Leu Leu Glu Phe Ile Asp Arg Pro
    130                 135                 140

Val Thr Lys Val Leu Phe Phe Asp Glu His Glu Arg Leu Lys Asp Leu
145                 150                 155                 160

Lys Glu Ser Leu Pro Asp Asp Phe Ser Lys Phe Asn Ile Met Phe
                165                 170                 175

Ser Lys Pro Phe Phe Leu Glu Phe Thr Asp Ile Asn Val Ser Lys Gly
            180                 185                 190

Asn Ala Leu Lys Phe Leu Thr Glu Tyr Tyr Gly Leu Lys Arg Glu Glu
        195                 200                 205

Val Met Ala Ile Gly Asp Gly Asp Asn Asp Ile Ser Met Ile Glu Tyr
    210                 215                 220

Ala Gly Ile Gly Val Ala Val Glu Asn Ala Val Glu Lys Leu Lys Glu
225                 230                 235                 240

Ala Ala Asp Phe Val Val Ala Lys Ser Asp Asp Ser Gly Phe Ala Gln
                245                 250                 255

Ala Ile Glu Lys Val Phe Asn Val His Phe
            260                 265

<210> SEQ ID NO 23
<211> LENGTH: 279
<212> TYPE: PRT
<213> ORGANISM: Caldicellulosiruptor bescii

<400> SEQUENCE: 23

Met Tyr Lys Leu Ile Ala Ile Asp Leu Asp Met Thr Leu Leu Asp Lys
1               5                   10                  15

Asn Lys Asn Ile Ser Ser Arg Asn Lys Arg Ala Ile Glu Leu Val Lys
            20                  25                  30

Gln Lys Gly Val Gln Ile Val Leu Cys Ser Gly Arg Ile Leu Lys Gly
        35                  40                  45

Val Met Tyr Phe Ala Lys Val Leu Gly Leu Tyr Asp Gln Val Ile Val
    50                  55                  60

Ala Cys Asn Gly Ala Ile Val Arg Asp Leu Lys Lys Asn Asn Asp Ile
65                  70                  75                  80
```

```
Tyr Tyr Ile Gly Leu Glu Asn Ser Lys Ser Leu Glu Ile Ala Arg Ile
                85                  90                  95

Cys Lys Glu Asn Asp Ile Tyr Tyr His Tyr Tyr Phe Gln Asp Thr Met
            100                 105                 110

Ile Ala Arg Arg Leu Asp Tyr Ser Ser Lys Phe Tyr Tyr Glu Lys Asn
        115                 120                 125

Lys Glu Leu Pro Glu Glu Arg Ile Asn Ile Ile Asp Asp Ser
130                 135                 140

Glu Asn Thr Ile Asn Ala Cys Gly Asp Leu Ile Thr Lys Phe Val Ile
145                 150                 155                 160

Ile Asp Lys Asp Leu Glu Lys Val Asn Tyr Val Arg Lys Ile Ile Glu
                165                 170                 175

Arg Glu Ile Pro Gly Val Glu Thr Thr Lys Ser Asp Ile Asn Ile Leu
            180                 185                 190

Glu Val Met Lys Glu Gly Val Asn Lys Lys Arg Ala Leu Glu Phe Val
        195                 200                 205

Ile Ser Tyr Leu Gly Ile Ala Pro Glu Glu Val Met Ala Ile Gly Asp
    210                 215                 220

Asn Glu Asn Asp Leu Glu Met Ile Glu Phe Ala Gly Leu Gly Val Ala
225                 230                 235                 240

Met Gly Asn Ala Ile Glu Glu Leu Lys Lys Ile Ala Asp Tyr Val Thr
                245                 250                 255

Ser Ser Tyr Glu Asn Asp Gly Val Ala Arg Ala Ile Glu Lys Phe Val
            260                 265                 270

Leu Gly Glu Ala Val Asn Val
        275

<210> SEQ ID NO 24
<211> LENGTH: 284
<212> TYPE: PRT
<213> ORGANISM: Caldicellulosiruptor bescii

<400> SEQUENCE: 24

Met Ile Lys Leu Ile Ala Leu Asp Ile Asp Gly Thr Leu Leu Asp Asp
1               5                   10                  15

Arg Gly Tyr Ile Pro Gln Ile Asn Arg Glu Phe Leu Lys Ile Ala Val
                20                  25                  30

Glu Lys Tyr Lys Ile Val Ile Val Leu Cys Thr Gly Arg Gly Ala Ser
            35                  40                  45

Ala Phe Lys Ile Ala Lys Asp Leu Gln Leu Pro Cys Ser Leu Ile Ser
        50                  55                  60

Ala Asn Gly Val Tyr Val Phe Glu Asn Pro Asn Phe Pro Pro Ile Ile
65                  70                  75                  80

Lys Asn Tyr Leu Thr Glu Arg Gln Lys Lys Val Leu Ile Glu Phe Leu
                85                  90                  95

Asp Asn Asn His Phe Glu Ile Asp Tyr Tyr Ile Val Leu Gly Tyr Glu
            100                 105                 110

Gln Asp Phe His Met Ile Tyr Lys Glu Arg Thr Asn Tyr Asp Ser Tyr
        115                 120                 125

Phe Leu Ser Phe Val Asn Gly Arg Lys Gln Phe Lys Ser Thr Tyr Pro
    130                 135                 140

Ala Glu Lys Leu Leu Lys Phe Leu Glu Tyr Pro Ile Ser His Thr Gly
145                 150                 155                 160

Ile Val Gly Lys Tyr Glu Lys Leu Lys Glu Ile Lys Glu Ile Leu Lys
                165                 170                 175
```

```
Thr Leu Glu Leu Asp Cys Asn Ile Ile Leu Tyr Tyr Ala Ser Asp Asn
            180                 185                 190

Lys Glu Tyr Gly Phe Leu Glu Val Leu Ser Asn Asn Ala Ser Lys Glu
            195                 200                 205

Lys Ala Leu Leu Gln Phe Met Asn Phe Lys Asn Ile Ser Ser Glu Glu
210                 215                 220

Leu Ile Ser Ile Gly Asp Asn Phe Asn Asp Val Gly Met Phe Lys Ile
225                 230                 235                 240

Ser Gly Ile Ser Val Ala Val Ala Asn Ala Pro Glu Val Lys Lys
            245                 250                 255

Ala Ala Lys Phe Val Thr Ser Arg Thr Asn Asn Glu Gly Ala Val Ala
            260                 265                 270

Glu Ala Ile Glu Met Phe Ile Ile Lys Arg Asp Gly
            275                 280

<210> SEQ ID NO 25
<211> LENGTH: 286
<212> TYPE: PRT
<213> ORGANISM: Caldilinea aerophila

<400> SEQUENCE: 25

Met Arg Pro Phe Asp Leu Val Val Leu Asp Leu Asp Gly Thr Ile Leu
1               5                   10                  15

Asn Ala Tyr Gln Arg Thr Arg Ile Ser Lys Ala Val His Asp Ala Ile
                20                  25                  30

Glu Ala Val Gln Ala Ala Gly Val Pro Val Thr Ile Gly Thr Gly Arg
            35                  40                  45

Thr Leu Asp Tyr Ile Arg Tyr His Leu Pro Gly Asp Leu His Leu Thr
        50                  55                  60

Tyr Pro Val Ile Ala Thr Gln Gly Ala Val Ile Gly Asp Pro Val Ser
65                  70                  75                  80

Gly Arg Val Leu Val Glu Ile Pro Leu Pro Leu Lys Glu Ala Arg Ala
                85                  90                  95

Ile Ala Ala Phe Val Asp Asp His Arg Tyr Thr Thr Ala Phe Tyr Phe
            100                 105                 110

Asn Asn Ala Asp Gly His Thr Val Ile Tyr Gln Asn Ala Ala Gly Ala
        115                 120                 125

Thr Ala Glu Glu Glu Ala Leu Leu His His Leu Leu Gly Val Pro Asn
130                 135                 140

Ala Leu Val Glu Gln Phe Ser Pro Leu Leu Ala Asn Glu Asp Ala His
145                 150                 155                 160

Pro Pro Ile Lys Val Ile Ser Phe Asn His Gly Leu Pro Asp Ala Val
                165                 170                 175

Asp Leu Leu His Glu Tyr Gln Arg Arg Phe Ser Pro Pro Leu Thr Val
            180                 185                 190

Thr Arg Thr His Glu Trp Leu Val Glu Ala Thr Ala Pro Gly Val Asp
        195                 200                 205

Lys Gly Ser Gly Leu Leu Arg Leu Cys Lys Leu Leu Gly Val Asp Pro
210                 215                 220

Gln Arg Val Leu Ala Ile Gly Asp Ser Asp Asn Asp Ile Pro Met Leu
225                 230                 235                 240

Glu Val Ala Gly Phe Ala Ile Ala Met Gly Asn Ala Asn Glu Arg Val
                245                 250                 255

Lys Ala Val Ala Asp Trp Val Ala Pro Ser Ile Asp Glu Glu Gly Ala
```

```
                260                 265                 270
Ala Val Ala Leu Arg Arg Trp Val Leu Glu Pro Met Ser Ala
            275                 280                 285

<210> SEQ ID NO 26
<211> LENGTH: 256
<212> TYPE: PRT
<213> ORGANISM: Caldilinea aerophila

<400> SEQUENCE: 26

Met Lys Asp Lys Thr Lys Val Leu Ala Leu Asp Leu Asp Thr Leu
1               5                   10                  15

Leu Arg Ser Asp Lys Ser Ile Gly Ala Ala Thr Leu Ala Ala Leu Asp
            20                  25                  30

Arg Trp Leu Ala Ala Gly His Glu Ile Val Val Ala Thr Gly Arg Pro
        35                  40                  45

Pro Arg Asn Val Ala Pro Val Leu Pro Pro Ser Leu Leu His Val Pro
    50                  55                  60

Arg Ile Val Tyr Asn Gly Ala Gln Ala Ile Leu Gly Asp Glu Ile Ile
65              70                  75                  80

Phe Asp Arg Pro Ile Pro Ala Gln Asp Val Arg His Ile Leu Glu Trp
                85                  90                  95

Ser Lys Arg Ser Gly Glu Ala Trp Tyr Ile Gly Leu Glu Ile Asn Asp
            100                 105                 110

Met Leu Tyr Val Asn Arg His Phe Glu Lys Pro Gly Thr Phe Gln Val
        115                 120                 125

Val Asp Leu Met Gln Leu Cys Asp Gln Pro Val Tyr Lys Ile Ile Phe
    130                 135                 140

Phe Phe Pro Asp Gly Arg Arg Asn Ile Glu Pro Leu Leu Ala Ala Met
145                 150                 155                 160

Pro Pro Thr Thr Arg Ala Leu Val Thr Pro Lys Phe Ser Leu Val Gln
                165                 170                 175

Leu Cys Ala Arg Asp Ala Asn Lys Phe Thr Ala Leu Lys Gln Leu Leu
            180                 185                 190

Ala Arg Arg Pro Leu Ala Pro Ala Val Ile Ala Val Gly Asp Asp
        195                 200                 205

Ile Asn Asp Ile Glu Met Val Arg Cys Ser Asp Ile Gly Val Ala Val
    210                 215                 220

Ala Asn Ala Leu Pro Glu Val Lys Ala Val Ala Asp Trp Ile Ala Pro
225                 230                 235                 240

Gly Ala Asp Asp Asp Gly Val Ala Tyr Val Ile Asp Arg Leu Leu Asn
                245                 250                 255

<210> SEQ ID NO 27
<211> LENGTH: 223
<212> TYPE: PRT
<213> ORGANISM: Caldilinea aerophila

<400> SEQUENCE: 27

Met Thr Ile Arg Ala Ile Leu Trp Asp Leu Asp Gly Thr Leu Ala Asp
1               5                   10                  15

Thr Thr Ala Leu His Tyr Gln Ala Trp Arg Lys Thr Met Gln Arg Tyr
            20                  25                  30

Gly Val Asp Leu Thr Tyr Glu Ser Phe Ile Lys Asp Tyr Gly Arg Asn
        35                  40                  45

Asn Ala Glu Ile Leu Ala Glu His Phe Gly Ile His Ala Val Ala Thr
```

```
            50                  55                  60
Ile Gln Gln Val Ala Asp Glu Lys Glu Ser Ala Phe Arg Ser Leu Ile
 65                  70                  75                  80

Thr Pro Gly Val Leu Gln Pro Leu Pro Gly Ala Leu Ala Trp Leu His
                 85                  90                  95

Cys Phe Arg Ser Leu Gly Met Ile Gln Val Ile Gly Ser Ser Gly Pro
                100                 105                 110

Met Ala Asn Ile Ala Ala Val Val His Ala Leu Gly Val Gly Asp Phe
                115                 120                 125

Phe Phe Gly Leu Val Ser Gly Val His Leu Pro Glu Gly Lys Pro Glu
            130                 135                 140

Pro Thr Ile Phe Leu Arg Cys Ala Ala Leu Ala Gly Ala Ala Pro Asp
145                 150                 155                 160

Glu Cys Leu Val Ile Glu Asp Ser Leu His Gly Ile Glu Ala Ala Met
                165                 170                 175

Arg Ala Gly Met Thr Ser Val Ala Val Gly Arg Ile Ala Ala Gln Pro
                180                 185                 190

Ala Leu Gln Asp Leu Ile Gln Lys Asn Pro Gly Leu Arg Cys Ile Val
                195                 200                 205

Thr Pro Ser Leu Ala Ser Ile Asp Asp Pro Lys Ser Ile Leu Thr
                210                 215                 220

<210> SEQ ID NO 28
<211> LENGTH: 275
<212> TYPE: PRT
<213> ORGANISM: Caldithrix abyssi

<400> SEQUENCE: 28

Met Ser Glu Val Met Lys Lys Met Leu Val Leu Asp Phe Asp Gly Thr
 1               5                  10                  15

Leu Phe Gln Pro Gly Lys Phe Ile Ser Asp Gln Asp Leu Lys Leu Leu
                20                  25                  30

Lys Ala Leu Ala Asn Met Asn Val Val Arg Val Ile Ala Thr Gly Arg
                35                  40                  45

Ser Leu Phe Ser Leu Lys Lys Val Ile Asp Met Ser Phe Pro Ile Asp
            50                  55                  60

Tyr Leu Ile Leu Ser Thr Gly Val Gly Ile Leu Asp Trp Arg Ser Gln
 65                  70                  75                  80

Lys Leu Ile Arg Ser Tyr Asp Met Glu Gly Gly Leu Val Asp Glu Ile
                85                  90                  95

Ile Ala Ile Leu Lys Arg Arg His Ser Phe Val His Gln Pro
                100                 105                 110

Ala Pro Gln Asn His Lys Phe Phe Tyr Tyr Asp Gly Ile Ala Pro Arg
            115                 120                 125

Gln Asp Phe Thr Arg Arg Phe Glu Leu Tyr Arg Asp Phe Ala Arg Pro
        130                 135                 140

Leu Lys Gln Arg Lys Arg Gly Met Ala Ala Gly Gln Ile Leu Val Ile
145                 150                 155                 160

Ser Glu Glu Leu Gln Gln Ile Lys Glu Glu Leu Gln Pro Leu Met His
                165                 170                 175

Arg Ile Asn Ile Ile Arg Thr Thr Ser Pro Leu Asp Gly Arg Ser Met
                180                 185                 190

Trp Val Glu Ile Phe Asp Lys Arg Val Asn Lys Ala Leu Ala Ala Gln
                195                 200                 205
```

```
Phe Leu Ala Glu Arg Leu Asn Ile Ser Val Arg Asn Ile Val Ala Leu
    210                 215                 220

Gly Asn Asp Tyr Asn Asp Leu Asp Leu Leu Asn Trp Ala Gly Ser Ala
225                 230                 235                 240

Phe Val Val His Thr Ala Pro Glu Glu Leu Lys Glu Lys Phe Gln Ile
                245                 250                 255

Ile Lys Asn Ala Asp Asp Gly Leu Leu Ile His Ile Met Pro Leu Leu
                260                 265                 270

Gln Arg Gly
        275
```

<210> SEQ ID NO 29
<211> LENGTH: 171
<212> TYPE: PRT
<213> ORGANISM: Caldithrix abyssi

<400> SEQUENCE: 29

```
Met Arg Lys Lys Leu Ser Gln Ile Gln Leu Ile Leu Met Asp Val Asp
1               5                   10                  15

Gly Val Leu Thr Ala Gly Glu Ile Ile Tyr Ser Ala Ala Gly Asp Glu
            20                  25                  30

Leu Lys Met Phe Asn Val Gln Asp Gly Met Gly Ile Thr Leu Ala Arg
        35                  40                  45

Met Ala Gly Leu Lys Thr Gly Ile Leu Thr Gly Arg Lys Ser Glu Leu
    50                  55                  60

Val Arg Arg Arg Ala Glu Glu Leu Lys Ile Asp Ile Val Ser Gln Gly
65                  70                  75                  80

Ser Phe Glu Lys Leu Pro Glu Tyr Glu Lys Ile Lys Gln Gln Met Gln
                85                  90                  95

Leu Ser Asp Glu Gln Ile Cys Tyr Ile Gly Asp Asp Val Leu Asp Ile
            100                 105                 110

Pro Val Leu Lys Arg Val Gly Phe Ser Val Ala Val Ala Asn Ala Arg
        115                 120                 125

Asp Glu Val Lys Ala Ile Ala Asp Tyr Val Thr Val Ala Glu Gly Gly
    130                 135                 140

Lys Gly Ala Val Arg Glu Val Ile Asp Lys Ile Leu Lys Trp Gln Asn
145                 150                 155                 160

Lys Leu His Ala Leu Ile Asp Gln Leu Ser Arg
                165                 170
```

<210> SEQ ID NO 30
<211> LENGTH: 354
<212> TYPE: PRT
<213> ORGANISM: Caldithrix abyssi

<400> SEQUENCE: 30

```
Met Lys Arg Gly His Arg Tyr Ile Val Phe Thr Met Ala Ile Phe Ser
1               5                   10                  15

Leu Ile Leu Ile Ala Cys Thr Lys Lys Glu Val Lys Pro Asp Leu Ala
            20                  25                  30

Phe Ala Gly Glu Lys His Leu Lys Asn Ile Arg Met Leu Thr Asn Gly
        35                  40                  45

Gly Glu Asn Ala Glu Ala Tyr Phe Ser Phe Asp Glu Ser Gln Leu Ile
    50                  55                  60

Tyr Gln Ser Lys His Asp Ser Ile Lys Cys Asp Gln Ile Phe Ile Met
65                  70                  75                  80
```

```
Asn Leu Asp Gly Ser Asp Lys Arg Met Val Ser Thr Gly Lys Gly Arg
                85                  90                  95

Thr Thr Cys Ser Tyr Phe Leu Pro Gly Asp Gln Gln Ile Ile Tyr Ala
            100                 105                 110

Ser Thr His Gly Val Asp Glu Asn Cys Pro Pro Pro Asp Phe Ser
            115                 120                 125

Arg Gly Tyr Val Trp Lys Val Tyr Ser Ser Tyr Asp Leu Tyr Ile Ala
        130                 135                 140

Asn Ala Asp Gly Ser Asp Pro Gln Pro Phe Leu Pro Ser Pro Gly Tyr
145                 150                 155                 160

Asp Ala Glu Ala Thr Val Ser Pro Arg Gly Asp Lys Ile Val Phe Thr
                165                 170                 175

Ser Gln Arg Asn Gly Asp Leu Asp Ile Tyr Thr Val Asn Ile Asp Gly
            180                 185                 190

Ser Gly Leu Lys Gln Leu Thr His Glu Ile Gly Tyr Asp Gly Gly Ala
        195                 200                 205

Phe Phe Ser Trp Asp Gly Ser Lys Ile Val Tyr Arg Ala Tyr His Pro
    210                 215                 220

Arg Thr Glu Glu Glu Leu Lys Arg Tyr Arg Lys Leu Leu Ala Glu Glu
225                 230                 235                 240

Leu Ile Glu Pro Asn Asn Phe Gln Leu Phe Val Met Asp Ala Asp Gly
                245                 250                 255

Ser Asn Lys Arg Gln Ile Thr His Asn Asp Phe Ala Asn Phe Ala Pro
            260                 265                 270

Phe Phe His Pro Asp Asn Lys Arg Ile Ile Phe Cys Ser Asn Met Gly
        275                 280                 285

Thr Thr Glu Ser Thr Gln Arg Asp Phe Asn Leu Trp Met Ile Asn Glu
    290                 295                 300

Asp Gly Thr Gly Leu Lys Gln Ile Thr Phe Phe Lys Gly Phe Asp Gly
305                 310                 315                 320

Phe Pro Met Phe Thr His Asp Gly Lys Lys Leu Val Phe Ala Ser Asn
                325                 330                 335

Arg Phe Asn Lys Lys Lys Gly Glu Thr Asn Val Phe Ile Ala Asp Trp
            340                 345                 350

Val Glu

<210> SEQ ID NO 31
<211> LENGTH: 222
<212> TYPE: PRT
<213> ORGANISM: Caldithrix abyssi

<400> SEQUENCE: 31

Met Arg Asn Lys Ala Val Leu Phe Asp Phe Asp Gly Val Val Val Lys
1               5                   10                  15

Ser Met Glu Gln His Phe Asn Ala Trp Arg Gln Ala Phe Leu Glu Lys
            20                  25                  30

Gly Val Glu Ile Lys Glu Asp Glu Phe Phe Val Leu Glu Gly Gln Gly
        35                  40                  45

Ile Asn Thr Ile Ala His His Leu Gly Lys Ile Tyr Gly Leu Asn Arg
50                  55                  60

Gln Gln Val Glu Glu Val Met Glu Arg Lys Val Asn Tyr Tyr Asn Gln
65                  70                  75                  80

Phe Met Thr Leu Glu Phe Tyr Asp His Phe His Glu Leu Val Glu His
                85                  90                  95
```

```
Leu His Arg Arg Gln Val Pro Met Gly Val Thr Gly Gly Asn Arg
             100                 105                 110

Ser Arg Val Glu Lys Ile Ile Asn Glu His Phe Asn His Tyr Phe Arg
             115                 120                 125

Ala Leu Val Thr Val Asp Asp Val Glu Arg Gly Lys Pro Phe Pro Asp
130                 135                 140

Pro Phe Leu Lys Ala Ala Gln Met Leu Asn Met Ala Pro Gln Asn Cys
145                 150                 155                 160

Ile Val Val Glu Asn Ala Pro Met Gly Ile Lys Gly Ala Lys Arg Ala
                 165                 170                 175

Gly Met Thr Val Val Ala Ile Thr Thr Thr Leu Lys Pro Asp Tyr Leu
                 180                 185                 190

Lys Gln Ala Asp Tyr Ile Ala His Asn Phe Leu Glu Val Glu Glu Ile
                 195                 200                 205

Leu Asn Thr Leu Leu Gly Ile Glu Arg Thr Glu Thr Ile Lys
                 210                 215                 220

<210> SEQ ID NO 32
<211> LENGTH: 268
<212> TYPE: PRT
<213> ORGANISM: Carboxydocella sp. UL01

<400> SEQUENCE: 32

Met Val Leu Val Lys Leu Ile Ala Ile Asp Leu Asp Asp Thr Leu Leu
1               5                   10                  15

Arg Thr Asp Cys Thr Ile Ser Pro Arg Ala Gln Ala Ala Ile Lys Ala
                20                  25                  30

Ala Ser Ala Arg Gly Val Ala Val Thr Leu Ala Thr Gly Arg Met Tyr
            35                  40                  45

Arg Ser Ala Arg Pro Tyr Ala Leu Glu Leu Gly Leu Asp Leu Pro Leu
        50                  55                  60

Ile Thr Tyr Gln Gly Ala Leu Ile Lys Ser Gly Leu Ser Gly Glu Glu
65                  70                  75                  80

Leu Trp His Cys Pro Leu Pro Pro Glu Met Ala Ala Glu Ile Ile Thr
                85                  90                  95

Leu Ala Arg Glu Glu Gly Ile His Ala Asn Ile Tyr Leu Asp Asp His
            100                 105                 110

Leu Tyr Val Glu Lys Ala Thr Ala Glu Ala Glu Ala Tyr Ser Gln Leu
        115                 120                 125

Ala Arg Val Pro Tyr Thr Val Glu Glu Asp Leu Arg Gly Arg Ile Leu
130                 135                 140

Ala Ser Gly Gln Gly Pro Ser Lys Ile Leu Leu Ile Ala Glu Pro Glu
145                 150                 155                 160

Arg Leu Asp Gln Leu Ala Ala Ala Leu Arg Pro Arg Trp Gln Gly Lys
                165                 170                 175

Val Gln Leu Ala Lys Ser Lys Asp His Tyr Leu Glu Phe Thr His Pro
            180                 185                 190

Glu Ala Ser Lys Gly Gln Ala Leu Ile Ala Leu Cys Arg Tyr Leu Asp
        195                 200                 205

Leu Glu Leu Lys Asp Ala Met Ala Ile Gly Asp Ser Phe Asn Asp Leu
210                 215                 220

Asp Met Ile Glu Leu Ala Gly Ile Gly Val Ala Met Gly Asn Ala Lys
225                 230                 235                 240

Pro Glu Val Lys Ala Ile Ala Asp Tyr Val Thr Leu Ala Asn Asp Asp
                245                 250                 255
```

```
Asp Gly Val Ala Glu Ala Ile His Arg Phe Val Leu
            260                 265
```

```
<210> SEQ ID NO 33
<211> LENGTH: 266
<212> TYPE: PRT
<213> ORGANISM: Carboxydothermus ferrireducens

<400> SEQUENCE: 33

Met Arg Tyr Arg Leu Leu Ala Val Asp Leu Asp Thr Phe Leu Asn
  1               5                  10                  15

Lys Glu Leu Gln Val Ser Pro Arg Val Gln Gln Ala Val Ile Glu Ala
                 20                  25                  30

Leu Lys Lys Gly Ile Ile Val Thr Leu Ala Thr Gly Arg Met Tyr Arg
             35                  40                  45

Ser Ala Lys Lys Tyr Ala Phe Ser Phe Leu Gly Asp Ile Pro Leu Ile
         50                  55                  60

Thr Tyr Asn Gly Ala Leu Ile Lys Tyr Ser Arg Ser Glu Arg Glu Ile
 65                  70                  75                  80

Tyr His Gln Pro Val Pro Gly Glu Leu Ala Leu Thr Ile Tyr Arg Arg
                 85                  90                  95

Val Lys Gly His Phe His Leu Asn Val Tyr Gln Asp Asp Glu Leu Phe
            100                 105                 110

Val Glu Glu Asp Asn Gln Tyr Ile Arg Asp Tyr Ser Lys Ile Ala Gly
            115                 120                 125

Val Pro Phe Arg Val Val Asn Asn Ile Glu Glu Leu Leu Gly Lys Lys
        130                 135                 140

Ala Pro Thr Lys Leu Leu Ala Ile Gly Asp Pro Glu Glu Leu Asp Gln
145                 150                 155                 160

Leu Trp Glu Glu Thr Asn Gly Glu Phe Arg Gly Val Leu His Ile Thr
                165                 170                 175

Lys Ser Lys Pro His Tyr Leu Glu Phe Leu Ala Ala Gly Val Asn Lys
            180                 185                 190

Gly Glu Ala Leu Lys Ile Leu Ala Gln His Leu Arg Ile Ser Leu Lys
        195                 200                 205

Glu Thr Val Ala Val Gly Asp Ser Tyr Asn Asp Leu Glu Met Leu Glu
    210                 215                 220

Ala Ala Gly Leu Gly Val Ala Met Gly Asn Ala Leu Pro Glu Val Lys
225                 230                 235                 240

Arg Arg Ala Asp Leu Val Val Pro Ala Asn Asp Glu Asp Gly Ile Ala
                245                 250                 255

Tyr Leu Ile Asn Glu Ile Ile Leu Lys Asn
            260                 265
```

```
<210> SEQ ID NO 34
<211> LENGTH: 231
<212> TYPE: PRT
<213> ORGANISM: Carboxydothermus ferrireducens

<400> SEQUENCE: 34

Met Ala Tyr Ile Leu Phe Asp Leu Asp Gly Thr Leu Pro Leu Asn
  1               5                  10                  15

Leu Asp Tyr Phe Leu Lys Leu Tyr Ile Gln Glu Val Lys Ser Tyr Val
                 20                  25                  30

Lys Gly Lys Phe Asp Pro Asp Leu Ile Val Lys Ala Ile Leu Lys Ala
             35                  40                  45
```

```
Thr Glu Glu Met Val Lys Asn Thr Gly Glu Lys Leu Asn Ser Glu Val
         50                  55                  60

Phe Trp Gln Ala Phe Asp Arg Val Tyr Pro Gly Thr Ala Asn Leu His
 65                  70                  75                  80

Asn Val Phe Glu Asp Phe Tyr His Thr Ser Phe Lys Asn Ile Gly Asn
                 85                  90                  95

Tyr Phe Lys Pro His Pro Leu Ala Arg Pro Met Ile Arg Tyr Leu His
                100                 105                 110

Lys Lys Gly His Thr Leu Ile Leu Ala Thr Asn Ala Leu Phe Pro Arg
            115                 120                 125

Ser Ala Ile Ile Glu Arg Leu Tyr Trp Ala Asn Leu Ser Pro Lys Tyr
130                 135                 140

Phe Arg Phe Ile Thr His Tyr Asp Asn Met His Tyr Cys Lys Pro Asn
145                 150                 155                 160

Pro Asn Tyr Tyr Lys Glu Ile Leu Glu Lys Ile Lys Ala Arg Pro Ser
                165                 170                 175

Asp Cys Leu Met Ile Gly Asn Asp Pro Ala Glu Asp Leu Val Ala Lys
                180                 185                 190

Glu Leu Gly Ile Lys Thr Phe Leu Val Lys Asp Tyr Gly Val Lys Arg
            195                 200                 205

Glu Asn Pro Arg Thr Pro Asp Tyr Ala Gly Asp Phe Tyr Glu Leu Tyr
210                 215                 220

Arg Phe Ile Arg Glu Asn Phe
225                 230

<210> SEQ ID NO 35
<211> LENGTH: 212
<212> TYPE: PRT
<213> ORGANISM: Carboxydothermus ferrireducens

<400> SEQUENCE: 35

Met Ile Lys Ala Val Phe Phe Asp Leu Asp Gly Thr Leu Leu Asp Thr
  1               5                  10                  15

Phe Asp Leu Ile Tyr Glu Ser Phe Lys His Val Tyr Lys Asn Phe Leu
                 20                  25                  30

Asn Lys Asp Ile Thr Arg Glu Glu Ile Tyr Pro Tyr Phe Gly Lys Pro
             35                  40                  45

Leu Ile Tyr Ser Phe Glu Asn Leu Asp Pro Glu Thr Ile Asp Gln Val
 50                  55                  60

Ile Ala Ala Tyr Arg Glu Phe Asn Leu Gln His His Asp Gln Met Val
 65                  70                  75                  80

Lys Pro Phe Pro Gly Ala Lys Glu Thr Leu Glu Lys Leu Lys Gln Arg
                 85                  90                  95

Gly Lys Ile Leu Ala Val Ile Thr Ser Lys Val Lys Ser Thr Ala Ile
            100                 105                 110

Arg Gly Leu Lys Leu Phe Asn Leu Asp Arg Tyr Phe Asp Leu Val Val
        115                 120                 125

Ala Leu Glu Asp Thr Glu Lys His Lys Pro Asp Pro Ala Pro Val Leu
130                 135                 140

Tyr Ala Leu Lys Phe Phe Gln Val Lys Pro Glu Gln Cys Leu Met Val
145                 150                 155                 160

Gly Asp Ser Pro His Asp Met Val Ser Ala Gln Arg Ala Gly Val Lys
                165                 170                 175

Thr Ala Ala Val Lys Trp Ser Val Leu Pro Trp Glu Asp Leu Val Lys
```

```
                180             185             190
Thr Lys Pro Asn Tyr Ile Leu Asn Ser Phe Asp Asp Leu Leu Lys Ile
            195                 200             205

Thr Gly Val Glu
        210
```

<210> SEQ ID NO 36
<211> LENGTH: 218
<212> TYPE: PRT
<213> ORGANISM: Chloroflexi bacterium 54-19

<400> SEQUENCE: 36

```
Met Asn Lys Phe Gln Gly Val Ile Leu Asp Ile Asp Gly Thr Leu Ile
1               5                   10                  15

Asp Ser Asn Asp Ala His Ala His Ser Trp Val Asp Thr Phe Ala Glu
            20                  25                  30

Ala Gly Ile Pro Val Pro Phe Glu Arg Val Arg Pro Leu Ile Gly Glu
            35                  40                  45

Gly Gly Asp Lys Leu Leu Pro Glu Val Ser Gly Phe Glu Ala Gly Ser
        50                  55                  60

Ala Glu Gly Lys Arg Leu Thr Lys Arg Thr Glu Ile Phe Lys Glu
65                  70                  75                  80

Lys Tyr Leu Pro His Ile Gln Pro Phe Pro Lys Thr Arg Glu Leu Ile
                85                  90                  95

Thr Ala Phe Glu Lys Arg Gly Leu Lys Leu Gln Ile Ala Thr Ser Ala
            100                 105                 110

Gln Glu Ala Glu Val Lys Asp Leu Leu Lys Val Ala Gly Thr Pro Glu
        115                 120                 125

Ile Ile Glu Gln Lys Thr Thr Ser Asp Asp Ala Glu Lys Ser Lys Pro
130                 135                 140

Asp Pro Asp Ile Ile His Ala Ala Leu Gln Lys Ile Gly Leu Glu Ala
145                 150                 155                 160

Gly Gln Val Val Met Leu Gly Asp Thr Pro Tyr Asp Val Ala Ala Ala
                165                 170                 175

Lys Lys Ala Gly Val Lys Ser Tyr Ala Phe Arg Cys Gly Gly Trp Trp
            180                 185                 190

Gln Asp Arg Asp Phe Glu Asp Ala Ala Ala Ile Phe Asp Gly Pro Ala
        195                 200                 205

Asp Leu Leu Glu Lys Leu Asp Asp Tyr Leu
        210                 215
```

<210> SEQ ID NO 37
<211> LENGTH: 284
<212> TYPE: PRT
<213> ORGANISM: Defluviitoga tunisiensis

<400> SEQUENCE: 37

```
Met Asn Tyr His Leu Asn Ser Ser Thr Lys Val Phe Val Phe Asp Phe
1               5                   10                  15

Asp Gly Thr Leu Leu Asn Ser Glu Val Arg Ile Ser Pro Arg Thr Phe
            20                  25                  30

Glu Ala Leu Lys Lys Leu Lys Glu His Gly His Thr Ile Ile Leu Cys
        35                  40                  45

Ser Gly Arg Met Tyr Ala Ser Met Leu Phe Ile Val Glu Asn Phe Leu
    50                  55                  60

Pro Phe Leu Lys Gly Tyr Ala His Ile Val Ser Tyr Asn Gly Gly Tyr
```

```
                65                  70                  75                  80
        Ile Val Asn Asn Lys Gly Glu Leu Leu Phe Glu Glu Gly Leu Asp Lys
                        85                  90                  95

Asp Val Ala Ile Asp Cys Ile Glu Phe Leu Arg Glu Leu Asn Val His
                    100                 105                 110

Arg His Val Tyr Ile Asn Asp Glu Leu Ile Ser Glu Gln Asp Asp Gln
                    115                 120                 125

Glu Ile Lys Asp Tyr Ser Lys His Ser Phe Val Ala Tyr Lys Leu Val
                    130                 135                 140

Asp Asp Leu Val Asp Thr Ile Lys Asn Ser Glu His Pro Thr Leu Lys
        145                 150                 155                 160

Ile Leu Gly Ile Cys Glu Gln Glu Lys Leu Asn Met Val Gln Ser Leu
                        165                 170                 175

Ala Glu Lys Lys Phe Glu Gly Lys Ile Asn Ile Met Arg Ser Phe Ser
                    180                 185                 190

Thr Tyr Leu Asp Phe Met Pro Phe Gly Val Ser Lys Gly Glu Ala Leu
                    195                 200                 205

Lys Ile Leu Ser Lys Ile Tyr Asn Phe Asn Val Glu Glu Val Tyr Val
                    210                 215                 220

Phe Gly Asp Ser Gln Asn Asp Ile Asp Met Leu Arg Ile Ser Arg Asn
        225                 230                 235                 240

Ser Phe Ala Met Gly Asn Ala Gln Lys Asp Val Lys Glu Val Ala Arg
                        245                 250                 255

Tyr Val Ile Pro Ser Asn Asp Glu Asp Gly Val Ala Phe Ala Ile Glu
                    260                 265                 270

Lys Ile Leu Ser Asp Asp Leu Asp Asn Val Asn Ile
                    275                 280

<210> SEQ ID NO 38
<211> LENGTH: 231
<212> TYPE: PRT
<213> ORGANISM: Deinococcus aerius

<400> SEQUENCE: 38

Met Thr Val Pro Gln Pro Thr Asp Pro Ala Thr Val Leu Asn Pro Glu
        1               5                   10                  15

Arg Leu Arg Gly Val Leu Leu Asp Val Asp Gly Thr Leu Ile Asp Ser
                        20                  25                  30

Asn Asp Ala His Ala Arg Ala Trp Val Glu Ala Leu Arg Glu Glu Gly
                    35                  40                  45

Phe Glu Arg Ser Phe Gly Glu Val Arg Pro Leu Ile Gly Met Gly Gly
                50                  55                  60

Asp Gln Leu Val Pro Arg Leu Thr Gly Glu Asp Gly Glu Ser Glu Val
        65                  70                  75                  80

Gly Lys Arg Leu Thr Gln Gly Trp Leu Lys His Phe Lys Pro Leu Val
                        85                  90                  95

Pro Gly Leu Arg Pro Thr Arg Gly Asn Arg Ala Leu Ile Glu Gly Leu
                    100                 105                 110

Arg Ser Arg Gly Leu Lys Val Val Leu Ala Thr Ser Gly Glu Ala Glu
                    115                 120                 125

Ile Val Asp Ser Leu Leu Lys Gln Ala Asn Leu Gly Asp Leu Asn Leu
                    130                 135                 140

Asp Arg Val Ser Ser Ser Glu Val Gly Ser Ser Lys Pro Ala Pro Asp
        145                 150                 155                 160
```

```
Leu Val Gln Val Gly Leu Asp Lys Leu Gly Leu Pro Ala Gly Ala Ala
                165                 170                 175

Leu Met Val Gly Asp Thr Pro Phe Asp Ala Glu Ala Ala His Gly Ala
            180                 185                 190

Gly Val Pro Cys Ala Leu Leu Arg Cys Gly Gly Asp Ser Glu Glu Glu
            195                 200                 205

Leu Gly Arg Thr Gly Ala Leu Val Leu Asn Asp Pro Gln Ala Leu Leu
        210                 215                 220

Glu Ala Leu Glu Gly Ala Ser
225                 230
```

<210> SEQ ID NO 39
<211> LENGTH: 231
<212> TYPE: PRT
<213> ORGANISM: Deinococcus apachensis

<400> SEQUENCE: 39

```
Met Thr Ala Leu Gln Pro Ala Asp Pro Ala Ala Leu Asn Pro Asp
1               5                   10                  15

Arg Leu Arg Gly Val Leu Leu Asp Val Asp Gly Thr Leu Ile Asp Ser
                20                  25                  30

Asn Asp Ala His Ala Arg Ala Trp Val Glu Ala Leu Arg Glu Glu Gly
            35                  40                  45

Phe Glu Arg Ser Phe Gly Glu Val Arg Pro Leu Ile Gly Met Gly Gly
        50                  55                  60

Asp Gln Leu Ile Pro Arg Leu Thr Gly Glu Asp Gly Glu Ser Glu Leu
65                  70                  75                  80

Gly Lys Arg Leu Thr Gln Gly Trp Leu Lys His Phe Lys Pro Leu Ile
                85                  90                  95

Pro Glu Leu Gln Pro Thr Arg Gly Asn Arg Ala Leu Ile Glu Gly Leu
            100                 105                 110

Arg Ala Arg Gly Leu Arg Val Ala Leu Ala Thr Ser Gly Glu Ala Glu
        115                 120                 125

Ile Val Asp Gly Leu Leu Lys Gln Ala Gly Leu Asp Asp Leu Asn Leu
130                 135                 140

Asp Arg Val Ser Ser Ser Glu Val Glu Ser Ser Lys Pro Glu Pro Asp
145                 150                 155                 160

Leu Val Glu Ala Gly Leu Asn Lys Leu Gly Leu Pro Ala Asp Ala Ala
                165                 170                 175

Leu Met Val Gly Asp Thr Pro Phe Asp Ala Glu Ala Ala His Lys Ala
            180                 185                 190

Gly Val Pro Cys Val Leu Leu Arg Cys Gly Gly Asp Ser Asp Glu Glu
            195                 200                 205

Leu Gly Arg Ala Pro Ala Leu Val Leu Asp Asp Pro Gln Ala Leu Leu
        210                 215                 220

Glu Ala Leu Glu Gly Thr Ser
225                 230
```

<210> SEQ ID NO 40
<211> LENGTH: 228
<212> TYPE: PRT
<213> ORGANISM: Deinococcus aquatilis

<400> SEQUENCE: 40

```
Met Arg Arg Ala Glu Asp Val Tyr Leu Asp Arg Met Tyr Lys Gly Val
1               5                   10                  15
```

```
Ile Phe Asp Ile Asp Gly Thr Leu Val Asp Ser Asn Asp Ala His Ala
            20                  25                  30

Arg Ala Trp Val Lys Ala Phe Ala Asp Glu His Ile Thr Val Pro Phe
        35                  40                  45

Asp Gln Val Arg Pro Leu Ile Gly Met Gly Ser Asp Gln Met Val Pro
    50                  55                  60

Arg Leu Thr Asp Val Gln Lys Asp Ser Pro Thr Phe Lys Arg Leu Gly
65                  70                  75                  80

Glu Ala Trp Lys Gln His Phe Gln Ala Glu Glu Met Pro His Leu Lys
                85                  90                  95

Ala Gln Pro Gly Val Arg Ala Leu Ile Glu Arg Leu Gln Glu Arg Gly
            100                 105                 110

Leu Arg Leu Ile Val Gly Thr Ser Ala Asp Glu Ala Leu Val Ala Asp
        115                 120                 125

Leu Leu Arg Val Ala Gly Val Asp Asp Leu Leu Thr Glu Tyr Thr Thr
130                 135                 140

Ala Ser Asp Val Glu Ser Ser Lys Pro Glu Pro Asp Ile Val Gln Ala
145                 150                 155                 160

Ala Val Thr Lys Leu Gly Leu Ala Pro Ala Glu Val Leu Met Val Gly
            165                 170                 175

Asp Thr Pro Phe Asp Ile Glu Ser Ala His Lys Ala Gly Val Ala Thr
        180                 185                 190

Val Ala Leu Arg Cys Gly Gly Asp Thr Arg Phe Glu Gly Ala Ala Ala
    195                 200                 205

Val Tyr Ala Asp Pro Gln Glu Trp Leu Glu Gln Leu Asp Gln Ser Pro
210                 215                 220

Leu Gly Lys Gly
225

<210> SEQ ID NO 41
<211> LENGTH: 229
<212> TYPE: PRT
<213> ORGANISM: Deinococcus geothermalis

<400> SEQUENCE: 41

Met Ser His Pro Glu Pro Thr Ala Pro Ala Ala Leu Asp Pro Lys
1               5                   10                  15

Arg Leu Arg Gly Val Leu Leu Asp Val Asp Gly Thr Leu Ile Asp Ser
            20                  25                  30

Asn Asp Ala His Ala Arg Ala Trp Val Glu Ala Leu Arg Glu Ala Gly
        35                  40                  45

Phe Glu Arg Thr Phe Glu Glu Val Arg Pro Leu Ile Gly Met Gly Gly
    50                  55                  60

Asp Gln Leu Ile Pro Arg Leu Thr Gly Leu Asp Ser Gln Ser Glu Glu
65                  70                  75                  80

Gly Gln Arg Leu Thr Gln Gly Trp Leu Arg His Phe Lys Pro Leu Ile
                85                  90                  95

Pro Thr Leu His Ala Thr Arg Gly Ala Arg Ala Leu Val Gln Gly Leu
            100                 105                 110

His Ala Arg Gly Leu Gln Val Leu Leu Ala Thr Ser Gly Glu Ala Glu
        115                 120                 125

Ile Val Asp Glu Leu Leu Lys Gln Ala His Leu Asp Asp Leu Gln Leu
    130                 135                 140

Glu Arg Val Ser Ser Ser Glu Val Glu Ser Ser Lys Pro Ala Pro Asp
145                 150                 155                 160
```

Leu Val Gln Ala Gly Leu Glu Lys Leu Gly Leu Pro Ala Gly Glu Ala
                165                 170                 175

Leu Leu Val Gly Asp Thr Pro Tyr Asp Ala Gln Ala Ala His Lys Ala
            180                 185                 190

Gly Val Pro Cys Val Leu Leu Arg Cys Gly Gly Asn Thr Gly Leu Glu
        195                 200                 205

Glu His Ala Pro Thr Leu Asp Asp Pro Gln Ala Leu Leu Glu Val Leu
    210                 215                 220

Glu Gly Thr Lys Gly
225

<210> SEQ ID NO 42
<211> LENGTH: 225
<212> TYPE: PRT
<213> ORGANISM: Deinococcus hopiensis

<400> SEQUENCE: 42

Met Ser Leu Lys Asp Leu Leu Ser Pro Ser His Leu Arg Gly Val Leu
1               5                   10                  15

Leu Asp Val Asp Gly Thr Leu Ile Asp Ser Asn Gly Ala His Ala Arg
            20                  25                  30

Ala Trp Val Gln Ala Leu Arg Asp Glu Gly Phe Ala Arg Thr Phe Glu
        35                  40                  45

Asp Val Arg Pro Leu Ile Gly Met Gly Gly Asp Lys Leu Val Pro Glu
    50                  55                  60

Leu Thr Gly Glu Asp Pro Glu Gly Glu Arg Ala Lys Arg Met Lys Asp
65                  70                  75                  80

Ala Trp Leu Lys His Phe Gln Pro Met Ile Pro Lys Leu Gln Pro Thr
                85                  90                  95

Arg Gly Ala Arg Glu Met Ile Glu Gly Leu Leu Ala Arg Asp Leu Arg
            100                 105                 110

Val Ala Ile Ala Thr Ser Gly Glu Ala Glu Ile Val Glu Gly Leu Leu
        115                 120                 125

Ala Arg Val Gly Val Ala His Leu Lys Leu Asp Arg Val Ser Ser Ser
    130                 135                 140

Glu Val Asp His Ser Lys Pro Asp Pro Asp Leu Ile Gln Val Gly Leu
145                 150                 155                 160

Asn Lys Leu Gly Val Ser Ala Glu Gln Ala Leu Met Val Gly Asp Thr
                165                 170                 175

Pro Phe Asp Ala Glu Ala Ala Arg Lys Ala Gly Val Pro Ser Val Leu
            180                 185                 190

Leu Arg Cys Gly Gly Asp Ala Arg Val Glu Gln His Ala Tyr Val Leu
        195                 200                 205

Asp Asp Pro Arg Ala Leu Leu Glu Ala Leu Pro Asp Gly Ser Gln Thr
    210                 215                 220

Val
225

<210> SEQ ID NO 43
<211> LENGTH: 214
<212> TYPE: PRT
<213> ORGANISM: Deinococcus maricopensis

<400> SEQUENCE: 43

Met Ser Ile Arg Ala Val Ile Met Asp Leu Asp Gly Thr Leu Val Asp
1               5                   10                  15

-continued

Ser Asn Asp Ala His Ala Arg Ala Trp Val Ala Ala Leu Arg Asp Phe
                20                  25                  30

Gly Ile Glu Arg Thr Phe Glu Asp Val Arg Pro Leu Ile Gly Met Gly
        35                  40                  45

Gly Asp Gln Leu Leu Pro Arg Val Ala Asp Val Asp Pro Asn Ser Glu
    50                  55                  60

Arg Gly Glu Gly Leu Thr Gln Ala Trp Ala Glu His Phe Lys Pro Met
65                  70                  75                  80

Ile Pro Glu Leu Arg Ala Thr Arg Gly Ala Arg Glu Leu Leu Glu Ala
                85                  90                  95

Leu His Gly Arg Gly Leu Arg Val Ile Leu Gly Thr Ser Gly Asp Ser
            100                 105                 110

Asp Val Ile Asp Pro Leu Leu Glu His Ile Gly Val Arg Asp Leu Val
        115                 120                 125

Pro Asp Arg Val Thr Ala Asp Val Glu Ala Ser Lys Pro Glu Pro
    130                 135                 140

Asp Ile Leu His Ala Ala Leu Gln Lys Leu Gly Val Gly Ala His Glu
145                 150                 155                 160

Ala Leu Met Val Gly Asp Thr Pro Phe Asp Ala Glu Ala Ala Lys Arg
                165                 170                 175

Ala Asn Val Arg Val Ala Leu Leu Arg Ala Gly Gly Asp Glu Arg Val
            180                 185                 190

Asn Ala Glu Ala Phe Thr Phe Asp Asp Pro Ala Asp Leu Ala Ala His
        195                 200                 205

Leu Asp Asp Val Leu Arg
    210

<210> SEQ ID NO 44
<211> LENGTH: 261
<212> TYPE: PRT
<213> ORGANISM: Deinococcus murrayi

<400> SEQUENCE: 44

Met Leu Leu Ala Phe Asp Leu Asp Gly Thr Leu Ile Pro Asp Leu Gly
1               5                   10                  15

Arg Glu Val Pro Ala Ala Thr Val Arg Ala Leu Ala Arg Leu Arg Gly
                20                  25                  30

Leu Gly Ala Arg Val Ala Val Ile Thr Gly Arg Asp Ala Ala Pro Pro
            35                  40                  45

Gln Val Leu Glu Ala Ala Gln Pro Asp Ala Val Ala Thr Asn Asn Gly
        50                  55                  60

Gly Arg Val Glu Leu Gln Gly Glu Leu His Arg Glu Ala Arg Phe Ser
65                  70                  75                  80

Glu Asp Glu Leu Ala Ala Val Leu Ala His Glu Leu Glu Glu Ala Arg
                85                  90                  95

Val Val Val Phe Arg Pro Ser Gly Leu Tyr Ala Glu Leu Pro Pro Gly
            100                 105                 110

His Ala Pro Glu Ala Trp Met Val Glu Arg Gly Val Arg Pro Leu Ala
        115                 120                 125

Gln Ala Pro Ala Gly Glu Pro Thr Leu Lys Val Gly Phe Tyr His Pro
    130                 135                 140

Gly Val Ala Asp Phe Ala Ala Arg Leu Arg Val Ser His Pro His Leu
145                 150                 155                 160

Val Leu Thr Gly Ala Gln Pro Pro Tyr Ser Glu Phe Leu Thr Val Thr

```
                         165                 170                 175
Pro Ala Gly Ala His Lys Gly Ala Ala Leu Thr Leu Ile Ala Gln Gly
                180                 185                 190
Leu Gly Val Glu Leu Glu Arg Thr Val Val Phe Gly Asp Ser Asp Asn
            195                 200                 205
Asp Val Ala Met Leu Glu Ile Ala Gly Tyr Ala Val Gln Val Gly His
        210                 215                 220
Leu Pro Leu Leu Ala Pro His Ala Asp Asp Arg Val Ser Gly Pro Gln
225                 230                 235                 240
Ala Leu Gly Pro Tyr Leu Glu Glu Leu Ala Asp Arg Leu Glu Ala Ala
                245                 250                 255
Glu Ala Pro Ala Thr
            260

<210> SEQ ID NO 45
<211> LENGTH: 225
<212> TYPE: PRT
<213> ORGANISM: Deinococcus murrayi

<400> SEQUENCE: 45

Met Thr His His Asp Leu Leu Ser Pro Glu Arg Leu Arg Gly Val Leu
1               5                   10                  15
Leu Asp Val Asp Gly Thr Leu Ala Asp Ser Asn His Ala His Ala Arg
            20                  25                  30
Ala Trp Ala Ala Ala Leu Arg Asp Glu Gly Phe Glu Lys Ser Pro Glu
        35                  40                  45
Ala Ile Phe Pro Leu Ile Gly Met Gly Gly Asp Lys Leu Val Pro Glu
    50                  55                  60
Leu Thr Gly Leu Asp Ala Glu Ser Glu Arg Gly Gln Arg Met Thr Glu
65                  70                  75                  80
Gly Trp Val Arg His Phe Gln Glu Leu Ile Pro Asp Leu Arg Pro Thr
                85                  90                  95
Pro Gly Ala Arg Ala Leu Val Glu Gly Leu Arg Ala Arg Gly Leu Arg
            100                 105                 110
Val Val Leu Ala Thr Ser Gly Glu Ala Glu Val Val Asp Ala Leu Leu
        115                 120                 125
Arg Gln Ile Gly Leu Asp Asp Leu Glu Leu Glu Arg Val Ser Ser Thr
    130                 135                 140
Asp Val Glu Asn Ser Lys Pro Asp Pro Asp Leu Val Gln Ala Gly Leu
145                 150                 155                 160
Arg Thr Leu Gly Leu Pro Ala Glu Ala Thr Leu Met Val Gly Asp Thr
                165                 170                 175
Pro Tyr Asp Ala Glu Ala Ala Arg Lys Ala Gly Val Pro Cys Val Leu
            180                 185                 190
Leu Arg Cys Gly Gly His Pro Gly Val Glu Glu His Asp Pro Val Tyr
        195                 200                 205
Asp His Pro Gln Ala Leu Leu Glu Ala Leu Asp Gln Ala Phe Pro Val
    210                 215                 220
Glu
225

<210> SEQ ID NO 46
<211> LENGTH: 229
<212> TYPE: PRT
<213> ORGANISM: Deinococcus reticulitermitis
```

```
<400> SEQUENCE: 46

Met Ala Asp Leu Gln Leu Ser Ser Pro Ala Leu Pro Ala Val Ser Arg
1               5                   10                  15

Leu Lys Gly Leu Leu Leu Asp Leu Asp Gly Thr Leu Val Asp Ser Asn
            20                  25                  30

Gly Ala His Thr Glu Ala Trp Val Gln Ala Leu Ala Asp Gln Gly Phe
            35                  40                  45

Thr Arg Pro Pro Ala Glu Val Arg Pro Leu Ile Gly Met Gly Gly Asp
    50                  55                  60

Gln Leu Val Pro Arg Leu Thr Gly Leu Asp Glu Gly Ser Glu Thr Gly
65                  70                  75                  80

Lys Ala Leu Val Glu Gly Trp Gln Thr His Phe Lys Ser Arg Met Pro
                85                  90                  95

Ser Val Arg Thr Phe Pro Gly Ala Arg Glu Leu Leu Glu Trp Ala Arg
            100                 105                 110

Glu Val Gly Leu Pro Val Val Leu Ala Ser Ser Gly Glu Asp Glu Ile
            115                 120                 125

Val Glu Gly Leu Leu Ala Gln Ala Gly Leu Leu Glu Leu Val Thr Asp
130                 135                 140

Arg Val Arg Ser Asp Glu Val Asn Gln Thr Lys Pro Arg Pro Asp Val
145                 150                 155                 160

Val Gln Ala Ala Leu Lys Lys Ala Gly Val Ala Pro Glu Glu Ala Leu
                165                 170                 175

Phe Val Gly Asp Thr Val His Asp Ala Arg Ala Arg Ala Ala Gly
            180                 185                 190

Val Pro Cys Val Leu Val Arg Ala Gly Gly Ser Pro Gly Leu Asp Ala
            195                 200                 205

Glu Pro His Val Leu Gly Asp Leu Met Glu Leu Leu Ala Ala Leu Lys
            210                 215                 220

Ala Gly Ser Thr Thr
225

<210> SEQ ID NO 47
<211> LENGTH: 227
<212> TYPE: PRT
<213> ORGANISM: Deinococcus wulumuqiensis

<400> SEQUENCE: 47

Met Arg Leu Ser Pro Gln Thr Pro Ala Leu Pro Ala Val Pro Asp Leu
1               5                   10                  15

Arg Ala Leu Leu Leu Asp Leu Asp Gly Thr Leu Ala Asp Ser Asn Asp
            20                  25                  30

Ala His Ala Arg Ala Trp Val Gln Ala Leu Ala Asp Gln Asp Ile Thr
            35                  40                  45

Arg Glu Glu Ser Glu Val Arg Pro Leu Ile Gly Met Gly Gly Asp Gln
    50                  55                  60

Leu Val Pro Ala Leu Thr Gly Glu Ser Asp Arg Ser Glu Leu Gly Lys
65                  70                  75                  80

Ala Leu Val Gln Gly Trp Gln Asp His Phe Gly Pro Met Ile Pro Glu
                85                  90                  95

Ile Ala Pro Leu Gly Gly Ala Arg Glu Leu Leu Glu Trp Ala Arg Thr
            100                 105                 110

Gln Gly Leu Lys Val Val Leu Ala Ser Ser Gly Glu Asp Asp Ile Val
            115                 120                 125
```

Asp Ala Leu Leu Glu Gln Ile Gly Val Gly Asp Leu Val Pro Leu Arg
    130                 135                 140

Val Arg Ser Asp Glu Val Gln Arg Thr Lys Pro Ala Pro Asp Val Leu
145                 150                 155                 160

Gln Ala Ala Leu Ala Lys Ala Gly Val Ser Ala Ala Gln Ala Leu Phe
                165                 170                 175

Val Gly Asp Thr Thr Tyr Asp Ala Arg Ala Arg Ala Ala Gly Val
            180                 185                 190

Ala Cys Val Val Leu Arg Ala Gly Gly Ser Pro Gly Leu Asn Thr Glu
            195                 200                 205

Pro His Val Leu Ser Asp Pro Ala Glu Leu Leu Ala Glu Leu Lys Lys
    210                 215                 220

Ala Thr Ser
225

<210> SEQ ID NO 48
<211> LENGTH: 224
<212> TYPE: PRT
<213> ORGANISM: Deinococcus sp. Leaf326

<400> SEQUENCE: 48

Met Ser Ser Tyr Leu Gly Val Ile Phe Asp Leu Asp Gly Thr Leu Val
1               5                   10                  15

Asp Ser Asn Asp Gly His Ala Arg Ala Trp Val Arg Ala Phe Ala Asp
            20                  25                  30

Gln Gly Ile Glu Val Thr Phe Gly Gln Val Arg Pro Leu Met Gly Met
        35                  40                  45

Gly Gly Asp Gln Leu Val Pro His Leu Thr Gly Ile Gly Lys Asp Asp
    50                  55                  60

Pro Arg Tyr Glu Ala Leu Ser Asp Gly Trp Lys Arg His Phe Gln Ala
65                  70                  75                  80

Glu Glu Leu Pro Arg Leu Arg Ala Gln Pro Gly Val Arg Pro Leu Leu
                85                  90                  95

Val Ala Leu Gln Ala Gln Gly Leu Arg Leu Ile Val Gly Thr Ser Ala
            100                 105                 110

Asp Glu Ala Leu Val Arg Asp Leu Leu Gly Val Ala Gly Ala Gln Asp
        115                 120                 125

Leu Phe Thr Glu Tyr Thr Thr Ala Ser Glu Val Glu Glu Ser Lys Pro
    130                 135                 140

Gln Pro Asp Ile Val Gln Ala Ala Val Arg Lys Leu Gly Leu Asp Pro
145                 150                 155                 160

Ala Gln Val Leu Met Val Gly Asp Thr Ser Phe Asp Ile Glu Ser Ala
                165                 170                 175

Arg Gly Ala Gly Val Ala Thr Val Ala Leu Arg Ser Gly Gly Thr Ala
            180                 185                 190

Gln Phe Thr Gly Ala Ala Ala Val Tyr Asp Ser Pro Gln Asp Trp Leu
        195                 200                 205

Asp His Leu Ala Ala Ser Pro Leu Gly Pro Asp Gln Pro Ser Ala Ser
    210                 215                 220

<210> SEQ ID NO 49
<211> LENGTH: 225
<212> TYPE: PRT
<213> ORGANISM: Deinococcus phoenicis

<400> SEQUENCE: 49

Met Thr Pro Ser Leu Glu Ala Leu Asn Pro Asp Arg Leu Arg Gly
1               5                   10                  15

Val Leu Leu Asp Val Asp Gly Thr Leu Ile Asp Ser Asn Asp Ala His
            20                  25                  30

Ala Arg Ala Trp Val Glu Ala Leu Arg Asp Glu Gly Phe Glu Lys Thr
        35                  40                  45

Val Gly Glu Val Arg Pro Leu Ile Gly Met Gly Gly Asp Gln Met Ile
50                  55                  60

Pro Arg Leu Thr Gly Lys Gly Ser Glu Ser Glu Val Gly Gln Arg Leu
65                  70                  75                  80

Thr Asp Gly Trp Leu Lys His Phe Lys Pro Leu Ile Pro Glu Leu His
                85                  90                  95

Ala Thr Arg Gly Ala Arg Ala Leu Val Glu Gly Leu Arg Ala Arg Gly
            100                 105                 110

Leu Arg Val Val Leu Ala Thr Ser Gly Glu Ala Glu Val Val Asp Ala
        115                 120                 125

Leu Leu Lys Gln Ala Gly Leu Ala Asp Leu Asn Leu Asp Arg Val Ser
    130                 135                 140

Ser Ser Glu Val Glu Ser Ser Lys Pro Ala Pro Asp Leu Ile Gln Val
145                 150                 155                 160

Gly Leu Lys Lys Leu Gly Val Pro Ala Glu Ala Leu Met Val Gly
                165                 170                 175

Asp Thr Pro Tyr Asp Ala Glu Ala Ala Lys Ala Asp Val Pro Cys
                180                 185                 190

Ile Leu Leu Arg Cys Gly Gly Asp Thr Asp Leu Glu Lys His Ala Pro
            195                 200                 205

Val Leu Asp Asp Pro Gln Ala Leu Leu Glu Ala Leu Glu Lys Ala Thr
        210                 215                 220

Val
225

<210> SEQ ID NO 50
<211> LENGTH: 228
<212> TYPE: PRT
<213> ORGANISM: Deinococcus proteolyticus

<400> SEQUENCE: 50

Met Gln Leu Asn Pro Gln Gly Pro Ser Leu Pro Thr Ile Ala Asp Leu
1               5                   10                  15

Arg Ala Leu Phe Val Asp Leu Asp Gly Thr Leu Val Asp Ser Asn Asp
            20                  25                  30

Ala His Ala Arg Ala Trp Val Gln Ala Leu Ala Asp Gln Asp Ile Thr
        35                  40                  45

Arg Asp Gln Gly Glu Val Arg Pro Leu Ile Gly Met Gly Gly Asp Gln
50                  55                  60

Leu Val Pro Glu Leu Thr Gly Lys Ser Asp Ser Ser Glu Leu Gly Glu
65                  70                  75                  80

Ala Leu Val Gln Gly Trp Gln Asp His Phe Lys Pro Leu Ile Ala Gly
                85                  90                  95

Leu Glu Val Leu Pro Gly Ala Arg Glu Leu Leu Glu Trp Ala Arg Gly
            100                 105                 110

Gln Gly Leu Thr Val Val Leu Ala Ser Ser Gly Glu Asp Asp Ile Val
        115                 120                 125

Glu Ala Leu Leu Glu His Ala Gly Leu Thr Asp Leu Ile Asp Leu Arg
    130                 135                 140

```
Val Arg Ser Asp Glu Val Gln Gln Thr Lys Pro Glu Pro Asp Ile Leu
145                 150                 155                 160

Gln Ala Ala Leu Asn Lys Ala Gly Val Gln Pro Gln Ala Leu Phe
            165                 170                 175

Val Gly Asp Thr Arg Phe Asp Ala Glu Ala Gln Lys Ala Gly Val
            180                 185                 190

Pro Cys Val Leu Leu Arg Ala Gly Gly Ser Pro Asp Leu Glu Glu Ala
            195                 200                 205

Gln Tyr Val Leu Ala Asn Ala His Glu Leu Leu Ser Ala Leu Gln Ala
210                 215                 220

Ala Thr Gln Asp
225

<210> SEQ ID NO 51
<211> LENGTH: 216
<212> TYPE: PRT
<213> ORGANISM: Deinococcus sp. 17bor-2

<400> SEQUENCE: 51

Met Thr Thr Ser Leu Gln Ala Ala Ile Leu Asp Leu Asp Gly Thr Leu
1               5                   10                  15

Ile Asp Ser Asn Asp Ala His Ala Arg Ala Trp Val Thr Ser Leu Lys
            20                  25                  30

Arg His Gly Phe Asp Ile Pro Phe Glu Arg Val Arg Pro Leu Ile Gly
        35                  40                  45

Met Gly Gly Asp Lys Leu Ile Pro Glu Leu Thr Gly Leu Asp Pro Glu
    50                  55                  60

Ser Glu Thr Gly Lys Ala Leu Thr Gln Gly Trp Gly Asp Ala Phe Lys
65                  70                  75                  80

Pro Met Ile Pro Ser Leu Gln Ala Thr Pro Gly Ala Arg Glu Leu Val
                85                  90                  95

Ala Gly Leu Arg Glu Leu Gly Trp Lys Leu Met Leu Gly Ser Ser Gly
            100                 105                 110

Glu Asp Glu Val Val Glu Gln Glu Leu Glu His Leu Gly Leu Glu Asp
        115                 120                 125

Leu Lys Asn Ser Arg Val Thr Ser Ser Glu Val Glu Glu Ser Lys Pro
130                 135                 140

Asp Ala Asp Ile Leu Ala Val Ala Leu Arg Lys Leu Gly Val Pro Ala
145                 150                 155                 160

Gly Ala Ala Leu Met Val Gly Asp Thr Lys Tyr Asp Ala Glu Ala Ala
                165                 170                 175

Arg Arg Ala Gly Val Arg Cys Val Leu Leu Arg Cys Gly Gly Asn Pro
            180                 185                 190

Asp Leu Pro Gly Glu Val Tyr Ala Ser Pro Ala Asp Leu Leu Gly Ala
        195                 200                 205

Leu Arg Ser Gly Asp Trp Gly Arg
    210                 215

<210> SEQ ID NO 52
<211> LENGTH: 225
<212> TYPE: PRT
<213> ORGANISM: Deinococcus sp. NW-56

<400> SEQUENCE: 52

Met Thr Gln His Asp Leu Leu Ala Pro Asp Arg Leu Arg Gly Val Leu
1               5                   10                  15
```

Leu Asp Val Asp Gly Thr Leu Ala Asp Ser Asn Leu Ala His Ala Arg
            20                  25                  30

Ala Trp Ala Ala Ala Leu Ala Asp Glu Gly Phe Glu Lys Thr Pro Glu
        35                  40                  45

Asp Ile Phe Pro Leu Ile Gly Met Gly Gly Asp Lys Leu Val Pro Glu
    50                  55                  60

Leu Thr Gly Leu Asp Ala Glu Ser Glu Arg Gly Gln Arg Leu Thr Asp
65                  70                  75                  80

Gly Trp Val Arg His Phe Arg Glu Leu Ile Pro Asp Leu Arg Pro Thr
                85                  90                  95

Pro Gly Ala Arg Ala Leu Ile Glu Gly Leu Arg Ala Arg Gly Leu Arg
            100                 105                 110

Val Ala Leu Ala Thr Ser Gly Glu Ala Glu Ile Val Asp Ala Leu Leu
        115                 120                 125

Glu Gln Ile Gly Leu Asp Asp Leu Lys Leu Glu Arg Val Ser Ser Ser
130                 135                 140

Asp Val Glu Asn Ser Lys Pro Asp Pro Asp Leu Val Lys Ala Gly Leu
145                 150                 155                 160

His Thr Leu Gly Leu Pro Ala Gly Ala Ala Leu Met Val Gly Asp Thr
                165                 170                 175

Pro Tyr Asp Ala Glu Ala Ala Arg Gly Ala Gly Val Pro Cys Val Leu
            180                 185                 190

Leu Arg Cys Gly Gly His Pro Gly Ala Glu Gly His Asp Pro Leu Tyr
        195                 200                 205

Asp Asp Pro Gln Ala Leu Leu Ala Ala Leu Asn Glu Ala Phe Pro Val
    210                 215                 220

Glu
225

<210> SEQ ID NO 53
<211> LENGTH: 225
<212> TYPE: PRT
<213> ORGANISM: Deinococcus sp. RL

<400> SEQUENCE: 53

Met Thr Gln Gly Asp Leu Leu Ser Pro Lys Arg Leu Arg Gly Val Leu
1               5                   10                  15

Leu Asp Val Asp Gly Thr Leu Ala Asp Ser Asn Met Ala His Ala Arg
            20                  25                  30

Ala Trp Ala Ala Ala Leu Arg Asp Glu Gly Phe Glu Gln Ser Pro Glu
        35                  40                  45

Ala Ile Leu Pro Leu Ile Gly Met Gly Gly Asp Lys Leu Val Pro Glu
    50                  55                  60

Leu Thr Gly Leu Asp Ala Glu Ser Glu Arg Gly Gln Arg Leu Thr Asp
65                  70                  75                  80

Gly Trp Ala Arg His Phe Arg Ala Leu Ile Pro Asp Leu Arg Pro Thr
                85                  90                  95

Pro Gly Ala Arg Ala Leu Leu Glu Gly Leu Arg Ala Arg Gly Leu Arg
            100                 105                 110

Val Ala Leu Ala Thr Ser Gly Glu Ala Glu Val Val Asp Ala Leu Leu
        115                 120                 125

Gln Gln Ile Gly Leu Asp Asp Leu Glu Leu Glu Arg Val Ser Ser Ser
130                 135                 140

Asp Val Glu Asn Ser Lys Pro Asp Pro Asp Leu Val Gln Ala Gly Leu

```
                145                 150                 155                 160
Arg Thr Leu Gly Leu Pro Ala Glu Ala Thr Leu Met Val Gly Asp Thr
                    165                 170                 175

Pro Tyr Asp Ala Glu Ala Arg Lys Ala Gly Val Pro Cys Val Leu
                180                 185                 190

Leu Arg Cys Gly Gly His Pro Gly Val Glu Glu His Asp Pro Val Tyr
                195                 200                 205

Asp His Pro Gln Ala Leu Leu Glu Ala Leu Asp Gln Ala Phe Pro Val
            210                 215                 220

Glu
225

<210> SEQ ID NO 54
<211> LENGTH: 198
<212> TYPE: PRT
<213> ORGANISM: Deinococcus sp. RL

<400> SEQUENCE: 54

Met Ala His Ala Arg Ala Trp Ala Ala Leu Arg Asp Glu Gly Phe
1               5                   10                  15

Glu Gln Ser Pro Glu Ala Ile Leu Pro Leu Ile Gly Met Gly Gly Asp
                20                  25                  30

Lys Leu Val Pro Glu Leu Thr Gly Leu Asp Ala Glu Ser Glu Arg Gly
            35                  40                  45

Gln Arg Leu Thr Asp Gly Trp Ala Arg His Phe Arg Ala Leu Ile Pro
        50                  55                  60

Asp Leu Arg Pro Thr Pro Gly Ala Arg Ala Leu Glu Gly Leu Arg
65                  70                  75                  80

Ala Arg Gly Leu Arg Val Ala Leu Ala Thr Ser Gly Glu Ala Glu Val
                85                  90                  95

Val Asp Ala Leu Leu Gln Gln Ile Gly Leu Asp Asp Leu Glu Leu Glu
                100                 105                 110

Arg Val Ser Ser Ser Asp Val Glu Asn Ser Lys Pro Asp Pro Asp Leu
            115                 120                 125

Val Gln Ala Gly Leu Arg Thr Leu Gly Leu Pro Ala Glu Ala Thr Leu
        130                 135                 140

Met Val Gly Asp Thr Pro Tyr Asp Ala Glu Ala Ala Arg Lys Ala Gly
145                 150                 155                 160

Val Pro Cys Val Leu Leu Arg Cys Gly Gly His Pro Gly Val Glu Glu
                165                 170                 175

His Asp Pro Val Tyr Asp His Pro Gln Ala Leu Leu Glu Ala Leu Asp
                180                 185                 190

Gln Ala Phe Pro Val Glu
        195

<210> SEQ ID NO 55
<211> LENGTH: 223
<212> TYPE: PRT
<213> ORGANISM: Deinococcus sp. YIM 77859

<400> SEQUENCE: 55

Met Ile Ala Glu Glu Leu Leu Ser Pro Asp Arg Leu Arg Gly Val Leu
1               5                   10                  15

Leu Asp Val Asp Gly Thr Leu Val Asp Ser Asn Asp Ala His Ala Tyr
                20                  25                  30

Ala Trp Leu Glu Ala Leu Arg Glu Glu Gly Phe Thr Arg Thr Phe Glu
```

```
                    35                  40                  45
Glu Val Arg Pro Leu Ile Gly Met Gly Gly Asp Gln Leu Val Pro Arg
 50                  55                  60

Leu Thr Gly Glu Asp Gly Glu Ser Glu Arg Gly Lys Arg Leu Thr Arg
 65                  70                  75                  80

Gly Trp Leu Asn His Phe Lys Pro Arg Ile Pro Gln Leu Gln Ala Thr
                     85                  90                  95

Arg Gly Ala Arg Ala Leu Val Glu Gly Leu Gln Ala Arg Gly Leu Arg
                100                 105                 110

Val Val Leu Ala Thr Ser Gly Glu Ala Asp Ile Val Asp Gly Leu Leu
            115                 120                 125

Lys Arg Ala His Leu Glu Asp Leu Asn Leu Asp Arg Val Ser Ser Ser
130                 135                 140

Glu Val Glu Ser Ser Lys Pro Ala Pro Asp Leu Ile Gln Ala Gly Leu
145                 150                 155                 160

Lys Lys Leu Gly Leu Pro Ala Glu Ala Ala Leu Met Val Gly Asp Thr
                165                 170                 175

Pro Tyr Asp Ala Glu Ala Ala Arg Lys Ala Gly Val Pro Tyr Val Leu
                180                 185                 190

Leu Arg Cys Gly Gly Asn Thr Gly Leu Glu Glu His Gly Pro Thr Leu
                195                 200                 205

Asp Asp Pro Gln Ala Leu Leu Glu Ala Leu Glu Lys Ala Ser Ala
            210                 215                 220

<210> SEQ ID NO 56
<211> LENGTH: 240
<212> TYPE: PRT
<213> ORGANISM: Desulfurococcus mucosus

<400> SEQUENCE: 56

Met Ala Val Lys Ile Val Phe Thr Asp Ile Asp Gly Thr Leu Thr Val
 1               5                  10                  15

Asn Arg Glu Ser Tyr Arg Leu Ala Val Glu Ala Val Glu Ala Leu Arg
                 20                  25                  30

Met Leu Val Asp Lys Gly Val Ile Val Ser Leu Val Ser Ser Asn Ala
             35                  40                  45

Leu Pro Val Val Ala Leu Ser Arg Tyr Ile Gly Leu Asn Gly Pro
         50                  55                  60

Val Val Gly Glu Ser Gly Ala Leu Val Tyr His Asp Glu Trp Gly Leu
 65                  70                  75                  80

Val Glu Leu Ala Gly Glu Ser Ala Arg Gln Val Tyr Met Asp Leu Leu
                 85                  90                  95

Gly Asn Tyr Arg Glu Tyr Val Asp Ser Trp Gln Asn Lys Phe Arg
                100                 105                 110

Leu Tyr Glu Tyr Ala Leu Lys Leu Arg Glu His Arg Gly Arg Ala
            115                 120                 125

Arg Glu Val Val Asp Glu Leu Arg Arg Tyr Val Glu Ser Lys Tyr Lys
130                 135                 140

Gly Phe Thr Val Asp Tyr Ser Gly Tyr Ala Ile His Val His Ala Lys
145                 150                 155                 160

Gly Val Gly Lys Gly Val Ala Val Asp Tyr Ile Leu Arg Arg Leu Gly
                165                 170                 175

Leu Ser Gly Gly Glu Ala Leu Gly Ile Gly Asp Ser Tyr Met Asp Val
                180                 185                 190
```

```
Asp Phe Ile Ala Arg Leu Gly Tyr Arg Ala Ala Val Gly Ala Asp
            195                 200                 205

Glu Glu Leu Val Arg Val Cys Asn Ile Val Ala Glu Ala Pro Ser Gly
    210                 215                 220

Leu Gly Val Ala Glu Val Val His Arg Ile Leu Gly Glu Arg His Glu
225                 230                 235                 240

<210> SEQ ID NO 57
<211> LENGTH: 230
<212> TYPE: PRT
<213> ORGANISM: Desulfurococcus mucosus

<400> SEQUENCE: 57

Met Asn Ser Leu Leu Arg Gly Ile Arg Leu Ile Leu Phe Asp Leu Asp
1               5                   10                  15

Gly Thr Ile Val Asp Ser Glu Asp Phe Ile Val Trp Ser Phe Val Glu
            20                  25                  30

Ala Gly Arg Leu Thr Gly Ile Arg Val Asp Pro Leu Lys Val Arg Glu
        35                  40                  45

Leu Ile Gly Phe Pro Leu Glu Ser Ile Leu Glu Ala Val Val Gly Thr
    50                  55                  60

Gly Leu Ser Arg Glu Asp Ala Ala Arg Phe Ile Glu Val Arg Arg Lys
65                  70                  75                  80

Leu Val Gln Glu Asn Trp Phe Lys His Val Arg Leu Phe Pro Asp Val
                85                  90                  95

Ile Pro Val Leu Arg Gln Leu Ser Ser Thr Gly Tyr Met Leu Gly Val
            100                 105                 110

Ala Ser Ser Ser Ile Arg Glu Arg Val Glu Leu Phe Leu Ser His Leu
        115                 120                 125

Gly Val Ser Gly Tyr Phe Lys Val Val Ser Gly Leu Glu Pro Gly Val
    130                 135                 140

Lys Gly Lys Pro Glu Pro Asp Val Ile Val Asn Ala Leu Lys Ala Ala
145                 150                 155                 160

Gly Val Pro Arg Ser Glu Ala Leu Tyr Val Gly Asp Arg Met Val Asp
                165                 170                 175

Cys Ile Ala Ala Arg Arg Ala Gly Val Lys Val Ile Val Asp Arg
            180                 185                 190

Gly Ser Val Asn Arg Trp Lys Gln Glu Glu Cys Val Pro Asp Ala Trp
        195                 200                 205

Ile Ser Ser Leu Leu Glu Leu Val Asp Asp Ala Ser Thr Pro Thr Arg
    210                 215                 220

Glu Ala Thr Arg His Asp
225                 230

<210> SEQ ID NO 58
<211> LENGTH: 224
<212> TYPE: PRT
<213> ORGANISM: Desulfurococcus mucosus

<400> SEQUENCE: 58

Met Arg Ile Arg Leu Val Val Met Asp Tyr Asp Leu Ser Met Val Tyr
1               5                   10                  15

Asn Leu Ser Asp Phe Tyr Glu Ala Tyr Ser Gly Ala Leu Lys Ser Tyr
            20                  25                  30

Gly Gly Gly Phe Ile Ser Phe Asp Glu Phe Leu Asn Leu Leu Asn Glu
        35                  40                  45
```

```
Asp Arg Leu Ser Glu Arg Ile Pro Gly Gly Val Arg Glu Glu Glu Phe
         50                  55                  60

Trp Leu Leu Phe Arg Arg Ile Tyr Val Ser Arg His Pro Ile Pro Met
 65                  70                  75                  80

Asp Gly Val Val Asp Leu Leu Arg Leu Leu Lys Ser Leu Pro Val Lys
                 85                  90                  95

Ile Ala Val Val Ser Gly Arg Glu Thr Ser Gly Glu Tyr Ile Trp Arg
                100                 105                 110

Asp Leu Arg Met Leu Gly Leu Asp Glu Tyr Val Asp Glu Val Tyr Thr
            115                 120                 125

Val Ser Asp Leu Gln Arg Leu Asn Gly Leu Glu Glu Tyr Leu Phe Asp
130                 135                 140

Lys Ser Trp Ile Ile Ser Tyr Ile Leu Arg Lys His Gly Val Ala Pro
145                 150                 155                 160

Cys Asn Ala Leu Cys Ile Gly Asp Phe Thr Thr Asp Leu Leu Ser Cys
                165                 170                 175

Arg Lys Leu Gly Ile Pro Phe Ile Gly Val Asn Lys Asp Glu Tyr Arg
            180                 185                 190

Gly Met Leu Leu Lys Lys Arg Gly Ala Ala Ile Val Val Lys Asn Leu
        195                 200                 205

Phe Glu Val Val Gln Trp Ile Pro Glu Leu Glu Lys Asp Ser Thr Cys
210                 215                 220

<210> SEQ ID NO 59
<211> LENGTH: 265
<212> TYPE: PRT
<213> ORGANISM: Dictyoglomus turgidum

<400> SEQUENCE: 59

Met Lys Arg Ile Leu Glu Val Ala Ile Lys Thr Ile Lys Glu Ser Gly
 1               5                  10                  15

Asn Ile Leu Leu Asn Tyr Ile Gly Glu Lys Glu Ile Glu Leu Lys
             20                  25                  30

Gly Ile Ser Asn Leu Val Thr Gln Val Asp Lys Leu Ser Glu Arg His
             35                  40                  45

Ile Leu Lys Ser Ile Glu Glu Asn Phe Pro Asp His Ser Ile Leu Thr
 50                  55                  60

Glu Glu Thr Gly Phe Ile Asn Lys Asn Ser Glu Tyr Thr Trp Ile Val
 65                  70                  75                  80

Asp Pro Leu Asp Gly Thr Thr Asn Tyr Ala His Asn Phe Pro Phe Phe
                 85                  90                  95

Gly Ile Ser Ile Ala Leu Ile Lys Asn Lys Glu Ile Ile Leu Gly Leu
                100                 105                 110

Ile Tyr Asp Pro Ile Arg Asp Glu Leu Phe Tyr Ala Ile Lys Asn Glu
            115                 120                 125

Gly Ala Tyr Leu Asn Asp Arg Arg Ile Glu Val Ser Lys Thr Glu Ser
130                 135                 140

Leu Glu Asn Ser Leu Ile Ser Phe Ala Phe Pro Tyr Glu Leu Ser Leu
145                 150                 155                 160

Glu Glu Lys Asn Phe Ile Pro Phe Ile Asn Phe Ser Ser Arg Thr His
                165                 170                 175

Gly Ile Arg Arg Thr Gly Ser Ala Ala Ile Glu Ile Ala Tyr Val Gly
            180                 185                 190

Cys Gly Arg Leu Asp Gly Phe Trp Ala Lys Lys Leu Lys Pro Trp Asp
        195                 200                 205
```

```
Ile Ser Ala Gly Ile Leu Ile Val Glu Glu Ala Lys Gly Lys Val Thr
    210                 215                 220

Asp Phe Ser Gly Asn Asn Ile Asp Ile His Thr Asp Asn Ile Leu Phe
225                 230                 235                 240

Ser Asn Gly Lys Ile His Gln Glu Met Ile Lys Ile Leu Asn Leu Gly
                245                 250                 255

Lys Ile Phe Ile Arg Asn Glu Lys Phe
            260                 265

<210> SEQ ID NO 60
<211> LENGTH: 249
<212> TYPE: PRT
<213> ORGANISM: Dictyoglomus turgidum

<400> SEQUENCE: 60

Met Tyr Lys Leu Phe Ile Thr Asp Leu Asp Gly Ser Ile Met Asp Gly
1               5                   10                  15

Ser Glu Val Ile Ser Thr Lys Asn Leu Lys Ala Ile Lys Ile Leu Arg
            20                  25                  30

Glu Asn Asn Ile Glu Ile Thr Ile Ala Thr Gly Arg Arg Trp Ser Ser
        35                  40                  45

Ile Ser Lys Ile Val Glu Pro Leu Ser Leu Thr Leu Pro Val Ile Leu
    50                  55                  60

Tyr Asn Gly Ala Gly Ile Tyr Asp Pro Leu Arg Lys Ser Phe Leu Tyr
65                  70                  75                  80

Leu Gln His Leu Ser Lys Glu Val Ile Gly Ala Leu Lys Val Ile
                85                  90                  95

His Tyr Tyr Leu Ser Phe Val Lys Leu Gly Ile Tyr His Asp Asp Lys
                100                 105                 110

Leu Tyr Glu Asp Ser Glu Ala Leu Glu Phe Leu Lys Asp Asn Lys Asn
            115                 120                 125

Gly Ile Ile Lys Ile Phe Ile Glu Gly Leu Lys Glu Leu Leu Lys Glu
        130                 135                 140

Leu Lys Asn Arg Leu Glu Lys Ile Tyr Leu Asn Val Val Phe Ser Ser
145                 150                 155                 160

Tyr Lys Tyr Leu Glu Ile Leu Pro Lys Gly Ala Ser Lys Gly Lys Ala
                165                 170                 175

Leu Lys Lys Leu Leu Lys Asn Leu Asp Ile Lys Leu Glu Glu Val Ile
            180                 185                 190

Ala Leu Gly Asp Tyr Asp Asn Asp Glu Glu Met Leu Lys Leu Ser Gly
        195                 200                 205

Leu Gly Ile Thr Leu Lys Asn Ala Ser Glu Arg Leu Lys Lys Ile Ala
    210                 215                 220

Asp Tyr Val Ile Asp Ala Ser Pro Ser Glu Ser Val His Tyr Ile Ile
225                 230                 235                 240

Gln Gln Val Leu Asn Phe Glu Arg Arg
                245

<210> SEQ ID NO 61
<211> LENGTH: 213
<212> TYPE: PRT
<213> ORGANISM: Dictyoglomus turgidum

<400> SEQUENCE: 61

Met Glu Leu Lys Gly Ile Ile Phe Asp Trp Asp Gly Thr Leu Val Asp
1               5                   10                  15
```

```
Ser Phe Pro Ala Cys Ile Lys Ala Thr Lys Glu Ile Phe Lys Lys Phe
            20                  25                  30

Gly Phe Ile Ile Ser Glu Glu Glu Tyr Arg Glu Lys Phe Ser Pro Asn
        35                  40                  45

Trp Tyr Asp Ile Tyr Arg Lys His Asn Ile Pro Glu Lys Tyr Trp Lys
    50                  55                  60

Glu Ile Asp Leu Leu Trp Lys Asp Tyr Phe Asp Tyr Ser Leu Val Lys
65                  70                  75                  80

Trp Arg Glu Gly Ala Val Glu Asn Leu Thr Phe Leu Lys Lys Leu Asn
                85                  90                  95

Leu Lys Ile Gly Val Val Thr Ala Ser Thr Lys Glu Asp Ile Glu Arg
            100                 105                 110

Glu Lys Pro Tyr Leu Asn Pro Glu Glu Tyr Ile Asp Gly Trp Ile Thr
        115                 120                 125

Trp Glu Asp Ser Glu Lys Pro Lys Pro Asp Pro Leu Pro Leu Leu Lys
    130                 135                 140

Ile Leu Lys Lys Leu Ser Leu Ser Pro Leu Glu Val Ile Tyr Val Gly
145                 150                 155                 160

Asp Thr Lys Glu Asp Ile Glu Met Ser Lys Lys Leu Asn Ile Leu Thr
                165                 170                 175

Ile Gly Val Leu Ser Pro Phe Thr Gln Lys Glu Lys Leu Val Ser Ser
            180                 185                 190

Asn Pro Asn Phe Leu Phe Asn Asn Leu Phe Glu Leu Leu Lys Phe Trp
        195                 200                 205

Lys Asp Leu Phe Leu
    210

<210> SEQ ID NO 62
<211> LENGTH: 213
<212> TYPE: PRT
<213> ORGANISM: Effusibacillus pohliae

<400> SEQUENCE: 62

Met Lys Tyr Pro Tyr Ile Leu Phe Asp Leu Asp Gly Thr Leu Val Asp
1               5                   10                  15

Thr Asn Glu Leu Ile Leu Gln Ser Phe Glu His Thr Leu Glu His Tyr
            20                  25                  30

Phe Pro Gly Arg Tyr Ser Arg Gln Asp Val Leu Pro Tyr Met Gly Glu
        35                  40                  45

Pro Leu Val Lys Gln Phe Ala Arg Trp Ala Pro Pro Glu Gln Val Ser
    50                  55                  60

Glu Leu Val Gln Ala Tyr Arg Lys Tyr Asn Val Glu Asn His Asp Arg
65                  70                  75                  80

Leu Ala Thr Ile Phe Pro Asn Val Pro Glu Val Leu Ala Glu Leu Lys
                85                  90                  95

Ala Gln Gly Cys Arg Met Ala Val Val Thr Asn Lys Met Arg Leu Thr
            100                 105                 110

Ala Glu Arg Gly Leu Arg Leu Phe Gly Leu Asp Arg Tyr Leu Glu Thr
        115                 120                 125

Val Val Thr Val Glu Asp Thr Asp Gln His Lys Pro His Pro Ala Pro
    130                 135                 140

Leu Gln Ile Ala Ile Glu Arg Leu Gly Gly Glu Pro Ala Gly Thr Leu
145                 150                 155                 160

Met Val Gly Asp Ser Pro Tyr Asp Ile Leu Ala Gly Gln Ala Ala Gly
```

```
                    165                 170                 175

Thr Ala Thr Cys Ala Val Ala Trp Ser Leu Arg Gly Cys Glu Gly Leu
            180                 185                 190

Ala Ser Tyr Lys Pro Asp Tyr Leu Ile Asp Glu Met Arg Glu Leu Leu
        195                 200                 205

Glu Ile Val Arg Gly
    210

<210> SEQ ID NO 63
<211> LENGTH: 215
<212> TYPE: PRT
<213> ORGANISM: Fervidobacterium gondwanense

<400> SEQUENCE: 63

Met Arg Pro Lys Ala Cys Ile Phe Asp Leu Asp Gly Val Ile Val Asp
1               5                   10                  15

Thr Ala Lys Tyr His Tyr Leu Ala Trp Lys Arg Leu Ala Lys Glu Leu
            20                  25                  30

Gly Phe Glu Phe Thr Glu Lys Asp Asn Glu Arg Leu Lys Gly Val Ser
        35                  40                  45

Arg Met Glu Ser Leu Glu Ile Leu Leu Ser Val Gly Gly Ile Lys Ile
    50                  55                  60

Glu Asp Gln Lys Leu Lys Glu Gln Leu Ser Asp Lys Lys Asn Asn Trp
65                  70                  75                  80

Tyr Val Glu Tyr Ile Ser Gln Met Thr Lys Asp Glu Ile Leu Pro Gly
                85                  90                  95

Val Glu Glu Phe Leu Arg Lys Leu Lys Asn Ala Gly Ile Lys Ile Ala
            100                 105                 110

Ile Gly Ser Ala Ser Lys Asn Thr Met Thr Ile Leu Arg Arg Ile Glu
        115                 120                 125

Leu Val Asp Leu Phe Asp Ser Ile Ile Asp Gly Thr Lys Ile Thr Lys
    130                 135                 140

Ala Lys Pro Asp Pro Glu Val Phe Leu Lys Ala Ala Glu Glu Leu Asn
145                 150                 155                 160

Val Asp Pro Lys Asp Cys Cys Val Phe Glu Asp Ala Val Ala Gly Ile
                165                 170                 175

Glu Ala Ala Lys Arg Ala Gly Met Lys Val Ile Gly Val Gly Asp His
            180                 185                 190

Glu Ile Leu Lys Asp Ala Asp Arg Val Ile Thr Ser Phe Val Gly His
        195                 200                 205

Gly Ile Glu Leu Val Glu Phe
    210                 215

<210> SEQ ID NO 64
<211> LENGTH: 305
<212> TYPE: PRT
<213> ORGANISM: Fervidobacterium islandicum

<400> SEQUENCE: 64

Met Lys Glu Trp Arg Glu Glu Leu Ser Asn Lys Ser Lys Cys Lys
1               5                   10                  15

Arg Thr Phe Val Phe Asp Leu Asp Gly Thr Val Leu Asn Ser Lys Asn
            20                  25                  30

Glu Phe Pro Lys Glu Thr Lys Thr Leu Val Gln Asn Ile Val Gly Asn
        35                  40                  45

Gly Asp Asn Val Val Phe Ala Thr Gly Arg Met His Ile Ser Ala Lys
```

```
                    50                  55                  60
Lys Leu Leu Asp Asn Val Phe Gly Glu Asp Ile Phe Pro Ile Ile Ser
 65                  70                  75                  80

Tyr Asn Gly Ala Val Ile Tyr Val Pro Gly Glu Gly Phe Ile Tyr Glu
                 85                  90                  95

Lys Thr Leu Asp Ile Glu Thr Ala Tyr Lys Val Ile Asp Phe Leu Arg
            100                 105                 110

Glu Lys Asn Ile His Ile Gln Thr Tyr Val Asp Asp Asn Leu Tyr Ser
            115                 120                 125

Glu Lys Asp Asp Asp Glu Ile Arg Leu Tyr Ala Lys His Ala Asp Val
130                 135                 140

Pro Tyr Tyr Val Val Glu Asp Leu Lys Ala Leu Glu His Pro Pro Ile
145                 150                 155                 160

Lys Met Leu Ala Ile Ala Glu Glu Ala Ile Leu Asp Ser Leu Ile Glu
                165                 170                 175

Pro Leu Lys Glu Ile Val Asp Gly Lys Ala Asn Val Phe Lys Ser Phe
            180                 185                 190

Pro Ile Phe Leu Asp Ile Val Pro Ala Asp Ala Asn Lys Gly Ile Ala
            195                 200                 205

Leu Lys Phe Leu Ala Asp Tyr Leu Asn Phe Asp Leu Gly Ser Thr Ile
210                 215                 220

Val Phe Gly Asp Asn Glu Asn Asp Ile Tyr Met Phe Lys Val Ala Ser
225                 230                 235                 240

Lys Arg Ile Ala Val Ser Asn Ala Val Trp Arg Leu Lys Glu Val Ala
                245                 250                 255

Asp Phe Val Ser Lys Ser Asn Glu Glu Asn Gly Val Leu His Ala Phe
            260                 265                 270

Val His Leu Phe Pro Glu Tyr Val Arg Gly Ile Asp Phe Ser Ser Gly
            275                 280                 285

His Thr Asn Ser Asn Ile Val Asn Thr Thr Ser Asp Asn Lys Ala Ala
290                 295                 300

Glu
305

<210> SEQ ID NO 65
<211> LENGTH: 278
<212> TYPE: PRT
<213> ORGANISM: Fervidobacterium islandicum

<400> SEQUENCE: 65

Met Val Lys Leu Ile Val Thr Asp Leu Asp Gly Thr Leu Leu Asn Asp
 1               5                  10                  15

Glu Lys His Ile Pro Lys Glu Asn Ile Glu Val Leu Arg Ala Ala Met
                20                  25                  30

Glu Lys Gly Ile His Val Ser Val Ala Thr Gly Arg Asn Phe Tyr Ser
             35                  40                  45

Ala Lys Pro Tyr Val Glu Glu Leu Gly Leu Asp Val Pro Val Ile Phe
 50                  55                  60

Gln Asn Gly Ala Phe Ile Tyr Gln Trp Met Glu Asn Lys Ile Ile Tyr
 65                  70                  75                  80

Lys Ser Ala Leu Gly Ser Glu Ile Ala Thr Lys Val Ile Glu Thr Ala
                 85                  90                  95

Arg Arg His Lys Leu Phe Tyr Ile Leu Tyr Arg Asp Phe Leu Glu Glu
            100                 105                 110
```

```
Lys Asp Met Tyr Ile Asp Met Pro Tyr Thr Gly Ser Phe Ser Leu Tyr
            115                 120                 125

Leu Gly Gln Asn Gln Trp Arg Leu Asn Ile Val Asp Asp Val Leu Lys
        130                 135                 140

Tyr Ile Lys Thr Lys Asp Ala Val Ala Glu Val Ala Leu Val Gly Glu
145                 150                 155                 160

Glu Leu Val Ile Arg Gln Ala Ile Asn Glu Ala Leu Asp Gly Leu Glu
                165                 170                 175

Ser Gln Thr Ser Val Val Lys Asn Thr Thr Ile Gly Asn Glu Thr Phe
            180                 185                 190

Tyr Glu Ile Phe Gly Pro Asn Ser Ser Lys Glu Leu Ser Ile Lys His
        195                 200                 205

Leu Phe Glu Tyr Phe Lys Val Ala Pro Glu Glu Thr Met Tyr Leu Gly
210                 215                 220

Asp Ser Phe Asn Asp Ile Gly Leu Leu Lys Met Val Gly Tyr Pro Ile
225                 230                 235                 240

Val Met Glu Asn Gly His Asp Glu Val Lys Gln Tyr Ala Arg Tyr Ile
                245                 250                 255

Thr Lys Ser Asn Asn Glu Ala Gly Val Ala Tyr Ala Val Lys Lys Trp
            260                 265                 270

Ala Leu Gly Ile Asp Asp
        275

<210> SEQ ID NO 66
<211> LENGTH: 270
<212> TYPE: PRT
<213> ORGANISM: Fervidobacterium nodosum

<400> SEQUENCE: 66

Met Val Arg Lys Thr Lys Thr Phe Val Phe Asp Leu Asp Gly Thr Val
1               5                   10                  15

Leu Thr Pro Lys Asn Glu Phe Pro Leu Glu Thr Lys Glu Leu Ile Met
            20                  25                  30

Asn Ile Leu Lys Lys Gly Asp Asn Val Val Phe Ala Thr Gly Arg Met
        35                  40                  45

His Ile Ser Ala Lys Lys Leu Leu Asp Arg Val Phe Gly Glu Asp Val
    50                  55                  60

Phe Pro Ile Ile Ser Tyr Asn Gly Ala Val Val Tyr Val Pro Asp Lys
65                  70                  75                  80

Gly Phe Ile Phe Glu Lys Thr Leu Glu Leu Ser Thr Ala His Lys Val
                85                  90                  95

Ile Asp Phe Phe Arg Arg Asn Asn Ile His Val Gln Thr Tyr Val Glu
            100                 105                 110

Asp Ile Leu Tyr Thr Glu Lys Asp Asn Glu Glu Ile Lys Leu Tyr Ser
        115                 120                 125

Lys His Ala Glu Val Pro Tyr Thr Val Val Asp Asp Leu Lys Ala Ile
    130                 135                 140

His Gln Pro Pro Ile Lys Ile Leu Gly Ile Gly Asp Gln Glu Leu Leu
145                 150                 155                 160

Asp Arg Leu Ile Pro Asp Leu Lys Asn Val Val Gly Asn Ser Ala Thr
                165                 170                 175

Val Phe Lys Ser Phe Ser Ile Phe Leu Asp Val Val Pro Ala Asp Ala
            180                 185                 190

Asn Lys Gly Ile Ala Leu Arg Phe Leu Ala Asp Tyr Leu Lys Phe Asp
        195                 200                 205
```

```
Leu Ser Glu Thr Ile Val Phe Gly Asp Asn Glu Asn Asp Ile Phe Met
    210                 215                 220

Phe Glu Val Ala Gly Arg Lys Ile Ala Val Ser Asn Ala Val Glu Lys
225                 230                 235                 240

Leu Lys Glu Val Ala Asp Phe Val Ser Lys Ser Asn Glu Glu Asn Gly
                245                 250                 255

Val Tyr Phe Ala Phe Thr Gln Leu Phe Pro Glu Tyr Ile Val
            260                 265                 270

<210> SEQ ID NO 67
<211> LENGTH: 276
<212> TYPE: PRT
<213> ORGANISM: Fervidobacterium nodosum

<400> SEQUENCE: 67

Met Val Lys Leu Ile Val Thr Asp Leu Asp Gly Thr Leu Leu Asn Asp
1               5                   10                  15

Asp Lys His Ile Pro Asp Asp Asn Ile Ile Ala Leu Arg Glu Ala Met
                20                  25                  30

Glu Lys Gly Val His Val Ser Ile Ala Thr Gly Arg Asn Phe Gly Ser
            35                  40                  45

Ala Lys Arg Tyr Ile Lys Glu Leu Gly Leu Asp Val Pro Val Ile Phe
50                  55                  60

Gln Asn Gly Ala Phe Ile Tyr Gln Trp Met Glu Asp Lys Val Ile Tyr
65                  70                  75                  80

Lys Ser Asp Leu Lys Ser Glu Ile Ala Lys Leu Ile Val Glu Lys Ala
                85                  90                  95

Arg Glu Lys Gly Leu Phe Tyr Val Val Tyr Ile Asp Phe Leu Glu Glu
            100                 105                 110

Lys Asp Met Tyr Ile Asp Ala Asn Tyr Ser Gly Glu Phe Leu Ser Tyr
        115                 120                 125

Leu Lys Gln Asn Glu Trp Arg Ile Asn Tyr Val Ser Asp Val Val Asn
    130                 135                 140

Tyr Ile Ser Asn Arg Asp Ser Ile Ala Glu Val Ala Leu Val Gly Asp
145                 150                 155                 160

Glu Glu Lys Ile Lys Asn Ile Val Glu Asp Leu Phe Ile Phe Gly
                165                 170                 175

Glu Ser Val Ser Val Val Lys Asn Asn Arg Ile Asn Ser Glu Val Phe
            180                 185                 190

Tyr Glu Phe Phe Gly Pro Asn Ser Ser Lys Asp Ile Ser Phe Asn Tyr
        195                 200                 205

Leu Leu Lys Tyr Phe Asn Val Lys Pro Glu Glu Thr Met Tyr Leu Gly
    210                 215                 220

Asp Asn Tyr Asn Asp Ile Gly Met Leu Lys Ile Val Gly Tyr Pro Val
225                 230                 235                 240

Val Met Glu Asn Ala Pro Asp Glu Val Lys Lys Tyr Ala Lys Tyr Val
                245                 250                 255

Ser Lys Ser Asn Asn Glu Ala Gly Val Ala Tyr Ala Val Arg Lys Leu
            260                 265                 270

Val Leu Gly Tyr
        275

<210> SEQ ID NO 68
<211> LENGTH: 281
<212> TYPE: PRT
```

<213> ORGANISM: Fervidobacterium pennivorans

<400> SEQUENCE: 68

```
Met Ser Asn Ile Arg Lys Leu Lys Asn Ala Lys Thr Phe Val Phe Asp
1               5                   10                  15

Leu Asp Gly Thr Val Leu Asn Ser Lys Asn Glu Phe Pro Gln Glu Thr
            20                  25                  30

Lys Gln Leu Ile Leu Asn Ile Leu Glu Asn Gly Asp Asn Val Ile Phe
        35                  40                  45

Ala Thr Gly Arg Met His Ile Ser Ala Lys Lys Leu Leu Glu Asn Val
    50                  55                  60

Phe Gly Glu Asp Ile Phe Pro Ile Ile Ser Tyr Asn Gly Ala Val Val
65                  70                  75                  80

Tyr Val Pro Asn Val Gly Phe Ile Tyr Glu Lys Thr Leu Asp Met Glu
                85                  90                  95

Thr Val His Lys Val Ile Gly Phe Leu Arg Gln Arg Asn Ile His Val
            100                 105                 110

Gln Thr Tyr Val Asp Asp Lys Leu Tyr Ser Glu Lys Asp Asn Glu Glu
        115                 120                 125

Ile Lys Leu Tyr Ala Lys His Ala Asp Val Pro Tyr Tyr Val Val Asn
    130                 135                 140

Asp Leu Lys Ala Ile Glu His Pro Pro Ile Lys Met Leu Ala Ile Ala
145                 150                 155                 160

Glu Gln Gly Ile Leu Asp Asn Leu Ile Glu Pro Leu Lys Glu Ile Val
                165                 170                 175

Asp Gly Arg Ala Asn Val Phe Lys Ser Phe Pro Ile Phe Leu Asp Ile
            180                 185                 190

Val Pro Ala Asp Ala Asn Lys Gly Asn Ala Leu Lys Phe Leu Ala Asp
        195                 200                 205

Tyr Leu Gly Phe Asp Leu Lys Asn Thr Val Val Phe Gly Asp Asn Glu
    210                 215                 220

Asn Asp Ile Tyr Met Phe Glu Val Ala Gly Thr Lys Val Ala Val Glu
225                 230                 235                 240

Asn Ala Val Asp Lys Leu Lys Glu Val Ala Asp Phe Val Ser Lys Ser
                245                 250                 255

Asn Glu Glu Asn Gly Val Leu Tyr Ser Phe Val Arg Leu Phe Pro Glu
            260                 265                 270

Tyr Leu Arg Gly Ile Glu Ser Ser Asn
        275                 280
```

<210> SEQ ID NO 69
<211> LENGTH: 278
<212> TYPE: PRT
<213> ORGANISM: Fervidobacterium pennivorans

<400> SEQUENCE: 69

```
Met Val Lys Leu Ile Val Thr Asp Leu Asp Gly Thr Leu Leu Asn Asp
1               5                   10                  15

Glu Lys His Ile Pro Arg Glu Asn Ile Glu Ala Leu Lys Ala Ala Met
            20                  25                  30

Asp Lys Gly Ile His Val Ser Val Ala Thr Gly Arg Asn Phe Tyr Ser
        35                  40                  45

Ala Lys Pro Tyr Val Glu Lys Leu Gly Leu Asp Val Pro Val Ile Phe
    50                  55                  60

Gln Asn Gly Ala Phe Ile Tyr Gln Trp Met Glu Asp Lys Val Ile Tyr
```

```
                65                  70                  75                  80
Lys Ser Glu Leu Lys Thr Glu Ile Ala Glu Arg Val Ile Glu Thr Ala
                    85                  90                  95
Arg Lys Tyr Lys Ile Phe Tyr Ile Leu Tyr Arg Asp Phe Leu Glu Glu
                100                 105                 110
Lys Asp Met Tyr Ile Asp Gln Pro Tyr Ser Gly Asn Phe Ser Leu Tyr
                115                 120                 125
Leu Asn Gln Asn Arg Trp Arg Leu Asn Ile Val Asp Asp Val Leu Lys
            130                 135                 140
Tyr Leu Lys Asn Lys Leu Thr Val Ala Glu Val Ala Leu Val Gly Asn
145                 150                 155                 160
Glu Glu Arg Ile Met Leu Ala Leu Asn Glu Ser Leu Gly Glu Val Arg
                165                 170                 175
Asn Ala Thr Ser Ile Val Lys Asn Asn Thr Ile Asn Glu Glu Thr Phe
                180                 185                 190
Tyr Glu Val Phe Gly Pro Asn Ala Ser Lys Glu Leu Ser Ile Lys Tyr
                195                 200                 205
Leu Phe Glu Tyr Phe Asn Val Ala Pro Glu Glu Thr Met Tyr Leu Gly
            210                 215                 220
Asp Ser Phe Asn Asp Ile Gly Leu Leu Lys Met Val Gly Tyr Pro Val
225                 230                 235                 240
Val Met Glu Asn Gly His Ser Glu Val Lys Gln Tyr Ala Arg Tyr Ile
                245                 250                 255
Thr Lys Ser Asn Asn Glu Ala Gly Val Ala Tyr Ala Val Arg Lys Trp
                260                 265                 270
Ala Leu Gly Ile Asp Glu
            275

<210> SEQ ID NO 70
<211> LENGTH: 215
<212> TYPE: PRT
<213> ORGANISM: Fervidobacterium pennivorans

<400> SEQUENCE: 70

Met Lys Pro Lys Ala Cys Ile Phe Asp Leu Asp Gly Val Ile Val Asp
1               5                   10                  15
Thr Ala Lys Tyr His Tyr Leu Ala Trp Lys Arg Leu Ala Lys Glu Leu
                20                  25                  30
Gly Phe Glu Phe Thr Glu Lys Asp Asn Glu Arg Leu Lys Gly Val Ser
            35                  40                  45
Arg Met Glu Ser Leu Glu Ile Leu Leu Ser Val Gly Gly Ile Lys Ile
        50                  55                  60
Asp Asp Glu Asn Val Lys Leu Gln Leu Ala Lys Lys Asn Lys Trp
65                  70                  75                  80
Tyr Val Glu Tyr Ile Asn Gln Met Thr Lys Asp Glu Ile Leu Pro Gly
                85                  90                  95
Val Ile Glu Phe Leu Glu Leu Leu Lys Ser Ala Gly Ile Lys Val Ala
                100                 105                 110
Ile Gly Ser Ala Ser Lys Asn Thr Ile Thr Ile Leu Glu Arg Ile Gly
            115                 120                 125
Leu Lys Asp Phe Phe Asp Val Ile Asp Gly Thr Lys Ile Ser Lys
        130                 135                 140
Ala Lys Pro Asp Pro Glu Val Phe Leu Lys Ala Glu Glu Leu Ser
145                 150                 155                 160
```

```
Val Arg Pro Glu Glu Cys Cys Val Phe Glu Asp Ala Val Ala Gly Ile
            165                 170                 175

Gln Ala Ala Lys Ser Ala Gly Met Lys Val Ile Gly Val Gly Asp Pro
            180                 185                 190

Thr Ile Leu Lys Asp Ala Asp Lys Val Ile Gln Ser Phe Gln Gly Gln
            195                 200                 205

Thr Leu Gly Leu Ile Glu Phe
            210             215

<210> SEQ ID NO 71
<211> LENGTH: 222
<212> TYPE: PRT
<213> ORGANISM: Geobacillus sp.

<400> SEQUENCE: 71

Met Thr Ile Arg Thr Ile Leu Phe Asp Leu Asp Gly Thr Leu Ile Asp
1               5                   10                  15

Thr Asn Glu Leu Ile Ile Gln Ser Phe Leu His Thr Leu Glu Lys Tyr
            20                  25                  30

Tyr Pro Gly Arg Tyr Gly Arg Glu Asp Val Leu Pro Phe Ile Gly Pro
            35                  40                  45

Ser Leu Tyr Glu Thr Phe Ser Ser Leu Asp Pro Glu Arg Ala Glu Glu
    50                  55                  60

Met Val Lys Thr Tyr Arg Thr Phe Asn His Ala Arg His Asp Glu Leu
65                  70                  75                  80

Ile Arg Glu Phe Asp Thr Val Tyr Glu Thr Ile Glu Thr Leu His Arg
                85                  90                  95

His Gly Phe Arg Leu Gly Val Val Thr Thr Lys Met His Asp Thr Ala
            100                 105                 110

Leu Met Gly Leu Arg Lys Thr Arg Leu Glu Pro Phe Phe Ser Cys Val
            115                 120                 125

Ile Gly Leu Asp Asp Val Ser Arg Pro Lys Pro Asp Pro Glu Pro Ile
            130                 135                 140

His Lys Ala Leu Glu Ala Leu Gln Ser Lys Ser Asp Glu Ala Leu Met
145                 150                 155                 160

Val Gly Asp Asn Tyr His Asp Ile Leu Ala Gly Lys Asn Ala Gly Val
                165                 170                 175

Lys Thr Ala Gly Val Ala Trp Ala Ile Lys Gly Arg Gly Tyr Leu Glu
            180                 185                 190

Gln Tyr Glu Pro Asp Tyr Met Leu Gly Lys Met Ser Asp Leu Leu Ala
            195                 200                 205

Ile Val Gly Ile Asn Glu Arg Lys Glu Glu Thr Ser Ser Gln
            210                 215                 220

<210> SEQ ID NO 72
<211> LENGTH: 264
<212> TYPE: PRT
<213> ORGANISM: Geobacillus stearothermophilus

<400> SEQUENCE: 72

Met Ala Glu Lys Trp Glu Glu Ile Asp Arg Tyr Ala Arg Gln Trp Ile
1               5                   10                  15

Asp Glu Ala Gly Lys Arg Ile Arg Ala Ser Phe Ala Lys Gln Leu Thr
            20                  25                  30

Val Glu Ala Lys Glu Asn Pro Asn Asp Leu Val Thr Asn Val Asp Arg
            35                  40                  45
```

Ala Ile Glu Gln Phe Phe Ala Glu His Ile Arg Arg Gln Phe Pro Ser
    50                  55                  60

His Arg Leu Leu Gly Glu Glu Gly Phe Gly Asp Arg Ile Asp Ala Leu
65                  70                  75                  80

Asp Gly Val Val Trp Val Ile Asp Pro Ile Asp Gly Thr Met Asn Phe
                85                  90                  95

Val His Gln Arg Arg His Phe Ala Val Ser Ile Gly Ile Phe Glu Asp
            100                 105                 110

Gly Ile Gly Gln Leu Gly Tyr Val Tyr Asp Val Val Phe Asp Glu Leu
        115                 120                 125

Tyr Ala Ala Gln Lys Gly Arg Gly Val Phe Leu Asn Gly Glu Pro Leu
130                 135                 140

Gly Leu Leu Gln Pro Ala Pro Val Ala Glu Ser Ile Ile Ala Ile Asn
145                 150                 155                 160

Gly Thr Trp Leu Met Glu Asn Lys Arg Leu Asp His Arg Pro Leu Met
                165                 170                 175

Arg Leu Ala Lys Glu Ala Arg Gly Thr Arg Ser Tyr Gly Ser Ala Ala
            180                 185                 190

Leu Glu Leu Ala Tyr Val Ala Ala Gly Arg Leu Asp Ala Tyr Ile Ser
        195                 200                 205

Pro Arg Leu Ser Pro Trp Asp Phe Ala Gly Gly Met Ile Leu Ile Glu
    210                 215                 220

Glu Ala Gly Gly Met Val Thr Thr Leu Asp Gly Lys Pro Leu Asp Leu
225                 230                 235                 240

Leu Gly Arg Asn Ser Val Leu Ala Ala Lys Pro Gly Val His Glu Glu
                245                 250                 255

Ile Leu Arg Arg Tyr Leu His Asp
            260

<210> SEQ ID NO 73
<211> LENGTH: 283
<212> TYPE: PRT
<213> ORGANISM: Geobacillus stearothermophilus

<400> SEQUENCE: 73

Met Leu Ile Ala Leu Asp Met Asp Gly Thr Leu Leu Asn Gly Glu Gly
1               5                   10                  15

Lys Ile Ser Glu Arg Asn Arg Lys Ala Met Met Ala Ala Gln Lys Glu
            20                  25                  30

Gly His Ile Val Ala Val Ile Thr Gly Arg Ala Arg Lys Asp Ala Leu
        35                  40                  45

Ala Pro Leu Arg Glu Ala Gly Leu Val Cys Pro Ile Ala Ser Leu Asn
    50                  55                  60

Gly Ala Ile Val Thr Leu Glu Asp Gly Thr Val Ile Gly Glu Ala Pro
65                  70                  75                  80

Leu Ala Arg Thr Ala Val Arg Pro Thr Leu Glu Trp Val Arg Lys Gln
                85                  90                  95

Ser Asp Leu Tyr Cys Glu Thr Tyr Thr Gly Asp Ala Val Tyr Val Gly
            100                 105                 110

Leu His Asn Arg Ala Gln Trp Glu Ser Leu Ala Ser Glu Met Ala Asp
        115                 120                 125

Ala Ala Pro Asp Val Lys Trp Leu Val Asn Lys Gln Phe Gln Gln Ala
    130                 135                 140

Arg Val Thr Tyr Val Asp Asp Ile Arg Thr Val Trp Asp Asp Pro Gln
145                 150                 155                 160

```
Leu Thr Leu Tyr Lys Leu Leu Ile Phe Ala Leu Asp Arg Glu Arg Leu
                165                 170                 175

Arg Asp Ala Ala Ser Arg Phe Ala Ala Leu Pro Ser Val Thr Val Thr
            180                 185                 190

Ser Ser His Pro His Asn Ile Glu Met Asn Asn Glu Arg Ala Thr Lys
        195                 200                 205

Gly Glu Ala Leu Lys Gln Leu Ala Ala His Tyr Gly Ile Asp Leu Cys
    210                 215                 220

Asp Thr Val Ala Phe Gly Asp Ser His Asn Asp Leu Ser Met Phe Glu
225                 230                 235                 240

Val Ala Gly Cys Arg Val Ala Met Ala Asn Ala Ala Pro Glu Leu Lys
                245                 250                 255

Ala Lys Ala Asp Ile Val Thr Cys Ser His Glu Glu Asp Gly Val Ala
            260                 265                 270

Ala Gly Leu Glu Arg Val Leu Ala Lys Arg Val
        275                 280

<210> SEQ ID NO 74
<211> LENGTH: 268
<212> TYPE: PRT
<213> ORGANISM: Geobacillus stearothermophilus

<400> SEQUENCE: 74

Met Lys Pro Tyr Leu Ile Ala Leu Asp Leu Asp Gly Thr Leu Leu Lys
1               5                   10                  15

Glu Asp Lys Thr Ile Ser Pro Phe Thr Lys Asp Val Ile Arg Arg Ala
            20                  25                  30

Ile Asp Thr Gly His Phe Val Val Ile Ala Thr Gly Arg Pro Tyr Arg
        35                  40                  45

Ala Ser Ser Met Tyr Tyr Glu Glu Leu Gly Leu Ala Thr Pro Ile Val
    50                  55                  60

Asn Phe Asn Gly Ala Phe Val His His Pro Arg Gln Pro Ser Trp Gly
65                  70                  75                  80

Met His His Tyr Pro Leu Pro Leu Ala Val Val Lys Asp Ile Val Glu
                85                  90                  95

Ile Ser Glu Ser Tyr Gly Ile Lys Asn Met Met Ala Glu Val Leu Asp
            100                 105                 110

Asn Val Tyr Phe His Gln His Asp Glu Val Leu Leu Asp Ile Val Arg
        115                 120                 125

Leu Gly Asn Pro Thr Val Glu Ile Gly Asp Leu Arg Arg Ser Leu Gly
    130                 135                 140

Lys Asp Pro Thr Ser Val Leu Val Tyr Thr Asp Asp His Ile Glu
145                 150                 155                 160

Arg Ile Gln Ser His Leu Ala Asn Val Tyr Ala Asn Val Ile His Gln
                165                 170                 175

Arg Arg Trp Ser Glu Pro Trp His Val Ile Glu Ile Arg His Gly
            180                 185                 190

Val His Lys Ala Ala Gly Leu Lys Gln Val Ala Asp Tyr Phe Gly Ile
        195                 200                 205

Pro Arg Glu Arg Val Ile Ala Phe Gly Asp Glu Asn Asp Leu Glu
    210                 215                 220

Met Ile Asp Trp Ala Gly Leu Gly Val Ala Met Gly Asn Ala Ile Glu
225                 230                 235                 240

Pro Leu Lys Thr Ile Ala Asp Asp Val Ala Lys Thr Asn Glu Glu Asp
```

```
                    245                 250                 255
Gly Val Gly Val Tyr Leu Gln Asp Leu Leu Arg Leu
            260                 265

<210> SEQ ID NO 75
<211> LENGTH: 287
<212> TYPE: PRT
<213> ORGANISM: Geobacillus stearothermophilus

<400> SEQUENCE: 75

Met Tyr Lys Leu Leu Ala Leu Asn Ile Asp Gly Thr Ile Leu Lys Asn
1               5                   10                  15

Asn Gly Arg Leu Pro Arg Glu Thr Lys Glu Ala Val Asp Tyr Val Lys
            20                  25                  30

Lys Lys Gly Val Tyr Val Thr Leu Ile Thr Ser Arg Asn Leu Leu Ser
        35                  40                  45

Ala Arg Lys Val Ala Lys Ala Leu Arg Leu Asp Gly Met Leu Ile Ala
    50                  55                  60

Phe Gln Gly Ala Met Ile Ala Arg Thr Leu Asp Asp Arg Leu Phe Asp
65                  70                  75                  80

Ala Val Ile Pro Glu Glu Arg Thr Phe Asn Ile Val Gln Ile Leu Glu
                85                  90                  95

Asn Phe Asn Cys Asn Ile Arg Leu Met His Glu Arg Tyr Ser Leu Gly
            100                 105                 110

Asn Arg Lys Lys Val Lys Lys Asn Leu Val Val Gln Thr Val Leu Ser
        115                 120                 125

Ser Ser Asp Pro Phe Phe Tyr Pro Thr Gln Phe Val Asp Ser Leu Gly
    130                 135                 140

Asp Val Leu Met Asp Glu Pro Ile Ala Val Pro Lys Ile Asp Val Tyr
145                 150                 155                 160

Phe Ala Thr Asp Glu Glu Arg Asp Ala Ala Ala Leu Leu Thr Lys
                165                 170                 175

Ser Ile Pro Ser Ile Asp Met Ile Met Gln Pro Asn Gly Lys Met Glu
            180                 185                 190

Ile Val Pro Gln Gly Val Ser Lys Leu Ala Gly Leu Arg Arg Leu Val
        195                 200                 205

Gln His Ile Gly Val Ser Leu Lys Glu Thr Val Met Ile Gly Asp Gly
    210                 215                 220

Leu Asp Asp Leu Pro Ala Ile Glu Ala Ala Gly Leu Gly Val Ala Met
225                 230                 235                 240

Gly Asn Ala Pro Leu Glu Val Lys Arg Ala Ala Asp Trp Val Thr Arg
                245                 250                 255

Ser Asn Glu Gln Leu Gly Val Ala Tyr Met Val Lys Glu His Phe Arg
            260                 265                 270

Lys Gln Gln Arg Ile Glu Phe Leu Gln Lys Leu Lys Thr Lys Gln
        275                 280                 285

<210> SEQ ID NO 76
<211> LENGTH: 258
<212> TYPE: PRT
<213> ORGANISM: Geobacillus stearothermophilus

<400> SEQUENCE: 76

Met Gly Arg Lys Ile Val Phe Phe Asp Ile Asp Gly Thr Leu Leu Asp
1               5                   10                  15

Glu Gln Lys Gln Leu Pro Leu Ser Thr Ile Glu Ala Val Arg Arg Leu
```

```
                20                  25                  30
Lys Gln Ser Gly Val Tyr Val Ala Ile Ala Thr Gly Arg Ala Pro Phe
            35                  40                  45

Met Phe Glu His Val Arg Lys Gln Leu Gly Ile Asp Ser Phe Val Ser
 50                  55                  60

Phe Asn Gly Gln Tyr Val Phe Glu Gly Asn Val Leu Tyr Lys Gln
 65                  70                  75                  80

Pro Leu Arg Arg Glu Lys Val Arg Ala Leu Thr Glu Glu Ala His Lys
                85                  90                  95

Asn Gly His Pro Leu Val Phe Met Asp Ala Glu Lys Met Arg Ala Ser
            100                 105                 110

Ile Ser Asp His Pro His Ile His Val Ser Met Ala Ser Leu Lys Phe
            115                 120                 125

Ala His Pro Pro Val Asp Pro Leu Tyr Tyr Glu Asn Lys Asp Ile Tyr
            130                 135                 140

Gln Ala Leu Leu Phe Cys Arg Ala Glu Glu Glu Pro Tyr Val Arg
145                 150                 155                 160

Asn Tyr Pro Glu Phe Arg Phe Val Arg Trp His Asp Val Ser Thr Asp
                165                 170                 175

Val Leu Pro Ala Gly Gly Ser Lys Ala Glu Gly Ile Arg Met Met Ile
            180                 185                 190

Glu Lys Leu Gly Ile Asp Lys Lys Asp Val Tyr Ala Phe Gly Asp Gly
            195                 200                 205

Leu Asn Asp Ile Glu Met Leu Ser Phe Val Gly Thr Gly Val Ala Met
210                 215                 220

Gly Asn Ala His Glu Glu Val Lys Arg Val Ala Asp Phe Val Thr Lys
225                 230                 235                 240

Pro Val Asp Lys Glu Gly Ile Trp Tyr Gly Leu Lys Gln Leu Gln Leu
                245                 250                 255

Ile Arg

<210> SEQ ID NO 77
<211> LENGTH: 237
<212> TYPE: PRT
<213> ORGANISM: Halococcus salifodinae

<400> SEQUENCE: 77

Met Asn Arg Ala Asp Ala Ala Pro Glu Ala Arg Pro Pro Leu Ala Val
 1               5                   10                  15

Asp Ile Asp Gly Thr Leu Thr Asp Arg Asn Arg Val Val Asp Pro Arg
                20                  25                  30

Val Phe Asp Ala Leu Arg Glu Trp Pro Ala Pro Val Val Leu Ala Thr
            35                  40                  45

Gly Lys Ala Leu Pro Tyr Pro Val Ala Leu Cys Glu Phe Ala Gly Leu
 50                  55                  60

Ala Thr Leu Val Val Ala Glu Asn Gly Gly Val Val Cys Leu Asp Thr
 65                  70                  75                  80

Glu Thr Arg Asp Asp Ile Val Val Asp Gly Asp Arg Thr Ala Ala Asp
                85                  90                  95

Arg Val Ala Ala Ala Tyr Arg Asp Ala Gly His Asp Leu Gly Trp Gly
            100                 105                 110

Ser Leu Asp Leu Val Asn Arg Trp Arg Glu Thr Glu Ile Ala Val Ser
            115                 120                 125

Arg Asp Ala Pro Leu Asp Pro Leu Arg Glu Ile Ala Val Glu Tyr Gly
```

```
              130                 135                 140
Leu Asp Val Val Asp Thr Gly Phe Ala Tyr His Val Val Ser Pro Asp
145                 150                 155                 160

Val Asp Lys Gly Arg Gly Leu Ser Ile Val Ala Asp Arg Leu Gly Arg
                165                 170                 175

Asp Pro Glu Glu Phe Val Ala Ile Gly Asp Ser Ala Asn Asp Val Ala
            180                 185                 190

Thr Phe Glu Val Val Gly Arg Ser Phe Ala Val Ala Asn Ala Asp Glu
        195                 200                 205

Ala Ala Thr Gln Ala Ala Asp Leu Val Thr Asp Ala Ala Tyr Ala Asp
    210                 215                 220

Gly Phe Ile Glu Ala Leu Ser Thr Val Arg Ser Ser Ser
225                 230                 235

<210> SEQ ID NO 78
<211> LENGTH: 237
<212> TYPE: PRT
<213> ORGANISM: Halococcus salifodinae

<400> SEQUENCE: 78

Met Asn Arg Ala Asp Ala Ala Pro Glu Ala Arg Pro Pro Leu Ala Val
1               5                   10                  15

Asp Ile Asp Gly Thr Leu Thr Asp Arg Asn Arg Val Val Asp Pro Arg
            20                  25                  30

Val Phe Asp Ala Leu Arg Glu Trp Pro Ala Pro Val Val Leu Ala Thr
        35                  40                  45

Gly Lys Ala Leu Pro Tyr Pro Val Ala Leu Cys Glu Phe Ala Gly Leu
    50                  55                  60

Ala Thr Leu Val Val Ala Glu Asn Gly Gly Val Val Cys Leu Asp Thr
65                  70                  75                  80

Glu Thr Arg Asp Asp Ile Val Val Asp Gly Asp Arg Thr Ala Ala Asp
                85                  90                  95

Arg Val Ala Ala Ala Tyr Arg Asp Ala Gly His Asp Leu Gly Trp Gly
            100                 105                 110

Ser Leu Asp Leu Val Asn Arg Trp Arg Glu Thr Glu Ile Ala Val Ser
        115                 120                 125

Arg Asp Ala Pro Leu Asp Pro Leu Arg Glu Ile Ala Val Glu Tyr Gly
    130                 135                 140

Leu Asp Val Val Asp Thr Gly Phe Ala Tyr His Val Val Ser Pro Asp
145                 150                 155                 160

Val Asp Lys Gly Arg Gly Leu Ser Ile Val Ala Asp Arg Leu Gly Arg
                165                 170                 175

Asp Pro Glu Glu Phe Val Ala Ile Gly Asp Ser Ala Asn Asp Val Ala
            180                 185                 190

Thr Phe Glu Val Val Gly Arg Ser Phe Ala Val Ala Asn Ala Asp Glu
        195                 200                 205

Ala Ala Thr Gln Ala Ala Asp Leu Val Thr Asp Ala Ala Tyr Ala Asp
    210                 215                 220

Gly Phe Ile Glu Ala Leu Ser Thr Val Arg Ser Ser Ser
225                 230                 235

<210> SEQ ID NO 79
<211> LENGTH: 183
<212> TYPE: PRT
<213> ORGANISM: Halococcus salifodinae
```

-continued

```
<400> SEQUENCE: 79

Met Thr Val Thr Ile Pro Asp Asp Thr Glu Ala Val Val Tyr Asp Leu
1               5                   10                  15

Asp Gly Thr Leu Val Arg Leu Ala Val Asp Trp Asp Ala Ala Ala Thr
            20                  25                  30

Asp Ala Ala Ala Leu Asp Gly Cys Gly Val Asp Thr Asp Gly Met
        35                  40                  45

Asp Leu Trp Arg Met Leu Glu Arg Ala Asp Glu Leu Gly His Arg Asp
    50                  55                  60

Ala Val Glu Glu Ala Ile Ala Gly His Glu Arg Gly Ala Arg Arg
65                  70                  75                  80

Ser Glu Arg Leu Ala Phe Ala Asp Glu Leu Val Thr Asp Arg Pro Val
            85                  90                  95

Gly Val Cys Ser Leu Asn Cys Glu Asp Ala Cys Arg Ile Ala Leu Asp
        100                 105                 110

Val His Asp Leu Ala Glu His Val Ala Cys Val Val Gly Arg Asp Thr
    115                 120                 125

Val Ala Thr Phe Lys Pro Asp Pro Glu Ser Leu Leu Ala Ala Val Glu
    130                 135                 140

His Leu Asp Ala Thr Pro Glu Arg Thr Leu Phe Ile Gly Asp Ser Glu
145                 150                 155                 160

Gly Asp Ala Glu Thr Ala Asp Arg Ala Gly Thr Arg Phe Ser Tyr Val
            165                 170                 175

Gly Asp Gly Pro Thr Thr Tyr
            180

<210> SEQ ID NO 80
<211> LENGTH: 212
<212> TYPE: PRT
<213> ORGANISM: Hydrogenivirga sp. 128-5-R1-1

<400> SEQUENCE: 80

Met Lys Ala Val Leu Phe Asp Leu Asp Gly Thr Leu Ile Asp Ser Ala
1               5                   10                  15

Asp Asp Ile Ala Leu Ala Leu Arg Leu Thr Leu Glu Glu Leu Gly Met
            20                  25                  30

Glu Glu Lys Met Pro Pro Ser Val Arg Ser Leu Ile Gly Gly Gly Val
        35                  40                  45

Lys Ala Leu Leu Glu Arg Val Leu Gly Asp Asp Phe Arg Glu Gln His
    50                  55                  60

Val Lys Val Phe Arg Arg His Tyr Ile Gly Asn Pro Val Val Asn Thr
65                  70                  75                  80

Thr Pro Tyr Pro Gly Val Met Glu Thr Leu Arg Ala Leu Arg Gly Arg
            85                  90                  95

Gly Ile Asn Leu Val Val Val Thr Asn Lys Leu Glu Glu Leu Ser Val
        100                 105                 110

Glu Ile Leu Lys Arg Leu Gly Met Leu Glu Phe Phe Asp Leu Val Val
    115                 120                 125

Gly Gly Asp Thr Phe Pro Glu Lys Lys Pro Ser Pro Leu Pro Val Leu
    130                 135                 140

Lys Ser Leu Glu Phe Val Gly Val Glu Ser Ser Gln Ala Leu Met Val
145                 150                 155                 160

Gly Asp Thr Ser Ala Asp Ile Glu Ala Gly Lys Arg Ala Gly Val Arg
            165                 170                 175
```

```
Thr Ala Leu Ala Ala Trp Gly Tyr Val Lys Leu Asn Ser Val Lys Pro
            180                 185                 190

Asp Tyr Ile Phe Asn Ser Pro Ala Asp Ile Leu Ser Leu Ala Ser Gln
        195                 200                 205

Val Ser Gly Ala
    210

<210> SEQ ID NO 81
<211> LENGTH: 211
<212> TYPE: PRT
<213> ORGANISM: Hydrogenobacter hydrogenophilus

<400> SEQUENCE: 81

Met Arg Leu Lys Leu Phe Ile Phe Asp Leu Asp Gly Thr Leu Ile Asp
1               5                   10                  15

Ser Tyr Met Asp Ile Gly Met Cys Val Asn Met Val Leu Gln Glu Met
            20                  25                  30

Gly Arg Asn Pro Ile Asp Pro Glu Arg Val Lys Ala Trp Ile Gly Gly
        35                  40                  45

Gly Ala Arg Arg Leu Leu Glu Lys Leu Phe Pro Asp Glu Glu Leu Asn
    50                  55                  60

Thr Ala Leu Glu Leu Phe Arg Arg Phe Tyr Arg Glu Asn Pro Val Val
65                  70                  75                  80

His Thr Lys Thr Tyr Glu Gly Ile Gln Glu Val Leu Ala Tyr Leu Arg
                85                  90                  95

Ser Arg Gly Ser Phe Leu Ala Val Val Thr Asn Lys Met Glu Asp Leu
            100                 105                 110

Ser Arg Glu Ile Leu Arg Arg Leu Glu Leu Leu Ser Tyr Phe Asp Val
        115                 120                 125

Val Val Gly Gly Asp Thr Phe Pro Glu Lys Lys Pro Ser Pro Leu Pro
    130                 135                 140

Ile Lys Gln Val Met Glu Arg Leu Arg Val Arg Pro Gln Glu Ser Val
145                 150                 155                 160

Ile Val Gly Asp Thr Ser Ala Asp Ile Cys Ala Gly Lys Asp Ala Gly
                165                 170                 175

Ile Trp Thr Ala Leu Ala Lys Trp Gly Tyr Val Arg Leu Asp Ser Val
            180                 185                 190

Met Pro Asp Phe Phe Leu Ser Glu Pro Lys Asp Val Ile Asp Leu Phe
        195                 200                 205

Glu Lys Val
    210

<210> SEQ ID NO 82
<211> LENGTH: 262
<212> TYPE: PRT
<213> ORGANISM: Hydrogenobacter hydrogenophilus

<400> SEQUENCE: 82

Met Asp Lys Val Glu Ser Phe Leu Lys Val Ala Lys Glu Ser Ala Leu
1               5                   10                  15

Ile Gly Gly Leu Ile Leu Lys Glu His Phe Gly Lys Leu Thr Gln Lys
            20                  25                  30

Asp Val Gln Glu Lys Ser Glu Lys Asp Val Val Ser Phe Val Asp Lys
        35                  40                  45

Ser Ser Glu Glu Arg Ile Arg Lys Tyr Ile Lys Ile Asn Phe Pro Asp
    50                  55                  60
```

```
His Asp Val Val Gly Glu Glu Gly Gly Thr Asp Asn Ser Asp Tyr
 65                  70                  75                  80

Val Trp Tyr Ile Asp Pro Leu Asp Gly Thr Lys Asn Tyr Ile Ala Gly
                 85                  90                  95

Phe Pro Ile Phe Gly Val Ser Val Gly Leu Thr Tyr Arg Lys Glu Pro
            100                 105                 110

Ile Val Gly Ala Val Tyr Met Pro Leu Tyr Asp Thr Leu Tyr Trp Ala
            115                 120                 125

Tyr Lys Gly Gly Gly Ala Tyr Lys Asn Gly Lys Ser Ile Glu Val Ser
        130                 135                 140

Lys Arg Val Gln Val Lys Ser Phe Phe Ile Ala Tyr Gly Phe Pro Ser
145                 150                 155                 160

Arg Ala Lys Arg Asn Leu Asp Ile Tyr Trp Asn Ile Phe Lys Glu Leu
                165                 170                 175

Phe Glu Lys Val Gly Ala Met Arg Arg Pro Gly Ala Ala Ile Asp
            180                 185                 190

Leu Cys Phe Thr Ala Glu Gly Ile Phe Asp Gly Leu Ile Glu Phe Glu
        195                 200                 205

Leu Asn Pro Trp Asp Val Cys Ala Gly Ile Leu Ile Leu Gln Glu Ala
    210                 215                 220

Gly Gly Lys Val His Leu Thr Lys Asp Leu Thr Lys Gly Thr Asp Val
225                 230                 235                 240

Ile Ala Gly Thr Pro Thr Ala Phe Pro Tyr Ile Glu Asn Thr Val Lys
                245                 250                 255

Ser Asn Leu Glu Gly Leu
            260

<210> SEQ ID NO 83
<211> LENGTH: 211
<212> TYPE: PRT
<213> ORGANISM: Hydrogenobacter thermophilus

<400> SEQUENCE: 83

Met Arg Leu Lys Leu Phe Ile Phe Asp Leu Asp Gly Thr Leu Ile Asp
  1               5                  10                  15

Ser Tyr Met Asp Ile Gly Met Cys Val Asn Gly Val Leu Arg Ser Met
             20                  25                  30

Gly Arg Gln Glu Ile Glu Pro Asp Ser Val Lys Asn Trp Ile Gly Gly
         35                  40                  45

Gly Ala Arg Gly Leu Leu Glu Lys Leu Phe Pro Ser Glu Glu Ile Asp
     50                  55                  60

Arg Ala Leu Glu Leu Phe Arg Lys Tyr Tyr Arg Glu Asn Pro Val Val
 65                  70                  75                  80

Tyr Thr Lys Ala Tyr Lys Gly Ile Arg Glu Val Leu Thr His Leu Lys
                 85                  90                  95

Ala Met Glu Lys Arg Leu Ala Val Val Thr Asn Lys Met Glu Asp Leu
            100                 105                 110

Ser Val Glu Ile Leu Lys Arg Leu Asn Leu Tyr His Tyr Phe Asp Met
        115                 120                 125

Val Val Gly Gly Asp Thr Phe Pro Glu Lys Lys Pro Ser Pro Val Pro
    130                 135                 140

Ile Lys Glu Val Leu Arg Trp Leu Gly Val Asp Ala Lys Glu Ala Val
145                 150                 155                 160

Met Ile Gly Asp Thr Asp Ala Asp Val Arg Ala Gly Lys Asp Ala Gly
                165                 170                 175
```

-continued

Val Trp Thr Ala Leu Ala Asn Trp Gly Tyr Val Arg Met Asp Gly Val
            180                 185                 190

Lys Pro Asp Phe Val Leu His Lys Pro Glu Asp Ile Ile Asn Leu Pro
        195                 200                 205

Gly Arg Ala
    210

<210> SEQ ID NO 84
<211> LENGTH: 247
<212> TYPE: PRT
<213> ORGANISM: Hyperthermus butylicus

<400> SEQUENCE: 84

Met Ala Glu Ala Val Arg Ile Glu Leu Pro Ala Arg Val Cys Gly Leu
1               5                   10                  15

Ala Leu Asp Ile Asp Gly Thr Leu Thr Glu Lys Lys Arg Leu Gly Glu
            20                  25                  30

Phe Asn Ile Ser Leu Glu Ala Val Glu Ala Val Arg Arg Ala Glu Ala
        35                  40                  45

Ala Gly Ile Pro Val Met Leu Val Thr Gly Asn Ser Val Tyr Val Val
    50                  55                  60

Ala Gly Val Ala Arg Tyr Ile Gly Ala Ser Gly Pro His Val Ala Glu
65                  70                  75                  80

Asn Gly Cys Ile Val Tyr Asp Asn Gly Thr Ile Tyr Arg Val Cys Arg
                85                  90                  95

Asp Thr Ala Arg Arg Ala Ala Arg Leu Ile Glu Glu Glu Leu Ala Gly
            100                 105                 110

Val Leu Lys Pro Ser Trp Gln Asn Pro Cys Arg Leu His Asp Tyr Ala
        115                 120                 125

Phe Ile Pro Lys Leu Leu Glu Pro Gly Glu Ala Leu Glu Ala Val Lys
    130                 135                 140

Arg Val Leu Ser Ser Arg Gly Ile Asn Val Lys Val Gly Phe Ser Gly
145                 150                 155                 160

Tyr Ala Ile His Leu Arg Pro Val Asp Ala Ser Lys Gly Arg Gly Leu
                165                 170                 175

Lys Leu Ala Leu Lys Leu Arg Gly Leu Glu Pro Asp Cys Val Val Ala
            180                 185                 190

Val Gly Asp Ser Val Ile Asp Leu Glu Met Lys Asp Ala Gly Val Ile
        195                 200                 205

Leu Ala Ala Val Gly Asn Ala Asp Glu Lys Leu Lys Lys Asn Ala Asp
    210                 215                 220

Ile Val Leu Pro Gly Glu Ser Gly Arg Ser Val Lys Ala Leu Ile Asp
225                 230                 235                 240

Ala Ile Leu Ser Asn Arg Gly
                245

<210> SEQ ID NO 85
<211> LENGTH: 267
<212> TYPE: PRT
<213> ORGANISM: Kosmotoga arenicorallina

<400> SEQUENCE: 85

Met Lys Met Ile Glu Ala Phe Val Ile Asp Ile Asp Gly Thr Phe Ile
1               5                   10                  15

Asp Ser Lys Gly Asn Ile Pro Gln Glu Asn Leu Asp Ala Leu Lys Glu
            20                  25                  30

```
Ile Glu Glu Gly Ile Met Ile Phe Phe Ala Ser Gly Arg Met Leu
             35                  40                  45

Ser Ser Val Ile Lys Phe Gln Ser Ser Lys Leu Asn Lys Ile His Pro
 50                  55                  60

Ile Ile Ala Tyr Asn Gly Ala Val Val Trp Asn Gly Arg Asp Val Ile
 65                  70                  75                  80

Phe Ser Lys Asn Ile Thr Thr Glu Met Ala Lys Asp Ile Val Ser Tyr
                 85                  90                  95

Ser Leu Ser Lys Gly Leu Tyr Ile Gln Ala Tyr Val Asn Asp Glu Leu
            100                 105                 110

Val Val Pro Phe Asp Cys Glu Lys Ala Arg Glu Tyr Ala Lys His Ser
        115                 120                 125

Ala Val Asp Phe Arg Val Glu Glu Lys Phe Ile Glu Phe Val Thr Lys
    130                 135                 140

Asn Thr Pro Thr Lys Leu Leu Ile Ile Asp Thr Pro Glu Lys Val Glu
145                 150                 155                 160

Val Leu Ser Ala His Phe Ala Ala Arg Tyr Asn His Leu Asn Val Phe
                165                 170                 175

Arg Ser Phe Ala Thr Tyr Leu Asp Leu Leu Pro Glu Gly Val Asn Lys
            180                 185                 190

Gly Leu Gly Leu Lys Tyr Leu Cys Glu Asp Leu His Val Asp Pro Ala
        195                 200                 205

Cys Val Val Ala Phe Gly Asp Asn Asp Asn Asp Val Pro Leu Phe Glu
    210                 215                 220

Glu Ala Gly Phe Ser Val Ala Val Ala Asn Ala Thr Pro Asn Ala Arg
225                 230                 235                 240

Lys Ala Ala Asp Val Ile Ala Ser Ala Asn Tyr Glu Ala Gly Phe Gly
                245                 250                 255

Arg Thr Ala Met Lys Leu Ile Lys Leu Leu Lys
            260                 265

<210> SEQ ID NO 86
<211> LENGTH: 265
<212> TYPE: PRT
<213> ORGANISM: Kosmotoga olearia

<400> SEQUENCE: 86

Met Ile Asn Gly Val Val Ile Asp Ile Asp Gly Thr Phe Ile Asp Ser
 1               5                  10                  15

Glu Glu Lys Ile Pro Ile Glu Asn Leu Glu Val Phe Arg Glu Leu Glu
             20                  25                  30

Ala Lys Gly Leu Arg Val Ile Phe Ala Ser Gly Arg Met Leu Thr Ser
             35                  40                  45

Val Lys Asn Phe Ile Ser Lys Ile Ser Asp Lys Ala Tyr Pro Ile Ile
 50                  55                  60

Ala Tyr Asn Gly Ala Val Val Tyr Val Asn Gly Glu Asn Ile Phe Asn
 65                  70                  75                  80

Gln Val Leu Leu Gln Asp Thr Ala Val Arg Ile Val Glu Arg Ala Leu
                 85                  90                  95

Ser Asn Asn Met Tyr Ile Gln Ala Tyr Val Asp Asp Arg Leu Val Val
            100                 105                 110

Pro Lys Asp Cys Glu Glu Ala Arg Ser Tyr Ala Ser His Ser Gly Val
        115                 120                 125

Asp Phe Met Val Val Glu Asp Leu Thr Asn Tyr Leu Ser Lys His Pro
```

```
                130                 135                 140
Thr Ile Lys Leu Leu Met Ile Ala Pro Ser Glu Gln Ile Asp Asn Leu
145                 150                 155                 160

Arg Leu Glu Phe Ser Glu Ile Phe Pro Glu Val Asp Phe Val Arg Ser
                165                 170                 175

Phe Ser Thr Tyr Leu Asp Ile Val Pro Lys Gly Val Ser Lys Gly Lys
            180                 185                 190

Ala Leu Glu Ile Leu Cys Lys His Leu Glu Ile Asp Ile Gly Lys Leu
            195                 200                 205

Ile Ala Phe Gly Asp Asn Asp Asn Asp Ile Ser Leu Phe Glu Arg Cys
            210                 215                 220

Gly Phe Ser Ile Ala Met Ala Asn Ala Thr Gln Arg Ala Lys Lys Ala
225                 230                 235                 240

Ala Asp Val Ile Ala Pro Ser Asn Asp Glu Ala Gly Phe Ala Arg Val
                245                 250                 255

Met Lys Lys Leu Leu Thr Leu Cys Asp
                260                 265

<210> SEQ ID NO 87
<211> LENGTH: 280
<212> TYPE: PRT
<213> ORGANISM: Kosmotoga olearia

<400> SEQUENCE: 87

Met Ile Lys Leu Ile Ala Ile Asp Leu Asp Gly Thr Leu Leu Asn Asn
1               5                   10                  15

Lys Lys Glu Ile Ser Leu Glu Asn Thr Ala Ala Leu Thr Glu Ala Met
                20                  25                  30

Glu Lys Gly Leu His Val Ser Ile Phe Thr Gly Arg Ser Tyr Ile Ser
            35                  40                  45

Gly Ser Glu Tyr Ala Lys Lys Leu Gly Leu Arg Val Pro Val Val Tyr
50                  55                  60

Gln Asn Gly Ala Leu Ile Ile Asn Ser Asp Asp Gly Asn Lys Gly Val
65                  70                  75                  80

Ile Arg Lys Val Ile Leu Ser Ala Lys Arg Ala Arg Glu Ile Val Glu
                85                  90                  95

Ala Ala Lys Lys Tyr Gly Leu Thr Tyr Ile Val Phe Thr Asn Phe Phe
            100                 105                 110

Asp Leu Pro Asp Met Phe Met Glu Arg Ile Pro Glu Asn Ser Pro Phe
            115                 120                 125

Lys Gly Tyr Phe Arg Ala Asn Leu Tyr Arg Ile Thr Ile Val Asn Asp
            130                 135                 140

Pro Ala Asp Phe Ile Arg Asp Glu Gly Ile Ala Glu Val Ala Val Glu
145                 150                 155                 160

Gly Pro Glu Asn Arg Ile Leu Ser Met Val Glu Glu Leu Gly Gln Pro
                165                 170                 175

Met Asn Asp Leu Ser Ile Val Lys Asn Asn Arg Ile Asn Glu His Thr
            180                 185                 190

Phe Tyr Glu Phe Phe Gly Pro Asn Val Gly Lys Asn Gln Ala Leu Asp
            195                 200                 205

Tyr Val Met His His Leu Ala Leu Thr Pro Asp Glu Ile Ala Tyr Ile
            210                 215                 220

Gly Asp Asn Tyr Asn Asp Val Glu Ile Met Lys Val Val Gly Leu Pro
225                 230                 235                 240
```

Ile Ala Met Ala Asn Ala Pro Lys Glu Val Lys Asp Phe Ala Arg Tyr
                245                 250                 255

Val Thr Thr Arg Thr Asn Asn Glu His Gly Val Ala Gly Ala Val Arg
            260                 265                 270

Lys Ile Ile Arg Glu Glu Ile Arg
        275                 280

<210> SEQ ID NO 88
<211> LENGTH: 275
<212> TYPE: PRT
<213> ORGANISM: Marinitoga piezophila

<400> SEQUENCE: 88

Met His Asn Lys Thr Phe Ile Phe Asp Leu Asp Gly Thr Leu Leu Asn
1               5                   10                  15

Ser Asn Glu Ser Ile Ser Gln Arg Thr Val Glu Ser Ile Lys Lys Ile
            20                  25                  30

Phe Glu Met Gly Ser Phe Ile Ile Ala Ser Gly Arg Met Tyr Lys
            35                  40                  45

Ser Thr Arg Leu Ile Val Glu Lys Tyr Met Pro Phe Leu His Asn Asn
    50                  55                  60

Ile Pro Ile Val Ser Tyr Asn Gly Ala Tyr Val Ser His Thr Gly
65                  70                  75                  80

Glu Val Val Phe Glu Ser Asp Ile Leu Lys Asp Leu Ala Ile Lys Val
                85                  90                  95

Ile Glu Asp Leu Lys Lys His Asp Thr His Val Gln Ile Tyr Leu Asn
            100                 105                 110

Asp Asp Leu Ile Thr Asp Lys Asp Asn Asp Glu Ile Lys Gln Tyr Ala
        115                 120                 125

Lys His Ser Gly Val Glu Tyr Lys Ile Val Lys Asp Ile Val Glu His
    130                 135                 140

Ile Lys Gln His Gly Glu Pro Thr Lys Ile Leu Ala Ile Asn Gln Pro
145                 150                 155                 160

Glu Lys Leu Asp Ile Ile Gln Lys Ser Met Thr Glu Lys Tyr Gly Asn
                165                 170                 175

Thr Leu Asn Ile Val Arg Ser Phe Ser Ile Tyr Leu Asp Phe Leu Asn
            180                 185                 190

Lys Asp Ser Ser Lys Gly Leu Ala Leu Lys Lys Leu Lys Glu Ile Tyr
        195                 200                 205

Arg Phe Asn Leu Glu Glu Ala Tyr Ile Phe Gly Asp Ser Glu Asn Asp
    210                 215                 220

Ile Ser Met Leu Ser Leu Ser Lys Asn Ser Tyr Ala Met Ala Asn Ala
225                 230                 235                 240

Asn Glu His Val Lys Glu Ser Ala Arg Asn Ile Thr Leu Ser Asn Asp
                245                 250                 255

Glu Glu Gly Val Ala Ile Val Leu Glu Lys Ile Ile Ser Asn Phe Ser
            260                 265                 270

Asn Ser Asn
        275

<210> SEQ ID NO 89
<211> LENGTH: 213
<212> TYPE: PRT
<213> ORGANISM: Marinitoga piezophila

<400> SEQUENCE: 89

```
Met Met Lys Tyr Lys Tyr Leu Phe Phe Asp Met Asp Gly Thr Leu Phe
1               5                   10                  15

Glu Thr Ser Arg Gly Ile Ile Tyr Ser Leu Gln Lys Ala Tyr Lys Ile
            20                  25                  30

Asn Asn Leu Thr Pro Leu Pro Glu Asp Lys Ile Lys Lys Leu Ile Gly
                35                  40                  45

Pro Thr Leu Asp Glu Ile Met Asn Ile Leu Phe Gly Glu Glu Asn Thr
    50                  55                  60

Glu Leu Lys Met Lys Val Arg Glu Asp Phe Arg Met Thr Tyr Ala Lys
65                  70                  75                  80

Glu Gly Val Phe Met Leu Asp Leu Tyr Pro Glu Val Met Asp Thr Leu
                85                  90                  95

Glu Lys Leu Tyr Ser Lys Asn Arg Ile Met Tyr Ile Val Thr Ser Lys
                100                 105                 110

Pro Glu Ile Phe Ala Ser Gln Ile Leu Glu Lys Phe Asn Met Ser Arg
                115                 120                 125

Phe Phe Lys Lys Ile Cys Gly Val Pro Leu Asp Gly Lys Ile Pro Pro
            130                 135                 140

Lys Ser Glu Arg Leu Lys Asn Leu Ile Ile Glu Glu Asn Ile Pro Leu
145                 150                 155                 160

Lys Glu Gly Leu Met Ile Gly Asp Thr Leu Ser Asp Ala Lys Ala Ala
                165                 170                 175

Trp Glu Asn Asn Val Asp Phe Ala Trp Ile Ser Phe Gly Phe Gly His
                180                 185                 190

Glu Asn Glu Ile Lys Lys Tyr Asp Tyr Lys Ile Asn Asn Phe Ser Gln
                195                 200                 205

Leu Leu Asn Leu Lys
                210

<210> SEQ ID NO 90
<211> LENGTH: 217
<212> TYPE: PRT
<213> ORGANISM: Marinitoga piezophila

<400> SEQUENCE: 90

Met Asn Phe Ile Phe Asp Leu Asp Gly Thr Leu Ile Asn Thr Glu Asn
1               5                   10                  15

Ile Ala Ile Pro Ala Ile Arg Gln Leu Leu Lys Asp Leu Gly Tyr Asn
            20                  25                  30

Pro Asn Ile Glu Lys Glu Glu Ile Leu Gln Tyr Ile Gly Tyr Thr Ile
                35                  40                  45

Asp Asp Ile Phe Tyr Gly Leu Leu Asn Thr Lys Asp Pro Glu Ile Ile
    50                  55                  60

Glu Lys Ala Ile Lys Leu Leu Asp Lys Tyr Glu Ile Glu Ile Ile Glu
65                  70                  75                  80

Lys Leu Pro Lys Asn Glu Ile Phe Phe Asp Gly Ala Ile Glu Val Leu
                85                  90                  95

Lys Thr Leu Lys Asn Glu Asn His Thr Leu Tyr Ile Leu Ser Asn Cys
                100                 105                 110

Asn Lys Lys Tyr Leu Asn Ala Leu Leu Glu Lys Glu Leu Asn Lys Tyr
                115                 120                 125

Ile Asp Phe Pro His Cys Ser Glu Met Tyr Asn Trp Ala Glu Lys Asp
            130                 135                 140

Tyr Val Leu Lys Leu Ile Thr Asn Gly Lys Lys Asp Phe Val Met Ile
145                 150                 155                 160
```

```
Gly Asp Arg His Lys Asp Val Asp Ala Ala Lys Lys Asn Gly Ile Leu
            165                 170                 175

Ser Val Gly Cys Thr Tyr Gly Tyr Ala Leu Glu Val Lys Asp Ala
        180                 185                 190

Asp Phe Ile Ile Tyr Asp Ile Lys Glu Leu Leu Thr Ile Lys Asn Lys
            195                 200                 205

Ile Ile Glu Ser Ala Tyr Asn Thr Ile
        210                 215

<210> SEQ ID NO 91
<211> LENGTH: 258
<212> TYPE: PRT
<213> ORGANISM: Meiothermus cerbereus

<400> SEQUENCE: 91

Met Asp Leu Arg Val Tyr Leu Gln Thr Ala Leu Asp Ala Ala Tyr Leu
1               5                   10                  15

Ala Lys Gly Ile His Gln Tyr Tyr Gln Glu Lys Gly Phe Thr Leu Ser
            20                  25                  30

Ser Lys Ser Thr Pro Thr Asp Leu Val Thr Gln Ala Asp His Glu Ser
        35                  40                  45

Glu Ala Ala Ile Arg Glu Leu Ile Ala Ala Arg His Pro Asp His Val
    50                  55                  60

Val Leu Gly Glu Glu Gln Gly Gln Asp Arg Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
            100                 105                 110

Gly Val Ile Leu Asp Thr Ala Arg Gly Asp Leu Phe Thr Ala Thr Lys
        115                 120                 125

Gly Gly Gly Ala Phe Met Asn Gly Arg Pro Ile Arg Val Ser Pro Arg
    130                 135                 140

Ala Thr Leu Val Gly Ser Leu Leu Ala Thr Gly Phe Pro Tyr Asp Val
145                 150                 155                 160

Ser Lys Asp Thr Glu Asn Leu Val Tyr Phe Gln Arg Ala Leu Thr Arg
                165                 170                 175

Gly Leu Met Val Arg Arg Pro Gly Ala Ala Leu Asp Leu Ala Tyr
            180                 185                 190

Val Ala Ala Gly Arg Leu Asp Gly Phe Trp Glu Val Lys Leu Asn Pro
        195                 200                 205

Trp Asp Val Ala Ala Gly Trp Leu Ile Ile Arg Glu Ala Gly Gly Thr
    210                 215                 220

Val Thr Gly Met Glu Gly Glu Ala Tyr Arg Leu Gly Asn Arg Tyr Leu
225                 230                 235                 240

Val Ala Ser Asn Gly Leu Ile His Gln Pro Leu Leu Asp Thr Ile His
                245                 250                 255

Gly Arg

<210> SEQ ID NO 92
<211> LENGTH: 216
<212> TYPE: PRT
<213> ORGANISM: Meiothermus cerbereus

<400> SEQUENCE: 92
```

```
Met Lys Leu Lys Ala Leu Leu Phe Asp Leu Asp Gly Thr Leu Ala Asp
1               5                   10                  15

Thr Asp Arg Leu His Glu Gln Ala Trp Leu Glu Gly Leu Ser Arg Tyr
            20                  25                  30

Gly Leu Gln Gly Asp His Thr Phe Tyr Gln Thr Gln Ile Ser Gly Gly
                35                  40                  45

Leu Asn Pro Glu Ile Val Gln Arg Leu Leu Pro Gln Leu Ser Gln Ala
    50                  55                  60

Glu Ala Glu Ala Phe Leu Glu Gln Lys Glu Ala Arg Phe Arg Glu Leu
65                  70                  75                  80

Ala Ser Glu Val Gln Pro Leu Pro Gly Leu Gly Thr Leu Trp Asp Trp
                85                  90                  95

Ala Gln Glu Gln Asn Leu Arg Arg Ala Leu Val Ser Asn Ala Pro Arg
                100                 105                 110

Glu Asn Ala Gln Tyr Leu Leu Lys Arg Leu Gly Leu Val Phe Asp His
                115                 120                 125

Ile Val Leu Ser Glu Glu Leu Pro Ala Gly Lys Pro Asp Pro Leu Pro
    130                 135                 140

Tyr Arg Thr Ala Leu Gln Ala Leu Asn Ile Gly Pro Ser Glu Ala Leu
145                 150                 155                 160

Ala Phe Glu Asp Ser Pro Ser Gly Val Arg Ser Ala Val Gly Ala Gly
                165                 170                 175

Ile Arg Thr Val Ala Leu Thr Thr Gly His Pro Ala His Ala Leu Glu
                180                 185                 190

Gln Ala Gly Ala Phe Leu Cys Ile Pro Asn Phe Ala Asp Pro Arg Leu
                195                 200                 205

Trp Ala Tyr Leu His Lys Met Gly
    210                 215

<210> SEQ ID NO 93
<211> LENGTH: 258
<212> TYPE: PRT
<213> ORGANISM: Meiothermus chliarophilus

<400> SEQUENCE: 93

Met Asp Leu Arg Pro Phe Leu Glu Thr Ala Leu Ala Ala Ala Tyr Val
1               5                   10                  15

Ala Arg Gly Ile His Gln Leu Tyr Gln Asp Lys Gly Phe Thr Gln Ser
            20                  25                  30

Thr Lys Ser Thr Pro Thr Asp Val Val Thr Gln Ala Asp Lys Glu Ala
            35                  40                  45

Glu Ala Ala Ile Arg Ala Leu Ile Glu Gln Arg His Pro Gly His Val
50                  55                  60

Val Leu Gly Glu Glu Gly Gln Gln Gly Gly Glu Tyr Arg Trp
65                  70                  75                  80

Ile Val Asp Pro Leu Asp Gly Thr Val Asn Tyr Ala His Gly Phe Pro
                85                  90                  95

Phe Tyr Cys Val Ser Ile Gly Leu Glu Val Arg Gly Glu Val Met Val
                100                 105                 110

Gly Val Val Leu Asp Thr Ala Arg Gly Asp Leu Phe Thr Ala Thr Arg
                115                 120                 125

Gly Gly Gly Ala Tyr Phe Asn Gly Arg Pro Met Arg Val Ser Arg Ser
    130                 135                 140

Pro Lys Leu Leu Gly Ser Leu Ile Ala Thr Gly Phe Pro Tyr Asp Val
145                 150                 155                 160
```

```
Ala Arg Asp Arg Glu Asn Leu Thr Tyr Leu Glu Arg Val Leu Phe Lys
            165                 170                 175

Gly Ile Thr Val Arg Arg Pro Gly Ala Ala Leu Asp Leu Ala Tyr
        180                 185                 190

Val Ala Cys Gly Arg Leu Asp Gly Phe Trp Glu Val Lys Leu Asn Pro
            195                 200                 205

Trp Asp Val Ala Ala Gly Trp Leu Leu Val Glu Glu Ala Gly Gly Arg
210                 215                 220

Ile Thr Gly Ile His Gly Glu Pro Tyr Arg Met Gly Asn Arg Tyr Leu
225                 230                 235                 240

Met Ala Ser Asn Gly His Ile His Glu Glu Leu Leu Ala Thr Ile His
            245                 250                 255

Gly Arg

<210> SEQ ID NO 94
<211> LENGTH: 262
<212> TYPE: PRT
<213> ORGANISM: Meiothermus chliarophilus

<400> SEQUENCE: 94

Met Asp Leu Asp Trp Thr Leu Val His Pro Ser Gln Gly Val Pro Glu
1               5                   10                  15

Ser Ala Trp Arg Ala Val Glu Glu Ala Arg Ala Ala Gly Val Arg Leu
            20                  25                  30

Ala Val Ala Thr Gly Arg Pro Phe Gly Gly Phe Gly Leu Glu Tyr Ala
            35                  40                  45

Leu Arg Met Asn Pro Glu Gly Tyr His Ala Phe Ser Asn Gly Ser Leu
50                  55                  60

Ile Ala Arg Gly Ala Glu Leu Val His Arg Val Ala Met Pro Glu Ala
65                  70                  75                  80

Thr Tyr Arg Arg Met Val Leu His Ser Arg Glu Gln Gly Leu Pro Phe
                85                  90                  95

Tyr Val Ser Gly Ala Ser Gly Arg Leu Tyr Ser Glu Asn Pro Pro Arg
            100                 105                 110

Glu Leu His Arg Phe Ala Leu Arg Met Gly Val Gly Tyr Glu Arg Val
            115                 120                 125

Asp Leu Leu Glu Leu Pro Glu Pro Cys Val Gly Gly Val Phe Val Ile
        130                 135                 140

Thr Gly Gly Leu Trp Asp Ser Leu Arg Pro Ser Leu Thr Ala Val Glu
145                 150                 155                 160

Gly Leu Asp Trp Leu Glu Tyr Val Val Gly Glu Gly Val Val Ala
                165                 170                 175

Val Ala Asp Pro Lys Gly Val Ser Lys Ala Ser Ala Leu Arg Trp Met
            180                 185                 190

Ala Glu Arg Tyr Gly Leu Ala Met Glu Glu Val Ala Met Ile Gly Asp
            195                 200                 205

Ser Leu Asn Asp Leu Glu Ala Ile Arg Gln Val Gly Leu Gly Ile Ala
        210                 215                 220

Met Gly Asn Ala Glu Pro Ala Ile Leu Glu Ala Ala Asp Ala Val Val
225                 230                 235                 240

Gly Arg Leu Glu Glu Asp Gly Phe Ala Gln Ala Val Arg Leu Cys Leu
                245                 250                 255

Glu Pro Ser Glu Val Arg
            260
```

<210> SEQ ID NO 95
<211> LENGTH: 258
<212> TYPE: PRT
<213> ORGANISM: Meiothermus ruber

<400> SEQUENCE: 95

Met Asp Leu Arg Ala Tyr Leu Gln Thr Ala Leu Asp Ala Ala Tyr Leu
1               5                   10                  15

Ala Lys Gly Ile His Gln Tyr Tyr Gln Glu Lys Gly Phe Thr Gln Ser
            20                  25                  30

Thr Lys Ser Thr Pro Thr Asp Leu Val Thr Gln Ala Asp His Glu Ser
        35                  40                  45

Glu Ala Ala Ile Arg Glu Leu Ile Ala Ser Arg His Pro Asp His Val
    50                  55                  60

Val Leu Gly Glu Glu Gln Gly Gln Asp Lys Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
            100                 105                 110

Gly Val Val Leu Asp Thr Ala Arg Gly Glu Leu Phe Thr Ala Thr Lys
        115                 120                 125

Gly Gly Gly Ala Tyr Leu Asn Gly Arg Pro Ile Arg Val Ser Thr Arg
    130                 135                 140

Ser Thr Leu Val Gly Ser Leu Leu Ala Thr Gly Phe Pro Tyr Asp Val
145                 150                 155                 160

Ser Lys Asp Thr Glu Asn Leu Val Tyr Phe Gln Arg Ala Leu Thr Lys
                165                 170                 175

Gly Leu Met Val Arg Arg Pro Gly Ala Ala Ala Leu Asp Leu Ala Tyr
            180                 185                 190

Val Ala Ala Gly Arg Leu Asp Gly Phe Trp Glu Val Lys Leu Asn Pro
        195                 200                 205

Trp Asp Val Ala Ala Gly Trp Leu Ile Val Ser Glu Ala Gly Gly Arg
    210                 215                 220

Ile Thr Gly Leu Gln Gly Glu Asp Tyr Arg Leu Gly Asn Arg Tyr Leu
225                 230                 235                 240

Val Ala Ser Asn Gly Leu Ile His Gly Pro Leu Leu Asp Thr Ile His
                245                 250                 255

Gly Arg

<210> SEQ ID NO 96
<211> LENGTH: 272
<212> TYPE: PRT
<213> ORGANISM: Meiothermus ruber

<400> SEQUENCE: 96

Met Ile Arg Leu Val Ala Leu Asp Leu Asp Gly Thr Phe Tyr Ala Gly
1               5                   10                  15

Arg Ser Leu Gly Val Pro Ala Ser Ala Trp Glu Ala Val Glu Lys Gly
            20                  25                  30

Arg Arg His Gly Leu Arg Phe Ala Val Cys Thr Gly Arg Pro Gln Gly
        35                  40                  45

Gly Tyr Gly Leu Glu Tyr Ala Lys Arg Leu Glu Pro Asn Gly Ala His
    50                  55                  60

-continued

```
Val Phe Asn Asp Gly Ala Ser Val Cys Asp Ala Thr Gly Arg Ser Leu
 65                  70                  75                  80

Gln Ala Asp Pro Leu Pro His Leu Ser Glu Leu Val Gly Leu Ala Arg
             85                  90                  95

Ala His Ala Leu Pro Phe Asp Leu Met Gly Ala Glu Gly Gly Arg Tyr
        100                 105                 110

Tyr Glu Glu Gly Leu Met Pro Pro Glu Leu Leu Ser His Ile Glu Thr
        115                 120                 125

Thr Gly Val Glu Ala Arg Ser Ala Arg Leu Glu Ile Glu Glu Thr
        130                 135                 140

Leu Val Arg Leu Trp Phe Val Val Gly Asp Leu Gly Leu Trp Glu Ser
145                 150                 155                 160

Val Lys Pro Glu Leu Val Ala Leu Pro Ser Ile Asp Leu Ala Glu Tyr
                165                 170                 175

Ile Ser Pro Arg Glu Val Ile Ala Gly Val Ile Arg Lys Gly Val Ser
            180                 185                 190

Lys Ala Thr Gly Leu Arg Trp Leu Ala Gln Tyr Tyr Gly Leu Ser Leu
        195                 200                 205

Ser Glu Ile Ala Met Ile Gly Asp Ser His Asn Asp Leu Glu Ala Ile
        210                 215                 220

Arg Glu Ala Gly Leu Gly Ile Ala Met Gly Asn Ala Val Glu Ala Ile
225                 230                 235                 240

Arg Ala Ala Ala Arg His Ile Thr Gly His Val Arg Glu Asp Gly Phe
                245                 250                 255

Ala Glu Ala Val Glu Tyr Ile Leu Ala Tyr Asn Arg Gln Asn Gln Leu
            260                 265                 270
```

<210> SEQ ID NO 97
<211> LENGTH: 278
<212> TYPE: PRT
<213> ORGANISM: Meiothermus ruber

<400> SEQUENCE: 97

```
Met Leu Gln Lys Ile Ser Arg Leu Pro Ile Gln Leu Val Leu Ile Asp
 1               5                  10                  15

Ile Asp Gly Thr Leu Phe Gly Pro Gln Gly Val Pro Glu Cys Ala Trp
                20                  25                  30

Glu Ala Ala Gln Arg Ala Arg Ala Ala Gly Leu His Leu Ser Ile Cys
            35                  40                  45

Thr Gly Arg Pro Gly Arg Gly Phe Ala Leu Glu Tyr Ala Lys Arg Leu
        50                  55                  60

Asp Pro Ala Gly Leu His Ile Phe Glu Ser Gly Ala Val Val Ser
 65                  70                  75                  80

Gly Gln Gly Glu Val Val Gln Ala Ser Thr Leu Pro Pro Ser Val Tyr
                85                  90                  95

Gln Arg Leu Leu Ala Leu Ser Arg Ala Tyr Gly Leu Pro Phe Glu Val
            100                 105                 110

Tyr Thr Ala Glu Gly Gly Phe Tyr Arg Glu Ser Gln His Pro Asp Leu
        115                 120                 125

Val Phe His Glu Ser Met Leu Gly Cys Pro Ala Val Cys Gly Leu
        130                 135                 140

Asp Asp Val Gly Ala Gln Val Val Arg Val Gln Phe Val Trp Arg Ala
145                 150                 155                 160

Ser Pro Ala Trp Gln Ala Val Arg Ala Gln Ile Ala Gln Met Thr Glu
                165                 170                 175
```

Val Glu Leu His Glu Ala Thr Ser Pro Gly Met Pro Gly Val Gly Phe
            180                 185                 190

Ser Ser Val Thr Ala Ala Gly Val Ser Lys Arg Ala Ala Ala Glu Trp
        195                 200                 205

Val Ala Ala Arg Leu Asp Leu Asp Leu Ser Arg Cys Ala Met Val Gly
210                 215                 220

Asp Gly Glu Asn Asp Leu Glu Leu Ile Gln Ala Ala Gly Leu Gly Ile
225                 230                 235                 240

Ala Met Gly Asn Ala Pro Glu Arg Val Lys Gln Ala Ala Gln Arg Val
                245                 250                 255

Val Gly Pro Val Glu Ala Cys Gly Leu Glu Gln Ala Leu Glu Ile Ile
            260                 265                 270

Gln Asn His Ala Arg Ser
            275

<210> SEQ ID NO 98
<211> LENGTH: 216
<212> TYPE: PRT
<213> ORGANISM: Meiothermus ruber

<400> SEQUENCE: 98

Met Lys Leu Arg Ala Leu Leu Phe Asp Leu Asp Gly Thr Leu Ala Asp
1               5                   10                  15

Thr Asp Arg Leu His Glu Gln Ala Trp Leu Gly Leu Ser Arg Tyr
                20                  25                  30

Gly Ile Gln Gly Asp His His Phe Tyr Gln Thr Gln Ile Ser Gly Gly
            35                  40                  45

Leu Asn Pro Glu Ile Val Gln Arg Leu Leu Pro Gln Leu Ser Glu Ala
        50                  55                  60

Glu Gly Gln Arg Phe Ile Glu Gln Lys Glu Ala Arg Phe Arg Glu Leu
65              70                  75                  80

Ala Thr Thr Val Gln Pro Leu Pro Gly Leu Arg Val Leu Trp Asn Trp
                85                  90                  95

Ala Gly Glu Arg Gly Leu Gly Arg Ala Leu Val Ser Asn Ala Pro Arg
            100                 105                 110

Gly Asn Ala Leu Tyr Leu Leu Glu Arg Leu Gly Leu Val Phe Asp His
        115                 120                 125

Ile Val Leu Ser Glu Asp Leu Pro Ala Gly Lys Pro Asp Pro Leu Pro
130                 135                 140

Tyr Arg Met Ala Leu Gln His Leu Asn Leu Ala Pro Gln Glu Ala Leu
145                 150                 155                 160

Ala Phe Glu Asp Ser Pro Ser Gly Val Arg Ser Ala Val Gly Ala Gly
                165                 170                 175

Leu Pro Thr Val Ala Leu Thr Thr Gly His Pro Pro Glu Ala Leu Ala
            180                 185                 190

Gln Ala Gly Ala Phe Leu Cys Ile Pro Asp Tyr Thr Asp Pro Arg Leu
        195                 200                 205

Trp Asp Trp Leu Arg Ala Leu Gly
    210                 215

<210> SEQ ID NO 99
<211> LENGTH: 258
<212> TYPE: PRT
<213> ORGANISM: Meiothermus ruber

<400> SEQUENCE: 99

```
Met Asp Leu Arg Pro Tyr Leu Glu Ala Ala Leu Asp Ala Ala Tyr Leu
1               5                   10                  15

Ala Lys Gly Ile His Gln Tyr Tyr Gln Glu Lys Gly Phe Thr His Ser
            20                  25                  30

Thr Lys Ser Thr Pro Thr Asp Val Val Thr Gln Ala Asp His Glu Ala
        35                  40                  45

Glu Ala Ala Ile Arg Ala Leu Ile Ala Glu Arg Phe Pro Asp His Val
    50                  55                  60

Val Leu Gly Glu Glu Gln Gly Gln Glu Gly Glu Phe Arg Trp
65                  70                  75                  80

Ile Val Asp Pro Leu Asp Gly Thr Val Asn Tyr Ala His Gly Phe Pro
                85                  90                  95

Phe Tyr Gly Val Ser Ile Gly Leu Glu Val Arg Gly Glu Val Val Leu
                100                 105                 110

Gly Val Val Leu Asp Thr Ala Arg Gly Asp Leu Phe Thr Ala Thr Lys
            115                 120                 125

Gly Gly Gly Ala Tyr Leu Asn Gly Arg Pro Leu Arg Val Ser Gln Arg
        130                 135                 140

Thr Thr Leu Val Gly Ser Leu Leu Ala Thr Gly Phe Pro Tyr Asp Val
145                 150                 155                 160

Ala Arg Asp Pro Glu Asn Leu Thr Tyr Phe Gln Arg Ala Leu Ala Lys
                165                 170                 175

Gly Leu Thr Val Arg Arg Pro Gly Ala Ala Ala Leu Asp Leu Ala Asn
            180                 185                 190

Val Ala Ala Gly Arg Leu Asp Gly Phe Trp Glu Val Lys Leu Asn Pro
        195                 200                 205

Trp Asp Val Ala Ala Gly Trp Leu Leu Ile Thr Glu Ala Gly Gly Gln
    210                 215                 220

Val Thr Gly Phe Gln Gly Glu Ala Tyr Arg Leu Gly Asn Arg Tyr Leu
225                 230                 235                 240

Val Ala Ser Asn Gly Arg Ile His Gln Ala Leu Leu Glu Ala Leu Gln
                245                 250                 255

Gly Arg

<210> SEQ ID NO 100
<211> LENGTH: 258
<212> TYPE: PRT
<213> ORGANISM: Meiothermus silvanus

<400> SEQUENCE: 100

Met Asp Leu Gln Arg Tyr Leu Glu Ala Ala Leu Asp Ala Ala Tyr Leu
1               5                   10                  15

Ala Arg Gly Ile His Leu Tyr Tyr Arg Glu Lys Gly Phe Ala Leu Glu
            20                  25                  30

Ser Lys Thr Ser Pro Thr Asp Leu Val Thr Gln Ala Asp Arg Glu Ser
        35                  40                  45

Glu Glu Ala Ile Arg Ser Leu Leu Leu Glu Arg Phe Pro Asp His Val
    50                  55                  60

Val Leu Gly Glu Glu Gly Gly Gln Glu Gly His Ser Asp Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Ala Leu Glu Val Gly Gly Glu Val Val Val
                100                 105                 110
```

```
Gly Ala Val Leu Asp Thr Ala Arg Gly Glu Leu Phe Thr Ala Leu Lys
            115                 120                 125
Gly Glu Gly Ala Phe Gln Asn Gly Arg Pro Ile Arg Val Ser Ser Thr
        130                 135                 140
Ala Thr Leu Ile Gly Ser Leu Leu Ala Thr Gly Phe Pro Tyr Asp Val
145                 150                 155                 160
Ala Lys Asp Ala Glu Asn Leu Thr Tyr Phe Gln Arg Ala Leu Ala Lys
                165                 170                 175
Gly Leu Thr Val Arg Arg Pro Gly Ala Ala Leu Asp Leu Ala Tyr
            180                 185                 190
Val Ala Ala Gly Arg Leu Glu Gly Phe Trp Glu Val Lys Leu Asn Pro
            195                 200                 205
Trp Asp Val Ala Ala Gly Trp Leu Leu Ile Thr Glu Ala Gly Gly Thr
    210                 215                 220
Val Ser Gly Ile Gln Gly Glu Pro Tyr Arg Leu Gly Asn Arg Tyr Leu
225                 230                 235                 240
Val Ala Ser Asn Gly Lys Ile His Glu Gln Leu Leu Asp Thr Leu His
                245                 250                 255
Gly Arg

<210> SEQ ID NO 101
<211> LENGTH: 213
<212> TYPE: PRT
<213> ORGANISM: Meiothermus silvanus

<400> SEQUENCE: 101

Met Arg Ala Leu Leu Phe Asp Leu Asp Gly Thr Leu Ala Asn Thr Asp
1               5                   10                  15
Arg Leu His Glu Gln Ala Trp Leu Glu Thr Leu Arg Phe Tyr Gly Ile
                20                  25                  30
Glu Gly Asp His His Phe Tyr Gln Thr Gln Ile Ser Gly Gly Leu Asn
            35                  40                  45
Pro Glu Ile Val Arg Arg Leu Leu Pro Gln Leu Ser Glu Ala Glu Gly
    50                  55                  60
Glu Ala Phe Ile Ala Arg Lys Glu Arg Phe Arg Glu Leu Ala Gln
65                  70                  75                  80
Asp Leu Arg Ala Leu Pro Gly Leu Asp Ala Leu Leu Ala Trp Ala Arg
                85                  90                  95
Arg Lys Lys Leu Leu Thr Gly Leu Val Thr Asn Ala Pro His Glu Asn
            100                 105                 110
Ala Arg His Val Thr Gln Ala Leu Gly Leu Ser Phe Asp Val Val Val
        115                 120                 125
Leu Ala Glu Glu Leu Ala Ala Gly Lys Pro Asp Pro Leu Pro Tyr Arg
    130                 135                 140
Val Ala Leu Glu Arg Leu Asp Leu Gly Ala Gln Glu Ala Leu Ala Phe
145                 150                 155                 160
Glu Asp Ser Pro Ala Gly Val Lys Ala Ala Val Gly Ala Gly Ile Pro
                165                 170                 175
Thr Ile Gly Leu Thr Thr Gly His Pro Pro Glu Ala Leu Lys Ala Ala
            180                 185                 190
Gly Ala Phe Leu Leu Ile Ala Asp Phe Thr Asp Pro Gln Leu Trp Lys
        195                 200                 205
Tyr Leu Glu Arg Ser
    210
```

<210> SEQ ID NO 102
<211> LENGTH: 258
<212> TYPE: PRT
<213> ORGANISM: Meiothermus taiwanensis

<400> SEQUENCE: 102

Met Asp Leu Arg Ala Tyr Leu Gln Thr Ala Leu Asp Ala Ala Tyr Leu
1               5                   10                  15

Ala Lys Gly Ile His Gln Tyr Gln Glu Lys Gly Phe Thr Gln Ser
            20                  25                  30

Ser Lys Ser Thr Pro Thr Asp Leu Val Thr Gln Ala Asp His Glu Ser
        35                  40                  45

Glu Ala Ala Ile Arg Glu Leu Ile Ala Ala Arg His Pro Asp His Val
    50                  55                  60

Val Leu Gly Glu Glu Gln Gly Gln Asp Lys Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
            100                 105                 110

Gly Val Val Leu Asp Thr Ala Arg Gly Glu Leu Phe Thr Ala Thr Lys
        115                 120                 125

Gly Gly Gly Ala Tyr Leu Asn Gly Arg Pro Ile Arg Val Ser Thr Arg
    130                 135                 140

Ser Thr Leu Val Gly Ser Leu Leu Ala Thr Gly Phe Pro Tyr Asp Val
145                 150                 155                 160

Ser Lys Asp Thr Glu Asn Leu Thr Tyr Phe Gln Arg Ala Leu Thr Lys
                165                 170                 175

Gly Leu Met Val Arg Arg Pro Gly Ala Ala Ala Leu Asp Leu Ala Tyr
            180                 185                 190

Val Ala Ala Gly Arg Leu Asp Gly Phe Trp Glu Val Lys Leu Asn Pro
        195                 200                 205

Trp Asp Val Ala Ala Gly Trp Leu Ile Val Ser Glu Ala Gly Gly Arg
    210                 215                 220

Val Ser Gly Leu Gln Gly Glu Asp Tyr Arg Leu Gly Asn Arg Tyr Leu
225                 230                 235                 240

Val Ala Ser Asn Gly Leu Ile His Gln Pro Leu Leu Asp Thr Leu His
                245                 250                 255

Gly Arg

<210> SEQ ID NO 103
<211> LENGTH: 216
<212> TYPE: PRT
<213> ORGANISM: Meiothermus taiwanensis

<400> SEQUENCE: 103

Met Lys Leu Arg Ala Leu Leu Phe Asp Leu Asp Gly Thr Leu Ala Asp
1               5                   10                  15

Thr Asp Arg Leu His Glu Gln Ala Trp Leu Glu Gly Leu Ser Arg Tyr
            20                  25                  30

Gly Ile Gln Gly Asp His Arg Phe Tyr Gln Ala Gln Ile Ser Gly Gly
        35                  40                  45

Leu Asn Pro Glu Ile Val Ala Arg Leu Leu Pro Gln Leu Ser Pro Asp
    50                  55                  60

```
Glu Gln Val Ala Phe Ile Glu Gln Lys Glu Ala Arg Phe Arg Glu Leu
 65                  70                  75                  80

Ala Ser Glu Val Gln Pro Leu Pro Gly Leu Arg Val Leu Trp Asp Trp
                 85                  90                  95

Ala Gln Ser Gln Gly Leu Arg Arg Ala Leu Val Ser Asn Ala Pro Arg
            100                 105                 110

Glu Asn Ala His Tyr Leu Leu Glu Arg Leu Gly Leu Met Phe Asp Ala
        115                 120                 125

Ile Val Leu Ser Glu Asp Leu Pro Ala Gly Lys Pro Asp Pro Leu Pro
   130                 135                 140

Tyr Arg Thr Ala Leu Gln His Leu Asn Ile Gly Pro Gln Glu Ala Leu
145                 150                 155                 160

Ala Phe Glu Asp Ser Pro Ser Gly Val Arg Ser Ala Val Gly Ala Gly
                165                 170                 175

Leu Arg Thr Val Ala Leu Thr Thr Gly His Pro Pro His Ala Leu Glu
            180                 185                 190

Gln Ala Gly Ala Phe Leu Cys Ile Pro Asp Phe Thr Asp Pro Arg Leu
        195                 200                 205

Trp Asp Trp Leu Gln Lys Met Gly
   210                 215

<210> SEQ ID NO 104
<211> LENGTH: 271
<212> TYPE: PRT
<213> ORGANISM: Meiothermus timidus

<400> SEQUENCE: 104

Met Ile Gly Leu Val Leu Ile Asp Val Asp Gly Thr Leu Tyr Gly Pro
 1               5                  10                  15

Asp Gly Val Pro Glu Cys Ala Trp Glu Ala Thr Gln Lys Ala Arg Ala
                 20                  25                  30

Ala Gly Ile His Leu Ala Leu Cys Thr Gly Arg Pro Gly Arg Gly Phe
            35                  40                  45

Ala Leu Glu Tyr Ala Arg Arg Ile Asp Pro Glu Gly Leu His Ile Phe
        50                  55                  60

Glu Ser Gly Ala Val Val Ala Gly Asn Gly Gln Val Ile Lys Ser
 65                  70                  75                  80

Ser Pro Leu Ser Pro Glu Ala Tyr Arg Glu Leu Leu Ala Leu Ser Arg
                 85                  90                  95

Glu Tyr Ala Ile Pro Phe Glu Val Tyr Thr Ala Asp Gly Gly Phe Phe
            100                 105                 110

Ile Glu Gln Asn His Pro Asp Leu Glu Ala His Gln Arg Met Leu Gly
        115                 120                 125

Phe Met Ala Lys Val Ala Pro Leu Asp Gln Pro Gly Glu Val Ile
   130                 135                 140

Arg Val Gln Tyr Val Thr Pro Leu Glu Gly Gln Trp Gln Glu Val Arg
145                 150                 155                 160

Gly Arg Val Gln Arg Ile Glu Gly Ala Glu Leu His Glu Ala Thr Ser
                165                 170                 175

Pro Gly Val Pro Gly Ile Gly Phe Asn Ser Val Thr Ala Ala Gly Val
            180                 185                 190

Ser Lys Leu Ser Ala Ala Arg Trp Val Ala Glu Arg Tyr Gly Leu Gly
        195                 200                 205

Leu Glu His Cys Ala Met Val Gly Asp Gly Glu Asn Asp Leu Glu Leu
   210                 215                 220
```

```
Ile Leu Ala Ala Gly Val Gly Ile Ala Met Gly Asn Ala Pro Gln Ser
225                 230                 235                 240

Val Lys Glu Arg Ser Lys Arg Val Val Gly Arg Val Glu Glu Cys Gly
                245                 250                 255

Leu Ala Gln Ala Leu Glu Trp Val Ala Ala Glu Gly Arg Ser
            260                 265                 270

<210> SEQ ID NO 105
<211> LENGTH: 214
<212> TYPE: PRT
<213> ORGANISM: Meiothermus timidus

<400> SEQUENCE: 105

Met Arg Pro Thr Thr Leu Leu Phe Asp Leu Asp Gly Thr Leu Leu Asp
1               5                   10                  15

Thr Glu Pro Gly Ile Leu Ala Cys Leu Arg His Thr Leu Glu His Phe
            20                  25                  30

Gly Leu Pro Thr Gln Gly Asp Ala Glu Leu Arg Arg Phe Ile Gly Pro
        35                  40                  45

Pro Leu Glu Gln Ala Trp Arg Glu Leu Val Gly Ala Ala His Val Glu
    50                  55                  60

Glu Ala Val Glu Ile Tyr Arg Arg Cys Tyr Asp Leu Lys Gly Lys Phe
65                  70                  75                  80

Lys Ala Ala Val Phe Glu Gly Ile Glu Ala Ala Leu His Glu Leu Ala
                85                  90                  95

Tyr His His Thr Leu Ile Val Ala Thr Ser Lys Arg Gln Val Phe Ala
            100                 105                 110

Glu Glu Met Leu Glu Arg Phe Gly Leu Ser Ser Tyr Phe Lys Ala Val
        115                 120                 125

Tyr Gly Val Thr Pro Pro Gln Leu Ser Glu Pro Lys Ala His Leu Ile
    130                 135                 140

Gly Arg Ile Leu Arg Asp His Gly Leu Ser Pro Gln Gln Ala Val Met
145                 150                 155                 160

Val Gly Asp Arg Glu Phe Asp Val Ile Gly Ala Lys Ala Asn Gly Met
                165                 170                 175

Ala Cys Val Gly Val Leu Trp Gly Tyr Gly Ser Arg Glu Glu Leu Ala
            180                 185                 190

Phe His Gly Ala Ser Leu Leu Cys Glu Ser Pro Arg Glu Leu Val Glu
        195                 200                 205

Ala Val Ala Gly Leu Ala
    210

<210> SEQ ID NO 106
<211> LENGTH: 223
<212> TYPE: PRT
<213> ORGANISM: Meiothermus timidus

<400> SEQUENCE: 106

Met Lys Arg Ala Val Leu Phe Asp Val Gly Asp Thr Leu Ile Leu Gly
1               5                   10                  15

His Pro Lys Leu Trp Leu Trp Pro Leu Leu Gln Glu Arg Gly Leu Ala
            20                  25                  30

Glu Lys Ala Asp Gly Ser Arg Leu Met Glu Ala Val Met Ala Ala Tyr
        35                  40                  45

Arg Val Tyr Asn Glu Arg His Met Gln Ala Thr Thr Ile Glu Ala Ala
    50                  55                  60
```

```
Leu Pro Val Trp Ala Glu Phe His Arg Thr Leu Ser Gly Ile Gly
 65                  70                  75                  80

Leu Gly Glu His Ala Gly Glu Ile Ser Gly Phe Leu Cys Glu Asn Trp
                 85                  90                  95

Arg Asn Pro Lys Val Trp Pro Leu Thr Pro Gly Ala Lys Glu Val Leu
            100                 105                 110

Gly Glu Leu Lys Gly Arg Gly Tyr Lys Leu Gly Val Val Ser Asn Trp
        115                 120                 125

Asp Ala Leu Leu Pro Gly Val Leu Glu Ala Thr Gly Leu Ala Pro Phe
    130                 135                 140

Phe Asp Phe Val Ala Ala Ser Ala Leu Val Gly Ala Ala Lys Pro Asp
145                 150                 155                 160

Pro Arg Ile Phe Arg Val Ala Leu Glu Gly Leu Gly Val Glu Pro His
                165                 170                 175

Gln Ala Leu His Val Gly Asp Ser Pro Asp Leu Gly Gly Ala Ala
            180                 185                 190

Ala Ala Gly Val Glu Ala Leu Leu Phe Asp Pro Tyr Arg Arg Asn Pro
        195                 200                 205

Glu Ala Leu His Glu Leu Ser Gly Val Leu Arg Leu Glu Ala
    210                 215                 220

<210> SEQ ID NO 107
<211> LENGTH: 198
<212> TYPE: PRT
<213> ORGANISM: Meiothermus timidus

<400> SEQUENCE: 107

Met Ser Lys Arg Ile Arg Ala Ile Cys Phe Asp Phe Asp Gly Thr Leu
 1               5                  10                  15

Ala Gln Phe Glu Gly Asp Phe Ala Arg Leu Thr Ala Leu Cys Cys Asp
                20                  25                  30

Gln Leu Gly Ile Asp Pro Gly Asp Arg Ala Phe Leu Ala Thr Tyr Glu
            35                  40                  45

Arg Glu Ile Arg Ala Glu Gly His Val Thr Phe Ala Leu Ala Leu Arg
 50                  55                  60

Arg Ala Leu Glu Thr His Gly Tyr Pro Val Pro Ala Gly Leu Glu Ala
 65                  70                  75                  80

Phe Ala Ala Glu Val Thr Ala Arg Tyr Ala Ala Glu Val Arg Leu Leu
                85                  90                  95

Pro Gly Val Arg Glu Leu Leu Ala Tyr Phe Ala Pro Leu Pro Lys Ala
            100                 105                 110

Ile Ile Thr Asn Gly Pro Ala Asp Met Gln Trp Ala Ala Ile Arg Ser
        115                 120                 125

Val Gly Leu Glu Arg Glu Phe Glu Ala Ile Val Ser Gly Asp Pro
    130                 135                 140

Asp Val Ala Val Arg Lys Pro His Pro Arg Ile Phe His Leu Ala Cys
145                 150                 155                 160

Glu Arg Leu Gly Val Pro Pro His Glu Thr Leu Met Ile Gly Asp His
                165                 170                 175

Leu Glu Ala Asp Ile Gln Gly Ala Ile Ala Ala Gly Leu Gln Gly Leu
            180                 185                 190

His Arg Pro Asn Ser Ala
        195
```

<210> SEQ ID NO 108
<211> LENGTH: 237
<212> TYPE: PRT
<213> ORGANISM: Meiothermus timidus

<400> SEQUENCE: 108

Met Ile Pro Glu Glu Leu Ala Leu Leu Ala Arg Gln Pro Leu Leu Val
1               5                   10                  15

Ile Cys Asp Tyr Asp Gly Thr Leu Ala Pro Ile Ala Ile His Pro Ser
            20                  25                  30

Gln Ala Phe Pro Gln Arg Gly Ala Arg Glu Ala Leu Arg Ala Leu Gln
        35                  40                  45

His His Pro Lys His Gln Ile Met Val Leu Thr Gly Arg Arg Ala Gln
    50                  55                  60

Glu Val Leu Asp Phe Leu Glu Leu Pro Gly Leu Arg Val Ile Gly Leu
65                  70                  75                  80

His Gly Leu Glu Trp Pro Gly Arg Pro Glu Pro Pro Arg Asp Arg Glu
                85                  90                  95

Ala Ile Gln Arg Ile Val Ser Arg Leu Pro Pro Leu Glu Gly Leu Trp
            100                 105                 110

Leu Glu Asp Lys Gly Trp Thr Leu Ala Val His Tyr Arg Asp Ala Pro
        115                 120                 125

Glu Ser Gln Gln Ser Lys Ala Ala Glu Leu Leu Ala Ala Val Pro Leu
    130                 135                 140

Pro Glu Gly Trp Glu Ala Met Pro Gly Lys Lys Val Cys Glu Tyr Arg
145                 150                 155                 160

Pro Ile Gly Tyr Gly Lys Gly Trp Ala Val Glu Gln Leu Met Leu Asp
                165                 170                 175

His Pro Ser His His Pro Val Phe Ile Gly Asp Asp Arg Thr Asp Glu
            180                 185                 190

Glu Gly Phe Ala Ala Val Leu Arg Leu Gly Gly Thr Ala Val Lys Val
        195                 200                 205

Gly Gly Gly Glu Ser Leu Ala Pro Tyr Arg Leu Gly Asn Ser Leu Glu
    210                 215                 220

Val Val Glu Leu Leu Thr Arg Trp Ala Arg Gly Tyr Asp
225                 230                 235

<210> SEQ ID NO 109
<211> LENGTH: 249
<212> TYPE: PRT
<213> ORGANISM: Meiothermus timidus

<400> SEQUENCE: 109

Met Arg Ala Leu Ile Phe Asp Val Asp Gly Val Ile Ala Glu Thr Glu
1               5                   10                  15

Glu Gly His Arg Leu Ala Phe Asn Arg Ala Phe Ala Glu Ala Gly Leu
            20                  25                  30

Asp Ile Glu Trp Ser Gln Glu Leu Tyr Glu Arg Leu Leu Trp Val Thr
        35                  40                  45

Gly Gly Lys Glu Arg Ile Ala His Tyr Leu Tyr His Cys Pro Glu Cys
    50                  55                  60

Pro Lys Leu Leu Asp Ala Asp Ile Ala Arg Leu His Trp Arg Lys Thr
65                  70                  75                  80

Glu Leu Tyr Asn Gln Ile Val Ala Ala Gly Val Pro Phe Arg Pro
                85                  90                  95

Gly Val Leu Arg Leu Trp Arg Glu Ala Arg Ala Gln Gly Val Lys Leu

```
            100                 105                 110
Ala Ile Ala Thr Thr Thr Ser Leu Pro Asn Val Glu Val Leu Leu Arg
            115                 120                 125

Gln Ala Gly Glu Glu Val Leu Gly Trp Phe Glu Thr Ile Val Ala Gly
        130                 135                 140

Asp Met Val Pro Arg Lys Lys Pro Ala Pro Asp Val Tyr Leu Lys Val
145                 150                 155                 160

Leu Glu Asn Leu Gly Leu Ala Pro Glu Glu Ala Leu Ala Ile Glu Asp
                165                 170                 175

Ser Gln Asn Gly Leu Ile Ala Ala Gln Lys Ala Gly Ile Pro Thr Leu
            180                 185                 190

Ile Thr Tyr Ser His Tyr Thr Arg Glu Gln Arg Phe Glu Gly Ala Leu
        195                 200                 205

Ala Val Leu Glu His Leu Gly Glu Pro Glu Leu Pro Ala Arg Val Val
            210                 215                 220

Ala Gly Pro Arg Ser Cys Ala Met Val Val Ser Leu Glu Val Leu Arg
225                 230                 235                 240

Glu Trp Tyr Gly Arg Phe Val Arg Ala
                245

<210> SEQ ID NO 110
<211> LENGTH: 157
<212> TYPE: PRT
<213> ORGANISM: Meiothermus timidus

<400> SEQUENCE: 110

Met Leu Arg Pro Lys Ala Gln Leu Ser Ser Val Leu Glu Ile Thr Pro
1               5                   10                  15

Gln Trp Leu Lys Thr Arg Gly Ile Lys Gly Leu Leu Leu Asp Leu Asp
            20                  25                  30

Asn Thr Leu Val Pro Tyr Lys Phe Lys Gly Glu Pro Pro Glu Glu Leu
        35                  40                  45

Val Ala Trp Val Lys Ser Leu Glu Ala Ala Gly Ile Arg Val Phe Leu
    50                  55                  60

Val Ser Asn Ala Gln His Lys Arg Leu Arg Ala Trp Ser Ala Lys Leu
65                  70                  75                  80

Gly Val Glu Gly Ile Gly Leu Ala Gly Lys Pro Trp Phe Gly Ile Arg
                85                  90                  95

Lys Gly Leu Lys Arg Leu Gly Leu Ser Pro Ser Gln Val Ala Met Val
            100                 105                 110

Gly Asp Gln Val Phe Thr Asp Val Leu Gly Gly Asn Leu Ala Gly Val
        115                 120                 125

Tyr Thr Ile Leu Val Thr Pro Ile Ser Gln Lys Glu Leu Gly Tyr Thr
    130                 135                 140

Lys Leu Ile Arg Arg Leu Glu Arg Leu Ile Leu Lys Leu
145                 150                 155

<210> SEQ ID NO 111
<211> LENGTH: 221
<212> TYPE: PRT
<213> ORGANISM: Meiothermus timidus

<400> SEQUENCE: 111

Met Lys Ala Leu Val Phe Asp Phe Asp Gly Thr Ile Leu Asp Thr Glu
1               5                   10                  15

Gln Ala Glu Tyr Thr Ala Trp Thr Gln Ala Tyr Ala Arg Tyr Gly Gly
```

```
                20                  25                  30
Glu Leu Thr Leu His Asp Tyr Leu Pro Leu Ile Gly Thr Ala Glu Pro
                35                  40                  45

Val Phe Asp Leu Tyr Ala His Leu Glu Ala Gln Ile Gly Pro Tyr Asp
 50                  55                  60

Arg Glu Ala Phe Asp Arg Glu Arg Gln Glu Val Leu His Ser Leu Leu
 65                  70                  75                  80

Ala Gln Leu Glu Pro Leu Pro Gly Val Pro Glu Cys Leu Glu Gln Ala
                 85                  90                  95

Arg Lys Leu Gly Leu Lys Leu Ala Val Ala Ser Ser Ser Ala Ala
                100                 105                 110

Trp Val Leu Gly His Leu Glu Gln His His Leu Leu Gln Ala Phe Asp
                115                 120                 125

His Val Ile Thr Arg Glu Tyr Val Ala Arg Thr Lys Pro Asp Pro Ala
                130                 135                 140

Leu Phe Leu Lys Ala Ala Glu Ala Leu Gln Val Ala Pro Ala Glu Cys
145                 150                 155                 160

Val Ala Val Glu Asp Ser Leu Asn Gly Val Arg Ala Ala Arg Ala Ala
                165                 170                 175

Gly Met Phe Thr Ile Ala Val Pro Asn Pro Leu Thr Arg His Gln Asp
                180                 185                 190

Leu Arg Gln Ala Asp Val Leu Leu Pro Ser Leu Ala Gly Leu Glu Leu
                195                 200                 205

Glu Pro Phe Leu Ser Ser Leu Lys Pro Val His Pro Arg
                210                 215                 220

<210> SEQ ID NO 112
<211> LENGTH: 274
<212> TYPE: PRT
<213> ORGANISM: Meiothermus timidus

<400> SEQUENCE: 112

Met Gly Gly Arg Cys Arg Gly Pro Val Val Ile Arg Leu Ile Gly Val
 1                   5                  10                  15

Asp Leu Asp Trp Thr Phe Val His Pro Ser Gln Gly Val Pro Ala Ser
                 20                  25                  30

Ala Trp Gln Ala Val Glu Glu Ala Lys Ala Ala Gly Met Arg Phe Ala
                 35                  40                  45

Val Val Thr Gly Arg Pro Phe Gly Gly Tyr Gly Leu Glu Tyr Ala Leu
 50                  55                  60

Lys Met Glu Pro Gln Gly Tyr His Ala Phe Ser Asn Gly Ser Leu Ile
 65                  70                  75                  80

Thr Gln Gly Ala Thr Leu Val His Ser Val Ala Met Ser Pro Ser Thr
                 85                  90                  95

Tyr Arg Arg Met Val Leu His Ser Arg Ala Gln Gly Leu Pro Phe Tyr
                100                 105                 110

Val Ser Gly Ala Ser Gly Arg Leu Tyr Ser Glu Asn Pro Pro Arg Glu
                115                 120                 125

Leu His Arg Phe Ala Glu Arg Met Gly Val Ser Tyr Gln Arg Ile Asp
                130                 135                 140

Leu Leu Glu Leu Pro Glu Pro Cys Val Gly Val Phe Val Leu Asp
145                 150                 155                 160

Gly Gln Leu Trp Asn Asp Leu Arg Gln Ala Ile Thr Ala Val Glu Gly
                165                 170                 175
```

```
Leu Asp Trp Leu Glu Tyr Leu Val Gly Gly Glu Val Ala Val
            180                 185                 190

Ala Asp Pro Lys Gly Thr Ser Lys Ala Ser Ala Leu Arg Trp Met Ala
        195                 200                 205

Glu Arg Tyr Gly Leu Ala Met Glu Glu Val Ala Met Ile Gly Asp Ser
    210                 215                 220

Leu Asn Asp Leu Glu Ala Ile Lys Gln Val Gly Leu Gly Ile Ala Met
225                 230                 235                 240

Gly Asn Ala Glu Glu Val Val Arg Glu Ala Ser Val Val Ala
                245                 250                 255

Gly Leu Glu Glu Asp Gly Phe Ala Gln Ala Val Arg Leu Cys Leu Ala
            260                 265                 270

Arg Arg

<210> SEQ ID NO 113
<211> LENGTH: 216
<212> TYPE: PRT
<213> ORGANISM: Meiothermus timidus

<400> SEQUENCE: 113

Met Arg Ala Leu Leu Phe Asp Leu Asp Gly Thr Leu Ala Asp Thr Asp
1               5                   10                  15

Arg Leu His Glu Gln Ala Trp Leu Glu Val Leu Leu Pro Tyr Gly Ile
            20                  25                  30

Arg Gly Asp His Ala Phe Tyr Gln Gln His Ile Ser Gly His Leu Asn
        35                  40                  45

Pro Glu Ile Val Ser Arg Leu Leu Pro His Leu Pro Pro Leu Glu Arg
    50                  55                  60

Thr Ala Leu Ile Glu Val Lys Glu Arg Arg Phe Arg Glu Leu Ala Gln
65                  70                  75                  80

Gly Leu Lys Ala Leu Pro Gly Leu Glu Gly Leu Trp Arg Trp Ala Arg
                85                  90                  95

Glu Arg Gly Leu Thr Leu Ala Leu Val Thr Asn Ala Pro Arg Pro Asn
            100                 105                 110

Ala Glu His Val Leu Gln Ala Leu Gly Ala Glu Phe Asp Leu Val Val
        115                 120                 125

Leu Ala Glu Glu Leu Ala Ala Gly Lys Pro Asp Pro Leu Pro Tyr Arg
    130                 135                 140

Thr Ala Leu Gly Arg Leu Gly Leu Asp Pro Ala Glu Ala Leu Ala Phe
145                 150                 155                 160

Glu Asp Ser Pro Ser Gly Val Arg Ser Ala Val Gly Ala Gly Ile Arg
                165                 170                 175

Thr Ile Gly Leu Thr Thr Gly His Asp Pro Arg Gly Leu Leu Glu Ala
            180                 185                 190

Gly Ala Phe Leu Leu Ile Asp Asp Phe Ser Asp Gly Arg Leu Trp Glu
        195                 200                 205

Tyr Leu Glu Gly Glu Ser Asp Ser
    210                 215

<210> SEQ ID NO 114
<211> LENGTH: 223
<212> TYPE: PRT
<213> ORGANISM: Meiothermus rufus

<400> SEQUENCE: 114

Met Lys Leu Lys Ala Leu Leu Phe Asp Leu Asp Gly Thr Leu Ala Asp
```

-continued

```
          1               5                  10                 15
        Thr Asp Arg Leu His Glu Gln Ala Trp Leu Glu Gly Leu Ala Arg Tyr
                        20                 25                 30
        Gly Ile Gln Ala Asp His His Tyr Tyr Gln Thr Gln Ile Ser Gly Gly
                        35                 40                 45
        Leu Asn Pro Glu Ile Val Ala Arg Leu Leu Pro Gln Leu Ser Pro Ala
         50                 55                 60
        Glu Ala Ala Phe Ile Glu Gln Lys Glu Ala Arg Phe Arg Glu Leu
         65                 70                 75                 80
        Ala Ala Gly Val Thr Pro Leu Pro Gly Leu Gln Glu Leu Trp Ala Trp
                        85                 90                 95
        Ala Asn Gly His Arg Leu Arg Leu Ala Leu Val Ser Asn Ala Pro Arg
                       100                105                110
        Gln Asn Ala Glu His Met Leu Lys Arg Leu Gly Leu His Phe Asp Cys
                       115                120                125
        Thr Val Leu Ser Glu Glu Leu Pro Ala Gly Lys Pro Asp Pro Leu Pro
        130                135                140
        Tyr Arg Thr Ala Leu Ala Gln Leu Gly Leu Gly Pro Glu Glu Ala Leu
        145                150                155                160
        Ala Phe Glu Asp Ser Pro Ser Gly Val Arg Ser Ala Val Gly Ala Gly
                       165                170                175
        Leu Arg Thr Val Ala Leu Thr Thr Gly His Pro Ala His Arg Leu Glu
                       180                185                190
        Glu Ala Gly Ala Phe Leu Ala Val Ala Asp Phe Thr Asp Glu Arg Leu
                       195                200                205
        Trp Ala Trp Leu Glu Gln Gln Ser Pro Pro Ser Thr Pro Arg Glu
                       210                215                220
```

<210> SEQ ID NO 115
<211> LENGTH: 218
<212> TYPE: PRT
<213> ORGANISM: Mesotoga infera

<400> SEQUENCE: 115

```
        Met Ile Lys Ala Ala Ile Phe Asp Met Asp Gly Val Ile Ile Asp Ser
         1                  5                 10                 15
        Glu Lys Ile Tyr Arg Arg Ala Cys Thr Glu Leu Val Asp Glu Leu Gly
                        20                 25                 30
        Gly Lys Ile Ser Val Glu Leu Phe Glu Arg Gln Met Gly Leu Lys Met
                        35                 40                 45
        Ser Glu Thr Gln Lys Val Val Val Gln Thr Ala Gly Leu Glu Ile Glu
         50                 55                 60
        Pro Glu Glu Phe Gly Lys Arg Tyr Met Glu Arg Tyr Leu Glu Leu Ala
         65                 70                 75                 80
        Arg Glu Thr Leu Val Pro Asn Pro Gly Leu Val Asn Leu Leu Asp Phe
                        85                 90                 95
        Leu Ser Glu Lys Val Glu Leu Ala Ile Ala Ser Ser Thr Glu Lys Ala
                       100                105                110
        Ala Val Glu Glu Leu Met Lys Arg Ile Gly Val Leu Asp Tyr Phe Glu
                       115                120                125
        Ile Ile Val Gly Gly Asp Glu Val Asp Glu Ser Lys Pro Ser Pro Met
                       130                135                140
        Ile Tyr Leu Lys Ala Ser Glu Leu Leu Gly Val Asn Pro Glu Glu Cys
        145                150                155                160
```

Ile Val Ile Glu Asp Ser Pro Asn Gly Ile Lys Ser Gly Ile Gly Ala
            165                 170                 175

Gly Met Glu Val Leu Gly Val Arg His Gly Glu Asn Ala His Leu Asp
            180                 185                 190

Leu Ser Ala Ser Ser His Val Phe Asp Asp Leu Tyr Gly Val Lys Glu
            195                 200                 205

Tyr Leu Glu Thr Val Leu Asn Gly Asn Ala
            210                 215

<210> SEQ ID NO 116
<211> LENGTH: 222
<212> TYPE: PRT
<213> ORGANISM: Metallosphaera sedula

<400> SEQUENCE: 116

Met Trp Ile Val Ala Ser Asp Phe Asp Arg Thr Leu Ser His Glu Asp
1               5                   10                  15

Asp Ser Phe Val Met Arg Lys Glu Val Ala Ser Lys Ile Asn His Phe
            20                  25                  30

Ser Thr Ile His Arg Phe Phe Val Val Thr Gly Arg Glu Glu Arg Tyr
        35                  40                  45

Met Arg Val Leu Ala Pro Asp Leu Arg Pro Thr Gly Trp Val Leu Glu
    50                  55                  60

Asn Gly Ala Leu Leu Ile Leu Gly Asp Arg Arg Ile Leu Asn Val Pro
65                  70                  75                  80

Glu Asp Trp Phe Glu Thr Arg Lys Ile Ile Gly Glu Lys Leu Thr Lys
                85                  90                  95

Phe Gly Ile Ser Tyr Ser Leu Gly Asp Val Ile Ile Tyr Val Asn Ser
            100                 105                 110

Trp Asn Gly Lys Leu Asp Leu Gly Pro Glu Val Arg Ile Glu Arg Asn
        115                 120                 125

Arg Glu Asp Ala Met Ile Leu Pro Gly Asn Val Asp Lys Gly Thr Gly
    130                 135                 140

Leu Arg Arg Ala Ile Gln Glu Met His Leu Glu Gly Lys Ile Val Ala
145                 150                 155                 160

Val Gly Asp Ala Glu Asn Asp Glu Ser Leu Phe Lys Val Ala Asp Val
                165                 170                 175

Lys Val Ala Val Ala Asn Ala Ile Pro Pro Ile Lys Arg Met Ala Asp
            180                 185                 190

Leu Val Met Glu Lys Glu Asp Gly Gly Val Glu Leu Leu Asp
            195                 200                 205

Met Ile Leu Ser Gly Arg Phe Pro Lys Asn Val Asp Val Asn
    210                 215                 220

<210> SEQ ID NO 117
<211> LENGTH: 224
<212> TYPE: PRT
<213> ORGANISM: Methanocella conradii

<400> SEQUENCE: 117

Met Ile Lys Ala Val Val Ala Asp Ile Asp Gly Thr Leu Thr Asp Met
1               5                   10                  15

Gln Arg Arg Ile Ser Val Glu Ala Ile Val Ala Ile Arg Lys Leu Pro
            20                  25                  30

Ile Pro Val Val Leu Ala Ser Gly Asn Val Ile Cys Phe Met Arg Ala
        35                  40                  45

```
Ala Ser Lys Leu Ile Gly Ala Ser Glu Ala Met Ile Gly Glu Asn Gly
    50                  55                  60

Gly Val Gln Val Gly Tyr Asp Ser Pro Val Phe Ala Asp
65                  70                  75                  80

Ile Glu Glu Cys Arg Arg Ala Ala Leu Leu Gln Arg Arg Phe Pro
                    85                  90                  95

Gly Leu Glu Gln Leu Asp Ala Arg Tyr Arg Leu Ser Glu Leu Ala Phe
                100                 105                 110

Arg Arg Thr Val Asp Ala Asn Glu Leu Arg Ala Ala Leu Asp Met Glu
                115                 120                 125

Tyr Pro Ser Leu Glu Val Val Asp Thr Gln Phe Ala Leu His Leu Lys
            130                 135                 140

His Lys Ser Val Asn Lys Gly Thr Gly Leu Val Asn Val Ala Ser Met
145                 150                 155                 160

Met Gly Phe Lys Pro Glu Glu Phe Ala Ala Leu Gly Asp Ser Ala Asn
                165                 170                 175

Asp Leu Pro Met Phe Glu Ala Ala Gly Leu Gly Leu Ala Val Gly Asn
            180                 185                 190

Ala Val Pro Glu Leu Lys Asp Val Ala Asp Tyr Val Ala Val Lys Pro
            195                 200                 205

Tyr Gly Glu Gly Ala Ala Glu Ala Leu Arg Trp Leu Ala Arg Gln Leu
210                 215                 220

<210> SEQ ID NO 118
<211> LENGTH: 237
<212> TYPE: PRT
<213> ORGANISM: Methanocella conradii

<400> SEQUENCE: 118

Met Ala Glu Arg Cys Ser Val Lys Ile Phe Leu Tyr Arg Ala Val Leu
1               5                   10                  15

Phe Asp Met Asp Gly Val Ile Ala Asp Thr Met Pro Leu His Tyr Glu
                20                  25                  30

Ala Trp Arg Arg Ala Phe Glu Ala Phe Gly Val His Val Asp Lys Met
            35                  40                  45

Asp Val Tyr Leu Arg Glu Gly Met Thr Thr Met Glu Met Gly Lys Asp
            50                  55                  60

Ile Ala Arg Ser Lys Gly Met Glu Leu Ser Glu Gly Glu Leu Asn Ser
65                  70                  75                  80

Ile Val Glu Leu Lys Thr Arg Ile Phe Asn Glu Leu Val Asp Ser Ser
                85                  90                  95

Val Arg Leu Tyr Glu Gly Val Pro Glu Thr Leu Thr Met Leu Arg Asn
                100                 105                 110

Asn Gly Met Lys Leu Ala Leu Val Thr Gly Ser Arg Arg Thr Ser Ala
            115                 120                 125

Met Ala Val Leu Lys Lys Val Gly Leu Glu Gly Ala Phe Asp Ala Ile
            130                 135                 140

Val Ala Ala Glu Asp Val Arg Arg Gly Lys Pro Asp Ala Glu Pro Tyr
145                 150                 155                 160

Leu Val Ala Met Arg Ala Val Asp Val Pro Ala Leu Asn Cys Val Val
            165                 170                 175

Val Glu Asn Ala Pro Leu Gly Ile Arg Ala Arg Ala Ala Lys Val
            180                 185                 190

Gly Tyr Ile Ile Ala Ile Ala Thr Thr Leu Asp Glu Ala His Leu Lys
            195                 200                 205
```

```
Glu Ala Asp Glu Val Ala Pro Ser Phe Pro Glu Leu Glu Gln Cys Ile
    210                 215                 220

Ala Arg Arg Phe Glu Ala Arg Pro Gly Arg Ala Ile Met
225                 230                 235

<210> SEQ ID NO 119
<211> LENGTH: 209
<212> TYPE: PRT
<213> ORGANISM: Methanocella conradii

<400> SEQUENCE: 119

Met Pro Arg Ile Arg Gly Leu Ile Phe Asp Leu Asp Gly Thr Leu Ile
1               5                   10                  15

Asp Asn Tyr Asp Gly Tyr Met Glu Leu Met Leu Arg Arg Val Gly Arg
            20                  25                  30

Asp Leu Gly Arg Glu Phe Thr Leu Ser His Ala Lys Glu Leu Trp Tyr
        35                  40                  45

Ser Ile Asn Ser Glu Ser Arg Asp Glu Val Ile Met Arg Trp Gly Val
    50                  55                  60

Asn Pro Asp Arg Phe Trp Thr Val Phe Asn Arg Tyr Glu Asp Ile Asn
65                  70                  75                  80

Glu Lys Leu Glu Asn Thr Tyr Leu His Asp Asp Ala Asp Ile Leu Lys
                85                  90                  95

Gly Leu Asn Ile Pro Lys Gly Ile Val Thr His Thr Ser Tyr Glu His
            100                 105                 110

Thr Asp Arg Leu Leu Gln Lys Val Gly Met Arg Gln Tyr Phe Arg Pro
        115                 120                 125

Ile Ile Ala Cys Thr Glu Asp Thr Gly Tyr Lys Pro Ser Pro Leu Pro
    130                 135                 140

Ile Ile Tyr Cys Val Val Gly Met Lys Leu Lys Pro Glu Glu Val Ala
145                 150                 155                 160

Tyr Val Gly Asp Thr Leu Ser Asp Met Leu Ala Ala Arg Tyr Ala Gly
                165                 170                 175

Val Lys Ser Ile Tyr Ile Asn Arg Tyr Asn Arg Pro Ile Lys Ala Ser
            180                 185                 190

Pro Asp Tyr Glu Ile Lys Arg Met Asp Glu Leu Leu Glu Ile Leu Gly
        195                 200                 205

Gln

<210> SEQ ID NO 120
<211> LENGTH: 216
<212> TYPE: PRT
<213> ORGANISM: Methanococcoides methylutens

<400> SEQUENCE: 120

Met Leu Asn Ser Leu Ile Phe Asp Ala Asp Gly Val Leu Met Asp Ser
1               5                   10                  15

Met Pro Cys His Ala Asp Ala Trp Val His Thr Phe Ser Glu Val Gly
            20                  25                  30

Ile Asp Ile Val Arg Gln Asp Ile Tyr Asp Ile Glu Gly Ser Asn His
        35                  40                  45

Val Gly Val Ile Lys Leu Ile Phe Lys Lys Ala Gly Arg Glu Ala Asp
    50                  55                  60

Pro Glu Ile Ile Glu Lys Leu Arg Val Arg Lys Arg Glu Leu Phe Leu
65                  70                  75                  80
```

```
Lys Lys Lys Asn Ile Asp Pro Phe Asp Gly Met Tyr Asn Leu Leu Lys
                85                  90                  95

Lys Leu Lys Asn Asp Phe His Leu Ala Val Val Ser Gly Ser Asp Arg
            100                 105                 110

Pro Ile Val Asp Ser Met Ile Asn Glu Phe Tyr Pro Asp Ile Phe Glu
            115                 120                 125

Val Thr Ile Ser Gly Ala Asp Val Asn Asn Gly Lys Pro Asp Pro Glu
            130                 135                 140

Pro Tyr Leu Lys Ala Met Glu Ile Leu Lys Val Lys Lys Glu Asn Cys
145                 150                 155                 160

Leu Val Ile Glu Asn Ala Pro Leu Gly Val Asp Ser Ala Lys Asn Ala
                165                 170                 175

Gly Ile Tyr Cys Val Ala Val Pro Thr Tyr Val Asp Ala Glu Lys Leu
                180                 185                 190

Lys Arg Ala Asp Gln Ile Ile Gln Asp His Lys Gln Leu Ile Glu Phe
            195                 200                 205

Leu Ser Asp Ile Glu Ser Pro Arg
210                 215

<210> SEQ ID NO 121
<211> LENGTH: 227
<212> TYPE: PRT
<213> ORGANISM: Methanococcoides methylutens

<400> SEQUENCE: 121

Met Val Phe Lys Ala Leu Val Val Asp Ile Asp Gly Thr Ile Thr Asn
1               5                   10                  15

Pro Asp Arg Ser Leu Asp Leu Arg Val Ala Lys Arg Phe Arg Glu Leu
            20                  25                  30

Arg Val Pro Val Val Leu Ser Thr Gly Asn Pro Leu Cys Tyr Val His
            35                  40                  45

Ala Ala Ala Lys Leu Ile Gly Leu Gly Gly Ile Val Ile Ala Glu Asn
        50                  55                  60

Gly Gly Val Ile Ser Thr Gly Phe Asp Lys Pro Ser Ile Ile Ala Asp
65                  70                  75                  80

Gly Met Glu Lys Cys Glu Glu Ala Tyr Glu Leu Leu Ser Asn Tyr Phe
                85                  90                  95

Asp Leu Glu Lys Leu Asp Ala Ala Tyr Arg Lys Thr Glu Val Val Leu
            100                 105                 110

Arg Arg Gly Met Asp Ile Ser Gln Leu Arg Glu Ile Val Glu Asp Asn
            115                 120                 125

Gly Met Glu Val Glu Ile Ile Asp Thr Gly Tyr Ala Val His Ile Lys
            130                 135                 140

Asp Gly Lys Ile Asn Lys Gly Thr Gly Leu His Thr Val Ala Glu Leu
145                 150                 155                 160

Met Gly Ile Asp Thr Lys Asp Phe Leu Ala Ile Gly Asp Ser Cys Asn
                165                 170                 175

Asp Ala Glu Met Met Arg Glu Ala Gly Leu Gly Ile Ala Val Gly Asn
            180                 185                 190

Ala Asp Asp Asp Ala Arg Lys Ala Ala Ser Met Val Thr Lys Ala Ser
            195                 200                 205

Phe Gly Glu Gly Met Leu Glu Ala Ile Glu Tyr Ala Phe Ser Asn Gly
            210                 215                 220

Leu Leu Glu
225
```

<210> SEQ ID NO 122
<211> LENGTH: 234
<212> TYPE: PRT
<213> ORGANISM: Methanohalobium evestigatum

<400> SEQUENCE: 122

Met Lys Tyr Lys Ala Leu Val Ala Asp Ile Asp Gly Thr Ile Thr His
1               5                   10                  15

Gln Asn Arg Arg Leu Asn Leu Lys Ala Glu Met Leu Tyr Arg Leu
            20                  25                  30

Asn Asp Glu Ser Gly Ile Pro Val Val Leu Ala Thr Gly Asn Ile Leu
            35                  40                  45

Cys Phe Ser His Ala Ala Ser Lys Leu Ile Gly Leu Ser Gly Tyr Val
50                  55                  60

Ile Ala Glu Asn Gly Gly Val Val Ser Glu Gly Phe Asp Thr Asn Pro
65                  70                  75                  80

Tyr Ile Met Gly Asp Ile Lys Glu Cys Arg Lys Ala Phe Ser Phe Leu
                85                  90                  95

Ser Glu Tyr Ile Pro Leu Thr Lys Leu Asp Pro Glu Tyr Arg Lys Thr
            100                 105                 110

Glu Ile Ala Leu Arg Arg Asn Phe Asp Leu Glu Tyr Ala Lys Asn Val
            115                 120                 125

Ile Lys Ser Gly Lys Tyr Asn Val Asp Leu Ile Asp Thr Gly Tyr Ala
130                 135                 140

Val His Ile Lys Ser Asn Thr Met Asn Lys Gly Thr Gly Leu Val Lys
145                 150                 155                 160

Ile Ala Glu Leu Met Gly Leu Asn Pro Lys Glu Phe Val Ala Ile Gly
                165                 170                 175

Asp Ser Glu Asn Asp Leu Glu Met Ile Glu Phe Ala Gly Ile Gly Ile
            180                 185                 190

Ala Val Ala Asn Ser Asp Gln Lys Thr Arg Ser Ile Ala Asp Ile Val
            195                 200                 205

Thr Asp Ala Ser Tyr Gly Glu Gly Val Val Glu Ala Ile Glu Arg Leu
    210                 215                 220

Tyr Ser Cys Asp Trp Asn Asp Thr Cys Leu
225                 230

<210> SEQ ID NO 123
<211> LENGTH: 217
<212> TYPE: PRT
<213> ORGANISM: Methanohalobium evestigatum

<400> SEQUENCE: 123

Met Leu Lys Ala Ile Ile Phe Asp Phe Asp Gly Val Leu Ala Asp Ser
1               5                   10                  15

Met Pro Tyr His Ala Gln Ala Trp Lys Ile Ala Phe Glu Lys Ala Gly
            20                  25                  30

Ile Glu Ile Asn Lys Asp Asp Ile Tyr Glu Ile Glu Gly Ser Asn His
        35                  40                  45

Val Gly Ile Ile Gln Leu Met Phe Gln Lys Met Gly Lys Ser Pro Gln
    50                  55                  60

Pro His Gln Phe Asp Glu Ile Ala Gln Glu Lys Arg Lys Ile Phe Ser
65                  70                  75                  80

Gln Ile Ala Asn Leu Lys Asn Phe Glu Asp Met Asp Lys Cys Leu Ser
                85                  90                  95

```
Gln Leu Lys Asn Lys Phe Lys Leu Ala Val Val Ser Gly Ala Asp Arg
            100                 105                 110

Asn Ala Val Phe Asn Met Val Gly Arg Phe Tyr Pro Asp Val Phe Asp
        115                 120                 125

Val Ile Val Thr Gly Glu Asp Val Asp Asn Gly Lys Pro Ser Pro Glu
    130                 135                 140

Pro Tyr Leu Lys Ala Leu Gly Met Leu Asn Val Glu Lys Asn Glu Cys
145                 150                 155                 160

Leu Val Val Glu Asn Ala Pro Leu Gly Val Asp Ser Ala Lys Asn Ala
                165                 170                 175

Gly Leu Tyr Cys Val Ala Val Pro Thr Tyr Val Asp Pro Glu Lys Leu
            180                 185                 190

Asp Lys Ala Asp Val Val Glu Asp His Ser Asp Leu Lys Lys Tyr
        195                 200                 205

Leu Gln Lys Ile Tyr Ser Glu Gln Ala
    210                 215
```

<210> SEQ ID NO 124
<211> LENGTH: 226
<212> TYPE: PRT
<213> ORGANISM: Methanolobus tindarius

<400> SEQUENCE: 124

```
Met Lys Phe Lys Ala Ile Val Ile Asp Ile Asp Gly Thr Ile Thr His
1               5                   10                  15

Arg Asp Arg Lys Leu Ser Leu Thr Ala Ala Lys Leu Arg Ala Leu
            20                  25                  30

Asp Ile Pro Val Val Ile Ala Thr Gly Asn Val Leu Cys Tyr Ala Lys
        35                  40                  45

Ala Thr Ala Lys Leu Val Gly Val Cys Cys Asn Ile Ile Ala Glu Asn
    50                  55                  60

Gly Gly Val Ile Ile Asp Gly Phe Asp Asn Asp Pro Ile Val Ser Asp
65                  70                  75                  80

Val Ile His Glu Cys Glu Glu Ala Tyr Glu Phe Leu Ser Ser Glu Phe
                85                  90                  95

Asn Met Glu Lys Leu Asp Ser Val His Arg Arg Thr Glu Ile Val Leu
            100                 105                 110

Arg Ser Asn Phe Asp Val Glu Lys Ala Arg Glu Val Leu Gly Thr His
        115                 120                 125

Phe Pro Asn Val Glu Ile Ile Asp Thr His Phe Ala Ile His Ile Lys
    130                 135                 140

Ser Lys Lys Ile Asn Lys Gly Thr Gly Leu Phe Lys Met Ala Glu Met
145                 150                 155                 160

Met Gly Leu Glu Thr Thr Asp Phe Val Ala Ile Gly Asp Ser Ile Asn
                165                 170                 175

Asp Leu Glu Met Leu Gln Glu Ala Gly Phe Ala Val Ala Val Gly Asn
            180                 185                 190

Ala Asp Asp Phe Leu Lys Asp Ile Ala Asp Tyr Val Ser Glu Ala Ser
        195                 200                 205

Tyr Gly Asp Gly Thr Val Glu Ala Ile Asp Tyr Leu Ile Ser Ser Gly
    210                 215                 220

Leu Ile
225
```

<210> SEQ ID NO 125
<211> LENGTH: 217
<212> TYPE: PRT
<213> ORGANISM: Methanolobus tindarius

<400> SEQUENCE: 125

Met Ile Lys Gly Ile Ile Phe Asp Ser Asp Gly Val Leu Val Asn Ser
1               5                   10                  15

Met Pro Phe His Ala Lys Ala Trp Val Glu Val Phe Ala Glu Tyr Gly
            20                  25                  30

Ile Glu Val Thr Glu Glu Asp Ile Tyr Glu Ile Glu Gly Ser Asn His
        35                  40                  45

Val Gly Val Ile Asn Ile Phe Phe Gly Lys Ala Gly Arg Thr Pro Glu
    50                  55                  60

Pro Glu Ile Tyr Ala Glu Ile Leu Glu Lys Lys Arg Ala His Phe Leu
65                  70                  75                  80

Glu Asn Asn Arg Ala Glu Val Phe Glu Gly Met Tyr Asp Cys Leu Ser
                85                  90                  95

Ser Leu Lys Asn Lys Phe Lys Leu Ala Val Ala Ser Gly Ala Asp Arg
            100                 105                 110

Thr Ile Val Thr Ser Leu Met Asp Lys Phe Tyr Pro Gly Val Phe Asp
        115                 120                 125

Ala Ile Ile Ser Gly Glu Asp Val Glu Asn Gly Lys Pro Asp Pro Glu
    130                 135                 140

Pro Tyr Glu Lys Ala Ile Val Lys Leu Gly Leu Ser Lys Asp Glu Cys
145                 150                 155                 160

Leu Val Val Glu Asn Ala Pro Leu Gly Val Glu Ser Ala Lys Asn Ala
                165                 170                 175

Gly Val Phe Cys Val Gly Val Pro Thr Tyr Leu Asp Glu Ser Lys Leu
            180                 185                 190

Lys Glu Ala Asp Phe Val Val Arg Asn His Ser Glu Leu Ile Glu Tyr
        195                 200                 205

Leu Thr Asp Leu Lys Asp Ser Ser Leu
    210                 215

<210> SEQ ID NO 126
<211> LENGTH: 228
<212> TYPE: PRT
<213> ORGANISM: Methanolobus tindarius

<400> SEQUENCE: 126

Met Leu Met Lys Phe Lys Ala Ile Val Ile Asp Ile Asp Gly Thr Ile
1               5                   10                  15

Thr His Arg Asp Arg Lys Leu Ser Leu Thr Ala Ala Ala Lys Leu Arg
            20                  25                  30

Ala Leu Asp Ile Pro Val Val Ile Ala Thr Gly Asn Val Leu Cys Tyr
        35                  40                  45

Ala Lys Ala Thr Ala Lys Leu Val Gly Val Cys Cys Asn Ile Ile Ala
    50                  55                  60

Glu Asn Gly Gly Val Ile Ile Asp Gly Phe Asn Asp Pro Ile Val
65                  70                  75                  80

Ser Asp Val Ile His Glu Cys Glu Glu Ala Tyr Glu Phe Leu Ser Ser
                85                  90                  95

Glu Phe Asn Met Glu Lys Leu Asp Ser Val His Arg Arg Thr Glu Ile
            100                 105                 110

Val Leu Arg Ser Asn Phe Asp Val Glu Lys Ala Arg Glu Val Leu Gly

```
              115                 120                 125
Thr His Phe Pro Asn Val Glu Ile Ile Asp Thr His Phe Ala Ile His
    130                 135                 140

Ile Lys Ser Lys Lys Ile Asn Lys Gly Thr Gly Leu Phe Lys Met Ala
145                 150                 155                 160

Glu Met Met Gly Leu Glu Thr Thr Asp Phe Val Ala Ile Gly Asp Ser
                165                 170                 175

Ile Asn Asp Leu Glu Met Leu Gln Glu Ala Gly Phe Ala Val Ala Val
            180                 185                 190

Gly Asn Ala Asp Asp Phe Leu Lys Asp Ile Ala Asp Tyr Val Ser Glu
        195                 200                 205

Ala Ser Tyr Gly Asp Gly Thr Val Glu Ala Ile Asp Tyr Leu Ile Ser
    210                 215                 220

Ser Gly Leu Ile
225

<210> SEQ ID NO 127
<211> LENGTH: 218
<212> TYPE: PRT
<213> ORGANISM: Methanosarcina siciliae

<400> SEQUENCE: 127

Met Leu Lys Ala Ile Ile Phe Asp Val Asp Gly Val Leu Val Asp Ser
1               5                   10                  15

Met Arg Phe Gln Ala Glu Ala Trp Val Lys Thr Leu Lys Glu Val Gly
            20                  25                  30

Val Thr Val Ser Arg Glu Asp Ile Tyr Glu Leu Glu Gly Ser Asn Asn
        35                  40                  45

Leu Gly Leu Ile Lys Leu Val Phe Glu Lys Ala Gly Lys Glu Pro Glu
    50                  55                  60

Pro Trp His Tyr Glu Gln Leu Pro Val Lys Lys Arg Glu Val Leu Glu
65              70                  75                  80

Phe Asp Arg Ile Lys Pro Phe Glu Gly Met Pro Ser Cys Leu Asn Gln
                85                  90                  95

Leu Lys Arg His Phe Arg Leu Ala Met Val Ser Gly Ser Asn Phe Asp
            100                 105                 110

Ile Val Ser Thr Phe Ala Asn Ser Phe Phe Pro Asp Cys Phe Glu Val
        115                 120                 125

Ile Val Thr Gly Gly Asp Leu Glu Arg Gly Lys Pro Cys Pro Asp Pro
    130                 135                 140

Tyr Ile Lys Ala Leu Glu Lys Leu Asp Leu Ala Thr Asn Glu Cys Ile
145                 150                 155                 160

Val Val Glu Asn Ala Pro Leu Gly Ile Thr Ala Ala Lys Arg Ala Gly
                165                 170                 175

Leu Tyr Cys Val Ala Val Ala Ser Met Leu Ser Pro Glu Lys Val Lys
            180                 185                 190

His Ala Asp Ile Val Phe Glu Asn His Ala Val Leu Leu Asp Tyr Leu
        195                 200                 205

Lys Ser Leu Ile Pro Gly Glu Ser His Thr
    210                 215

<210> SEQ ID NO 128
<211> LENGTH: 253
<212> TYPE: PRT
<213> ORGANISM: Methanosarcina siciliae
```

```
<400> SEQUENCE: 128

Met Ser Ser Ile Ile Asn Tyr Gly Ser Ile Ile Asn Tyr Glu Trp Gly
1               5                   10                  15

Ser Ile Leu Ser Pro Leu Ser His Leu Phe Ser Met Lys Phe Lys Ala
            20                  25                  30

Ile Val Val Asp Ile Asp Gly Thr Ile Thr Cys Glu Asn Arg Glu Leu
        35                  40                  45

His Leu Gly Ala Val Lys Lys Ile Arg Ser Leu Lys Val Pro Val Val
    50                  55                  60

Leu Ala Thr Gly Asn Ile Ile Cys Tyr Ala Arg Thr Ala Ser Lys Leu
65                  70                  75                  80

Ile Gly Leu Glu Gly Ala Val Val Ala Glu Asn Gly Gly Ala Val Thr
                85                  90                  95

Val Arg Tyr Asp Leu Asn Gly Thr Phe Glu Ser Leu Glu Glu Cys
                100                 105                 110

Glu Lys Ala Phe Ser Phe Leu Ser Glu His Phe Gln Leu Thr Lys Leu
                115                 120                 125

Asp Pro Phe Tyr Arg Lys Thr Glu Ile Ala Leu Arg Arg Asp Phe Asp
            130                 135                 140

Leu Glu Lys Ala Arg Ala Leu Leu Lys Thr Gln Leu Leu Asp Val Glu
145                 150                 155                 160

Met Val Asp Thr Lys Tyr Ala Val His Ile Lys Ser Thr Arg Ile Asn
                165                 170                 175

Lys Gly Ser Gly Leu Arg Lys Leu Ala Glu Met Met Gly Leu Glu Ala
                180                 185                 190

Lys Asp Phe Val Ala Ile Gly Asp Ser Glu Asn Asp Val Glu Met Phe
            195                 200                 205

Lys Ala Ala Gly Phe Gly Ile Ala Val Ala Asn Gly Asp Thr Lys Ile
            210                 215                 220

Lys Glu Ala Ala Asp Tyr Val Thr Glu Ala Ser Phe Gly Lys Gly Ala
225                 230                 235                 240

Val Glu Ala Phe Glu Tyr Leu Glu Ser Lys Gly Leu Ile
                245                 250

<210> SEQ ID NO 129
<211> LENGTH: 213
<212> TYPE: PRT
<213> ORGANISM: Methanosarcina siciliae

<400> SEQUENCE: 129

Met Lys Tyr Asn Thr Val Ile Phe Asp Phe Asp Tyr Thr Leu Ala Asp
1               5                   10                  15

Ala Thr Asp Gly Ile Val Ser Ser Phe Asn His Ala Phe Ser Glu Leu
            20                  25                  30

Asp Leu Ala Ser Tyr Asp Ile Glu Ser Ile Lys Arg Thr Val Gly Leu
        35                  40                  45

Ser Leu Asp Glu Ala Phe Val Gln Leu Thr Ala Glu Asp Lys Ala
50                  55                  60

Leu Arg Asn Arg Phe Lys Ile Leu Phe Lys Glu Lys Ala Asp Glu Val
65                  70                  75                  80

Met Ser Lys Asn Thr Val Leu Phe Asp Asp Thr Ile Ser Thr Leu Arg
                85                  90                  95

Gln Leu Lys Arg Asp Gly Leu Asn Thr Gly Ile Val Thr Thr Lys Tyr
            100                 105                 110
```

His Tyr Arg Ile Met Glu Thr Leu Asn Thr Tyr Gly Ile Ser Asp Leu
            115                 120                 125

Val Asp Ile Ile Val Gly Gly Glu Asp Val Lys Ala Pro Lys Pro Ser
    130                 135                 140

Pro Glu Gly Leu Leu Leu Ala Ile Asp Ser Leu Asn Ser Arg Gln Asn
145                 150                 155                 160

Asn Val Leu Tyr Ile Gly Asp Ser Leu Val Asp Ala Lys Thr Ala Leu
                165                 170                 175

Ala Ala Asn Val Asp Phe Val Ala Val Thr Thr Gly Thr Thr Glu Val
            180                 185                 190

Lys Glu Phe Ser Gln Tyr Pro Cys Ile Arg Ile Leu Lys Asn Leu Ser
        195                 200                 205

Glu Leu Phe Asp Arg
    210

<210> SEQ ID NO 130
<211> LENGTH: 224
<212> TYPE: PRT
<213> ORGANISM: Methanothermus fervidus

<400> SEQUENCE: 130

Met Lys Ile Glu Ala Ile Ala Val Asp Ile Asp Gly Thr Ile Thr Asp
1               5                   10                  15

Thr Lys Arg Arg Leu Cys Ile Asp Ala Ile Lys Ala Leu Arg Asp Ala
            20                  25                  30

Glu Lys Leu Gly Ile Lys Val Thr Leu Val Thr Gly Asn Ile Leu Cys
        35                  40                  45

Tyr Ala Tyr Ala Thr Ser Thr Leu Ile Gly Leu Ser Gly Gly Val Val
    50                  55                  60

Ala Glu Asn Gly Gly Val Ile Tyr Val Asn Asp Glu Val Asn Val Leu
65                  70                  75                  80

Gly Asp Ile Lys Lys Ala Lys Lys Ala Tyr Asn Tyr Leu Lys Ser Ile
                85                  90                  95

Tyr Pro Val Glu Lys Val Gln Phe Ser Glu Leu Arg Val Ser Glu Ile
            100                 105                 110

Ala Ile Lys Arg Thr Ile Pro Val Glu Ile Lys Asp Ala Leu Lys
        115                 120                 125

Asp Phe Asp Val Glu Val Tyr Asp Thr Lys Phe Ala Ile His Leu Thr
    130                 135                 140

Asp Pro Lys Val Asp Lys Gly Ser Ser Leu Lys Ile Leu Thr Lys Lys
145                 150                 155                 160

Leu Gly Ile Asp Leu Glu Lys Thr Ile Ala Ile Gly Asp Ser Glu Asn
                165                 170                 175

Asp Leu Glu Phe Leu Asp Val Ala Gly Val Lys Val Ala Val Ala Asn
            180                 185                 190

Ala Asn Lys Glu Leu Lys Glu Ile Ala Asp Tyr Val Thr Lys Lys Pro
        195                 200                 205

Tyr Gly Ser Gly Val Ala Glu Ala Ile Lys Lys Tyr Val Thr Leu Ser
    210                 215                 220

<210> SEQ ID NO 131
<211> LENGTH: 277
<212> TYPE: PRT
<213> ORGANISM: Petrotoga mobilis

<400> SEQUENCE: 131

Met Lys Lys Thr Phe Val Phe Asp Leu Asp Gly Thr Leu Leu Asn Ser
1               5                   10                  15

Glu Val Arg Ile Ser Pro Lys Thr Tyr Gln Ala Leu Lys Arg Leu Lys
                20                  25                  30

Glu Glu Gly His Ile Ile Ile Ile Ala Ser Gly Arg Met Tyr Ala Ser
            35                  40                  45

Thr Met Tyr Val Val Glu Asn Phe Leu Pro Phe Leu Lys Gly Asn Val
        50                  55                  60

Ile Ile Ser Ser Tyr Asn Gly Gly Tyr Ile Val Asp His Asn Gly Lys
65                  70                  75                  80

Val Val Phe Glu Lys Gly Val Ala Asn Glu Ser Ala Ile Lys Cys Ile
                85                  90                  95

Lys Phe Leu Arg Asp Leu Asn Ile His Arg His Ile Tyr Ile Asn Asp
                100                 105                 110

Lys Leu Ile Ser Glu Ile Asp Lys Glu Ile Arg Asp Tyr Ser Lys
        115                 120                 125

His Ser Phe Val Asp Tyr Val Leu Val Asp Leu Ile Ala Glu Ile
        130                 135                 140

Glu Thr Ser Ser His Pro Thr Leu Lys Ile Leu Ala Ile Gly Glu Pro
145                 150                 155                 160

Asp Lys Ile Asp Val Ile Lys Lys Leu Ala Glu Asn Glu Leu Gln Gly
                165                 170                 175

Glu Phe Asn Leu Met Lys Ser Trp Asp Thr Tyr Leu Asp Phe Ile Pro
                180                 185                 190

Tyr Gly Val Ser Lys Gly Asn Ser Leu Lys Ile Ile Ser Lys Ile Tyr
                195                 200                 205

Asn Leu Asp Pro Asn Thr Leu Tyr Val Phe Gly Asp Ser Glu Asn Asp
210                 215                 220

Ile Asp Met Leu Glu Leu Thr Lys Asn Ser Phe Ala Met Gly Asn Ala
225                 230                 235                 240

Lys Glu Asp Val Lys Lys Val Ala Asn Tyr Leu Leu Pro Ser Asn Asp
                245                 250                 255

Glu Asp Gly Val Ala Tyr Ala Ile Glu Lys Ile Leu Ala Asp Asp Leu
            260                 265                 270

Asp Asn Val Asn Ile
        275

<210> SEQ ID NO 132
<211> LENGTH: 214
<212> TYPE: PRT
<213> ORGANISM: Petrotoga mobilis

<400> SEQUENCE: 132

Met Ile Lys Ala Cys Ile Phe Asp Leu Asp Gly Val Ile Val Asp Thr
1               5                   10                  15

Ala Lys Tyr His Tyr Met Ala Trp Lys Arg Leu Ala Asp Glu Leu Asn
                20                  25                  30

Ile Pro Phe Asn Glu Lys Asp Asn Glu Arg Leu Lys Gly Val Ser Arg
            35                  40                  45

Met Lys Ser Leu Glu Ile Ile Leu Asp Leu Gly Asn Val Asn Leu Ser
        50                  55                  60

Gln Glu Glu Lys Glu Glu Leu Ala Gln Lys Lys Asn Asn Trp Tyr Val
65                  70                  75                  80

Glu Cys Ile Ser Asn Met Asp Lys Ser Glu Leu Leu Pro Gly Val Glu
                85                  90                  95

```
Glu Phe Ile Lys Asn Leu Lys Arg Lys Gly Ile Lys Val Ala Ile Ala
            100                 105                 110

Ser Ala Ser Lys Asn Thr Lys Leu Ile Leu Lys Lys Leu Asn Leu Glu
            115                 120                 125

Asp Thr Phe Asp Ala Val Ile Asp Gly Thr Met Ile Asp Lys Ala Lys
130                 135                 140

Pro Asn Pro Glu Ile Phe Leu Lys Ala Ser Asp Tyr Leu Asn Val Lys
145                 150                 155                 160

Pro Glu Glu Cys Leu Val Phe Glu Asp Ala Val Ala Gly Val Gln Ala
                165                 170                 175

Ala Lys Lys Ala Gly Met Lys Val Ile Gly Val Gly Lys Lys Val
            180                 185                 190

Leu Lys Gly Ala Asp Lys Val Ile Lys Asn Phe Glu Asn Val Asp Leu
            195                 200                 205

Thr Leu Ile Glu Gly Ile
    210

<210> SEQ ID NO 133
<211> LENGTH: 236
<212> TYPE: PRT
<213> ORGANISM: Picrophilus torridus

<400> SEQUENCE: 133

Met Phe Met Thr Lys Asp Leu Phe Phe Val Tyr Ile Phe Thr Thr Met
1               5                   10                  15

Ile Lys Leu Val Val Leu Asp Val Asp Gly Thr Leu Thr Asp Lys Ser
            20                  25                  30

Arg Met Ile Ser Val Asn Ala Val Asn Ala Ile Arg Asn Leu Lys Thr
            35                  40                  45

Lys Val Ala Leu Val Ser Gly Asn Val Leu Pro Val Leu Tyr Gly Leu
50                  55                  60

Lys Ile Tyr Ile Gly Phe Asp Gly Tyr Ile Phe Ala Glu Asn Gly Gly
65                  70                  75                  80

Ile Ala Leu Ile Asn Asn Asn Ile Glu Lys Phe Phe Glu Lys Asp Gly
            85                  90                  95

Pro Glu Ser Phe Leu Asn Asp Ile Ser Gly Tyr Thr Ser Ala Arg Gly
            100                 105                 110

Ile Leu Thr Asn Arg Trp Arg Glu Thr Ser Met Ala Phe Thr Ala Asn
            115                 120                 125

His Asp Glu Met Asp Ile Ile Asp Arg Glu Ala Ala Ser Arg Asp Leu
130                 135                 140

Tyr Ile Val Asp Ser Gly Phe Thr Leu His Ile Leu Asn Lys Gly Gln
145                 150                 155                 160

Asp Lys Gly Phe Ala Val Lys Lys Met Ile Asp Ile Met Asn Ile Asp
                165                 170                 175

Tyr Asn Asn Val Leu Val Ile Gly Asp Ser Gln Asn Asp Glu Ser Met
            180                 185                 190

Phe Ser Leu Gly Thr Leu Ser Ala Cys Pro Gly Asn Ala Ser Glu Lys
            195                 200                 205

Ile Lys Glu Met Ser Asn Tyr Val Ser Gly Lys Cys Tyr Gly Asp Glu
            210                 215                 220

Leu Phe Asp Val Phe Arg His Phe Asp Leu Ile His
225                 230                 235
```

<210> SEQ ID NO 134
<211> LENGTH: 202
<212> TYPE: PRT
<213> ORGANISM: Picrophilus torridus

<400> SEQUENCE: 134

Met Phe Lys Ala Val Ile Phe Asp Leu Asp Gly Thr Ile Leu Asp Ser
1               5                   10                  15

Ile Pro Leu Arg Val Arg Ser Trp Gln Gln Ala Phe Asp Asp Tyr Asn
            20                  25                  30

Ile Ser Ala Asp Pro Glu Ile Ile Arg Leu Met Ile Gly Tyr Pro Gly
        35                  40                  45

Ser Met Leu Ile Lys Lys Val Asn Ala Met Asn Pro Glu Ile Glu Phe
    50                  55                  60

Arg Glu Glu Tyr Tyr Phe Lys Met His Leu Asp Glu Leu Arg Phe Phe
65                  70                  75                  80

Pro Asp Val Asp Asp Thr Phe Lys Glu Leu Arg Lys Leu Gly Val Lys
                85                  90                  95

Ile Ala Val Val Thr Ser Ser Arg Lys Asp Phe Val Met Arg Leu Asn
            100                 105                 110

Ile Lys Ala Asp Ala Ile Val Thr Ile Asp Asp Val Lys Asn Gly Lys
        115                 120                 125

Pro Asp Thr Glu Pro Tyr Ile Lys Ala Met Ser Met Met Asn Val Lys
    130                 135                 140

Pro Asp Glu Thr Val Val Gly Asp Ile Asp Asn Asp Leu Ile Pro
145                 150                 155                 160

Ser Arg Glu Leu Gly Cys Leu Ser Val Leu Val Arg His Asn Arg Asn
                165                 170                 175

Val Ser Ser Asp His Ala Asp Ile Ile Ile Glu Glu Ile Lys Glu Val
            180                 185                 190

Leu Asn Ile Phe Asn Asp Lys Lys Asp Leu
        195                 200

<210> SEQ ID NO 135
<211> LENGTH: 228
<212> TYPE: PRT
<213> ORGANISM: Pseudonocardia thermophila

<400> SEQUENCE: 135

Met Thr Asp Arg Ala Asp Thr Ala His Pro Asp Thr Ala His Pro Asp
1               5                   10                  15

Thr Ala Ile Val Asp Val Asp Gly Thr Leu Val Asp Thr Asn Tyr His
            20                  25                  30

His Ala Leu Ala Trp Phe Arg Ala Phe Arg Arg Phe Gly Val Thr Leu
        35                  40                  45

Pro Val Trp Arg Leu His Arg Ala Ile Gly Met Gly Gly Asp Gln Leu
    50                  55                  60

Val Pro Ala Val Ala Gly Asn Arg Phe Glu Asp Asp His Gly Asp Ala
65                  70                  75                  80

Val Arg Glu Ala Trp Lys Asp Glu Phe Asp Pro Leu Met Gly Glu Val
                85                  90                  95

Arg Pro Phe Gly Gly Val Cys Glu Leu Leu Thr Ala Phe Gly Glu Ser
            100                 105                 110

Gly Leu Lys Val Val Leu Ala Ser Ser Gly Ala Pro Glu His Val Asp
        115                 120                 125

Ala Tyr Leu Asp Leu Phe Asp Gly Arg Arg Leu Ala Asp Ala Trp Thr

```
        130                 135                 140
Thr Ser Glu Asp Val Asp Arg Thr Lys Pro Glu Pro Asp Leu Ile Thr
145                 150                 155                 160

Ala Ala Leu Asp Arg Val Arg Gly Glu Val Gly Ile Val Ile Gly Asp
                165                 170                 175

Ser Val Trp Asp Phe Arg Ala Ala Glu Arg Ala Gly Gln Arg Gly Tyr
            180                 185                 190

Ala Ile Arg Thr Gly Gly Phe Ser Glu Ser Glu Leu Arg Glu Ala Gly
        195                 200                 205

Ala Arg Asn Val Phe Glu Ser Leu Pro Glu Leu His Gln Ala Leu Pro
210                 215                 220

Arg Ile Leu Gly
225
```

<210> SEQ ID NO 136
<211> LENGTH: 273
<212> TYPE: PRT
<213> ORGANISM: Pyrococcus furiosus

<400> SEQUENCE: 136

```
Met Glu Met Arg Ile Val Phe Asp Met Asp Gly Val Leu Tyr Arg Gly
1               5                   10                  15

Asn Thr Pro Ile Glu Gly Ala Arg Glu Val Ile Glu Phe Leu Lys Glu
            20                  25                  30

Lys Gly Ile Lys Phe Ala Phe Leu Thr Asn Asn Ser Thr Lys Thr Pro
        35                  40                  45

Glu Met Tyr Arg Glu Arg Leu Leu Lys Met Gly Ile Asp Val Pro Ala
50                  55                  60

Asp Ser Ile Ile Thr Ser Gly Leu Ala Thr Arg Ile Tyr Met Lys Lys
65                  70                  75                  80

His Phe Glu Pro Gly Lys Ile Phe Val Ile Gly Gly Arg Gly Leu Val
                85                  90                  95

Glu Glu Met Glu Lys Leu Gly Trp Gly Ile Val Ser Val Glu Glu Ala
            100                 105                 110

Arg Glu Gly Ile Trp Lys Glu Val Lys Tyr Val Val Gly Leu Asp
        115                 120                 125

Pro Glu Leu Thr Tyr Glu Lys Leu Lys Tyr Gly Thr Leu Ala Ile Arg
130                 135                 140

Asn Gly Ala Glu Phe Ile Gly Thr Asn Pro Asp Arg Thr Tyr Pro Gly
145                 150                 155                 160

Glu Glu Gly Ile Tyr Pro Gly Ala Gly Ser Ile Ile Ala Ala Leu Glu
                165                 170                 175

Ala Ala Thr Asp Lys Lys Pro Leu Ile Ile Gly Lys Pro Asn Glu Pro
            180                 185                 190

Met Tyr Glu Val Leu Arg Glu Lys Leu Gly Glu Gly Glu Val Trp Met
        195                 200                 205

Val Gly Asp Arg Leu Asp Thr Asp Ile Leu Phe Ala Lys Lys Phe Gly
210                 215                 220

Met Lys Ala Ile Met Val Leu Thr Gly Val His Ser Leu Ser Asp Ile
225                 230                 235                 240

Glu Lys Ser Asp Ile Lys Pro Asp Leu Val Leu Pro Ser Ile Lys Glu
                245                 250                 255

Leu Leu Glu Tyr Leu Lys Ile Leu His Asp Glu Asp Lys Glu Gly Thr
            260                 265                 270
```

Lys

<210> SEQ ID NO 137
<211> LENGTH: 351
<212> TYPE: PRT
<213> ORGANISM: Pyrococcus furiosus

<400> SEQUENCE: 137

Met Ser Lys Pro Leu Phe Val Thr Pro Tyr Val Ser Thr Leu Leu
1               5                   10                  15

Thr Leu Ile Glu Tyr Cys Thr Trp Leu Ile Ser Cys Pro Ser Leu Lys
            20                  25                  30

Phe Pro Pro Cys Phe Ile Met Pro Thr Phe Trp Ala Gly Tyr Phe
            35                  40                  45

Cys Cys Trp Lys Ser Arg Asn Phe Leu Phe Asn Tyr Asn Tyr Ser Phe
50                  55                      60

Ile Arg Pro Met Leu Asp Phe Phe Cys Ser Ser Ile Cys Phe Gly Val
65                  70                  75                  80

Leu Arg Ile Tyr Arg Phe Leu Ile Thr Thr Phe Ser Thr Asp Lys Asp
            85                  90                  95

Ser Ser Pro Pro Val Gly Tyr His Asn Thr Pro Thr Phe Gly Ala Glu
            100                 105                 110

Phe His His Leu Ser His Pro His Thr Ser Gln Gly Gln Ser Leu Ile
            115                 120                 125

Val Gln Asn Lys Lys Phe Thr Leu His His Ser Leu Glu Gly Arg Cys
130                 135                     140

Met Lys Ile Ser Lys Ile Ile Glu Gln Ile Lys Ser Glu Leu Asp Lys
145                 150                 155                 160

Lys Asp Lys Leu Arg Glu Glu Ala Leu Glu Ile Thr Arg Asp Ile Ile
                165                 170                 175

Arg Leu Ser Gly Asp Ala Ile Lys Ala Met His Arg Gly Glu Leu Glu
                180                 185                 190

Leu Ala His Glu Arg Leu Glu Lys Ala Arg Gly Leu Val Lys Glu Leu
            195                 200                 205

Lys Glu Lys Leu Arg Glu His Pro Asp Leu Tyr Tyr Thr Gly Tyr Val
210                 215                 220

Gln Asn Ala Asn Gln Glu Phe Val Glu Ala Val Leu Met Tyr His Tyr
225                 230                 235                 240

Leu Thr Asp Arg Glu Phe Pro Ser His Val Asp Leu Gly Val Pro Ser
                245                 250                 255

Gln Asp Tyr Ile Leu Gly Val Gly Asp Phe Ile Gly Glu Leu Arg Arg
                260                 265                 270

Tyr Phe Leu Ile Asn Leu Met Lys Gly Asn Leu Asp Glu Ala Glu Ser
            275                 280                 285

Thr Tyr Arg Phe Met Glu Glu Val Tyr Glu Glu Leu Met Thr Leu Glu
290                 295                 300

Tyr Pro Lys Gly Leu Val Asn Ile Arg Gln Lys Gln Asp Gln Ala Arg
305                 310                 315                 320

Tyr Thr Leu Glu Arg Thr Leu Glu Asp Leu Thr Arg Ala Lys Val Asn
                325                 330                 335

Arg Arg Val Glu Glu Lys Leu Glu Ala Phe Leu Asn Asp Arg Ser
                340                 345                 350

<210> SEQ ID NO 138
<211> LENGTH: 207

```
<212> TYPE: PRT
<213> ORGANISM: Pyrococcus furiosus

<400> SEQUENCE: 138

Met Lys Ile Ser Lys Ile Ile Glu Gln Ile Lys Ser Glu Leu Asp Lys
1               5                   10                  15

Lys Asp Lys Leu Arg Glu Glu Ala Leu Glu Ile Thr Arg Asp Ile Ile
            20                  25                  30

Arg Leu Ser Gly Asp Ala Ile Lys Ala Met His Arg Gly Glu Leu Glu
        35                  40                  45

Leu Ala His Glu Arg Leu Glu Lys Ala Arg Gly Leu Val Lys Glu Leu
    50                  55                  60

Lys Glu Lys Leu Arg Glu His Pro Asp Leu Tyr Tyr Thr Gly Tyr Val
65                  70                  75                  80

Gln Asn Ala Asn Gln Glu Phe Val Glu Ala Val Leu Met Tyr His Tyr
                85                  90                  95

Leu Thr Asp Arg Glu Phe Pro Ser His Val Asp Leu Gly Val Pro Ser
            100                 105                 110

Gln Asp Tyr Ile Leu Gly Val Gly Asp Phe Ile Gly Glu Leu Arg Arg
        115                 120                 125

Tyr Phe Leu Ile Asn Leu Met Lys Gly Asn Leu Asp Glu Ala Glu Ser
    130                 135                 140

Thr Tyr Arg Phe Met Glu Glu Val Tyr Glu Glu Leu Met Thr Leu Glu
145                 150                 155                 160

Tyr Pro Lys Gly Leu Val Asn Ile Arg Gln Lys Gln Asp Gln Ala Arg
                165                 170                 175

Tyr Thr Leu Glu Arg Thr Leu Glu Asp Leu Thr Arg Ala Lys Val Asn
            180                 185                 190

Arg Arg Val Glu Glu Lys Leu Glu Ala Phe Leu Asn Asp Arg Ser
        195                 200                 205

<210> SEQ ID NO 139
<211> LENGTH: 204
<212> TYPE: PRT
<213> ORGANISM: Pyrococcus furiosus

<400> SEQUENCE: 139

Met Lys Gly Leu Ile Ala Phe Asp Leu Glu Gly Thr Leu Thr Asp Met
1               5                   10                  15

Ile Ser Trp Glu Ile Leu His Glu Lys Phe Gly Thr Cys Asp Lys Ala
            20                  25                  30

Arg Val His Thr Ser Leu Phe Leu Ser Gly Lys Ile Thr Tyr His Glu
        35                  40                  45

Trp Ala Glu Met Asp Val Arg Leu Trp Lys Gly Arg Arg Glu Glu
    50                  55                  60

Val Glu Glu Ala Phe Ser Gln Val Thr Leu Lys Pro Tyr Ala Arg Glu
65                  70                  75                  80

Leu Phe Glu Trp Leu Lys Lys Asn Asn Phe Lys Thr Ala Ile Ile Ser
                85                  90                  95

Gly Gly Leu Met Cys Leu Ala Arg Lys Val Gly Glu Lys Leu Gly Val
            100                 105                 110

Asp Phe Ile Val Ala Asn Glu Leu Lys Phe Asp Ser Gln Gly Arg Ile
        115                 120                 125

Glu Gly Val Ile Val Arg Val Thr Phe Asp Asn Lys Gly Glu Ile Leu
    130                 135                 140
```

```
Arg Gln Leu Lys Gln Lys Val Asn Pro Asn Val Thr Ile Ala Val Gly
145                 150                 155                 160

Asp Trp Lys Asn Asp Lys Ser Met Phe Glu Glu Ala Asp Ile Ser Ile
                165                 170                 175

Ser Leu Gly Asp Ile Asp Gly Asp Tyr Lys Ala Arg Asp Leu Arg Asp
            180                 185                 190

Val Leu Glu Ile Leu Lys Ser Ile Val Arg Asn Ile
        195                 200
```

```
<210> SEQ ID NO 140
<211> LENGTH: 235
<212> TYPE: PRT
<213> ORGANISM: Pyrococcus furiosus

<400> SEQUENCE: 140

Met Ala Ile Thr Leu Lys Leu Leu Gln Met Cys Ser Ser Leu Met Ile
1               5                   10                  15

Ile Ala Phe Asp Phe Asp Gly Thr Leu Val Asp Ser Tyr Ser Cys Ile
            20                  25                  30

Glu Glu Ala Phe Tyr Arg Ala Leu Lys Arg Thr Tyr Pro Trp Leu Pro
        35                  40                  45

Gly Lys Arg Tyr Ile Ala Lys Leu Leu Thr Lys Leu Glu Leu Gln Phe
50                  55                  60

Glu Arg Pro Lys Phe Gly Lys His Gly Arg Lys Ile Lys Pro Pro Met
65                  70                  75                  80

Lys Ile Phe Gln Gly Lys Phe Ala Arg Ala Trp Phe Glu Glu Arg Ala
                85                  90                  95

Lys Leu Thr Lys Pro Leu Asp Gly Ala Arg Glu Val Leu Glu Arg Leu
            100                 105                 110

Lys Glu Asp Gly His Ile Val Ile Ser Phe Ser Ala Glu Asp Phe Ile
        115                 120                 125

Pro Gly Ile Lys Glu Tyr Arg Leu Lys Ile Ser Gly Leu Tyr Asp Leu
    130                 135                 140

Phe Asp Asp Val Ile Ile Phe Gly Arg Asp Ile Thr Ile Cys Glu Ala
145                 150                 155                 160

Phe Ser Ile Val Arg Glu Lys Tyr Gly Tyr Asp Thr Phe Val Trp Val
                165                 170                 175

Asp Asp Lys Pro Trp Arg Phe Ile Gly Arg Gly Asp Glu Asn Thr Glu
            180                 185                 190

Tyr Val Trp Met Tyr Phe Pro Tyr Thr Ala Arg Phe Val Ser Asp Asp
        195                 200                 205

Ile Leu Ala Gln Ile Pro His Leu His Val Ile Tyr Asp Leu Trp Ser
    210                 215                 220

Leu Leu Asp Val Val Lys Asn Leu Lys Ser Arg
225                 230                 235
```

```
<210> SEQ ID NO 141
<211> LENGTH: 211
<212> TYPE: PRT
<213> ORGANISM: Pyrococcus furiosus

<400> SEQUENCE: 141

Met Leu Ile Ile Leu Asp Leu Asp Asp Thr Leu Cys Asn Thr Trp Glu
1               5                   10                  15

Ala Ile Arg Ile Ala Ala Ile Arg Leu Ile Pro Thr Leu Leu Arg Leu
            20                  25                  30
```

Arg Lys Phe Arg Met Phe Ala Tyr Ile Leu Thr Lys Arg Tyr Arg Glu
            35                  40                  45

Leu Glu Glu Ile Arg Glu Leu His Ile Leu Gly Phe Glu Glu Ile Leu
 50                  55                  60

Asp Arg Ile Ile Asn Lys Ile Tyr Lys Asn Leu Glu Asn Glu Val
65                  70                  75                  80

Gln Glu Ile Ala Asn Leu Phe Asp Arg Thr Phe Phe Ala Asn Leu Arg
                85                  90                  95

Leu Tyr Pro Asp Val Ile Pro Phe Leu Glu Lys Val Arg Glu Met Gly
               100                 105                 110

Ala Lys Ile Val Leu Val Thr Asp Ser Ser Ser Trp Gln Arg Arg
               115                 120                 125

Lys Leu Glu Val Leu Gly Ile Lys Asp Tyr Phe Asp Ala Ile Ile Val
   130                 135                 140

Ser Gly Asp Thr Gly His Ser Lys Phe Glu Pro Tyr Asn Phe His Leu
145                 150                 155                 160

Ala Arg Lys Lys Phe Pro Arg Glu Lys Lys Val Tyr Val Ile Gly Asp
               165                 170                 175

Arg Asp Asp Thr Asp Met Lys Gly Gly Lys Ala Ile His Ala Thr Thr
               180                 185                 190

Ile Leu Val Lys Arg Ala Thr Leu Lys Glu Gly Gly Gln Ser Met Gln
   195                 200                 205

Ile Met Leu
   210

<210> SEQ ID NO 142
<211> LENGTH: 238
<212> TYPE: PRT
<213> ORGANISM: Pyrococcus furiosus

<400> SEQUENCE: 142

Met Trp Ile Val Phe Asp Val Asp Gly Val Leu Ile Asp Thr Ser Glu
1               5                   10                  15

Ser Tyr Asp Met Ala Thr Lys Leu Thr Val Glu Tyr Phe Leu Ser His
                20                  25                  30

Leu Gly Ile Lys Lys Glu Val Ser Leu Glu Ile Ile Arg Asp Met Arg
            35                  40                  45

Lys Lys Gly Val Phe Ser Asp Asp Phe Glu Leu Ser Glu Ala Leu Ile
    50                  55                  60

Leu Met Tyr Leu Ser Gly Glu Asp Leu Pro Lys Gly Glu Gly Val Glu
65                  70                  75                  80

Tyr Leu Arg Gln Lys Leu Gly Ile Val Leu Asp Arg Lys Asp Ile Glu
                85                  90                  95

Arg Val Phe Asn Thr Phe Tyr Leu Gly Glu Ile Tyr Pro Asn Ser Ile
               100                 105                 110

Phe Lys Phe Glu Gly Leu Trp Arg Lys Glu Lys Arg Ile Val Asp Ile
           115                 120                 125

Glu Leu Leu Lys Lys Ala Lys Glu Thr Tyr Lys Leu Gly Ile Val Thr
    130                 135                 140

Gly Arg Asp Ser Leu Glu Met Lys Leu Ala Glu Glu Ile Ile Arg Phe
145                 150                 155                 160

Lys Phe Asp Lys Val Val Thr Arg Asp Met Phe Glu Lys Pro Asp Pro
               165                 170                 175

Arg Ala Leu Tyr Glu Val Thr Gln Gly Glu Glu Ala Ile Tyr Ile Gly
               180                 185                 190

Asp Ser Lys Val Asp Glu Leu Val Glu Arg Tyr Arg Arg Thr Phe
    195                 200                 205

Lys Gly Asn Val Thr Tyr Leu Met Val Gly Arg Asp Val Asn Asp Val
210                 215                 220

Asn Glu Ala Leu Lys Lys Ile Leu Phe Gln Ser Tyr Ile Arg
225                 230                 235

<210> SEQ ID NO 143
<211> LENGTH: 219
<212> TYPE: PRT
<213> ORGANISM: Pyrococcus furiosus

<400> SEQUENCE: 143

Met Val Arg Val Ile Phe Phe Asp Ile Asp Gly Thr Leu Leu Thr Glu
1               5                   10                  15

Trp Pro Leu Val Lys Leu Met Leu Pro Gln Val Tyr Glu Met Leu Ala
                20                  25                  30

Lys Lys Leu Gly Val Ser Lys Lys Glu Ala Arg Glu Ile Phe Leu Gly
            35                  40                  45

Glu Ile Glu Lys Arg Lys Gly Thr Tyr Glu Trp Tyr Asp Trp Asn Phe
50                  55                  60

Phe Phe Ser Tyr Phe Asn Leu Pro Leu Arg Tyr Glu Asp Phe Ile Arg
65                  70                  75                  80

Lys Tyr Pro Glu Lys Ile Glu Leu Tyr Pro Gly Val Arg Glu Val Leu
                85                  90                  95

Lys Glu Leu Ser Gly Lys Tyr Lys Leu Gly Ile Thr Ser Gly Pro
            100                 105                 110

His Tyr Gln Leu Leu Lys Leu Lys Val Thr Asp Ile Asp Lys Phe Phe
            115                 120                 125

Asp Val Ile Ile Thr Arg Asp Asp Val Lys Ala Val Lys Pro Ser Pro
130                 135                 140

Lys Ile Phe Leu Ala Gly Leu Glu Arg Val Arg Ala Lys Pro Thr Glu
145                 150                 155                 160

Ser Leu Met Val Gly Asp Ser Leu Glu Asn Asp Ile Leu Gly Ala Lys
                165                 170                 175

Ala Leu Gly Phe Lys Thr Val Trp Ile Asn Arg Gly Arg Glu Lys Gly
            180                 185                 190

Phe Asn Leu Pro Asp Phe Glu Ile Tyr Glu Met Lys Glu Leu Ile Arg
            195                 200                 205

Val Val Glu Val Ala Glu Asn Glu Lys Asp Ile
    210                 215

<210> SEQ ID NO 144
<211> LENGTH: 230
<212> TYPE: PRT
<213> ORGANISM: Pyrococcus furiosus

<400> SEQUENCE: 144

Met Ser Phe Leu Ala Ile Tyr Lys Thr Asp Val Lys Leu Leu Arg Arg
1               5                   10                  15

Asp Pro Met Leu Leu Tyr Ser Val Ile Met Val Phe Val Leu Leu Leu
                20                  25                  30

Ile Val Arg Tyr Phe Lys Asp Lys Val Gly Ile Tyr Tyr Tyr Pro Leu
            35                  40                  45

Ala Leu Leu Thr Met Leu Phe Ile Pro Met Ile Phe Gly Met Leu Pro
50                  55                  60

```
Gly Phe Val Met Ala Asp Glu Lys Glu Lys Thr Ile Gln Ala Leu
 65                  70                  75                  80

Gln Val Ile Pro Ile Ser Ser Glu Ala Phe Leu Ala Tyr Arg Leu Thr
                 85                  90                  95

Trp Ala Ser Ile Val Thr Ala Val Leu Gly Phe Ala Ser Pro Tyr Ile
            100                 105                 110

Leu Asp Ile Glu Leu Ser Arg Lys Gly Leu Ala Met Leu Ile Val Leu
        115                 120                 125

Phe Val Leu Glu Val Trp Ile Tyr Gly Leu Leu Ile Thr Val Phe Ser
130                 135                 140

Glu Ser Arg Met Gln Ala Ile Thr Val Ser Lys Val Leu Gly Trp Phe
145                 150                 155                 160

Leu Met Leu Pro Pro Leu Ile Lys Leu Val Leu Trp Arg Asn Leu
                165                 170                 175

Ser Arg Asp Trp Ser Glu Phe Thr Ala Phe Leu Pro Thr Tyr Trp Leu
            180                 185                 190

Tyr Lys Val Phe Glu Gly Ile Leu Gln Asn Asp Tyr Ser Asp Phe Leu
        195                 200                 205

Val Ala Phe Ile Val His Leu Ile Trp Leu Ile Pro Leu Ile Ala Leu
    210                 215                 220

Phe Lys Arg Arg Val Leu
225                 230

<210> SEQ ID NO 145
<211> LENGTH: 240
<212> TYPE: PRT
<213> ORGANISM: Pyrococcus furiosus

<400> SEQUENCE: 145

Met Arg Arg Ile Lys Val Ile Phe Phe Asp Leu Asp Asp Thr Leu Val
1               5                   10                  15

Asp Thr Ser Lys Leu Ala Glu Val Ala Arg Lys Asn Ala Ile Glu Asn
            20                  25                  30

Met Ile Arg His Gly Met Pro Val Asp Phe Asp Thr Ala Tyr Asn Glu
        35                  40                  45

Leu Leu Glu Leu Ile Lys Glu Tyr Gly Ser Asn Phe Pro Tyr His Phe
    50                  55                  60

Asp Tyr Leu Leu Arg Arg Leu Asp Leu Glu Tyr Asn Pro Lys Trp Val
65                  70                  75                  80

Ala Ala Gly Val Ile Ala Tyr His Asn Thr Lys Phe Thr Tyr Leu Arg
                85                  90                  95

Glu Val Pro Gly Ala Arg Lys Thr Leu Leu Arg Leu Lys Lys Glu Gly
            100                 105                 110

Tyr Met Thr Gly Ile Ile Thr Asp Gly Asn Pro Ile Lys Gln Trp Glu
        115                 120                 125

Lys Ile Leu Arg Leu Glu Leu Asp Asp Phe Phe Glu His Val Met Ile
    130                 135                 140

Ser Asp Phe Glu Gly Val Lys Lys Pro His Pro Lys Ile Phe Lys Lys
145                 150                 155                 160

Ala Leu Lys Ala Phe Asn Val Lys Pro Glu Glu Ala Ile Met Val Gly
                165                 170                 175

Asp Arg Leu Tyr Ser Asp Ile Tyr Gly Ala Lys Asn Val Gly Met Lys
            180                 185                 190

Thr Val Trp Phe Lys Tyr Gly Lys Tyr Ala Glu Leu Asp Leu Glu Tyr
```

195                 200                 205
Lys Glu Tyr Ala Asp Tyr Val Ile Thr Glu Leu Pro Gln Leu Leu Glu
            210                 215                 220
Val Leu Glu Arg Glu Asn Gly Ser Asp Lys Glu Val His Ser Ser Gly
225                 230                 235                 240

<210> SEQ ID NO 146
<211> LENGTH: 218
<212> TYPE: PRT
<213> ORGANISM: Pyrococcus furiosus

<400> SEQUENCE: 146

Met Ile Lys Gly Val Ile Phe Asp Val Asp Glu Thr Leu Val Tyr Tyr
1               5                   10                  15

Glu Gly Tyr Ser Leu Lys Glu Trp Tyr Glu Lys Ile Ala Lys Pro Thr
            20                  25                  30

Met Lys Lys Leu Gly Ile Leu Ile Asp Trp Glu Thr Phe Arg Lys Met
        35                  40                  45

Ala Lys Gly Glu Leu Pro Arg Ser Tyr Val Glu Glu Phe Gly Ile Asp
    50                  55                  60

His Val Thr Phe Trp Lys Ala Leu Asp Lys Ala Asn Arg Arg Tyr Arg
65                  70                  75                  80

Glu Glu Leu Leu Asn Glu Gly Lys Ile Arg Thr Tyr Asp Asp Val Glu
                85                  90                  95

Ala Ile Lys Glu Leu Lys Lys Leu Gly Leu Lys Leu Ala Ala Val Ser
            100                 105                 110

Asn Ala Ser Gln Asp Asn Thr Glu Leu Val Leu Lys Ala Phe Asn Leu
        115                 120                 125

Leu Asp Tyr Phe Asp Val Val Tyr Gly Lys Asp Tyr Thr Tyr Leu Asp
    130                 135                 140

Gly Val Lys Pro Asn Pro Tyr Leu Ile Asn Lys Ala Leu Asn Thr Leu
145                 150                 155                 160

Gly Leu Arg Pro Asp Glu Ala Ile Leu Val Gly Asp Ser Asp Leu Asp
                165                 170                 175

Ile Ile Ala Gly Lys Arg Ala Gly Val Thr Val Val Gln Ile Val Arg
            180                 185                 190

Glu Lys Lys Tyr Glu Gly Ala Asp Tyr Tyr Ile Gln Asn Leu Trp Glu
        195                 200                 205

Leu Val Asp Leu Ile Lys Arg Ser Arg Cys
    210                 215

<210> SEQ ID NO 147
<211> LENGTH: 234
<212> TYPE: PRT
<213> ORGANISM: Pyrococcus furiosus

<400> SEQUENCE: 147

Met Ile Lys Ala Val Phe Phe Asp Phe Ile Gly Thr Leu Leu Ser Gln
1               5                   10                  15

Glu Gly Glu Tyr Glu Thr His Leu Lys Ile Met Glu Glu Val Leu Gly
            20                  25                  30

Glu Asn Lys Lys Ile Ser Pro Glu Leu Leu Arg Glu Tyr Asp Ala
        35                  40                  45

Leu Thr Arg Glu Ala Phe Ser Gln Tyr Ala Gly Lys Pro Phe Lys Pro
    50                  55                  60

Ile Arg Ile Ile Glu Glu Glu Ile Met Lys Lys Leu Ala Glu Lys Tyr

```
                65                  70                  75                  80
Gly Phe Asp Tyr Pro Glu Asn Phe Trp Glu Ile His Leu Lys Ala His
                    85                  90                  95

Gln Arg Tyr Gly Lys Leu Tyr Pro Glu Val Glu Val Leu Asn Glu
                100                 105                 110

Leu Lys Lys Arg Glu Tyr His Val Gly Leu Ile Thr Asp Ser Asp Thr
            115                 120                 125

Ala Tyr Leu Arg Ala His Leu Glu Ala Leu Gly Ile Ala Glu Leu Phe
        130                 135                 140

Asp Ser Ile Thr Thr Ser Glu Glu Ala Gly Phe Phe Lys Pro His Pro
145                 150                 155                 160

Arg Ile Phe Glu Val Ala Leu Lys Lys Ala Gly Val Lys Gly Ser Glu
                165                 170                 175

Ala Val Tyr Val Gly Asp Asn Pro Ile Lys Asp Cys Gly Gly Ala Arg
                180                 185                 190

Gln Leu Asp Met Leu Ser Ile Leu Val Asp Arg Lys Gly Glu Lys Lys
            195                 200                 205

Glu Leu Trp Lys Glu Cys Glu Phe Val Ile Ser Asp Leu Arg Glu Val
        210                 215                 220

Ile Gln Ile Val Glu Glu Leu Asn Gly Gln
225                 230

<210> SEQ ID NO 148
<211> LENGTH: 254
<212> TYPE: PRT
<213> ORGANISM: Pyrococcus furiosus

<400> SEQUENCE: 148

Met Lys Leu Lys Phe Trp Arg Glu Val Ala Ile Asp Ile Ile Ser Asp
1               5                   10                  15

Phe Glu Thr Thr Ile Met Pro Phe Phe Gly Asn Pro Asp Gly Gly Lys
                20                  25                  30

Leu Val Lys Ile Ser Pro Ser Gly Asp Glu Thr Lys Leu Val Asp Lys
            35                  40                  45

Leu Ala Glu Asp Leu Ile Leu Ser Arg Ile Thr Glu Leu Gly Val Asn
        50                  55                  60

Val Val Ser Glu Glu Val Gly Val Ile Asp Asn Glu Ser Glu Tyr Thr
65                  70                  75                  80

Val Ile Val Asp Pro Leu Asp Gly Ser Tyr Asn Phe Ile Ala Gly Ile
                85                  90                  95

Pro Phe Phe Ala Leu Ser Leu Ala Val Phe Lys Lys Asp Lys Pro Ile
                100                 105                 110

Tyr Ala Ile Ile Tyr Glu Pro Met Thr Glu Arg Phe Phe Glu Gly Ile
            115                 120                 125

Pro Gly Glu Gly Ala Phe Leu Asn Gly Lys Arg Ile Lys Val Arg Lys
        130                 135                 140

Thr Pro Asp Glu Lys Pro Ser Ile Ser Phe Tyr Ser Arg Gly Lys Gly
145                 150                 155                 160

His Glu Ile Val Lys His Val Lys Arg Thr Arg Thr Leu Gly Ala Ile
                165                 170                 175

Ala Leu Glu Leu Ala Tyr Leu Ala Met Gly Ala Leu Asp Gly Val Val
            180                 185                 190

Asp Val Arg Lys Tyr Val Arg Pro Thr Asp Ile Ala Ala Gly Thr Ile
        195                 200                 205
```

Ile Ala Lys Glu Ala Gly Ala Leu Ile Lys Asp Ser Ala Gly Lys Asp
            210                 215                 220

Ile Asp Ile Ser Phe Asn Ala Thr Asp Arg Leu Asp Val Ile Ala Val
225                 230                 235                 240

Asn Ser Glu Glu Leu Leu Lys Thr Ile Leu Ser Leu Leu Glu
                245                 250

<210> SEQ ID NO 149
<211> LENGTH: 264
<212> TYPE: PRT
<213> ORGANISM: Pyrodictium occultum

<400> SEQUENCE: 149

Met Arg Gly Arg Gly Arg Gly Arg Leu Leu Gly Ala Val Leu Ala Gly
1               5                   10                  15

Val Ala Ser Ala Gly Glu Leu Ala Arg Leu Leu Pro Gly Arg Val Cys
            20                  25                  30

Gly Val Ala Val Asp Ile Asp Gly Thr Ile Thr Glu Arg Arg Val Ser
        35                  40                  45

Gly Asp Phe Arg Leu Ser Leu Glu Ala Val Glu Ala Leu Arg Arg Leu
    50                  55                  60

Glu Asp Ala Gly Val Arg Val Ile Leu Val Thr Gly Asn Ser Val Met
65                  70                  75                  80

Val Ala Ala Gly Val Ala Arg Tyr Ile Gly Val Arg Gly Pro His Val
                85                  90                  95

Ala Glu Asn Gly Cys Leu Val Tyr Gln Arg Gly Ser Val Val His Ala
            100                 105                 110

Cys Arg Gly Thr Ala Arg Ala Ala Glu Ala Leu Glu Glu Glu Leu
        115                 120                 125

Gly Gly Leu Leu Glu Pro Ser Trp Gln Asn Arg Cys Arg Ile His Asp
    130                 135                 140

Tyr Ala Phe Leu Val Arg Arg Val Gly Pro Glu Glu Ala Trp Arg Met
145                 150                 155                 160

Ala Glu Arg Val Leu Arg Glu Arg Gly Leu Arg Ala Lys Leu Ser His
                165                 170                 175

Ser Gly Tyr Ala Leu His Val Arg Pro Leu Glu Ala Ser Lys Gly Leu
            180                 185                 190

Gly Leu Arg Val Ala Met Arg Met Ala Gly Leu Glu Pro Gly Cys Val
        195                 200                 205

Val Ala Val Gly Asp Ser Ala Met Asp Leu Glu Met Arg Asp Ala Gly
    210                 215                 220

Val Thr Leu Ala Ala Val Gly Asn Ala Asp Pro Arg Leu Arg Glu Gly
225                 230                 235                 240

Ala Asp Leu Ile Leu Pro Gly Glu Ser Gly Gly Val Ala Leu Leu
                245                 250                 255

Ala Arg Ala Ile Leu Glu Ser Leu
            260

<210> SEQ ID NO 150
<211> LENGTH: 235
<212> TYPE: PRT
<213> ORGANISM: Rhodothermus marinus

<400> SEQUENCE: 150

Met His Leu Leu Leu Phe Asp Ile Asp Gly Thr Leu Ile Arg Thr Arg
1               5                   10                  15

Gly Phe Gly Arg Gln Thr Met Glu Ala Ala Leu Ser Glu Trp Leu Gly
            20                  25                  30

Arg Pro Val Thr Thr Glu Gly Val Asp Phe Ala Gly Arg Thr Asp Pro
        35                  40                  45

Ala Ile Leu Leu Asp Ile Leu Lys Ala Ser Gly Leu Pro Glu His Thr
 50                  55                  60

Ala Arg His Leu Leu Pro Glu Ala Leu Glu Val Tyr Ser Arg Ala Met
 65                  70                  75                  80

Ile Arg Arg Leu Arg Pro Glu His Leu Glu Val Leu Pro Gly Val Val
                85                  90                  95

Met Leu Leu Glu Glu Leu Ser Glu Trp Pro Asp Val Tyr Leu Gly Leu
            100                 105                 110

Val Thr Gly Asn Leu Arg Pro Val Ala Phe His Lys Leu Ala Met Ala
        115                 120                 125

Gly Leu Ala Gly Tyr Phe Gly Glu Gly Ala Phe Gly Cys Asp His Ala
130                 135                 140

Asn Arg Asn Glu Leu Pro Pro Leu Ala Ile Glu Arg Ile Arg Glu Ala
145                 150                 155                 160

Thr Gly Tyr Pro Phe Thr Gly Ala Asp Ala Val Ile Ile Gly Asp Thr
                165                 170                 175

Pro His Asp Val Ala Cys Ala Arg His Ala Gly Ala Ser Val Ala Val
            180                 185                 190

Val Cys Thr Gly Gly Tyr Ser Arg Asp Ala Leu Glu Ala Cys Arg Pro
        195                 200                 205

Asp Leu Leu Leu Glu Asp Leu Ser Asp Pro Gln Pro Leu Phe Lys Leu
210                 215                 220

Leu Thr Gln Gln Ala Leu Ser Arg Lys Ala Ser
225                 230                 235

<210> SEQ ID NO 151
<211> LENGTH: 279
<212> TYPE: PRT
<213> ORGANISM: Rhodothermus marinus

<400> SEQUENCE: 151

Met Phe Asp Leu Arg Arg Ala Asp Leu His Leu His Thr Ser Arg Ser
1               5                   10                  15

Asp Gly Arg Leu Ser Pro Ala Glu Leu Val Arg Arg Ala Arg Glu Ala
            20                  25                  30

Gly Leu Tyr Cys Val Ala Ile Thr Asp His Asp Thr Ile Asp Gly Leu
        35                  40                  45

Glu Glu Ala Arg Gln Ala Ala Arg Trp Ala Met Val Val Ile Pro
 50                  55                  60

Gly Val Glu Leu Ser Val Gln Val Glu Glu Glu Val His Leu Leu
65                  70                  75                  80

Gly Tyr Phe Phe Asp Pro Asp His Pro Ala Leu Arg Glu Ala Leu Thr
                85                  90                  95

Ala Tyr Arg Lys Ala Arg Glu Glu Arg Leu Ala Ala Met Leu Ala Arg
            100                 105                 110

Leu Gln Glu Val Gly Val Arg Leu Ser Glu Gln Val Gln Thr Ala
        115                 120                 125

Val Gly His Gly Val Pro Gly Arg Pro His Val Ala Arg Ala Leu Val
130                 135                 140

Ala Ala Gly Tyr Ala Glu Ser Tyr Arg Glu Ala Phe Gln Arg Tyr Leu
145                 150                 155                 160

```
Leu Pro Gly Gly Pro Gly Tyr Val Pro Lys Pro Ala Trp Thr Ala Glu
            165                 170                 175

Glu Ala Val Ala Val Leu His Glu Ala Gly Gly Ile Ala Val Leu Ala
            180                 185                 190

His Pro Gly Glu His Leu Arg Asp Arg Val Phe Arg Ala Leu Leu Gln
            195                 200                 205

Ala Gly Ile Asp Gly Ile Glu Val Ile His Pro Ala His Ser Tyr Tyr
            210                 215                 220

Leu Val Gln His Tyr Arg Gln Val Ala Arg Asp Phe Gly Leu Leu Glu
225                 230                 235                 240

Thr Gly Gly Ser Asp Tyr His Gly His Arg Pro Glu Asp Asp Ala Leu
            245                 250                 255

Leu Gly Ala Cys Thr Ile Pro Tyr Pro Arg Val Glu Arg Leu Arg Ala
            260                 265                 270

Thr Leu Gln Ala Thr Arg Ala
            275

<210> SEQ ID NO 152
<211> LENGTH: 846
<212> TYPE: PRT
<213> ORGANISM: Rhodothermus marinus

<400> SEQUENCE: 152

Met Ser Ser Arg Arg Phe Ala Thr Ser Asp Leu Val Leu Ala Leu Ala
1               5                   10                  15

Gly Val Ile Gly Leu Val Leu Gly Leu Trp Leu Leu Pro Arg Gln His
            20                  25                  30

Pro Asp Ala Ala Leu Gln His Met Leu Ser Ala Glu Ala Ala Arg His
            35                  40                  45

Arg Ala Ala Phe Leu Ala Gln Arg Gly Tyr Arg Val Asp Thr Thr
    50                  55                  60

His Ala Leu Val Val Leu Arg Arg Ala Pro Glu Leu Leu Arg Arg Trp
65                  70                  75                  80

Gln Thr Arg Trp Gly Arg Pro Glu Leu Val Arg Arg Leu Glu Asp Leu
            85                  90                  95

Pro Trp Leu Pro Val Tyr Arg Trp Val Val Tyr Arg Ser Ser Asp Glu
            100                 105                 110

Met Asn Gly Gln Arg Trp Gln Val Val Leu Ala Gly Asp Gly Thr Ile
            115                 120                 125

Trp Gly Phe Arg Gly Pro Glu Thr Pro Gly Asp Pro Ala Ala Arg
            130                 135                 140

Ala Ala Val Gly Ile Ala Ala Glu Ala Phe Asp Pro Leu Ala Ser Trp
145                 150                 155                 160

Gly Lys Leu Ser Gly Ala Pro Asp Ser Ser Glu Thr Pro Glu Arg Pro
            165                 170                 175

Gly Pro Ala Ala Ala Val Ala Leu Ala Arg Tyr His Leu Gln Arg Thr
            180                 185                 190

Ile Gly Ser Val Leu Pro Leu Arg Pro Asp Ser Val Gly Leu Leu Ala
            195                 200                 205

Thr Ser Ser Pro Gln Gln Ala Val Val Arg Phe Arg Gly Leu Ser Pro
            210                 215                 220

Thr Gly Asp Ser Val Thr Val Gln Val Val Thr Ala Ser Gly Gln
225                 230                 235                 240

Leu Arg Ala Leu Glu Ala Thr Trp Gly Thr Leu His Leu Pro Glu Pro
```

```
                    245                 250                 255
Ser Pro Leu Glu Glu Gly Pro Pro Arg Arg Gly Glu Arg Gly Phe Thr
                260                 265                 270

Val His Glu Val Gln Asp Leu Leu Ser Val Leu Leu Phe Ala Gly Leu
            275                 280                 285

Gly Ile Trp Leu Leu Thr Val Phe Leu Arg Arg Leu His Arg Arg Leu
        290                 295                 300

Leu Asp Thr Gln Gly Pro Leu Arg Asp Ala Val Leu Gly Gly Leu Ala
305                 310                 315                 320

Phe Thr Val Ala Thr Leu Gly Gly Ala Leu Pro Gly Ile Leu Gln Val
                325                 330                 335

Pro Asp Leu Trp Leu Arg Leu Ile Leu Leu Met Ser Thr Leu Val
            340                 345                 350

Val Gly Val Phe Gly Ala Ala Ser Val Phe Leu Leu Ala Gly Thr Ser
            355                 360                 365

Asp Ala Leu Ala Arg Asp Arg Trp Pro Glu Lys Leu Ala Val Leu Thr
        370                 375                 380

Leu Leu Arg Asn Gly Gln Val Arg Asn Val Val Gly Ala Ser Leu
385                 390                 395                 400

Leu Arg Gly Leu Ala Leu Gly Gly Leu Leu Leu Gly Met Thr Val Gly
                405                 410                 415

Leu Leu Gly Leu Trp Pro Arg Ala Ala Leu Arg Leu Asp Ala Gly Ala
            420                 425                 430

Trp Thr Val Pro Trp Pro Gly Met Gln Ala Ala Val Trp Leu Gly Phe
        435                 440                 445

Ala Val Trp Val Gly Met Leu Leu Val Tyr Leu Leu Leu Ala Val Met
450                 455                 460

Ala Arg Leu Pro Trp Arg Asp Gly Gly Arg Val Val Gly Thr Leu Thr
465                 470                 475                 480

Leu Leu Leu Leu Leu Ala Gly Val Ser Ala Ile Asp Leu Glu Gln Val
                485                 490                 495

Gly Phe Glu Leu Leu Val His Ala Leu Trp Gly Val Val Leu Ala Trp
            500                 505                 510

Ala Cys Trp Arg Tyr Glu Pro Ala Cys Ser Gly Ile Gly Ala Met Thr
        515                 520                 525

Ala Trp Ala Leu Trp Arg Ser Ala Ser Gly Trp Met Ala Pro Asp Gly
    530                 535                 540

Pro Phe Gly Pro Asp Gly Trp Ile Val Leu Ala Met Val Gly Thr Gly
545                 550                 555                 560

Leu Val Ile Gly Phe Val Gly Ile Arg Ser Arg Arg Ser Ala Ala Glu
                565                 570                 575

Leu Pro Arg Tyr Val Pro Ala Tyr Leu Gln Glu Leu Ala Arg Gln Glu
            580                 585                 590

Arg Leu Glu Arg Glu Leu Glu Ile Ala Arg Gln Ala Gln Ala Ser Leu
        595                 600                 605

Leu Pro Arg Thr Leu Pro Glu Val Pro Gly Ala Ala Met Ala Ala Leu
    610                 615                 620

Cys Arg Pro Ala Tyr Glu Val Gly Gly Asp Tyr Tyr Asp Val Phe Ala
625                 630                 635                 640

Leu Pro Asp Gly Arg Leu Ala Val Val Gly Asp Val Ser Gly Lys
                645                 650                 655

Gly Ile Gln Ala Ala Phe Phe Met Thr Leu Ile Lys Gly His Val Arg
            660                 665                 670
```

-continued

Ala Leu Ser Leu Ser Thr Arg Asp Pro Ala Asp Val Leu Arg His Leu
            675                 680                 685

Asn Arg Leu Phe Arg Glu Gln Ala Pro Arg Gly Leu Phe Val Thr Met
690                 695                 700

Ile Tyr Gly Val Leu Asp Pro Thr Thr Arg Thr Phe Thr Leu Ala Arg
705                 710                 715                 720

Ala Gly His Pro Pro Val Leu His Tyr Arg Ala Cys Thr Gln Gln Val
                725                 730                 735

Gln Cys Leu Arg Pro Ser Gly Met Gly Ile Gly Leu Ala Asp Ala Glu
            740                 745                 750

Leu Phe Asp Lys Ala Leu Glu Asn Cys Val Leu Arg Leu Glu Ala Gly
            755                 760                 765

Asp Arg Val Leu Leu Tyr Thr Asp Gly Ile Thr Glu Met Ala Gly Pro
770                 775                 780

Arg Gly Glu Arg Trp Gly Leu Glu Arg Leu Gln Gln Trp Leu Arg Glu
785                 790                 795                 800

Ser Ser Arg Arg Gly Tyr Ala Pro Glu Gln Ala Leu Gly Ala Leu Glu
                805                 810                 815

Glu Gln Leu Arg Ala Phe Ala Gly Thr Thr Glu Leu Ala Asp Asp Leu
            820                 825                 830

Thr Ala Ile Leu Leu Glu Ala Lys Gln Asp Gly Tyr Ala Asn
835                 840                 845

<210> SEQ ID NO 153
<211> LENGTH: 534
<212> TYPE: PRT
<213> ORGANISM: Rhodothermus marinus

<400> SEQUENCE: 153

Met Pro Ala Val Val Ala Glu Leu Glu Gln Ala Thr Arg Ser Pro Val
1               5                   10                  15

Arg Met Cys Val Ile Asp Leu Gly Thr Asn Ser Phe His Ala Val Ile
                20                  25                  30

Val Asp Ala Leu Pro Gly Thr Phe Arg Val Val Asp Arg Phe Lys Glu
            35                  40                  45

Met Val Arg Leu Gly Glu Gly Leu Gln Gly Gln Arg Leu Ser Glu
    50                  55                  60

Ala Ala Met Gln Arg Ala Ile Arg Ala Leu Arg Arg Ile Arg Gln Leu
65                  70                  75                  80

Ala Glu Gly Trp Gly Ala Thr Glu Phe Leu Ala Cys Ala Thr Ser Ala
                85                  90                  95

Ile Arg Glu Ala Glu Asn Gly Gly Glu Leu Leu Gln Arg Ile Arg Ser
            100                 105                 110

Glu Val Gly Leu His Val Arg Val Ile Asp Gly Leu Gln Glu Ala Arg
        115                 120                 125

Leu Ile Tyr Lys Gly Val Arg Arg Ala Val Pro Met Pro Glu Pro Val
    130                 135                 140

Leu Ile Met Asp Val Gly Gly Gly Ser Val Glu Phe Ile Val Gly Thr
145                 150                 155                 160

Ser Gln Gln Pro Leu His Leu Phe Ser Leu Lys Leu Gly Ala Ala Arg
                165                 170                 175

Met Thr Arg Arg Phe Val Arg His Asp Pro Ala Thr Arg Glu Glu Leu
            180                 185                 190

Lys Ala Leu Arg Ala Phe Tyr Arg Glu Gln Leu His Pro Val Phe Glu 195                 200                 205
Ala Ala Arg Ala His Gly Val Arg Glu Val Val Gly Ser Ser Gly Ala
    210                 215                 220

Met Glu Asn Leu Ala Ser Val Cys Ala Arg Met Arg Gly Glu Val Ala
225                 230                 235                 240

Arg Ser Ile Tyr Glu Gln Pro Phe Pro Ala Glu Asp Phe Arg Arg Val
                245                 250                 255

Ala Arg Arg Ile Met Arg Leu Ser Arg Glu Gln Arg Arg Arg Leu Arg
            260                 265                 270

Gly Ile Asp Pro Lys Arg Val Asp Gln Ile Val Ala Ala Ala Leu
            275                 280                 285

Ile Asp Val Val Leu Lys Asp Leu Ala Ile Glu Arg Val Arg Ile Ser
    290                 295                 300

Pro His Ala Leu Arg Glu Gly Leu Val Val Asp Phe Val Glu Arg Asn
305                 310                 315                 320

Ala Pro Leu Leu Ala Arg Leu Thr Ala Phe Ala Asp Val Arg Arg Arg
                325                 330                 335

Ser Ile Tyr Glu Met Gly Trp Arg Phe Asp Trp Glu Tyr Arg His Ala
            340                 345                 350

Gln Gln Val Ala Ala Leu Ala Leu Gln Leu Phe Asp Ala Thr Gln Ser
            355                 360                 365

Leu His Gly Leu His Val Asp Arg Glu Leu Leu Glu Tyr Ala Ala
    370                 375                 380

Leu Leu His Asp Ile Gly Tyr His Ile Ser His Arg Ser His His Lys
385                 390                 395                 400

His Gly Leu Tyr Leu Ile Lys His Ala Asp Leu Arg Gly Phe Thr Ser
                405                 410                 415

Glu Glu Ile Ala Val Leu Ala Asn Val Val Arg Tyr His Arg Gly Ser
            420                 425                 430

Leu Pro Lys Pro Thr His Ala Asp Tyr Met Ala Leu Ser Glu Glu Asn
            435                 440                 445

Arg Val Arg Val Cys Lys Leu Ala Ala Leu Leu Arg Leu Ala Glu Gly
    450                 455                 460

Leu Asp Arg Ser His Asn Gln Asn Val Arg Thr Leu His Val Arg Leu
465                 470                 475                 480

Glu Ser Asp Arg Leu Val Leu His Leu Glu Thr Arg Gly Asp Pro Glu
                485                 490                 495

Leu Glu Val Trp Gly Val Arg Arg Ser Ala Glu Leu Phe Glu Gln Thr
            500                 505                 510

Phe Gly Arg Thr Val Glu Val Ser Ala Thr Ala Glu Pro Pro Leu Leu
            515                 520                 525

Glu Glu Thr Ala Gly Ala
    530

<210> SEQ ID NO 154
<211> LENGTH: 336
<212> TYPE: PRT
<213> ORGANISM: Rhodothermus marinus

<400> SEQUENCE: 154

Met Thr Thr Asn His Ile Gln Glu Leu Leu Ser Lys Leu Asn Glu Leu
1               5                   10                  15

Arg Ala Val Phe Ile Leu Gly Gln Arg Ala Ile Pro Phe Ile Glu Glu
                20                  25                  30

```
Val Val Tyr Phe Leu Arg Glu Ile Ser Pro Leu Leu Ser Glu Val Asn
         35                  40                  45

Asp Ser Leu Ala Glu Ser Thr Arg Lys Met Pro Arg Ala Ser Ser Gln
 50                  55                  60

Leu Lys Ser Val Thr Gln Ala Thr Glu Met Ala Thr Thr Glu Ile Leu
 65                  70                  75                  80

Asp Leu Ile Asp Val Leu Asn Asp Leu Asp Thr Phe Arg Lys Ser
                 85                  90                  95

Trp Ala Ala Ala Pro Glu Ala Leu Gln Thr Leu Gln Ser Gln Glu Glu
                100                 105                 110

Gln Leu Trp Gln Pro Leu Pro Glu Ser Trp Asn Glu Arg Leu Gln Thr
            115                 120                 125

Leu Leu Glu Glu Arg Arg Gln His Tyr Ala Thr Leu Gln Ala Met Leu
130                 135                 140

Glu Ser Gln Gln Gln Leu Val Asp Ser Leu Arg Asp Arg Met Asn Arg
145                 150                 155                 160

Ile Met Met Ala Leu Gln Val Gln Asp Ile Thr Ala Gly Gln Leu Ala
                165                 170                 175

Ala Val Asn His Leu Ile Glu Ser Val Arg Tyr Arg Met Ala Gln Leu
                180                 185                 190

Ile Arg Arg Leu Gly Ser Glu Val Leu Asp Asp Leu Glu Leu Pro Arg
            195                 200                 205

Gln Leu Phe Ala Glu Gly Thr Phe Asp Pro His Ala Arg Tyr Asp Arg
210                 215                 220

Asp Gly Arg Arg Gln Gln Gln Val Asp Ala Leu Val Asp Ala Leu Gln
225                 230                 235                 240

His Asn Ala Ser Leu Pro Glu Asp Gly Glu Ser Thr Gly Pro Ala Ser
                245                 250                 255

Gln Asp Glu Ile Asp Ala Leu Phe Ser Gly Asn Ser Thr Pro Ala Ser
                260                 265                 270

Gln Asp Glu Ile Asp Ser Leu Phe Ser Ser Gly Thr Pro Thr Ser Gln
            275                 280                 285

Asp Glu Ile Asp Ala Leu Phe Gly Gly Gly Ser Thr Pro Ala Ser Gln
290                 295                 300

Asp Glu Ile Asp Ala Leu Phe Gly Gly Gly Ser Thr Pro Ala Ser Gln
305                 310                 315                 320

Asp Glu Ile Asp Ala Leu Phe Asn Pro Lys Arg Asn Asp Ser Asn Ser
                325                 330                 335
```

```
<210> SEQ ID NO 155
<211> LENGTH: 231
<212> TYPE: PRT
<213> ORGANISM: Rhodothermus marinus

<400> SEQUENCE: 155
```

```
Met Ser Leu Leu Phe Thr Glu Glu Leu Thr Arg Val Arg Glu Ala
 1               5                  10                  15

Val Ala Ala Ala Glu Gln Arg Thr Ala Gly Glu Ile Val Pro Val Ile
                 20                  25                  30

Val Pro Arg Ser Gly Ala Tyr Pro Glu Ala Val Trp Lys Gly Ala Val
             35                  40                  45

Leu Leu Met Leu Pro Val Leu Ala Val Ala Leu Leu Phe Asp Tyr Ile
 50                  55                  60

Tyr Gln Gly Trp Gly Leu Thr Leu Leu His Thr Gly Trp Gly Val Ala
 65                  70                  75                  80
```

```
Leu Leu Thr Ala Leu Ala Gly Leu Val Gly Gly Leu Gly Ala Tyr
                85                  90                  95

Val Ala Pro Val Gln Arg Trp Leu Val Gly Glu Ala Arg Met Ala Glu
            100                 105                 110

Gln Val His Leu Arg Ala Leu Gln Ala Phe Leu Glu Glu Val Phe
        115                 120                 125

Asn Thr Arg Asp Arg Thr Gly Ile Leu Ile Phe Val Ser Leu Phe Glu
    130                 135                 140

His Trp Val Glu Val Ile Gly Asp Ala Gly Ile Asn Gln Arg Val Gly
145                 150                 155                 160

Pro Glu Ala Trp Ala Glu Val Val Asp Arg Ile Arg Lys Gly Ile Arg
                165                 170                 175

Glu Gly Arg Pro Val Asp Gly Leu Val Ala Ala Ile Glu Gln Cys Gly
            180                 185                 190

Gln Leu Leu Ala Thr His Gly Val Ala Leu Arg Pro Asp Asp Thr Asn
        195                 200                 205

Glu Leu Ala Asp Thr Leu Arg Val Arg Gly Ala Pro Ser Lys Lys Arg
    210                 215                 220

Arg Gly Gly Arg Arg Lys Arg
225                 230

<210> SEQ ID NO 156
<211> LENGTH: 221
<212> TYPE: PRT
<213> ORGANISM: Rhodothermus marinus

<400> SEQUENCE: 156

Met Pro Ala Thr Thr Leu Tyr Phe Val Arg His Gly Glu Thr Asp Tyr
1               5                   10                  15

Asn Arg Asn Gly Ile Val Gln Gly Arg Gly Val Asp Ala Pro Leu Asn
                20                  25                  30

Glu Arg Gly Arg Arg Gln Ala Glu Ala Leu Ala Arg Arg Phe Ala Ala
            35                  40                  45

Val Pro Leu Asp Ala Ile Tyr Ala Ser Pro Leu Arg Arg Ala Leu Glu
        50                  55                  60

Thr Ala Glu Ala Val Arg Arg Tyr His Pro Glu Val Pro Phe Tyr Gln
65                  70                  75                  80

Leu Ala Asp Leu Glu Glu Met Asp Trp Gly Asp Leu Glu Gly Lys Pro
                85                  90                  95

Tyr Ala Pro Pro Tyr Asp Ala Lys Ile Arg Ala Ile Tyr Glu Arg Trp
            100                 105                 110

Arg Ala Gly Asp Tyr Asp Tyr Pro Val Pro Gly Gly Glu Ser Ile Leu
        115                 120                 125

Asp Val Gln Arg Arg Ala Leu Arg Ala Leu Glu Thr Ile Leu Ser Arg
    130                 135                 140

His Glu Gly Glu Thr Val Leu Ile Val Ala His Gly Arg Phe Leu Arg
145                 150                 155                 160

Ile Leu Leu Ala Ser Val Leu Ser Glu Tyr Gly Leu Ala Arg Met Glu
                165                 170                 175

Ala Leu Pro His Thr Asn Thr Ala Val Asn His Leu Val Tyr Glu Asn
            180                 185                 190

Gly Arg Phe Arg Ala Leu Arg Leu Asn Cys Thr Ala His Leu Glu Glu
        195                 200                 205

Ala Ala Val Asp Asp Gly Leu Pro Thr Glu Val Ala Ala
    210                 215                 220
```

<210> SEQ ID NO 157
<211> LENGTH: 162
<212> TYPE: PRT
<213> ORGANISM: Rhodothermus marinus

<400> SEQUENCE: 157

Met Arg Leu Cys Leu Leu Arg His Ala Glu Ala Tyr Pro Ala Ala Pro
1               5                   10                  15

Gly Arg Pro Asp Ala Glu Arg Ser Leu Thr Glu Val Gly Gln Gln Val
            20                  25                  30

Ala Arg Gln Met Gly Glu Ala Leu Arg Arg Leu Arg Leu Ala Pro Gly
        35                  40                  45

Ala Val Tyr Thr Ser Pro Tyr Arg Arg Ala Val Gln Thr Ala Gln Ala
    50                  55                  60

Val Ala Glu Ala Leu Gly Val Pro Val Val Glu Asp Arg Leu Leu Ala
65                  70                  75                  80

Pro Gly Cys Gly Pro Ala Glu Leu Glu Thr Leu Ile Gln Ala Tyr Ala
                85                  90                  95

Pro Gly Glu Thr Val Leu Val Val Gly His Gln Pro Asp Phe Gly Glu
            100                 105                 110

Leu Val Arg Trp Leu Thr Gly Ala Thr Ile Arg Leu Pro Ala Gly Gly
        115                 120                 125

Leu Ala Val Val Glu Thr Pro Ala Leu Arg Glu Arg Ala Gly Thr Leu
    130                 135                 140

His Gly Leu Tyr Asp Pro Ala Trp Leu Ala Ala Val Met Thr Gly Arg
145                 150                 155                 160

Thr Gly

<210> SEQ ID NO 158
<211> LENGTH: 249
<212> TYPE: PRT
<213> ORGANISM: Rhodothermus marinus

<400> SEQUENCE: 158

Met Asn Val Glu Val Phe Leu Thr Gly Ser His Val Thr Glu Glu Asp
1               5                   10                  15

Val Glu Gly Arg Thr Val Val Ile Asp Val Leu Arg Ala Ser Ser
            20                  25                  30

Thr Ile Ile Thr Ala Leu Ala Asn Gly Ala Arg Ala Val Ile Pro Val
        35                  40                  45

Ala Asp Met Asp Gln Ala Gly Lys Ile Ala Met Asn Leu Asp Pro Ser
    50                  55                  60

Thr Tyr Leu Leu Gly Gly Glu Arg Asp Gly Asp Arg Ile Asp Gly Tyr
65                  70                  75                  80

His Leu Gly Asn Ser Pro Leu Glu Tyr Thr Pro Asp Val Val Glu Gly
                85                  90                  95

Lys Thr Ile Ile Leu Asn Thr Thr Asn Gly Thr Arg Thr Ile Trp Asn
            100                 105                 110

Ala Arg Asn Ala Glu His Leu Ile Val Gly Gly Phe Leu Asn Ala Asn
        115                 120                 125

Arg Val Val Gln Phe Val Arg Glu Ala Gly Leu Asp Val Thr Ile Ile
    130                 135                 140

Cys Ala Gly Arg Asn Asn Arg Val Ala Leu Asp Asp Ala Leu Cys Ala
145                 150                 155                 160

```
Gly Leu Leu Leu His Arg Leu Trp Glu Gly Arg Glu Pro Glu Tyr Val
                165                 170                 175

Ser Asp Ala Ala His Ile Ala Leu Thr Gln Tyr Leu His Asp Arg Asp
            180                 185                 190

Arg Leu Ala Asp Ala Leu Arg His Ser Asn His Ala Arg Trp Leu Ile
        195                 200                 205

Glu Lys Gly Tyr Gly Ala Asp Val Glu Tyr Cys Leu Gln Leu Asp Ala
    210                 215                 220

Leu Pro Val Leu Pro Tyr Tyr Arg Glu Asn Arg Leu Val Leu Tyr Arg
225                 230                 235                 240

Glu Arg Gln Pro Ser Glu Ser Val Gly
                245
```

<210> SEQ ID NO 159
<211> LENGTH: 345
<212> TYPE: PRT
<213> ORGANISM: Rhodothermus marinus

<400> SEQUENCE: 159

```
Met Glu Thr Leu His Thr Arg Gly Arg Lys Val Val Glu Glu Phe Ile
1               5                   10                  15

Thr Leu Glu Gln Phe Ile Ile Asp Gln Gln Glu Arg Phe Pro His Ser
            20                  25                  30

Thr Gly Ala Phe Ser Arg Leu Leu Arg Asp Ile Ser Val Ala Ala Lys
        35                  40                  45

Ile Val Asn Arg Asp Ile Arg Arg Ala Gly Leu Val Asp Ile Phe Gly
    50                  55                  60

Thr Thr Gly Lys Val Asn Ile His Gly Glu Val Gln Gln Lys Leu Asp
65                  70                  75                  80

Ala Leu Ala His Glu Glu Phe Val Arg Ala Leu Arg Arg Gly Gly Glu
                85                  90                  95

Cys Cys Leu Ile Gly Ser Glu Glu His Ala Glu Ala Ile Pro Leu Ser
            100                 105                 110

Ala Asn Gly Glu Gly Asp Gly Arg Tyr Ile Val Leu Leu Asp Pro Leu
        115                 120                 125

Asp Gly Ser Ser Asn Val Asp Val Asn Val Ser Val Gly Thr Ile Phe
    130                 135                 140

Ser Ile Tyr Arg Leu Pro Asp Glu Tyr Glu Thr Pro Thr Leu Glu Ala
145                 150                 155                 160

Ala Leu Gln Pro Gly Ser Lys Gln Val Ala Ala Gly Tyr Ile Val Tyr
                165                 170                 175

Gly Ser Ser Thr Met Leu Val Tyr Thr Thr Gly Asn Gly Val Asn Gly
            180                 185                 190

Phe Thr Leu Asp Pro Ser Ile Gly Glu Phe Ile Leu Ser His Pro Asn
        195                 200                 205

Ile Arg Ile Pro Lys Thr Gly Ser Ile Tyr Ser Ile Asn Glu Gly Asn
    210                 215                 220

Phe Asn Ser Phe Glu Glu Gly Leu Lys Arg Phe Ile Arg Trp Ala Gln
225                 230                 235                 240

Glu Glu Asp Lys Ala Thr Gly Arg Pro Phe Ser Thr Arg Tyr Ile Gly
                245                 250                 255

Ser Phe Val Ser Asp Phe His Arg Asn Leu Leu Lys Gly Gly Ile Tyr
            260                 265                 270

Met Tyr Pro Ala Thr Lys Lys Asn Pro Glu Gly Lys Leu Arg Leu Met
```

```
                275                 280                 285
Tyr Glu Ala Asn Pro Met Ala Phe Ile Val Glu Gln Ala Gly Gly Arg
    290                 295                 300

Ala Ser Asp Gly His Arg Arg Ile Leu Asp Ile Val Pro Glu Lys Leu
305                 310                 315                 320

His Gln Arg Thr Pro Leu Phe Ile Gly Ser Glu Leu Val Arg Thr
                325                 330                 335

Val Glu Glu Phe Leu Gln Gly Lys Arg
            340                 345

<210> SEQ ID NO 160
<211> LENGTH: 197
<212> TYPE: PRT
<213> ORGANISM: Rhodothermus marinus

<400> SEQUENCE: 160

Met Lys Arg Arg Gly Leu Trp Ser Gly Thr Val Leu Ala Val Leu Ile
1               5                   10                  15

Thr Ala Ser Ala Gln Ala Gln Thr Ala Cys Asp Arg Pro Ala Leu Glu
                20                  25                  30

Leu Arg Leu Leu Cys Thr Val Tyr Arg Trp Asp Gly Pro Val Ala Ser
            35                  40                  45

Ala Tyr Phe Glu Thr Ile Asp Ala Thr Ala Tyr Pro Met Phe Ala Gly
        50                  55                  60

Leu Thr Ala Met Ala Trp Gly Val Leu Ala Gly Arg Leu Glu Arg
65                  70                  75                  80

Pro Ala Ala Glu Arg Val Thr Leu Ala Thr Ala Thr Thr Val Leu
                85                  90                  95

Val Phe Gly Leu Lys Ala Leu Ala Arg Arg Asn Arg Pro Phe Asp Ala
            100                 105                 110

Trp Asp Asp Ile Ala Pro Arg Gly Asp Pro Pro Thr Ser His Ala Phe
        115                 120                 125

Pro Ser Gly His Ala Ala Leu Ala Phe Thr Leu Ala Thr Ala Trp Gly
    130                 135                 140

Leu Glu Val Pro Arg Ile Tyr Val Ile Val Pro Ala Tyr Val Trp Ala
145                 150                 155                 160

Thr Ser Val Ala Val Gly Arg Val Trp Lys Gly Val His Tyr Pro Thr
                165                 170                 175

Asp Val Leu Ala Gly Ala Val Leu Gly Ala Gly Val Ala Trp Thr Val
            180                 185                 190

His Arg Ile Trp Arg
        195

<210> SEQ ID NO 161
<211> LENGTH: 269
<212> TYPE: PRT
<213> ORGANISM: Rhodothermus marinus

<400> SEQUENCE: 161

Met Ser Trp Trp Glu Ala Leu Ile Leu Gly Leu Leu Gln Gly Leu Thr
1               5                   10                  15

Glu Phe Leu Pro Val Ser Ser Gly His Leu Val Leu Gly Gln Tyr
                20                  25                  30

Val Leu Gly Leu Asn Pro Gly Gly Val Thr Phe Glu Val Phe Val His
            35                  40                  45

Phe Gly Thr Val Leu Ser Ile Leu Thr Val Tyr Arg Lys Arg Val Gly
```

```
            50                  55                  60
Ala Ile Val Gly Glu Val Trp Thr Ala Leu Pro Arg Pro Ala Glu Trp
 65                  70                  75                  80

Pro Met Arg Tyr Arg Glu Arg Asp Pro Phe Arg Leu Ala Val Trp Ile
                 85                  90                  95

Leu Ile Thr Met Ile Pro Thr Gly Leu Val Tyr Val Leu Leu Gly Asp
                100                 105                 110

Trp Ile Glu Gln Thr Phe Glu His Pro Arg Phe Ala Ala Gly Met Leu
                115                 120                 125

Val Val Thr Gly Val Leu Leu Ile Leu Thr Arg Leu Arg Arg His Pro
                130                 135                 140

Asp Gly Asp Leu Ser Pro Leu Lys Ala Phe Val Val Gly Val Ala Gln
145                 150                 155                 160

Ser Ala Ala Met Leu Pro Gly Ile Ser Arg Ser Gly Ser Thr Ile Cys
                165                 170                 175

Ala Ala Ile Tyr Gln Asn Val Arg Pro Glu Arg Ala Ala Asp Phe Ser
                180                 185                 190

Phe Leu Met Leu Leu Pro Val Val Leu Gly Ala Thr Leu Leu Lys Gly
                195                 200                 205

Ile Glu Leu Leu Asn Ser Pro Glu Ser Ile Gly Met Gly Pro Leu Val
                210                 215                 220

Leu Gly Thr Val Ala Ala Tyr Val Ser Gly Val Ala Ala Ile Arg Met
225                 230                 235                 240

Leu Leu Gln Val Val Arg Arg Gly Arg Leu Glu Tyr Phe Ala Tyr Tyr
                245                 250                 255

Cys Phe Leu Val Gly Leu Leu Gly Leu Trp Leu Ile Arg
                260                 265

<210> SEQ ID NO 162
<211> LENGTH: 366
<212> TYPE: PRT
<213> ORGANISM: Rhodothermus marinus

<400> SEQUENCE: 162

Met Ser Thr Arg Arg Ala Val Leu Asn Cys Phe Arg Arg His Gln Arg
 1               5                  10                  15

Phe Val Leu Thr Thr His Ile Lys Pro Asp Gly Asp Ala Leu Gly Ser
                20                  25                  30

Gln Leu Ala Leu Gly Arg Leu Leu Gln Lys Met Gly His Asp Val Tyr
                35                  40                  45

Leu Ile Asn Ser Asp Pro Pro Ser Asn Leu Thr Trp Ile Pro Gly
 50                  55                  60

Ile Glu Gln Val Glu Val Phe Asn Gly Ala Leu Ala Gln Arg Glu Arg
 65                  70                  75                  80

Ile Asp Gln Ala Asp Val Ile Cys Val Leu Asp Thr Asn Ala Leu Asp
                85                  90                  95

Arg Leu Gly Asp Leu Ala Pro Ala Val Glu Ala Ser Arg Ala Arg Lys
                100                 105                 110

Leu Leu Ile Asp His His Thr Ser Pro Glu Asp Trp Phe Asp Leu Gln
                115                 120                 125

Tyr Val Arg Asp Thr Ala Ser Ser Thr Gly Glu Leu Val Tyr Glu Leu
                130                 135                 140

Val Cys Ala Val Asp Pro Asn Leu Ile Asp His Glu Leu Ala Thr Ala
145                 150                 155                 160
```

```
Leu Tyr Val Ala Ile Met Thr Asp Thr Gly Ser Phe Arg Phe Asn Thr
                165                 170                 175

Val Thr Pro Thr Val His Arg Ile Val Ala Asp Leu Leu Glu Arg Gly
            180                 185                 190

Gly Leu Ser Thr Glu Ala Ile His Ser Ala Ile Phe Asp Thr Arg Thr
            195                 200                 205

Pro Glu Ser Met Arg Leu Leu Gly Leu Ala Leu Arg Asn Leu Gln Leu
        210                 215                 220

Arg Tyr Asp Gly Arg Val Ala Tyr Met Val Leu Ser Arg Arg Met Phe
225                 230                 235                 240

Asn Glu Thr Gly Ala Ser Thr Glu Asp Thr Glu Gly Phe Ile Asn His
                245                 250                 255

Leu Leu Ser Ile Arg Gly Val Arg Val Ala Leu Leu Phe Thr Glu Ile
                260                 265                 270

Glu Lys Gly Val Lys Ile Ser Phe Arg Ser Lys Gly Asp Tyr His Val
            275                 280                 285

Asn Glu Trp Ala Arg Ala Phe Gly Gly Gly His Arg Asn Ala Ala
        290                 295                 300

Gly Ala Phe Val Glu Asn Ala Ala Leu Asp Ala Leu Val Asp Ala Val
305                 310                 315                 320

Leu Ala Ala Ala Pro Arg Tyr Leu Pro Gln Leu Glu Ala Ser Ser Ala
                325                 330                 335

Gly Asn Ala Ser Gly Thr Leu Ser Ser Glu Asp Ala Ser Tyr Leu Ser
                340                 345                 350

Ala Leu Leu His Gln Lys Ser Gln Ala Ser Ser Thr Ala Ser
            355                 360                 365

<210> SEQ ID NO 163
<211> LENGTH: 174
<212> TYPE: PRT
<213> ORGANISM: Rhodothermus marinus

<400> SEQUENCE: 163

Met Ser Gln Thr Asn His Gln Pro Ile Arg Val Leu Phe Val Cys Leu
1               5                   10                  15

Gly Asn Ile Cys Arg Ser Pro Leu Ala Glu Gly Val Phe Arg Lys Leu
            20                  25                  30

Val Asp Glu Ala Gly Leu Thr Ala His Phe Glu Ile Asp Ser Ala Gly
        35                  40                  45

Thr Gly Pro Trp His Val Gly Glu Pro Ala Asp Arg Arg Met Gln Arg
    50                  55                  60

Thr Ala Arg Arg His Gly Val Asp Leu Ser Gly His Val Ala Arg Gln
65                  70                  75                  80

Leu Gly Arg Glu Asp Leu Ala Arg Tyr Asp His Ile Tyr Val Met Asp
                85                  90                  95

Arg Glu Asn Leu Glu Asp Val Leu Arg Leu Asp Arg Asp Gly Arg Phe
            100                 105                 110

Arg His Lys Val Glu Leu Phe Arg Thr Phe Asp Pro Glu Pro Gly Asp
        115                 120                 125

Gly Glu Val Pro Asp Pro Tyr Tyr Gly Gly Arg Gly Phe Glu Glu
    130                 135                 140

Val Tyr Gln Ile Val Glu Arg Thr Ala Arg Arg Leu Leu Glu His Leu
145                 150                 155                 160

Val Ser Leu Tyr Lys Leu Lys Glu Thr Ala Asp Leu Ser Arg
                165                 170
```

<210> SEQ ID NO 164
<211> LENGTH: 272
<212> TYPE: PRT
<213> ORGANISM: Rhodothermus marinus

<400> SEQUENCE: 164

Met Met Asp Ala Tyr Thr Leu Tyr Glu Glu Ala Arg Glu Val Ala Ala
1               5                   10                  15

Arg Leu Ala Arg Asp Ala Gly Gln Ile Ala Arg Tyr Tyr Ala Gly Arg
                20                  25                  30

Val Thr Val Arg Glu Lys Gly Tyr Asn Glu Leu Val Thr Gln Ala Asp
            35                  40                  45

Glu Glu Val Gln Arg Phe Leu Ile Glu Gln Ile His Arg His Phe Pro
        50                  55                  60

Glu His Ala Ile Leu Ala Glu Glu Asn Leu Ser Asp Met Gln Asp Gly
65                  70                  75                  80

Arg Glu Gly Ala Ser Phe Arg Trp Ile Ile Asp Pro Ile Asp Gly Thr
                85                  90                  95

Thr Asn Phe Thr His Gly Val Pro Pro Tyr Gly Ile Ser Leu Ala Leu
                100                 105                 110

Gln His Glu Gly Arg Thr Val Val Gly Val Val Tyr Asp Val Pro His
            115                 120                 125

Asp Glu Leu Phe Thr Ala Val Arg Gly Gly Gly Leu Tyr Val Asn Gly
        130                 135                 140

Val Arg Ala Arg Val Ser Gln Thr Glu Thr Leu Arg Glu Ala Leu Ile
145                 150                 155                 160

Thr Thr Gly Phe Pro Tyr Arg Glu Val Val His Leu Glu Glu Tyr Leu
                165                 170                 175

Glu Ala Leu Gly Arg Val Ile Arg Ala Thr Arg Gly Val Arg Arg Pro
                180                 185                 190

Gly Ala Ala Ser Val Asp Leu Ala Trp Val Ala Cys Gly Arg Phe Asp
            195                 200                 205

Gly Phe Phe Glu Thr Gly Leu Ser Pro Trp Asp Val Ala Ala Gly Ile
        210                 215                 220

Leu Leu Val Glu Glu Gly Gly Arg Val Thr Asp Phe His Gly Arg
225                 230                 235                 240

Pro Asp Pro Ile Phe Ala Arg Gln Met Leu Ala Thr Asn Gly Arg Ile
                245                 250                 255

His Glu Ala Leu Cys Glu Leu Val Ala Pro Leu His His Val Tyr Ala
                260                 265                 270

<210> SEQ ID NO 165
<211> LENGTH: 219
<212> TYPE: PRT
<213> ORGANISM: Slackia heliotrinireducens

<400> SEQUENCE: 165

Met Ile Leu Lys Ala Ala Leu Phe Asp Asn Asp Gly Thr Leu Val Asp
1               5                   10                  15

Ser Glu Glu Leu Ile Leu Ser Ser Phe Arg Tyr Ala Thr Lys Ser Val
                20                  25                  30

Leu Gly Glu Ala Leu Pro Asp Glu Val Leu Arg Arg Lys Val Gly Gln
            35                  40                  45

Pro Leu Arg Thr Gln Met Ala Asp Phe Thr Pro Asp Val Asp Lys Arg
        50                  55                  60

```
Glu Glu Leu Phe Arg Val Tyr Gln Glu Phe Asn Ala Arg Glu His Asp
 65                  70                  75                  80

Arg Met Ile Arg Leu Phe Pro Asp Val Ala Asn Thr Leu Gly Thr Met
                 85                  90                  95

Leu Gln Arg Gly Leu Arg Leu Gly Val Val Thr Ser Lys Leu Ser Glu
            100                 105                 110

Asn Cys Leu Gln Asn Leu Ser His Leu Gly Ile Asp Gly Tyr Phe Glu
            115                 120                 125

Cys Ile Val Ala Pro Asp Asn Cys Pro Leu His Lys Pro Asp Pro Gly
            130                 135                 140

Pro Val Leu Glu Gly Ala Lys Leu Leu Gly Ala Arg Pro Glu Gln Cys
145                 150                 155                 160

Val Tyr Val Gly Asp Ser Pro Tyr Asp Ile Ala Ala Gly Arg Asp Ala
                165                 170                 175

Gly Cys Thr Thr Ile Ala Val Thr Tyr Gly Val Phe Ser Arg Glu Asp
                180                 185                 190

Leu Lys Pro Glu Arg Pro Asp Tyr Phe Cys Asp Ser Phe Ala Glu Leu
            195                 200                 205

Leu Ser Val Leu Asp Gly Ile Val Arg Arg Gly
            210                 215

<210> SEQ ID NO 166
<211> LENGTH: 264
<212> TYPE: PRT
<213> ORGANISM: Slackia heliotrinireducens

<400> SEQUENCE: 166

Met Leu Ala His Gln Asn Glu Thr Met Thr Lys Tyr Leu Phe Phe Asp
1                5                  10                  15

Ile Asp Gly Thr Leu Ala Ala Gly Pro Ile Gly Asn Arg Val Val Pro
                 20                  25                  30

Glu Gly Thr Arg Asp Ala Leu Leu Arg Leu Arg Lys Asn Gly His Phe
             35                  40                  45

Thr Ala Ile Cys Thr Gly Arg Ser His Ala Met Ala Arg Ser Tyr Met
 50                  55                  60

Glu Glu Gln Gly Phe Thr Asn Met Val Ala Asp Gly Gly Asn Ser Thr
 65                  70                  75                  80

Val Ile Asp Gly Asn Leu Leu Gly Ile Glu Pro Leu Asp Arg Lys Arg
                 85                  90                  95

Cys Ile Gln Val Leu Glu Glu Cys Asp Arg Leu Lys Ile Pro Trp Ala
            100                 105                 110

Val Ser Ala Asp Asp Ser Asn Thr Arg Leu Ser Ile Asp Gly Arg Phe
            115                 120                 125

Ala Asp Leu Val Glu Lys Gly Tyr Met Val Thr Lys Thr Val Pro Asn
            130                 135                 140

Leu Asp Tyr His Ala Ile Pro Arg Phe Tyr Lys Leu Tyr Ile Ala Val
145                 150                 155                 160

Asn Ala Glu Asp Glu Lys Arg Ile Thr Thr Leu Asp Leu Val Pro His
                165                 170                 175

Val His Phe Ser Asp Thr Cys Leu Phe Val Glu Pro Ile Asp Lys Ser
            180                 185                 190

Arg Gly Ile Met Arg Ile Met Glu His Leu Gly Ala Pro Ile Glu Asp
            195                 200                 205

Val Val Val Phe Gly Asp Gly Met Asn Asp Leu Ser Met Phe Asp Pro
```

Arg Trp Leu Ser Ile Ala Met Gly Asn Ala Val Gln Pro Leu Lys Asp
225                 230                 235                 240

Ala Ala Asp Tyr Ile Thr Ala Asn Ala Asp Asp Gly Ile Arg Lys
            245                 250                 255

Ala Cys Glu His Phe Gly Trp Ile
            260

<210> SEQ ID NO 167
<211> LENGTH: 238
<212> TYPE: PRT
<213> ORGANISM: Staphylothermus marinus

<400> SEQUENCE: 167

Met Ile Arg Leu Ala Ala Phe Asp Ile Asp Gly Thr Leu Thr Ile Asn
1               5                   10                  15

Arg Ser Ser Thr Val Leu Cys Leu Glu Ala Ile Asp Ala Leu Arg Lys
            20                  25                  30

Leu Glu Lys Asn Gly Val Ile Val Leu Val Ser Ser Asn Ala Leu
        35                  40                  45

Pro Val Val Gly Leu Lys Lys Tyr Ile Gly Leu Ser Gly Pro Ala
    50                  55                  60

Ile Gly Glu Thr Gly Ala Leu Ile Tyr Tyr Gly Glu Glu Ile Val
65                  70                  75                  80

Ala Thr Thr Lys Tyr Ser Ala Lys Gln Ala Tyr Leu Asp Val Leu Glu
                85                  90                  95

Lys Tyr Asn Glu Tyr Val Tyr Gly Ser Trp Gln Asn Met Phe Arg Leu
            100                 105                 110

His Asp Tyr Ala Leu Lys Ile Arg Lys Gln Tyr Leu Ser Lys Asp Asn
        115                 120                 125

Glu Ile Tyr Ser Leu Ile Lys Glu Tyr Val Glu Asn Lys Tyr Pro Tyr
130                 135                 140

Ile Lys Val Gly Tyr Ser Gly Tyr Ala Ile His Leu Thr Pro Lys Asp
145                 150                 155                 160

Thr Gly Lys Gly Lys Ala Leu Lys Gln Ile Met Glu Lys His Gly Ile
                165                 170                 175

Arg Arg Glu Glu Thr Met Gly Val Gly Asp Ser Ile Met Asp Trp Glu
            180                 185                 190

Phe Ile Lys Glu Thr Lys Ile Lys Val Ala Val Ala Asn Ala Asp Pro
        195                 200                 205

Glu Leu Arg Arg Lys Ala Asp Ile Val Thr Thr Lys Pro Ser Gly Tyr
210                 215                 220

Gly Val Val Glu Ile Val Glu Lys Ile Leu Asp Lys Pro Pro
225                 230                 235

<210> SEQ ID NO 168
<211> LENGTH: 227
<212> TYPE: PRT
<213> ORGANISM: Staphylothermus marinus

<400> SEQUENCE: 168

Met Ala Arg Ile Lys Ala Val Leu Leu Asp Tyr Asp Leu Thr Leu Met
1               5                   10                  15

Asn Asn Leu Ile Asp Phe Tyr Asp Ala Tyr Asn Glu Ala Leu Lys Lys
            20                  25                  30

Phe Val Gly Lys Thr Leu Gly Phe Asn Glu Phe Phe His Leu Leu Ile

```
                35                  40                  45
Asn Tyr Ser Leu Gln Ala Tyr Ile Pro Pro Asp Val Asp Arg Phe Ser
 50                  55                  60

Phe Trp Arg Tyr Phe Arg Gln Val Tyr Arg Thr Arg Tyr Gly Tyr Pro
 65                  70                  75                  80

Met Glu Gly Ala Tyr Tyr Phe Leu Tyr Trp Val Lys Ala Leu Gly Leu
                 85                  90                  95

Lys Thr Ile Ile Val Ser Gly Arg Glu Cys His Glu Ser Ser Ile Trp
            100                 105                 110

Glu Glu Leu Lys Arg Phe Gly Leu Asn Glu Tyr Ile Asp Lys Val Tyr
        115                 120                 125

Thr Met Phe Asp Thr Leu Ile Leu Gly Gly Val Glu Glu Leu Phe
    130                 135                 140

Asp Lys Thr Trp Leu Ile Ser Tyr Ala Leu Ser Ser Tyr Gly Leu Asp
145                 150                 155                 160

Arg Asp Glu Val Val Tyr Ile Gly Asp Tyr Arg Gln Asp Leu Leu Ser
                165                 170                 175

Ser Gln Arg Thr Gly Ile Lys Phe Ile Gly Ile Ala Phe Ser Glu Lys
            180                 185                 190

Arg Lys Glu Cys Leu Arg Arg Leu Gly Ala Glu Tyr Val Gly Ser Asn
        195                 200                 205

Leu Tyr Asp Val Thr Tyr Tyr Leu Trp Gln Ile Arg Glu Val Glu
    210                 215                 220

Phe Lys Lys
225

<210> SEQ ID NO 169
<211> LENGTH: 222
<212> TYPE: PRT
<213> ORGANISM: Staphylothermus marinus

<400> SEQUENCE: 169

Met Thr Ser Thr Glu Val Val Lys Ala Val Leu Phe Asp Met Asp Gly
 1               5                  10                  15

Thr Ile Ile Asn Ser Val Glu Leu Ile Ala Glu Cys Trp Ser Lys Ala
             20                  25                  30

Phe Lys Lys His Gly Ile Arg Ile Glu Pro Gln Asp Ile Tyr Arg Val
         35                  40                  45

Val Gly Leu Pro Ala Asp Thr Ile Leu Glu Lys Tyr Thr Gly Thr Lys
     50                  55                  60

Asn Pro Arg Leu His Asn Ser Ile Leu Glu Gln Ala Arg Lys Cys Phe
 65                  70                  75                  80

Glu Glu Lys Met Asn Pro Asn Thr Leu Leu Tyr Asn Asp Val Leu Glu
                 85                  90                  95

Thr Ile Lys Gln Leu Arg Glu Asn Asn Lys Leu Cys Gly Ile Val Thr
            100                 105                 110

Ser Ser Ser Cys Lys Arg Thr Ile Glu Leu Leu Glu Lys Leu Asp Ile
        115                 120                 125

Ile Glu Tyr Phe Asp Thr Ile Gln Cys Tyr Gln Gly Lys Leu Arg Gly
    130                 135                 140

Lys Pro Tyr Pro Asp Leu Leu Leu Ser Ala Leu Asn Lys Leu Gly Ile
145                 150                 155                 160

Lys Pro Ser Gln Ala Ile Tyr Val Gly Asp Ser Tyr Ile Asp Tyr Leu
                165                 170                 175
```

```
Thr Ala Arg Asn Thr Gly Val Leu Phe Val Leu Val Lys Arg Ser Trp
            180                 185                 190

Asn Thr His Ile Val Asp Lys Cys Ser Glu Lys Cys Ile Val Ile Ser
            195                 200                 205

Asp Leu Arg Glu Ile Ser Asn Leu Ile Thr Asn Lys Ile Lys
    210                 215                 220

<210> SEQ ID NO 170
<211> LENGTH: 225
<212> TYPE: PRT
<213> ORGANISM: Sulfolobus acidocaldarius

<400> SEQUENCE: 170

Met Asn Lys Asp Ile Ile Phe Val Ser Asp Tyr Asp Arg Thr Leu Ser
1               5                   10                  15

Ser Glu Lys Asn Asn Phe Arg Ile Asp Lys Glu Val Ala Arg Ile Val
            20                  25                  30

Asn Asp Phe Ser Lys Thr Tyr Pro Phe Phe Val Val Thr Gly Arg Glu
        35                  40                  45

Lys Lys Phe Ile Asp Ile Leu Ala Pro Glu Leu Lys Pro Thr Gly Trp
50                  55                  60

Ile Leu Glu Asn Gly Ala Leu Met Tyr Val Asn Gly Glu Leu Ile Tyr
65                  70                  75                  80

Asn Ile Gln Pro Ser Trp Phe Asp Thr Arg Lys Asn Ile Ile Lys Ile
                85                  90                  95

Leu Asp Asn Tyr Asn Ile Ser Tyr Ser Leu Gly Asn Val Ile Val Tyr
            100                 105                 110

Val Asp Lys Ala His Glu Tyr Lys Gly Val Leu Asn Ser Ile Lys Asp
        115                 120                 125

Ala Thr Val Glu Trp Asn Arg Asn Asp Ala Met Ile Leu Pro Lys Gly
    130                 135                 140

Val Asp Lys Gly Ser Ala Val Ile Gln Leu Arg Glu Arg Leu Gly Tyr
145                 150                 155                 160

Arg Gly Lys Ile Val Ala Ile Gly Asp Ser Glu Asn Asp Ile Ser Met
                165                 170                 175

Phe Arg Val Ala Asp Ile Arg Val Ser Val Ala Asn Ala Leu Pro Met
            180                 185                 190

Ile Lys Glu Ile Ser Glu Leu Ile Leu Glu Lys Glu Asp Gly Glu Gly
        195                 200                 205

Val Lys Glu Phe Leu Leu Lys Val Leu Lys Gly Glu Ile Ile Leu Ile
    210                 215                 220

Lys
225

<210> SEQ ID NO 171
<211> LENGTH: 224
<212> TYPE: PRT
<213> ORGANISM: Sulfolobus acidocaldarius

<400> SEQUENCE: 171

Met Ile Tyr Asn Ile Phe Ile Phe Val Ile Lys Tyr Asn Phe Pro Val
1               5                   10                  15

Phe Lys Val Lys Gly Val Ile Phe Asp Leu Asp Gly Thr Leu Ala Asn
            20                  25                  30

Thr Ala Leu Ile His Lys Glu Ala Trp Glu Lys Ala Leu Asp Arg Leu
        35                  40                  45
```

Gly Ile Lys Ser Asp Val Lys Ile Asp Asn Leu Leu Gly Arg Lys Ser
    50                  55                  60

Ser Asp Ile Ala Lys Leu Leu Ala Pro Asn Asn Trp Ser Glu Leu Ile
65                  70                  75                  80

Asn Ile Lys Asn Gln Ile Tyr Val Glu Leu Val Lys Glu Lys Ala Ser
                85                  90                  95

Pro Thr Pro Cys Ala Leu Asp Leu Leu Ser Tyr Leu Arg Lys Lys Glu
            100                 105                 110

Ile Lys Thr Ala Ile Val Thr Ser Ser Asn Lys Leu Ser Ser Gly Ser
        115                 120                 125

Val Leu Lys Lys Leu Gly Ile Thr Ser Glu Val Leu Thr Gly Asp
    130                 135                 140

Asp Val Ile Asn Ser Lys Pro Asn Pro Glu Gly Ile Asn Lys Ala Leu
145                 150                 155                 160

Ser Leu Leu Tyr Leu Asp Gly Arg Asp Val Ile Gly Val Gly Asp Thr
                165                 170                 175

Glu Val Asp Val Glu Ala Tyr Tyr Lys Ala Gly Leu Gly Gly Ile Tyr
            180                 185                 190

Leu Val Lys Ser Gly Val Pro Phe Arg Glu Glu Val Val Lys Met Tyr
        195                 200                 205

Gly Gly Ile Val Ile Ser Ser Leu Cys Glu Leu Leu Glu Leu Ile Ser
    210                 215                 220

<210> SEQ ID NO 172
<211> LENGTH: 267
<212> TYPE: PRT
<213> ORGANISM: Sulfolobus acidocaldarius

<400> SEQUENCE: 172

Met Lys Arg Glu Asp Val Glu Lys Val Ala Ser Glu Ala Ser Lys Tyr
1               5                   10                  15

Ile Tyr Glu Glu Arg Glu Asn Lys Asp Val Asp Arg Val Ile Asn Val
            20                  25                  30

His Gly Asn Asp Val Thr Arg Ile Ile Asp Lys Arg Ser Glu Asp Phe
        35                  40                  45

Ile Val Asp Arg Leu Lys Ser Leu Gly Tyr Asn Ile Leu Ile Val Thr
50                  55                  60

Glu Glu Ser Gly Val Ile Asp Ser Tyr Gly Lys Asn Tyr Asp Tyr Ile
65                  70                  75                  80

Ala Ile Val Asp Pro Leu Asp Gly Ser Thr Asn Phe Val Ser Gly Ile
                85                  90                  95

Pro Trp Ser Ser Val Ser Ile Ala Ile Tyr Asn Arg Asp Glu Glu Asp
            100                 105                 110

Ile Leu Ser Ser Asn Val Gly Ala Val Ser Ser Ile Phe Thr Pro Tyr
        115                 120                 125

Thr Phe Ser Tyr Asp Glu Gly Ser Ala Tyr Val Asn Gly Val Lys Ile
    130                 135                 140

Ala Glu Ile Lys Lys Pro Glu Lys Ile Leu Leu Leu Ala Tyr Phe Ser
145                 150                 155                 160

Arg Ser Lys Leu Pro Asn Leu Leu Phe Phe Glu Lys Ile Gly Gln
                165                 170                 175

Gly Tyr Lys Ile Arg Ser Leu Gly Ser Ala Ser Leu Asp Met Ile Leu
            180                 185                 190

Val Cys Thr Gly Arg Ala Thr Met Phe Phe Asp Ile Arg Gly Lys Leu
        195                 200                 205

```
Arg Asn Val Asp Ile Ala Ala Ser Ser Asn Phe Cys Ser Arg Leu Gly
        210                 215                 220

Val Ile Pro Tyr Asp Ile Gly Leu Arg Lys Ile Lys Ser Ser Leu Thr
225                 230                 235                 240

Glu Val Ser Val Val Lys Asp Leu Val Ile Ser Leu Asp Glu Ser Leu
                245                 250                 255

Leu Arg Ser Phe Ser Leu Ala Leu Gln Thr Val
            260                 265

<210> SEQ ID NO 173
<211> LENGTH: 272
<212> TYPE: PRT
<213> ORGANISM: Thermanaerothrix daxensis

<400> SEQUENCE: 173

Met Thr Thr Thr Pro Ile Val Leu Ser Ile Asp Leu Asp Gly Thr Leu
1               5                   10                  15

Leu Ile Glu Glu Arg Glu Val His Pro Glu Asp Val His Leu Leu His
            20                  25                  30

His Pro Leu Pro Val Thr Leu Ile Leu Ala Thr Gly Arg Ser Leu Glu
        35                  40                  45

Ser Ala Arg Arg Val Leu Glu Arg Ala Gly Leu Tyr Arg His Glu Pro
50                  55                  60

Leu Pro Phe Pro Leu Val Leu Gln Asn Gly Ala Ala Ile Tyr Arg Pro
65                  70                  75                  80

Gln Glu Val Leu Glu Asp Tyr Phe Pro Ile Pro Pro Glu Ala Glu Thr
                85                  90                  95

Gln Leu His Ala Leu Ala Pro Gln Phe Ser Glu Ala Ala Leu Leu Trp
            100                 105                 110

Gln Gly Leu Asp Gly Ala Tyr Leu Glu Glu Ile Thr Pro Phe Gly Leu
        115                 120                 125

Gln Ala Ala Gly Arg Phe Gly Phe Leu Pro Arg Pro Leu Ser Glu Ala
    130                 135                 140

Pro Ala Gly Gln Gly Phe Gly Lys Leu Met Cys Leu Ser Asp Arg Pro
145                 150                 155                 160

Glu Val Leu Lys Ala Phe Ala Ala Thr Arg His Leu Pro Val Glu
                165                 170                 175

Gly Ser Tyr Ser Leu Asp Val Ile Tyr Glu Val Thr Arg Gln Gly Val
            180                 185                 190

His Lys Gly Phe Gly Leu Arg Ile Leu Leu Gln Arg Leu Gly Leu Thr
        195                 200                 205

His Ala Arg Leu Val Ala Val Gly Asp Gly Asp Asn Asp Val Pro Met
    210                 215                 220

Phe Ser Cys Ala Asp Leu Ala Ile Ala Pro Leu Asn Ala Ser Pro Leu
225                 230                 235                 240

Ala Arg Ser His Ala His Arg Leu Ile Asp Arg Arg Pro His Gly Leu
                245                 250                 255

Leu Thr Pro Val Leu Asp Leu Leu Arg Gln Glu Gly Trp Leu Asp Pro
            260                 265                 270

<210> SEQ ID NO 174
<211> LENGTH: 215
<212> TYPE: PRT
<213> ORGANISM: Thermoanaerobacter sp.

<400> SEQUENCE: 174
```

```
Met Asn Val Lys Ala Val Val Phe Asp Leu Asp Gly Thr Leu Ile Asp
1               5                   10                  15

Ser Lys Lys Asp Ile Ala Met Ala Ala Asn Lys Thr Leu Ser Glu Leu
            20                  25                  30

Gly Leu His Thr Leu Pro Glu Asp Thr Ile Ala Ser Phe Ile Gly Tyr
        35                  40                  45

Gly Gly Glu Leu Phe Ile Lys Arg Cys Ile Gly Glu Lys Asn Ile Asp
50                  55                  60

Lys Phe Glu Glu Ala Phe Lys Lys Phe Lys Glu Asn Tyr Ser Glu Leu
65                  70                  75                  80

Cys Ile Ile His Thr Ser Leu Phe Pro Gly Val Glu Glu Val Leu Glu
                85                  90                  95

Phe Leu Lys Lys Arg Lys Ile Asn Ile Ala Leu Ala Thr Asn Lys Met
            100                 105                 110

Ile Ser Leu Ser Lys Lys Ile Leu Lys His Leu Glu Val Glu Lys Tyr
        115                 120                 125

Phe Ser Ile Met Leu Gly Pro Glu Asp Val Thr Asn Arg Lys Pro His
130                 135                 140

Pro Glu Ile Ile Glu Ile Leu Leu Gln Asn Leu Asn Val Arg Pro Glu
145                 150                 155                 160

Glu Thr Leu Tyr Val Gly Asp Ser Glu Ile Asp Val Phe Cys Gly Lys
                165                 170                 175

Ser Ala Gly Val Tyr Thr Cys Ala Val Thr Tyr Gly Ile Gly Asp Ile
            180                 185                 190

Lys Ser Ile Ile Ala Ala Asp Pro Asp Phe Ile Ile Thr Asp Leu Thr
        195                 200                 205

Lys Leu Ile Ile Leu Leu Ser
210                 215

<210> SEQ ID NO 175
<211> LENGTH: 273
<212> TYPE: PRT
<213> ORGANISM: Thermoanaerobacter thermohydrosulfuricus

<400> SEQUENCE: 175

Met Tyr Lys Leu Phe Val Thr Asp Ala Asp Gly Ser Leu Leu Asn Ser
1               5                   10                  15

Asn Ser Glu Ile Ser Asp Lys Asn Lys Glu Ala Ile Lys Glu Val Ile
            20                  25                  30

Ser Arg Gly Val Ile Phe Thr Ile Ala Thr Gly Arg Met Phe Ser Ser
        35                  40                  45

Ile Leu Pro Tyr Ala Phe Glu Leu Asn Val Asn Ala Pro Val Ile Ser
50                  55                  60

Tyr Asn Gly Ala Leu Ile Lys Asp Ile Tyr Thr Lys Lys Val Tyr Tyr
65                  70                  75                  80

Tyr Asn Pro Ile Gln Thr Glu Asp Ala Ile Phe Ala Ile Arg Leu Leu
                85                  90                  95

Lys Glu Ser Gly Tyr His Ile Asn Leu Tyr Ile Asp Asp Glu Leu Tyr
            100                 105                 110

Val Glu Glu Ile Thr Asp Arg Val Glu Trp Tyr Leu Ser Phe Asn Asn
        115                 120                 125

Val Thr Val Asn Ala Val Gly Asn Leu Glu Glu Phe Leu Lys Arg Thr
130                 135                 140

Gly Gly Val Thr Ala Lys Ile Tyr Ala Ile Asn Asp Met Lys Asn Pro
```

```
            145                 150                 155                 160
Ile Ser Ile Asp Ala Glu Ile Tyr Asp Glu Ile Ser Lys Arg Leu Thr
                165                 170                 175
Ile Ser Thr Ser Gly Gly Gly His Leu Glu Ile Asn Ala Lys Gly Val
                180                 185                 190
Ser Lys Gly Asn Ala Leu Lys Thr Leu Ala Asn Met Tyr Ser Ile Lys
                195                 200                 205
Arg Glu Gln Val Val Ala Ile Gly Asp Asn Leu Asn Asp Leu Ser Met
            210                 215                 220
Ile Glu Tyr Ala Gly Leu Gly Val Ala Met Gly Asn Ala Pro Asp Ile
225                 230                 235                 240
Val Lys Ile Lys Ala Asp Tyr Thr Thr Leu Ser Asn Asp Glu Asp Gly
                245                 250                 255
Val Ala His Val Ile Asp Lys Phe Phe Leu Asn Lys Lys Thr Val Ala
                260                 265                 270
Val

<210> SEQ ID NO 176
<211> LENGTH: 273
<212> TYPE: PRT
<213> ORGANISM: Thermoanaerobacter thermohydrosulfuricus

<400> SEQUENCE: 176

Met Tyr Lys Leu Phe Val Thr Asp Ala Asp Gly Ser Leu Leu Asn Ser
1               5                   10                  15
Asn Ser Glu Ile Ser Asp Lys Asn Lys Glu Glu Ile Lys Glu Val Ile
                20                  25                  30
Ser Arg Gly Val Ile Phe Thr Ile Ala Thr Gly Arg Met Phe Ser Ser
            35                  40                  45
Ile Leu Pro Tyr Ala Phe Glu Leu Asn Val Asn Ala Pro Val Ile Ser
50                  55                  60
Tyr Asn Gly Ala Leu Ile Lys Asp Ile Tyr Thr Lys Lys Val Tyr Tyr
65                  70                  75                  80
Tyr Asn Pro Ile Gln Thr Glu Asp Ala Ile Phe Ala Ile Arg Leu Leu
                85                  90                  95
Lys Glu Ser Gly Tyr His Ile Asn Leu Tyr Ile Asp Asp Glu Leu Tyr
                100                 105                 110
Val Glu Glu Ile Thr Asp Arg Val Glu Trp Tyr Leu Ser Phe Asn Asn
            115                 120                 125
Val Thr Val Asn Ala Val Gly Asn Leu Glu Glu Phe Leu Lys Arg Thr
            130                 135                 140
Gly Gly Val Thr Ala Lys Ile Tyr Ala Ile Asn Asp Met Lys Asn Pro
145                 150                 155                 160
Ile Ser Ile Asp Ala Glu Ile Tyr Asp Glu Ile Ser Lys Arg Leu Thr
                165                 170                 175
Ile Ser Thr Ser Gly Gly Gly His Leu Glu Ile Asn Ala Lys Gly Val
                180                 185                 190
Ser Lys Gly Asn Ala Leu Lys Thr Leu Ala Asn Met Tyr Ser Ile Lys
                195                 200                 205
Arg Glu Gln Val Val Ala Ile Gly Asp Asn Leu Asn Asp Leu Ser Met
            210                 215                 220
Ile Glu Tyr Ala Gly Leu Gly Val Ala Met Gly Asn Ala Pro Asp Ile
225                 230                 235                 240
Val Lys Ile Lys Ala Asp Tyr Thr Thr Leu Ser Asn Asp Glu Asp Gly
```

-continued

```
                        245                 250                 255
Val Ala His Val Ile Asp Lys Phe Phe Leu Asn Lys Lys Thr Val Ala
                    260                 265                 270
Val

<210> SEQ ID NO 177
<211> LENGTH: 257
<212> TYPE: PRT
<213> ORGANISM: Thermoanaerobacter wiegelii

<400> SEQUENCE: 177

Met Lys Asp Glu Lys Gly Ile Val Asp Ile Ile Lys Lys Ala Gly
1               5                   10                  15

Glu Ile Leu Gln Asp Gly Trp Asn Lys Lys Asn Phe Lys Ile Tyr Arg
                20                  25                  30

Lys Gly Thr Ile Asn Leu Val Thr Glu Ile Asp Lys Lys Ile Glu Phe
            35                  40                  45

Leu Ile Ile Gln Leu Leu Lys Gln Tyr Phe Pro Asp Tyr Gly Ile Leu
        50                  55                  60

Thr Glu Glu Ser Lys Glu Ile Asn Ser Lys Ala Asn Val Arg Trp Ile
65                  70                  75                  80

Ile Asp Pro Leu Asp Gly Thr Thr Asn Tyr Ile Lys Gln Tyr Pro Phe
                85                  90                  95

Val Ala Ile Ser Ile Ala Leu Glu Lys Gly Glu Leu Ile Leu Gly
                    100                 105                 110

Val Val Tyr Asn Pro Ile Leu Asn Glu Met Phe Ile Ala Gln Lys Gly
            115                 120                 125

Cys Gly Ala Thr Tyr Asn Gly Lys Ser Ile His Val Ser Lys Ile Lys
        130                 135                 140

Glu Leu Gly Ser Ala Val Leu Ala Ser Gly Phe Pro Tyr Asp Ala Trp
145                 150                 155                 160

Glu Asn Pro Asp Asn Asn Ala Lys Gln Trp Arg Gln Phe Leu Thr Arg
                165                 170                 175

Ser Leu Ser Leu Arg Cys Asp Gly Ser Ala Ala Leu Asp Leu Cys Arg
            180                 185                 190

Val Ala Cys Gly Gln Leu Asp Gly Tyr Trp Glu Lys Gly Ile Ser Pro
        195                 200                 205

Trp Asp Val Ala Ala Gly Ile Val Ile Leu Arg Glu Ala Gly Gly Ile
    210                 215                 220

Ile Thr Asp Tyr Leu Gly Glu Glu Asn Phe Phe Lys Arg Gly Glu Val
225                 230                 235                 240

Val Ala Ala Asn Pro Val Leu His Ala Gln Met Leu Lys Val Leu Asn
                245                 250                 255

Asn

<210> SEQ ID NO 178
<211> LENGTH: 215
<212> TYPE: PRT
<213> ORGANISM: Thermoanaerobacter wiegelii

<400> SEQUENCE: 178

Met Asn Val Lys Thr Ile Ile Phe Asp Leu Asp Gly Thr Leu Ile Asp
1               5                   10                  15

Ser Lys Lys Asp Ile Val Met Ala Ile Asn Lys Thr Leu Arg Asp Leu
                20                  25                  30
```

```
Asp Ile Pro Thr Leu Pro Glu Asp Ile Ile Pro Phe Met Ser Tyr
             35                  40                  45

Gly Pro Glu Val Phe Ile Lys Gln Cys Ile Gly Glu Lys Asn Ala Asp
 50                  55                  60

Lys Phe Glu Arg Ala Phe Glu Lys Phe Lys Glu Asn Tyr Ser Glu Arg
 65                  70                  75                  80

Cys Ile Val Tyr Thr Ser Leu Phe Pro Gly Val Arg Glu Val Leu Glu
                 85                  90                  95

Phe Leu Lys Glu Arg Lys Ile Asn Ile Ala Leu Ala Thr Asn Lys Met
            100                 105                 110

Met Ser Leu Ser Lys Lys Ile Leu Gln His Phe Gly Leu Glu Lys Tyr
            115                 120                 125

Phe Ser Ile Met Leu Gly Pro Glu Asp Val Thr Asn Lys Lys Pro His
130                 135                 140

Pro Glu Ile Ile Glu Ile Ile Leu Gln Lys Leu Asn Val Lys Arg Glu
145                 150                 155                 160

Glu Ala Leu Tyr Val Gly Asp Ser Glu Ile Asp Val Leu Cys Gly Lys
                165                 170                 175

Ser Ala Gly Val Tyr Thr Cys Ala Val Thr Tyr Gly Ile Gly Asp Ile
            180                 185                 190

Lys Ser Ile Ile Ala Ala Asn Pro Asp Phe Ile Ile Thr Asp Leu Thr
            195                 200                 205

Lys Leu Ile Leu Leu Val Ser
210                 215

<210> SEQ ID NO 179
<211> LENGTH: 205
<212> TYPE: PRT
<213> ORGANISM: Thermoanaerobacterium xylanolyticum

<400> SEQUENCE: 179

Met Ser Thr Arg Leu Phe Ile Val Arg His Gly Glu Thr Leu Trp Asn
 1               5                  10                  15

Arg Gln Lys Lys Ile Gln Gly Ala Ser Asp Thr Gln Leu Ser Asp Glu
             20                  25                  30

Gly Met Lys Gln Ala Tyr Leu Leu Ser Gln Arg Leu Lys Asn Glu Ile
             35                  40                  45

Ile Asp Val Ile Phe Ser Ser Asp Leu Asp Arg Ala Tyr Lys Thr Ala
 50                  55                  60

Thr Phe Ile Ala Lys Asn Phe Asn Leu Asp Val Ile Lys Leu Pro Glu
 65                  70                  75                  80

Leu Arg Glu Ile Ser Phe Gly Val Trp Glu Gly Leu Thr Val Asp Glu
                 85                  90                  95

Ile Glu Lys Ser Tyr Lys Glu Leu Tyr His Thr Trp Lys Thr Asn Pro
            100                 105                 110

Pro Glu Ala Thr Ile Glu Gly Ala Glu Thr Leu Lys Ala Val Gln Asp
            115                 120                 125

Arg Ile Leu Asn Ala Thr Asn Lys Ile Ile Glu Gln Tyr Lys Asn Lys
            130                 135                 140

Asn Ile Leu Ile Val Ser His Gly Thr Thr Ile Lys Ala Leu Ile Leu
145                 150                 155                 160

Gly Met Leu Asn Leu Asp Leu Ser Phe Tyr Pro Lys Ile Arg Gln Asp
                165                 170                 175

Asn Thr Ala Leu Asn Ile Ile Asp Val Lys Asp Asp Gly Asn Cys Val
            180                 185                 190
```

Leu Val Leu Leu Asn Asp Thr Cys His Leu Arg Glu Arg
        195                 200                 205

<210> SEQ ID NO 180
<211> LENGTH: 595
<212> TYPE: PRT
<213> ORGANISM: Thermobifida halotolerans

<400> SEQUENCE: 180

Met Arg Tyr His Val Leu Ala Cys Asp Tyr Asp Glu Thr Ile Ala His
1               5                   10                  15

Gly Gly Arg Val Asp Asp Ala Thr Val Thr Ala Leu Glu His Leu Ser
            20                  25                  30

Arg Ser Gly Arg Arg Leu Val Met Val Thr Gly Arg Arg Leu Asp Asp
        35                  40                  45

Leu Phe Gly Val Phe Asp His Val Asp Leu Phe Asp Met Val Val Ala
    50                  55                  60

Glu Asn Gly Gly Val Leu Tyr Asp Pro Gly Arg Asp Arg Arg Pro
65                  70                  75                  80

Leu Ala Glu Arg Pro Pro Ala Glu Phe Val Glu Arg Leu Arg Arg His
                85                  90                  95

Gly Val Ser Pro Leu Ala Val Gly Glu Val Val Ala Thr Arg Glu
            100                 105                 110

Pro His Asp Arg Thr Val Leu Asp Ala Ile Arg Glu Leu Gly Leu Glu
            115                 120                 125

Leu Gln Val Ile Tyr Asn Lys Gly Ala Val Met Val Leu Pro Pro Gly
    130                 135                 140

Val Asn Lys Ala Ser Gly Leu Ala Ala Ala Leu Arg Arg Leu Glu Phe
145                 150                 155                 160

Ser Pro His Ser Thr Val Ala Val Gly Asp Ala Glu Asn Asp His Ala
                165                 170                 175

Met Leu His Met Cys Glu Cys Ala Val Ala Val Ala Gly Ala Leu Glu
            180                 185                 190

Ala Val Lys Arg Thr Ser Asp Leu Val Leu Glu Arg Pro Asp Gly Glu
        195                 200                 205

Gly Val Ala Glu Leu Val Asp Arg Leu Leu Ala Thr Asp Leu Ala Glu
    210                 215                 220

Val Pro Val Ser Arg His Asp Leu His Phe Gly Thr Ala Gly Ala Ala
225                 230                 235                 240

Pro Thr Ala Ile Ala Pro His Gly Arg Gly Ala Val Ala Gly Pro
                245                 250                 255

Ser Gly Ser Gly Lys Ser Thr Ala Ala Thr Ala Leu Leu Glu Arg Leu
            260                 265                 270

Gly Glu Ser Gly Tyr Gln Tyr Cys Val Ile Asp Pro Glu Gly Asp Tyr
        275                 280                 285

Ala Asp Phe Glu Gly Val Thr Ala Phe Gly Asp Ala Thr Arg Ala Pro
    290                 295                 300

Ser Ile Asp Glu Val Leu Thr Ala Leu Arg Asp Pro Asp His Asn Val
305                 310                 315                 320

Ala Val Asn Met Leu Ala Val Pro Leu Arg Asp Arg Pro Ala Phe Phe
                325                 330                 335

Ala Gly Leu Leu Pro Arg Leu Val Gly Leu Arg Ala Glu Leu Gly His
            340                 345                 350

Pro Ala Trp Leu Val Val Asp Glu Ala His His Leu Met Pro Val Glu

```
            355                 360                 365
Leu Ala Gln Leu Pro Leu Arg Val Pro Ala Asp Val Gly Gly Leu Met
        370                 375                 380
Leu Val Thr Val His Pro Glu Thr Leu Ser Pro Leu Val Leu Arg Leu
385                 390                 395                 400
Val Asp Thr Val Val Ala Val Gly Asp Pro Gly Gln Thr Leu Asp
            405                 410                 415
Ala Phe Ala Ala Ala Thr Gly His Arg Pro Ala Leu Glu Pro Ala
            420                 425                 430
Pro Ala Glu Pro Asp Arg Gln Gln Glu Ser Val Val Ser Asp Ile Ala
            435                 440                 445
Val Trp Arg Val Ala Glu Thr Ala Ala Gln Arg Val Lys Leu Ala Pro
        450                 455                 460
Gly Glu Thr His Arg Thr Arg His Arg Arg Lys Tyr Ala Ala Gly Thr
465                 470                 475                 480
Leu Ala Pro Asp Lys Ser Phe Tyr Phe Thr Gly Pro Gln Gly Arg Leu
            485                 490                 495
Arg Leu Arg Ala Arg Asn Leu His Ser Phe Val Glu Leu Ala Glu Gly
            500                 505                 510
Val Asp Asp Asp Thr Trp Thr His His Leu Arg Arg His Asp Tyr Ser
            515                 520                 525
Arg Trp Leu Arg Gly Ser Val Arg Asp Gly Glu Leu Ala Asp Leu Val
        530                 535                 540
Arg Arg Val Glu Gln Asp Thr Gly Arg Ala Pro Ser Asp Ser Arg Arg
545                 550                 555                 560
Glu Val Ala Arg Leu Ile Asp Glu Arg Tyr Thr Leu Pro Ala Glu Pro
            565                 570                 575
Thr Ser Tyr Asp Pro Asp Arg Gly Arg Glu Thr Gly Pro Ser Gly Arg
            580                 585                 590
Arg Arg Pro
        595

<210> SEQ ID NO 181
<211> LENGTH: 237
<212> TYPE: PRT
<213> ORGANISM: Thermobifida halotolerans

<400> SEQUENCE: 181

Met Gly Leu Arg Glu Thr Asp Thr Glu Phe Val Pro Pro Arg Ala Ala
1               5                   10                  15
Leu Phe Asp Leu Asp Gly Thr Leu Ile Asn Ser Glu Pro Arg Ser Ala
            20                  25                  30
Ala Val Trp Ala Arg Leu Leu Arg Ala Arg Gly Ile Thr Pro Asp Glu
        35                  40                  45
Ala Leu Leu Arg Arg Phe Met Gly Arg Gly Gly Asp Val Val Ala
        50                  55                  60
Glu Leu Pro His Leu Phe Pro Gly Glu Ser Leu Glu Gln Ile Phe Asp
65                  70                  75                  80
Glu Leu Trp Arg His Gly Gln Asp Pro Asp Leu Pro Gln Val Ala Pro
            85                  90                  95
Leu Pro Glu Ser Val Ala Phe Leu His His Leu His Ser Gln Gly Val
            100                 105                 110
Pro Phe Ala Leu Val Thr Ser Ala Gly Arg Glu Trp Ala Glu Ser Ala
        115                 120                 125
```

```
Leu Glu Trp Leu Gly Val Arg Gly Met Phe Arg Gly Leu Val Thr Ala
    130                 135                 140

Gly Asp Val Thr Val Gly Lys Pro His Pro Gln Gly Tyr Leu Gly Gly
145                 150                 155                 160

Ala Glu Ile Leu Gly His Glu Pro His Ile Val Val Phe Glu Asp
            165                 170                 175

Thr Pro Ala Gly Ile Met Ala Gly Arg Gly Ala Gly Met Arg Val Val
            180                 185                 190

Gly Ile Thr Thr Thr His Pro Pro Glu Ala Leu Thr Gln Ala Asp Leu
            195                 200                 205

Val Val Glu His Leu Thr Gln Val Ala Trp Pro Arg Leu Ser Leu Arg
210                 215                 220

Asp Pro Glu Pro Pro Arg Ser Ser Phe Ala Gly Arg Gly
225                 230                 235
```

<210> SEQ ID NO 182
<211> LENGTH: 236
<212> TYPE: PRT
<213> ORGANISM: Thermococcus celer

<400> SEQUENCE: 182

```
Met Gly Arg Val Lys Ala Ile Ser Leu Asp Ile Asp Gly Thr Ile Thr
1               5                   10                  15

Tyr Pro Asp Arg Arg Leu His Glu Glu Ala Met Arg Ala Ile Arg Leu
            20                  25                  30

Ala Glu Ser Leu Gly Val Pro Val Met Leu Val Thr Gly Asn Ser Val
            35                  40                  45

Pro Phe Ala Glu Ala Met Ala Ile Met Ile Gly Thr Ser Gly Pro Val
50                  55                  60

Val Ala Glu Asp Gly Gly Ala Leu Ser Ile Lys Asp Gly Arg Leu Arg
65                  70                  75                  80

Lys Arg Val Tyr Leu Thr Thr Met Asp Glu Glu Trp Ile Leu Trp Ser
                85                  90                  95

Glu Val Lys Lys Arg Tyr Pro Gly Ala Ile Leu Ser Phe Ser Met Pro
                100                 105                 110

Glu Arg Lys Ala Gly Leu Val Ile Leu Arg Thr Val Pro Val Glu Ala
            115                 120                 125

Val Arg Glu Leu Ile Lys Glu Leu Gly Leu Asn Leu Ile Ala Val Asp
            130                 135                 140

Ser Gly Phe Ala Ile His Val Lys Lys Pro Trp Ile Asn Lys Gly Thr
145                 150                 155                 160

Gly Ile Glu Lys Ala Cys Glu Val Leu Gly Ile Lys Pro Arg Glu Val
            165                 170                 175

Ala His Val Gly Asp Gly Glu Asn Asp Leu Asp Ala Phe Arg Val Val
            180                 185                 190

Gly Tyr Arg Val Ala Val Gly Gln Ala Pro Glu Ser Leu Lys Gly Glu
            195                 200                 205

Ala Asp Tyr Val Thr Glu Lys Thr Tyr Gly Ala Gly Gly Ala Glu Gly
210                 215                 220

Ile Leu His Val Leu Arg Glu Phe Gly Tyr Met Glu
225                 230                 235
```

<210> SEQ ID NO 183
<211> LENGTH: 236
<212> TYPE: PRT
<213> ORGANISM: Thermococcus celer

<400> SEQUENCE: 183

```
Met Gly Arg Val Lys Ala Ile Ser Leu Asp Ile Asp Gly Thr Ile Thr
1               5                   10                  15

Tyr Pro Asp Arg Arg Leu His Glu Glu Ala Met Arg Ala Ile Arg Leu
            20                  25                  30

Ala Glu Ser Leu Gly Val Pro Val Met Leu Val Thr Gly Asn Ser Val
        35                  40                  45

Pro Phe Ala Glu Ala Met Ala Ile Met Ile Gly Thr Ser Gly Pro Val
50                  55                  60

Val Ala Glu Asp Gly Gly Ala Leu Ser Ile Lys Asp Gly Arg Leu Arg
65                  70                  75                  80

Lys Arg Val Tyr Leu Thr Thr Met Asp Glu Glu Trp Ile Leu Trp Ser
                85                  90                  95

Glu Val Lys Lys Arg Tyr Pro Gly Ala Ile Leu Ser Phe Ser Met Pro
            100                 105                 110

Glu Arg Lys Ala Gly Leu Val Ile Leu Arg Thr Val Pro Val Glu Ala
        115                 120                 125

Val Arg Glu Leu Ile Lys Glu Leu Gly Leu Asn Leu Ile Ala Val Asp
130                 135                 140

Ser Gly Phe Ala Ile His Val Lys Lys Pro Trp Ile Asn Lys Gly Thr
145                 150                 155                 160

Gly Ile Glu Lys Ala Cys Glu Val Leu Gly Ile Lys Pro Arg Glu Val
                165                 170                 175

Ala His Val Gly Asp Gly Glu Asn Asp Leu Asp Ala Phe Arg Val Val
            180                 185                 190

Gly Tyr Arg Val Ala Val Gly Gln Ala Pro Glu Ser Leu Lys Gly Glu
        195                 200                 205

Ala Asp Tyr Val Thr Glu Lys Thr Tyr Gly Ala Gly Gly Ala Glu Gly
210                 215                 220

Ile Leu His Val Leu Arg Glu Phe Gly Tyr Met Glu
225                 230                 235
```

<210> SEQ ID NO 184
<211> LENGTH: 251
<212> TYPE: PRT
<213> ORGANISM: Thermococcus litoralis

<400> SEQUENCE: 184

```
Met Tyr Glu Trp Asn Glu Ile Ala Leu Asn Leu Ala Lys Asp Ile Glu
1               5                   10                  15

Arg Glu Val Met Pro Leu Phe Gly Thr Lys Lys Ala Gly Glu Phe Ile
            20                  25                  30

Gly Phe Ser Pro Ser Gly Asp Lys Thr Lys Leu Val Asp Lys Val Ala
        35                  40                  45

Glu Asp Val Val Leu Glu Tyr Leu Arg Pro Leu Gly Val Asn Val Val
50                  55                  60

Ser Glu Glu Ile Gly Asn Ile Glu Ala Gly Ser Glu Tyr Thr Ile Val
65                  70                  75                  80

Val Asp Pro Ile Asp Gly Ser Phe Asn Phe Ile Gln Gly Ile Pro Ile
                85                  90                  95

Phe Gly Phe Ser Phe Ala Val Phe Lys Asn Glu Lys Pro Val Tyr Ala
            100                 105                 110

Met Ile Tyr Glu Phe Ile Thr Lys Asn Val Tyr Glu Gly Ile Pro Gly
        115                 120                 125
```

Glu Gly Ala Tyr Leu Asn Gly Glu Arg Ile Arg Val Arg His Leu Asn
            130                 135                 140

Glu Lys Ser Ile Ser Ile Ser Phe Tyr Thr Arg Gly Arg Gly Ala Arg
145                 150                 155                 160

Leu Val Glu Lys Val Lys Arg Thr Arg Val Leu Gly Ala Ile Ala Val
                165                 170                 175

Glu Leu Ala Tyr Leu Ala Arg Gly Ser Leu Asp Gly Val Ile Asp Ile
            180                 185                 190

Arg Asn Tyr Val Arg Pro Thr Asp Ile Ala Ala Gly Tyr Ile Ile Ala
                195                 200                 205

Lys Glu Ala Gly Ala Ile Ile Thr Asp Asp Ser Gly Glu Glu Ile Lys
            210                 215                 220

Phe Arg Leu Asp Ala Arg Glu Lys Leu Asn Ile Ile Ala Val Asn Asp
225                 230                 235                 240

Lys Arg Leu Leu Lys Leu Ile Leu Glu Val Ile
                245                 250

<210> SEQ ID NO 185
<211> LENGTH: 237
<212> TYPE: PRT
<213> ORGANISM: Thermococcus profundus

<400> SEQUENCE: 185

Met Lys Val Arg Ala Ile Ser Leu Asp Ile Asp Gly Thr Ile Thr Tyr
1               5                   10                  15

Arg Asp Arg Arg Leu Ser Ile Glu Ala Leu Lys Ala Ile Arg Leu Ala
                20                  25                  30

Glu Ser Leu Gly Val Pro Val Met Leu Val Thr Gly Asn Ser Val Pro
            35                  40                  45

Phe Ala Glu Ala Ala Ile Phe Ile Gly Thr Ser Gly Pro Val Ile
    50                  55                  60

Ala Glu Asp Gly Gly Ala Leu Ser Leu Lys Gly Lys Gly Thr Met Arg
65                  70                  75                  80

Lys Arg Val Phe Leu Thr Asp Met Asp Glu Glu Trp Ile Leu Trp Ser
                85                  90                  95

Glu Leu Lys Lys Arg Tyr Pro Lys Ala Glu Leu Ser Phe Ser Thr Met
            100                 105                 110

Glu Arg Lys Ala Gly Leu Val Ile Arg Arg Thr Ile Pro Val Glu Ala
        115                 120                 125

Val Arg Glu Ile Ile Arg Glu Leu Gly Leu Asn Leu Val Ala Val Asp
    130                 135                 140

Ser Gly Phe Ala Ile His Val Lys Lys Pro Trp Ile Asn Lys Gly Thr
145                 150                 155                 160

Gly Ile Glu Lys Ala Cys Glu Tyr Leu Gly Ile Ser Pro Lys Glu Val
                165                 170                 175

Ala His Val Gly Asp Gly Glu Asn Asp Leu Asp Ala Phe Arg Val Val
            180                 185                 190

Gly Tyr Arg Val Ala Ile Ala Gln Ala Pro Glu Ser Val Lys Glu Lys
        195                 200                 205

Ala Asp Tyr Val Thr Gln Lys Pro Tyr Gly Asp Gly Gly Ala Glu Ala
    210                 215                 220

Val Met His Ile Leu Arg Lys Phe Gly Tyr Leu Glu Glu
225                 230                 235

<210> SEQ ID NO 186
<211> LENGTH: 215
<212> TYPE: PRT
<213> ORGANISM: Thermocrinis minerva

<400> SEQUENCE: 186

Met Phe Lys Leu Val Ile Phe Asp Leu Asp Gly Thr Leu Ile Asp Ser
1               5                   10                  15

Cys Gln Asp Ile Thr Leu Cys Leu Asn Met Thr Leu Arg Asp Phe Gly
            20                  25                  30

Lys Pro Gln Val Glu Ser Gln Thr Val Arg Arg Tyr Ile Gly Ser Gly
        35                  40                  45

Ala Arg Ala Leu Leu Glu Lys Phe Phe Pro Pro Glu Asp Val Asp Lys
    50                  55                  60

Ala Leu Glu Val Phe Arg Gly Tyr Tyr Arg Gln His Pro Val Val Tyr
65                  70                  75                  80

Thr Arg Pro Tyr Glu Gly Ile Pro Glu Ala Leu Glu Phe Leu Arg Ser
                85                  90                  95

Lys Gly Val Ile Met Thr Val Val Thr Asn Lys Met Glu Glu Ile Ser
            100                 105                 110

Tyr Lys Ile Leu Asp Thr Leu Lys Leu Leu Asp Tyr Phe Ser Leu Val
        115                 120                 125

Val Gly Gly Asp Thr Tyr His Glu Lys Lys Pro Ser Ala Leu Pro Ile
    130                 135                 140

Ile Lys Thr Leu Glu Lys Phe Ser Val Lys Pro Lys Glu Ser Leu Ile
145                 150                 155                 160

Val Gly Asp Thr Glu Ala Asp Ile Leu Ser Gly Lys Arg Ala Ser Val
                165                 170                 175

Tyr Thr Ala Leu Ala Leu Trp Gly Tyr Thr Lys Asp Met Gln Glu Glu
            180                 185                 190

Pro Asp Phe Ile Leu Asn Thr Pro Thr Glu Ile Ile Glu Leu Trp Asn
        195                 200                 205

Ser Arg Ser Thr Ser Arg Val
    210                 215

<210> SEQ ID NO 187
<211> LENGTH: 404
<212> TYPE: PRT
<213> ORGANISM: Thermocrinis ruber

<400> SEQUENCE: 187

Met Glu Gly Gly Ser Phe Leu Asn Leu Ile Glu Ser Leu Asp Lys Phe
1               5                   10                  15

Ala Val Gly Ile Phe Arg Gln Phe Leu Ile Arg Glu Asp Thr Asp Lys
            20                  25                  30

Ile Leu Ile Leu Thr Pro Asn Glu Glu Tyr Lys Arg Trp Ala Ile Ala
        35                  40                  45

Tyr Leu Ser Thr Arg Leu Lys Gly Phe Gly Lys Lys Val Val Val Glu
    50                  55                  60

Cys Glu Gly Glu Arg Lys Glu Gln Lys Glu Ile Glu Ser Pro Lys Asp
65                  70                  75                  80

Asn Leu Leu Asp Lys Tyr Thr Phe Glu Asn Phe Val Val Gly Pro Ser
                85                  90                  95

Asn Glu Leu Ala Tyr Lys Val Cys Leu Glu Val Thr Lys Asn Pro Gly
            100                 105                 110

Lys Leu Phe Asn Pro Leu Phe Ile Tyr Gly Arg Ser Gly Leu Gly Lys

```
                115                 120                 125
Thr His Leu Leu His Ala Ile Gly Asn Gln Leu Lys Ala Arg Tyr Arg
    130                 135                 140

Val Leu Tyr Ile Pro Leu Met Asp Phe Ser Asp Ser Met Val Lys Ala
145                 150                 155                 160

Phe Lys Glu Asn Arg Val Glu Glu Phe Glu Arg Phe Phe Asn Leu
                165                 170                 175

Asp Val Leu Leu Leu Asp Asp Val Gln Phe Leu Val Gly Lys Glu Arg
                180                 185                 190

Thr Gln Ile Glu Leu Phe Arg Ile Tyr Glu Lys Leu Gln Ala Glu Glu
                195                 200                 205

Lys Gln Ile Val Leu Val Ser Asp Arg His Pro Arg Asp Leu Lys Asp
    210                 215                 220

Val Ser Glu Arg Leu Val Ser Arg Phe Glu Ser Gly Leu Ile Ile Glu
225                 230                 235                 240

Ile Gly Leu Asp Glu Glu Thr Lys Arg Arg Ile Ile Lys Gln Lys Leu
                245                 250                 255

Ile Leu Tyr Gly Leu Pro Leu Asp Gln Glu Thr Ile Asp Tyr Val Phe
                260                 265                 270

Glu Asn Thr Gly Tyr Asn Val Arg Glu Ile Glu Gly Phe Val Lys Thr
                275                 280                 285

Leu Lys Val Ser Gly Ile Lys Arg Leu Pro Lys Ser Glu Glu Leu Asp
    290                 295                 300

Lys Glu Lys Lys Val Gln Leu Ile Ile Asn Thr Val Ala Lys Gly Phe
305                 310                 315                 320

Lys Leu Asn Pro Glu Leu Leu Lys Lys Asp Thr Lys Glu Arg Arg Met
                325                 330                 335

Ile Asn Ala Arg His Ile Ala Met Phe Leu Cys Lys Thr Ile Leu Asn
                340                 345                 350

Leu Pro Tyr Ser Gln Ile Gly Glu Phe Phe Gly Lys Lys Asp His Thr
                355                 360                 365

Ala Val Met Tyr Ala Val Lys Lys Val Glu Gln Arg Cys Arg Glu Asp
    370                 375                 380

Arg Lys Phe Met Tyr Met Val Ser Phe Glu Lys Ser Ile Arg Lys
385                 390                 395                 400

Ser Leu Gly Leu

<210> SEQ ID NO 188
<211> LENGTH: 222
<212> TYPE: PRT
<213> ORGANISM: Thermoflexus hugenholtzii

<400> SEQUENCE: 188

Met Ser Arg Gly Pro Ala Phe Leu Phe Asp Leu Asp Gly Thr Leu Val
1               5                   10                  15

Asp Ser Val Tyr Gln His Val Leu Ala Trp Arg Glu Ala Leu Glu Ala
                20                  25                  30

Val Gly Ile Ser Leu Ser Val Trp Arg Ile His Arg Arg Ile Gly Met
            35                  40                  45

Ser Gly Gly Leu Leu Leu Arg Ala Leu Leu Arg Glu Thr Gly Arg Glu
        50                  55                  60

Val Thr Ser Glu Glu Val Gln Arg Ile Gln Gln Gln His Ala Glu Ala
65                  70                  75                  80

Phe Ala Arg Leu Leu Pro Gln Val Arg Pro Leu Pro Gly Ala Arg Glu
```

```
                    85                  90                  95
Leu Leu Glu Ala Leu Thr Arg Ala Gly Ile Pro Trp Ala Ile Ala Thr
                100                 105                 110

Ser Gly Arg Arg Asp Val Ala Arg Pro Leu Leu Glu Leu Leu Gly Val
            115                 120                 125

Asp Glu Gly Ile Pro Val Ile Thr Arg Glu Asp Val Pro Tyr Ala Lys
        130                 135                 140

Pro Asp Pro Asp Leu Phe Leu Ala Ala Ala Arg Leu Gly Ile Pro
145                 150                 155                 160

Ile Ala Glu Cys Ile Val Val Gly Asp Ser Val Trp Asp Leu Leu Ala
                165                 170                 175

Ala Arg Arg Ala Gly Ala Leu Ser Val Gly Leu Leu Ser Gly Gly Tyr
            180                 185                 190

Gly Arg Glu Glu Leu Glu Arg Ala Gly Ala Tyr Arg Val Tyr Glu Asp
        195                 200                 205

Pro Ala Asp Leu Leu Arg His Leu Asp Glu Val Gly Val Arg
210                 215                 220

<210> SEQ ID NO 189
<211> LENGTH: 255
<212> TYPE: PRT
<213> ORGANISM: Thermotoga lettingae

<400> SEQUENCE: 189

Met Asp Arg Met Asp Phe Ser Ile Lys Ile Ala Arg Lys Val Gly Leu
1               5                   10                  15

Tyr Leu Met Glu His Trp Gly Asn Ala Glu Asn Val Arg Gln Lys Ser
                20                  25                  30

Ser Phe Gln Asp Leu Val Ser Asp Cys Asp Lys Gln Ala Gln Lys Met
            35                  40                  45

Ile Val Gln Lys Ile Lys Asp His Phe Pro Asp Ala Ile Leu Ala
        50                  55                  60

Glu Glu Gly Leu Phe Glu Lys Gly Asp Arg Met Trp Ile Ile Asp Pro
65                  70                  75                  80

Ile Asp Gly Thr Met Asn Tyr Val His Gly Leu Pro Ser Phe Ala Ile
                85                  90                  95

Gly Ile Ala Tyr Val Glu Lys Glu Gln Val Ile Leu Gly Val Ala His
            100                 105                 110

Asp Pro Val Leu Asn Glu Thr Tyr Tyr Ala Ile Lys Gly Gln Gly Ala
        115                 120                 125

Tyr Lys Asn Gly Glu Arg Ile Asn Val Ser Glu Asn Ser Leu Leu Lys
130                 135                 140

Asp Ser Ile Gly Asn Thr Gly Phe Tyr Thr Asp Phe Thr Gly Ile Phe
145                 150                 155                 160

Ile Ser Ala Ile Glu Lys Lys Val Arg Arg Val Arg Met Thr Gly Ser
                165                 170                 175

Ala Ile Leu Ala Gly Ala Tyr Val Ala Cys Gly Arg Phe Asp Phe Phe
            180                 185                 190

Ile Ala Lys Arg Ala Asn Ser Trp Asp Val Ala Pro Leu Phe Val Leu
        195                 200                 205

Val Pro Glu Ala Gly Gly Ile Val Thr Asp Leu Ser Gly Asn Gln Ala
210                 215                 220

His Leu Asn Thr Gly Asn Phe Leu Phe Ser Asn Gly Leu Leu His Asp
225                 230                 235                 240
```

```
Gln Val Leu Glu Val Ile Arg Glu Val Asn Lys Lys Val Arg Lys
                245                 250                 255
```

<210> SEQ ID NO 190
<211> LENGTH: 201
<212> TYPE: PRT
<213> ORGANISM: Thermotoga neapolitana

<400> SEQUENCE: 190

```
Met Arg Leu Tyr Leu Ile Arg His Gly Glu Thr Ile Trp Asn Glu Lys
1               5                   10                  15

Gly Leu Trp Gln Gly Ile Ala Asp Val Pro Leu Asn Glu Lys Gly Lys
            20                  25                  30

Asp Gln Ala Lys Lys Leu Ala Glu Arg Leu Lys Arg Val Asp Ala Ile
        35                  40                  45

Tyr Ser Ser Pro Leu Lys Arg Cys Leu Glu Thr Ala Arg Glu Ile Ala
50                  55                  60

Glu Arg Phe Lys Lys Glu Val Ile Val Glu Glu Asp Leu Arg Glu Cys
65                  70                  75                  80

Glu Ile Ser Leu Trp Asn Gly Leu Thr Val Glu Glu Ala Met Arg Glu
                85                  90                  95

Tyr Pro Glu Glu Phe Lys Arg Trp Ser Thr Asp Pro Asn Phe Gly Thr
            100                 105                 110

Lys Gly Leu Glu Ser Met Lys Ser Val Gln Asp Arg Met Val Lys Val
        115                 120                 125

Met Met Lys Ile Val Ser Gln Glu Arg Leu Asn Gly Ser Glu Asp Val
    130                 135                 140

Val Ile Val Ser His Ser Leu Ser Leu Arg Ser Phe Ile Cys Trp Val
145                 150                 155                 160

Leu Gly Leu Pro Leu Arg Leu His Arg Asn Phe Lys Leu Asp Asn Ala
                165                 170                 175

Ser Leu Ser Ile Val Asp Val Glu Ser Arg Pro Arg Leu Val Leu Leu
            180                 185                 190

Asn Asp Thr Cys His Leu Glu Asp Thr
        195                 200
```

<210> SEQ ID NO 191
<211> LENGTH: 268
<212> TYPE: PRT
<213> ORGANISM: Thermotoga neapolitana

<400> SEQUENCE: 191

```
Met Tyr Arg Val Phe Val Phe Asp Leu Asp Gly Thr Leu Leu Asn Asp
1               5                   10                  15

Ser Leu Glu Ile Ser Glu Lys Asp Arg Lys Val Ile Gly Arg Leu Ser
            20                  25                  30

Arg Asn Cys His Val Val Phe Ala Ser Gly Arg Met Leu Val Ser Thr
        35                  40                  45

Leu Asn Val Glu Lys Arg Tyr Phe Lys Arg Thr Phe Pro Thr Ile Ala
50                  55                  60

Tyr Asn Gly Ala Met Val Tyr Leu Pro Glu Glu Gly Val Val Leu Asn
65                  70                  75                  80

Glu Lys Ile Pro Pro Glu Val Ala Lys Asp Ile Ile Glu Tyr Ile Lys
                85                  90                  95

Pro Leu Asn Val His Trp Gln Ala Tyr Ile Asp Asp Val Leu Tyr Ser
            100                 105                 110
```

```
Glu Lys Asp Asn Glu Ile Lys Ser Tyr Ala Arg His Ser Asn Val
        115                 120                 125

Asp Tyr Arg Val Glu Pro Asn Leu Ser Glu Leu Val Ser Lys Met Gly
    130                 135                 140

Thr Thr Lys Leu Leu Leu Ile Asp Thr Pro Glu Arg Leu Asp Glu Leu
145                 150                 155                 160

Lys Glu Ile Leu Ser Glu Arg Phe Lys Asp Val Val Lys Val Phe Lys
                165                 170                 175

Ser Phe Pro Thr Tyr Leu Glu Ile Val Pro Lys Asn Val Asp Lys Gly
            180                 185                 190

Lys Ala Leu Lys Phe Leu Arg Gly Arg Met Asn Trp Lys Lys Glu Glu
        195                 200                 205

Ile Val Val Phe Gly Asp Asn Glu Asn Asp Leu Phe Met Phe Glu Glu
    210                 215                 220

Ala Gly Leu Arg Val Ala Met Gly Asn Ala Ile Asp Lys Val Lys Glu
225                 230                 235                 240

Ala Ala Asp Val Val Thr Leu Thr Asn Asn Asp Ser Gly Val Ser Tyr
                245                 250                 255

Val Leu Glu Arg Ile Ser Thr Asp Cys Leu Asp Glu
            260                 265

<210> SEQ ID NO 192
<211> LENGTH: 201
<212> TYPE: PRT
<213> ORGANISM: Thermotoga neapolitana

<400> SEQUENCE: 192

Met Ile Arg Asn Ile Val Phe Asp Leu Gly Gly Val Leu Ile Asp Trp
1               5                   10                  15

Arg Pro Cys Glu Tyr Leu Val Glu Ser Phe Pro Glu Asp Val Ala Lys
            20                  25                  30

Val Leu Glu Arg Glu Ile Phe Lys His Glu Asp Trp Lys Lys Met Asp
        35                  40                  45

Arg Gly Thr Leu Pro Glu Asn Asp Leu Trp Glu Lys Lys Lys Lys Glu
    50                  55                  60

Leu Ser Glu Tyr Arg Glu Tyr Val Glu Lys Leu Glu Arg Glu Val Pro
65                  70                  75                  80

Lys Leu Leu Lys Pro Ile Glu Glu Asn Val Lys Leu Leu Ser Ile Leu
                85                  90                  95

Lys Glu Lys Asn Phe Lys Leu Tyr Val Leu Ser Asn Tyr Gly Lys Ile
            100                 105                 110

Tyr Phe Glu Met Val Arg Arg Tyr Arg Phe Phe Asp Phe Asp
        115                 120                 125

Gly Met Val Ile Ser Ser His Val Gly Phe Ile Lys Pro Glu Lys Glu
    130                 135                 140

Ile Tyr Leu Glu Leu Ile Arg Lys Tyr Lys Ile Thr Pro Lys Glu Ser
145                 150                 155                 160

Leu Phe Ile Asp Asp Met Glu Glu Asn Val Lys Ala Ala Glu Glu Leu
                165                 170                 175

Gly Phe Asn Thr Ile His Leu Pro Glu Pro Ser Arg Leu Lys Glu Leu
            180                 185                 190

Leu Phe Glu Thr Leu Lys Ile Gly Arg
        195                 200

<210> SEQ ID NO 193
```

```
<211> LENGTH: 564
<212> TYPE: PRT
<213> ORGANISM: Thermotoga neapolitana

<400> SEQUENCE: 193
```

| | | | | | | | | | | | | | | |
|---|---|---|---|---|---|---|---|---|---|---|---|---|---|---|
| Met | Leu | Leu | Arg | Ile | Ile | Pro | Ser | Asp | Arg | Ile | Ser | Ser | Thr | Glu | Val |
| 1 | | | | 5 | | | | | 10 | | | | | 15 | |

Lys Thr Leu Glu Arg Val Tyr Val Gly His Arg Asn Pro Asp Thr
                20                  25                  30

Asp Ser Val Cys Ser Ala Ile Gly Tyr Ala His Tyr Lys Ala Glu Val
        35                      40                  45

Glu Lys Lys Lys Gln Phe Ile Pro Ala Arg Cys Gly Glu Leu Thr Asn
50                      55                      60

Glu Ala Leu Phe Val Leu Asp Tyr Phe Lys Val Arg Pro Pro Ile Phe
65                      70                      75                  80

Leu Glu Thr Leu Glu Pro Thr Val Glu Asp Leu Glu Leu Lys Asp Pro
                85                      90                      95

Ile Phe Val Ser Pro Asp Thr Pro Val Tyr Asp Val Ala Met Leu Met
                100                     105                     110

Glu Gly Lys Gly Ile Lys Asn Val Pro Val Val Ser Arg Gly Lys Met
            115                     120                     125

Ile Gly Val Val Thr Glu Ser Asn Leu Ala Arg Val Tyr Val Arg Arg
        130                     135                     140

Leu Lys Ile Glu Pro Leu Val Ile His Pro Val Pro Leu Glu Gln Leu
145                     150                     155                     160

Val Arg Val Leu Lys Ala Glu Val Val Cys Asp His Leu Lys Glu Lys
                165                     170                     175

Thr Ile Ser Gly Lys Val His Ile Ala Val Asp Ala Leu His Val Leu
            180                     185                     190

Leu Gly Lys Ile Glu Ile Gly Asp Val Val Ile Val Gly Asp Asn Glu
        195                     200                     205

Pro Ser Gln Ile Ala Leu Leu Glu Lys Gly Ala Lys Leu Met Ile Ile
    210                     215                     220

Val Asn Asn Ala Pro Val Ser Ser Arg Val Leu Glu Ile Ala Lys Glu
225                     230                     235                     240

Lys Gly Ala Ala Val Leu Arg Val Lys Phe Asp Ala Phe Gly Ala Ala
                245                     250                     255

Lys Leu Ile Asn Leu Ala Leu Pro Val Thr Leu Val Met Ser Lys Lys
            260                     265                     270

Phe Pro Thr Val Thr Lys Arg Asp Thr Leu Glu Asp Val Lys Asn Ile
        275                     280                     285

Val Phe Thr Ser Lys Leu Arg Ala Ala Phe Val Glu Asp Glu Lys Gly
    290                     295                     300

Lys Leu Leu Gly Val Ile Thr Arg Thr Asp Leu Met Lys Asp Val Arg
305                     310                     315                     320

Lys Lys Val Ile Leu Val Asp His Asn Glu Ile Thr Gln Ala Pro Glu
                325                     330                     335

Gly Val Glu Lys Ala Glu Ile Leu Glu Ile Ile Asp His His Arg Leu
            340                     345                     350

Gly Gly Leu Ser Thr Leu Asn Pro Val Phe Phe Tyr Asn Glu Pro Val
        355                     360                     365

Gly Ser Thr Ser Thr Ile Val Thr Glu Phe Phe Leu Arg Asp Gly Val
    370                     375                     380

Lys Met Glu Arg Glu Ile Ala Gly Val Leu Leu Ala Gly Ile Val Ser

```
                    385                 390                 395                 400
Asp Thr Leu Phe Phe Lys Leu Ser Thr Thr Thr Glu Lys Asp Arg Ala
                        405                 410                 415

Met Ala Gly Phe Leu Ala Arg Ile Thr Lys Leu Asp Leu Glu Lys Phe
                        420                 425                 430

Ala Lys Lys Val Leu Lys Glu Gly Met Lys Ile Pro Glu Asn Val Asp
                435                 440                 445

Pro Leu Asp Leu Leu Lys Arg Asp Val Lys Val Tyr Glu Met Gly Glu
450                 455                 460

Glu Ser Phe Ala Val Ser Gln Ile Met Thr Ser Asp Phe Ser Val Leu
465                 470                 475                 480

Leu Lys Glu Lys Glu Lys Phe Ala Thr Ala Leu Lys Ser Leu Lys Gly
                    485                 490                 495

Glu Leu Gly Val Thr His Cys Phe Val Leu Phe Thr Asn Pro Ile Glu
                500                 505                 510

Glu Ala Ser Leu Val Met Val Glu Gly Asp Gln Arg Ile Leu Glu Lys
                515                 520                 525

Ala Phe Asp Gly Ala Glu Lys Lys Asp Gly Leu Phe Leu Leu Lys Gly
                530                 535                 540

Val Met Ser Arg Lys Lys Asp Phe Val Pro Arg Ile Gly Asp Ile Leu
545                 550                 555                 560

Arg Arg Glu Arg

<210> SEQ ID NO 194
<211> LENGTH: 136
<212> TYPE: PRT
<213> ORGANISM: Thermotoga neapolitana

<400> SEQUENCE: 194

Met Asp Thr Phe Leu Tyr His Ile Leu Ala Ile Asp Val Lys Gly Tyr
1               5                   10                  15

Val Asp Pro Ser Leu Pro Val Glu Glu Ile Val Lys Arg Leu Lys Glu
                20                  25                  30

Gln Asn Ala Leu Val Ile Ala Ala His Pro Asp Arg Lys Lys Gln Asp
            35                  40                  45

Glu Glu His Leu Ser Trp Phe Leu Trp Val Asn Met Glu Arg Phe Lys
        50                  55                  60

Asp Met Phe Asp Ala Trp Glu Val Ala Asn Arg Asp Asp Leu Phe Asn
65                  70                  75                  80

Ser Ile Gly Val Lys Lys Tyr Arg Tyr Val Ala Asn Ser Asp Phe His
                85                  90                  95

Glu Val Trp His Val Tyr Ser Trp Lys Thr Leu Ile Arg Ser Glu Arg
                100                 105                 110

Asn Val Glu Ala Ile Lys Glu Ala Ile Arg Lys Asn Thr Asp Val Ala
            115                 120                 125

Ile Tyr Leu Met Arg Glu Lys Thr
        130                 135

<210> SEQ ID NO 195
<211> LENGTH: 443
<212> TYPE: PRT
<213> ORGANISM: Thermotoga neapolitana

<400> SEQUENCE: 195

Met Asn Glu Arg Asp Ile Cys Arg Arg Ile Ser Glu Ile Leu Gly Ile
1               5                   10                  15
```

```
Asp Tyr Asp Cys Thr Arg Gly Ile Asp Glu Leu Leu Lys Ile Leu Glu
             20                  25                  30

Tyr Glu Ile Asn Glu Tyr Lys Lys Ser Leu Glu Glu Gln Thr Ile Phe
         35                  40                  45

Met Glu Ala Gln Leu Glu Leu Ser Arg Ser Tyr Glu Glu Ile Ser
 50                  55                  60

Thr Leu Glu Ile Ser Glu Ile Phe Gly Phe Glu Phe Pro Met
 65                  70                  75                  80

Asn Leu Arg Glu Lys Leu Glu Lys Val Ile Pro Leu Leu Lys Lys Val
                 85                  90                  95

Val Lys Phe Lys Asp Tyr Ile Val Arg Val Glu Asp Leu Ser Ile Gly
             100                 105                 110

Asn Met Ser His Glu Glu Val Glu Arg Glu Ile Glu Glu Arg Glu Lys
             115                 120                 125

Thr Val Leu Ile Glu Pro Gly Glu Ser Lys Lys Phe Ser Asn Leu Leu
 130                 135                 140

Phe Val Pro Ile Ile Gly Asn Arg Tyr Tyr Gly Tyr Met Cys Phe Ser
145                 150                 155                 160

Gly Lys Glu Glu Gly Ile Val Phe Thr Ala Ser Asp Arg Arg Ile Thr
                 165                 170                 175

Glu Val Thr Ser Arg Tyr Ile Ala Asn Ala Leu Asp Arg Ile Asp Phe
             180                 185                 190

Leu Gln Lys Glu Ile Glu Arg Gln Arg Leu Glu Glu Gln Met Glu Ile
             195                 200                 205

Ala Arg Arg Ile Gln Ser Glu Leu Leu Pro Arg Glu Leu Pro Arg Thr
 210                 215                 220

Gly Phe Ile Asp Ile Thr Ala Cys Ser Arg Pro Ala Val Gln Val Gly
225                 230                 235                 240

Gly Asp Tyr Tyr Asp Val Phe Ala Ser Asp Gly Lys Val Leu Ala Val
                 245                 250                 255

Met Gly Asp Val Ala Gly Lys Ser Val Pro Ala Ala Leu Leu Met Ser
             260                 265                 270

Ala Val Arg Ser Tyr Leu Lys Val Leu Ser Thr Ser His Ser Asp Leu
             275                 280                 285

Glu Asp Leu Val Asn His Leu Asn Ser Ile Leu Cys Glu Asp Leu Ser
 290                 295                 300

Asn Asp Arg Phe Val Thr Met Val Phe Leu Glu Ile Phe Gln Asn Gly
305                 310                 315                 320

Thr Leu Asn Leu Val Asn Ala Gly His Asn Pro Val Tyr Phe Leu His
                 325                 330                 335

Asp Gly Glu Ile Val Lys Leu Gly Ala Ser Ala Ile Pro Ile Gly Ile
             340                 345                 350

Ala Glu Trp Asn Tyr Arg Arg His Thr Ile Gln Leu Lys Pro Asn Thr
             355                 360                 365

Phe Ile Val Val Tyr Thr Asp Gly Ile Thr Glu Ala Arg Asn Thr Leu
 370                 375                 380

Gly Glu Glu Tyr Gly Tyr Glu Arg Leu Glu Glu Thr Leu Arg Glu Tyr
385                 390                 395                 400

Asn Gly Asp Ser Ala Glu Asp Leu Leu Ser Lys Leu Lys Lys Ser Val
                 405                 410                 415

Glu Glu Phe Ser Lys Asp Val Pro Gln His Asp Asp Met Thr Ile Met
             420                 425                 430
```

Val Leu Lys Tyr Lys Gly Gln Gln Glu Val Glu
        435                 440

<210> SEQ ID NO 196
<211> LENGTH: 266
<212> TYPE: PRT
<213> ORGANISM: Thermotoga neapolitana

<400> SEQUENCE: 196

Met Ile Ala Leu Leu Asp Met Gly Ser Asn Ser Phe Ile Leu Leu Ile
1               5                   10                  15

Val Ser Glu Glu Gly Glu Val Ile Leu Glu Val His Glu Val Gly
            20                  25                  30

Ile Ala Ser Gly Asn Leu Gln Arg Ala Lys Glu Val Phe Arg Glu Cys
            35                  40                  45

Val Arg Lys Ser Glu Glu Leu Gly Ala Asp Leu His Ile Phe Gly Thr
        50                  55                  60

Ala Phe Phe Arg Lys Asn Pro Asp Val Phe Tyr Glu Ile Thr Gly Gly
65                  70                  75                  80

Arg Gly Lys Ile Leu Ser Glu Glu Glu Ala Arg Tyr Ser Tyr Ile
                85                  90                  95

Ser Val Val Arg Asp Phe Gly Lys Glu Asp Ile Leu Val Ala Asp Leu
            100                 105                 110

Gly Gly Gly Ser Leu Glu Leu Ala Trp Lys Asp Gly Tyr Thr Ser Leu
        115                 120                 125

Glu Leu Gly Thr His Ile Leu Asn Arg Ile Phe Ser Leu Thr Leu Pro
    130                 135                 140

Phe Arg Lys Ser Val Asp Asp Val Val Glu Tyr Val Met Asp Lys Leu
145                 150                 155                 160

Pro Asp Leu Ala Lys Ser Asp Leu Phe Gly Val Gly Ser Phe Val
                165                 170                 175

Ala Leu Ala Ala Leu Met Lys Gly Lys Trp Asp Leu Lys Ser Ile His
            180                 185                 190

Gly Ser Thr Leu Glu Ile Glu Arg Val Gln Lys Ile Val Asp Gln Ile
        195                 200                 205

Arg Lys Met Ser Phe Glu Asp Ile Arg Lys Leu Lys Ile Leu Pro Glu
    210                 215                 220

Gly Arg Glu Lys Thr Ile Leu Ala Gly Gly Ile Val Thr Ile Ala Leu
225                 230                 235                 240

Leu Lys Lys Tyr Ser Pro Lys Met Thr Val Ser Thr Lys Gly Tyr Arg
                245                 250                 255

Tyr Gly Ile Ala Trp Glu Ile Met Val Gln
            260                 265

<210> SEQ ID NO 197
<211> LENGTH: 208
<212> TYPE: PRT
<213> ORGANISM: Thermotoga neapolitana

<400> SEQUENCE: 197

Met Glu Leu Ile Lys Leu Lys Lys Gly Gly Val Met Val Gly Thr Phe
1               5                   10                  15

Arg Ile Tyr Val Ala Thr Thr Asn Pro His Lys Val Glu Glu Ile Lys
            20                  25                  30

Glu Ile Ala Pro Glu Trp Ala Gly Ile Leu Pro Ser Pro Glu Lys Ile
        35                  40                  45

```
Glu Val Ile Glu Asp Gly Glu Thr Phe Leu Glu Asn Ser Val Lys Lys
 50                  55                  60

Ala Ile Val Tyr Gly Lys Lys Leu Lys Ser Pro Val Ile Ala Asp Asp
 65                  70                  75                  80

Ser Gly Leu Val Ile Tyr Ser Leu Gly Gly Phe Pro Gly Val Met Ser
                 85                  90                  95

Ala Arg Phe Met Glu Glu Tyr Thr Tyr Glu Glu Lys Met Lys Thr Ile
                100                 105                 110

Leu Lys Met Leu Glu Gly Lys Asp Arg Lys Ala Ala Phe Val Cys Ser
            115                 120                 125

Ala Thr Phe Phe Asp Phe Gln Arg Asn Leu Leu Val Ser Val Glu Asp
        130                 135                 140

Arg Val Glu Gly Tyr Ile Ala Glu Glu Ile Arg Gly Thr Gly Gly Phe
145                 150                 155                 160

Gly Tyr Asp Pro Phe Phe Val Pro Glu Gly Tyr Asp Arg Thr Phe Gly
                165                 170                 175

Glu Met Pro Glu Leu Lys Lys Lys Leu Ser His Arg Ser Arg Ala Phe
            180                 185                 190

Arg Lys Leu Phe Ser Ile Leu Ser Lys Ile Ser Glu Ser Glu Ser Leu
        195                 200                 205
```

<210> SEQ ID NO 198
<211> LENGTH: 436
<212> TYPE: PRT
<213> ORGANISM: Thermotoga neapolitana

<400> SEQUENCE: 198

```
Met Ile Gln Val Arg Arg Leu Ile Val Leu Val Leu Ala Leu Leu Leu
  1               5                  10                  15

Val Ala Phe Ser Phe Ser Gln Val Lys Asn Ile Ile Tyr Phe Ile Gly
                 20                  25                  30

Asp Gly Met Gly Leu Ser Gln Ala Tyr Leu Thr Ser Leu Ile Glu Gly
             35                  40                  45

Arg Pro Leu Ser Phe Met Lys Thr Pro Tyr Thr Gly Leu Val Lys Thr
 50                  55                  60

His Ser Val Asp Ser Trp Val Thr Asp Ser Ala Ala Gly Thr Ala
 65                  70                  75                  80

Leu Ala Ser Gly Phe Lys Thr Lys Asn Gly Met Ile Asn Val Leu Pro
                 85                  90                  95

Asp Gly Thr Arg Val Pro Thr Ile Phe Glu Ile Ala Lys Ala Tyr Gly
                100                 105                 110

Ala Lys Thr Gly Ile Val Val Thr Cys Arg Val Thr His Ala Thr Pro
            115                 120                 125

Ala Ala Phe Tyr Ala His Val Lys Ser Arg Ser Glu Glu Asn Glu Ile
        130                 135                 140

Ala Arg Gln Leu Val Glu Ser Glu Thr Val Asp Leu Val Met Gly Gly
145                 150                 155                 160

Gly Trp Ala Asn Phe Leu Pro Glu Ser Leu Gly Gly Lys Arg Ser Asp
                165                 170                 175

Gly Leu Asn Leu Ile Glu Met Ala Lys Lys Gly Tyr Val Tyr Val
            180                 185                 190

Thr Lys Lys Glu Asp Leu Met Lys Leu Pro Glu Asn Thr Glu Lys Val
        195                 200                 205

Leu Ala Leu Phe Ala Pro Ser His Leu Asp Pro Ala Ser Ser Arg Glu
    210                 215                 220
```

```
Glu Gln Pro Met Leu Tyr Glu Met Val Lys Lys Ala Leu Glu Ile Leu
225                 230                 235                 240

Ser Asn Asp Glu Glu Pro Phe Phe Leu Met Val Glu Gly Ser Gln Ile
            245                 250                 255

Asp Trp Glu Ala His Asp Asn Asp Ile Tyr Gly Val Trp Lys Glu Val
                260                 265                 270

Val Glu Phe Asp Arg Ala Val Gln Val Ala Leu Asp Phe Ala Leu Lys
            275                 280                 285

Arg Gly Asp Thr Leu Val Ile Val Thr Ala Asp His Glu Thr Gly Gly
            290                 295                 300

Leu Ala Leu Ser Ser Gly Asp Tyr Arg Val Asp Val Asp Arg Ile Arg
305                 310                 315                 320

Lys Phe Ser Lys Thr Thr Asp Trp Ile Leu Ala Asn Tyr Ser Leu Lys
                325                 330                 335

Asp Arg Glu Ser Phe Lys Lys Ala Ile Glu Lys Tyr Phe Gly Leu Thr
            340                 345                 350

Leu Ser Asp Ser Asp Leu Asp Arg Ile Thr Ser Ser Asn Asn Ser Lys
            355                 360                 365

Val Glu Leu Gly Arg Val Leu Ser Glu Lys Val Asn Val Gly Trp Thr
370                 375                 380

Thr Thr Ser His Ser Gly Val Pro Val Pro Ile Tyr Ala Phe Gly Pro
385                 390                 395                 400

Gly Ala Glu Asn Phe Thr Gly Phe Leu Asp Asn Thr Asp Ile Pro Arg
                405                 410                 415

Ile Met Met Lys Leu Ala Gly Tyr Ser Leu Gln Tyr Pro Leu Val Lys
            420                 425                 430

Glu Pro Val Lys
        435

<210> SEQ ID NO 199
<211> LENGTH: 174
<212> TYPE: PRT
<213> ORGANISM: Thermotoga neapolitana

<400> SEQUENCE: 199

Met Lys Ile Leu Ile Thr Gly Arg Pro Gly Val Gly Lys Thr Thr Leu
1               5                   10                  15

Ile Lys Lys Ile Ser Ser Leu Leu Gln Asn Ala Gly Phe Tyr Thr
                20                  25                  30

Glu Glu Met Arg Glu Lys Gly Lys Arg Val Gly Phe Lys Ile Val Thr
            35                  40                  45

Leu Asp Gly Arg Glu Gly Ile Leu Ala Lys Val Gly Phe Pro Ser Gln
50                  55                  60

His Arg Val Gly Lys Tyr Gly Val Asn Leu Lys Asp Leu Glu Glu Leu
65                  70                  75                  80

Gly Val Asp Ser Val Glu Arg Ala Leu Glu Lys Ser Val Val Ile
            85                  90                  95

Ile Asp Glu Ile Gly Lys Met Glu Leu Leu Ser Glu Arg Phe Lys Arg
            100                 105                 110

Val Val Glu Lys Ala Phe Asn Ser Glu Lys Asp Leu Ile Ala Thr Ile
            115                 120                 125

Lys Lys Ser Ser Asp Pro Phe Val Glu Lys Ile Lys Asn Lys Lys Asp
130                 135                 140

Val Ile Ile Phe Glu Leu Asn Glu Arg Asn Arg Asp Leu Leu Leu Lys
```

```
                145                 150                 155                 160
Arg Ile Leu Asp Met Leu Lys Ser Asn Arg Gly Val Gly Glu
                    165                 170

<210> SEQ ID NO 200
<211> LENGTH: 508
<212> TYPE: PRT
<213> ORGANISM: Thermotoga neapolitana

<400> SEQUENCE: 200

Met Arg Arg Tyr Leu Val Leu Phe Val Leu Leu Ser Val Phe
1               5                   10                  15

Leu Leu Gly Val Arg Leu Thr Ile Leu His Val Asn Asp Thr His Gly
                20                  25                  30

His Ala Trp Thr Phe Asp Glu Tyr Gln Asn Pro Gly Ile Gly Gly Leu
            35                  40                      45

Ala Ala Ile Ala Thr Ile Val Glu Val Lys Arg Glu Val Glu Glu
        50                  55                  60

Gln Gly Gly Tyr Val Ile Phe Leu His Ala Gly Asp Leu Asn Thr Gly
65                      70                  75                  80

Val Pro Glu Ser Asp Leu Gln Asp Ala Ile Pro Asp Ile Val Gly Tyr
                    85                  90                  95

Asn Met Ile Gly Leu Ser Ala Met Ala Val Gly Asn His Glu Phe Asp
                    100                 105                 110

Asn Pro Arg Asp Val Leu Leu Lys Gln Met Lys Phe Ala Asp Phe Pro
                115                 120                 125

Phe Leu Ser Ala Asn Ile Leu Lys Glu Asn Gly Glu Pro Phe Phe Thr
    130                 135                 140

Pro Tyr Ile Leu Lys Asp Phe Gly Lys Leu Lys Val Ala Ile Ile Gly
145                 150                 155                 160

Phe Thr Thr Glu Glu Thr Thr Ile Leu Glu Pro Leu Tyr Leu Glu Asp
                    165                 170                 175

Leu Lys Phe Glu Asn Ala Leu Lys Val Ala Gln Lys Ile Ala Pro Glu
                180                 185                 190

Leu Lys Asn Gln Ala Asp Val Val Ile Ala Leu Ala His Leu Asp Trp
            195                 200                 205

Gly Glu Pro Lys Lys Glu Asn Ile Thr Thr Thr His Gln Leu Ala Lys
    210                 215                 220

Val Asp Gly Ile Asp Val Val Ala Gly His Ser His Val Leu Gly
225                 230                 235                 240

Ser Glu Val Val Asp Glu Lys Ile Ile Val Ser Ala Gly Glu Tyr Gly
                    245                 250                 255

Lys Tyr Val Gly Arg Leu Asp Leu Asp Ile Glu Asp Gly Lys Ile Val
                260                 265                 270

Ala Trp His Trp Gln Ala Ile Pro Val Asn Leu Lys Ala Tyr Arg Asp
            275                 280                 285

Gly Lys Tyr Glu Tyr Val Gly Lys Pro Tyr Leu Glu Asn Arg Tyr Val
    290                 295                 300

Ala Lys Ala Leu Glu Tyr Phe Arg Lys Val Gly Asn Glu Lys Leu Asp
305                 310                 315                 320

Thr Val Ile Gly Glu Thr Lys Ile Phe Leu Asp Gly Glu Arg Glu His
                    325                 330                 335

Val Arg Ser Arg Asn Thr Asn Leu Thr Asn Leu Ile Thr Asp Ala Met
                340                 345                 350
```

-continued

Arg Trp Lys Val Lys Ala Asp Ile Ala Leu Thr Asn Gly Glu Gly Ile
         355                 360                 365

Arg Ala Ser Ile Lys Pro Gly Lys Ile Thr Val Arg Asp Ile Leu Thr
    370                 375                 380

Val Leu Pro Phe Gly Asn Thr Leu Tyr Val Leu Glu Leu Thr Gly Glu
385                 390                 395                 400

Gln Ile Met Lys Val Leu Glu Tyr Ser Ala Thr Ile Pro Glu Gly Lys
                405                 410                 415

Gly Ala Phe Leu Gln Val Ser Gly Leu Thr Trp Lys Ser Lys Asp Gly
            420                 425                 430

Lys Val Val Glu Val Leu Val Asn Gly Glu Pro Leu Asp Pro Lys Lys
        435                 440                 445

Thr Tyr Arg Val Val Thr Asn Asn Tyr Met Ala Gly Gly Asp Gly
    450                 455                 460

Tyr Thr Met Leu Lys Glu Trp Gly Gly Tyr Asp Thr Gly Phe Leu Met
465                 470                 475                 480

Ser Asp Ala Val Ile Glu Tyr Ile Gln Asn Val Leu Asn Gly Val Ile
                485                 490                 495

Glu Glu Tyr Asp Asn Ser Gln Arg Tyr Val Arg Glu
            500                 505

<210> SEQ ID NO 201
<211> LENGTH: 154
<212> TYPE: PRT
<213> ORGANISM: Thermotoga neapolitana

<400> SEQUENCE: 201

Met Asp Ala Lys Ile Val Asn Ala Leu Ile Gly Ser Val Tyr Glu Thr
1               5                   10                  15

Ile Lys Ser Val Leu Arg Val Glu Pro Lys Leu Gly Lys Pro Ser Ala
            20                  25                  30

Val Ser His Ile Glu Ile Pro His Ser Val Val Thr Val Ile Gly Val
        35                  40                  45

Thr Gly Ser Ile Glu Gly Ser Leu Ile Tyr Ser Phe Ser Ser Glu Thr
    50                  55                  60

Ala Leu Lys Val Val Ser Ala Met Met Gly Met Glu Tyr Gly Gln Leu
65                  70                  75                  80

Asp Glu Leu Ala Met Ser Ala Ile Gly Glu Leu Gly Asn Met Thr Ala
                85                  90                  95

Gly Lys Leu Ala Met Lys Leu Glu Thr Leu Gly Lys His Val Asp Ile
            100                 105                 110

Thr Pro Pro Thr Val Val Ser Gly Lys Asp Leu Lys Ile Lys Ser Phe
        115                 120                 125

Gly Thr Val Leu Lys Leu Pro Ile Ser Val Phe Ser Asn Glu Asp Phe
    130                 135                 140

Asp Leu His Leu Ser Val Lys Ser Gly Gly
145                 150

<210> SEQ ID NO 202
<211> LENGTH: 333
<212> TYPE: PRT
<213> ORGANISM: Thermotoga neapolitana

<400> SEQUENCE: 202

Met Lys Glu Ile Val Asp Ala Ile Ser Gln Tyr Asn Arg Ile Leu Val
1               5                   10                  15

Val Gly His Ile Met Pro Asp Gly Asp Cys Val Ser Val Leu Ser
            20                  25                  30

Leu Thr Leu Gly Leu Glu Arg Ile Gly Lys Glu Val Arg Ala Ala Ile
            35                  40                  45

Asp Tyr Arg Val Pro Tyr Val Phe Glu Asn Phe Pro His Ile Glu Arg
 50                  55                  60

Ile Glu Gln Asn Val Asp Phe Glu Pro Glu Leu Val Ile Val Val Asp
65                  70                  75                  80

Ala Ser Ser Pro Asp Arg Ile Gly Arg Phe Gln Asp Leu Leu Lys Glu
                85                  90                  95

Val Pro Ser Ala Val Ile Asp His His Ser Thr Asn Val Leu Phe Gly
            100                 105                 110

Lys Trp Asn Trp Val Asp Pro Ser Phe Ala Ala Thr Ala Gln Met Val
            115                 120                 125

Phe Arg Leu Asn Arg Lys Leu Gly Val Glu Tyr Asp Pro Val Leu Ala
            130                 135                 140

Thr Leu Asn Tyr Leu Gly Ile Ala Thr Asp Thr Gly Phe Phe Arg His
145                 150                 155                 160

Ser Asn Thr Asp Ala Arg Val Phe Glu Asp Ala Tyr Glu Leu Val Lys
                165                 170                 175

Ile Gly Ala Asp Ala His Phe Val Ala Lys Glu Ile Leu Glu Asn Lys
            180                 185                 190

Arg Phe Glu Gln Phe Lys Leu Phe Ala Glu Val Leu Glu Arg Leu Gln
            195                 200                 205

Leu Leu Glu Asn Gly Arg Ile Ala Tyr Ser Tyr Ile Asp Tyr Asp Thr
210                 215                 220

Tyr Leu Arg His Asn Cys Thr Asp Glu Asp Ser Ala Gly Phe Val Gly
225                 230                 235                 240

Glu Leu Arg Ser Ile Arg Gly Val Glu Val Ala Val Leu Phe Met Glu
                245                 250                 255

Phe Pro Lys Gly Lys Ile His Val Ser Met Arg Ser Lys Asp Trp Phe
            260                 265                 270

Asn Val Asn Glu Val Ala Phe Glu Leu Gly Gly Gly His Pro Arg
            275                 280                 285

Ala Ala Gly Val Thr Phe Glu Gly Glu Lys Leu Glu Asn Val Ile Ser
290                 295                 300

Arg Val Ile Asp His Leu Leu Gly Arg Phe Lys Gly Val Ser Arg
305                 310                 315                 320

Glu Gly Glu Lys Thr Ser Gln Arg Ser Val Leu Gly Arg
                325                 330

<210> SEQ ID NO 203
<211> LENGTH: 295
<212> TYPE: PRT
<213> ORGANISM: Thermotoga neapolitana

<400> SEQUENCE: 203

Met Ile Leu Arg Arg Arg Gly Ile Val Leu Ser Phe His Ser Asn Met
1               5                   10                  15

Val Thr Val Glu Asp Glu Thr Gly Glu Arg Leu Leu Cys Lys Leu
            20                  25                  30

Arg Gly Lys Phe Arg Leu Gln Asn Leu Lys Ile Tyr Val Gly Asp Arg
            35                  40                  45

Val Glu Tyr Thr Pro Asp Gly Thr Gly Ser Gly Val Ile Glu Asn Val
50                  55                  60

```
Leu His Arg Lys Asn Leu Leu Val Lys Pro His Val Ala Asn Val Asp
 65                  70                  75                  80

Gln Ala Ile Leu Val Thr Val Lys Met Pro Glu Thr Ser Thr Tyr
                 85                  90                  95

Ile Ile Asp Lys Phe Leu Val Leu Thr Glu Lys Asn Glu Leu Glu Thr
                100                 105                 110

Val Leu Val Ile Asn Lys Met Asp Ile Tyr Asp Glu Asp Leu Glu
            115                 120                 125

Lys Val Lys Glu Leu Glu Arg Ile Tyr Ser Lys Leu Tyr Pro Ile Val
130                 135                 140

Lys Thr Ser Ala Lys Thr Gly Met Gly Ile Glu Glu Leu Lys Lys Tyr
145                 150                 155                 160

Leu Lys Gly Lys Ile Ser Thr Met Ala Gly Leu Ser Gly Val Gly Lys
                165                 170                 175

Ser Ser Leu Leu Asn Ala Ile Asn Pro Gly Leu Lys Leu Arg Val Ser
            180                 185                 190

Glu Val Ser Gln Lys Leu Gln Arg Gly Arg His Thr Thr Thr Ser Ala
            195                 200                 205

Gln Leu Leu Arg Phe Asp Phe Gly Gly Tyr Val Val Asp Thr Pro Gly
210                 215                 220

Phe Ala Asn Leu Glu Ile Gly Asp Ile Glu Pro Glu Glu Leu Lys Tyr
225                 230                 235                 240

Tyr Phe Lys Glu Phe Asn Glu Lys Gln Cys Phe Ser Asp Cys Asn
                245                 250                 255

His Ile Asp Glu Pro Glu Cys Gly Val Lys Glu Ala Val Glu Asn Gly
            260                 265                 270

Glu Ile Ala Glu Ser Arg Tyr Glu Asn Tyr Val Lys Met Phe His Glu
            275                 280                 285

Leu Leu Gly Arg Gly Lys Ser
    290                 295

<210> SEQ ID NO 204
<211> LENGTH: 528
<212> TYPE: PRT
<213> ORGANISM: Thermotoga neapolitana

<400> SEQUENCE: 204

Met Lys Lys Ile Thr Gly Arg Phe Leu Lys Thr Ile Ile Lys Lys Ala
1               5                  10                  15

Thr Glu Asn Leu Leu Lys His Lys Asp Glu Ile Asn Ala Leu Asn Val
            20                  25                  30

Phe Pro Val Pro Asp Gly Asp Thr Gly Ser Asn Met Cys Ser Thr Met
        35                  40                  45

Leu Glu Ala Cys Lys Tyr Ile Asp Asn Leu Lys Ser Asp Asp Leu Ser
 50                  55                  60

Glu Val Trp Lys Ala Ile Lys Glu Gly Ala Leu Met Gly Ala Arg Gly
 65                  70                  75                  80

Asn Ser Gly Val Ile Leu Ser Gln Ile Leu Arg Gly Leu Ala Asp Ala
                 85                  90                  95

Ser Pro Glu Asn Tyr Ile Thr Pro Gly Asp Phe Ile Lys Met Ile Ser
                100                 105                 110

Asn Ala Arg Lys Val Ala Tyr Ser Ala Val Met Arg Pro Val Glu Gly
            115                 120                 125

Thr Met Leu Thr Val Val Arg Glu Leu Asp Glu Lys Leu Lys Gly Arg
```

```
                130                 135                 140
Ser Phe Glu Thr Phe Glu Leu Phe Asp Gln Ile Val Glu Met Ile
145                 150                 155                 160

Lys Asp Thr Val Asn Arg Thr Pro Ser Met Leu Ser Lys Leu Arg Glu
                165                 170                 175

Ala Gly Val Val Asp Ala Gly Ala Lys Gly Leu Tyr Tyr Leu Phe Glu
                180                 185                 190

Gly Met Arg Asp Ala Ile Lys Gly Asp Ile Glu Val Asn Leu Glu Gln
            195                 200                 205

Val Glu Gln Ala Ser Val Glu Asp Leu Lys Arg Met Ala Leu Glu Glu
    210                 215                 220

Ile Thr Asn Gln Tyr Cys Thr Glu Val Ala Val Arg Arg Lys Arg Val
225                 230                 235                 240

Phe Glu Lys Ser Glu Leu Glu Ser Phe Leu Asn Glu Ile Gly Asp Ser
                245                 250                 255

Val Val Leu Val Glu Gln Asp Asp Ile Phe Arg Leu His Val His Thr
                260                 265                 270

Asn His Pro Gly Gln Val Leu Glu Lys Val Leu Asp Phe Gly Glu Ile
            275                 280                 285

Ile Lys Val Lys Val Asp Asn Met Lys Leu Gln His Glu His Ile Ile
    290                 295                 300

Ser Ala Gln Val Glu Lys Glu Ile Gly Val Val Ala Val Ser Pro Gly
305                 310                 315                 320

Lys Gly Ile Ser Glu Ile Leu Lys Ser Leu Gly Val Asp Glu Ile Val
                325                 330                 335

Pro Gly Gly Gln Thr Met Asn Pro Ser Phe Ala Asp Leu Lys Ala Ala
                340                 345                 350

Val Asp Lys Thr His Ala Lys Val Val Phe Leu Phe Pro Asn Asn Ala
            355                 360                 365

Asn Val Leu Leu Thr Ala Lys Gln Val Ala Glu Ser Val Asp Asp Lys
    370                 375                 380

Arg Val Ile Val Gln Thr Ser His Val Gln Glu Cys Val Ala Ala
385                 390                 395                 400

Met Val Glu Tyr Asp Pro Asp Glu Asp Pro Glu Leu Lys Arg Arg
                405                 410                 415

Phe Glu Glu Ala Ile Asn Gln Cys Val Pro Ile Ser Ile Thr Arg Ala
                420                 425                 430

Val Arg Asp Ser Arg Tyr Gly Lys Arg Ile Arg Lys Gly Glu Tyr
            435                 440                 445

Leu Val Phe Val Arg Lys Glu Leu Leu Ala His Gly Phe Asn Leu Val
    450                 455                 460

Lys Ala Leu Lys Asp Val Leu Glu Lys Glu Asn Ala Arg Glu Lys Glu
465                 470                 475                 480

Ile Leu Thr Val Phe Leu Gly Asp Asn Tyr Arg Lys Ala Glu Leu Glu
                485                 490                 495

Lys Ile Gln Asn Leu Ile Gly Glu Glu Phe Pro Asn Leu Asp Leu Glu
                500                 505                 510

Ile His Glu Gly Gly Gln Pro His Tyr Pro Phe Leu Met Leu Leu Gln
            515                 520                 525

<210> SEQ ID NO 205
<211> LENGTH: 263
<212> TYPE: PRT
<213> ORGANISM: Thermotoga neapolitana
```

<400> SEQUENCE: 205

```
Met Glu Gly Gly Ile Glu Leu Asp Arg Leu Asp Phe Ser Ile Lys Leu
1               5                   10                  15

Leu Arg Arg Val Gly His Phe Leu Met Leu His Trp Gly Lys Val Asp
            20                  25                  30

Ser Val Glu Lys Lys Thr Gly Phe Lys Asp Ile Val Thr Glu Ile Asp
        35                  40                  45

Lys Lys Ala Gln Glu Met Ile Val Glu Glu Ile Arg Lys Val Phe Pro
50                  55                  60

Asp Glu Asn Ile Ile Ala Glu Glu Gly Ile Ser Glu Asn Gly Lys Lys
65                  70                  75                  80

Leu Trp Ile Ile Asp Pro Ile Asp Gly Thr Ile Asn Phe Val His Gly
                85                  90                  95

Leu Pro Asn Phe Ser Ile Ser Ile Ala Tyr Val Glu Asn Gly Glu Val
            100                 105                 110

Lys Met Gly Val Val His Ala Pro Ala Leu Asn Glu Thr Leu Tyr Ala
        115                 120                 125

Glu Glu Asn Gly Gly Ala Phe Leu Asn Gly Glu Arg Ile Arg Val Ser
130                 135                 140

Gly Asn Thr Ser Leu Glu Glu Cys Val Gly Ser Thr Gly Ser Tyr Val
145                 150                 155                 160

Asp Phe Thr Gly Lys Phe Ile Glu Lys Met Glu Lys Lys Thr Arg Arg
                165                 170                 175

Val Arg Ile Leu Gly Ser Ala Ala Leu Asn Ala Cys Tyr Val Gly Ala
            180                 185                 190

Gly Arg Val Asp Phe Phe Val Thr Trp Arg Ile Asn Pro Trp Asp Ile
        195                 200                 205

Ala Ala Gly Leu Ile Val Val Lys Glu Ala Gly Gly Thr Val Thr Asp
210                 215                 220

Phe Ala Gly Lys Glu Ala Asn Val Phe Ser Lys Asn Phe Val Phe Ser
225                 230                 235                 240

Asn Gly Leu Val His Glu Glu Val Leu Glu Val Val Asn Glu Val Leu
                245                 250                 255

Lys Glu Ile Gly Glu Gly Lys
            260
```

<210> SEQ ID NO 206
<211> LENGTH: 90
<212> TYPE: PRT
<213> ORGANISM: Thermotoga neapolitana

<400> SEQUENCE: 206

```
Met Lys Ala Leu Lys Ile Arg Val Glu Gly Ile Val Gln Gly Val Gly
1               5                   10                  15

Phe Arg Tyr Phe Thr Arg Arg Ile Ala Arg Thr Leu Gly Ile Lys Gly
            20                  25                  30

Tyr Val Met Asn Met Asp Asp Gly Ser Val Phe Ile His Ala Glu Gly
        35                  40                  45

Glu Glu Glu Lys Leu Arg Arg Phe Leu Asn Val Ser Lys Gly Pro
50                  55                  60

Pro Ala Ala Val Val Thr Asn Ile Ser Val Glu Glu Thr Ser Pro Glu
65                  70                  75                  80

Gly Tyr Glu Asp Phe Ala Ile Arg Tyr Tyr
                85                  90
```

<210> SEQ ID NO 207
<211> LENGTH: 401
<212> TYPE: PRT
<213> ORGANISM: Thermotoga neapolitana

<400> SEQUENCE: 207

```
Met Leu Ser Phe Phe Cys Glu Thr Pro Phe Gln Ile Leu Pro Tyr Gly
1               5                   10                  15

Lys Glu Glu Leu Asp Ser Met Gln Leu Glu Arg Leu Asp Glu Gly Leu
            20                  25                  30

Phe Tyr Pro His Tyr Asn Gly Tyr Ser Ile Val Asn Phe Ser Asn Thr
        35                  40                  45

Ile Leu Ser Ile Phe Gly Glu Lys Thr Leu His Arg Pro Phe Pro Leu
50                  55                  60

Pro Glu Arg Phe Leu Glu Asn Val Arg Lys Val Val Leu Val Val
65                  70                  75                  80

Asp Ala Leu Ser Tyr Asp Val Phe Ser Asn Thr Ile Gln Asp Asp
                85                  90                  95

Val Gln Val Phe Pro Cys Ser Ser Val Phe Pro Thr Thr Ala Ala
            100                 105                 110

Ala Leu Pro Ser Leu Tyr Ser Gly Leu Thr Pro Leu Glu His Gly Phe
        115                 120                 125

Leu Gly Tyr Ile Leu Tyr Leu Arg Glu Val Gly Ser Pro Val Asn Met
130                 135                 140

Ile Glu Met Ala Pro Pro Gly Phe Pro Arg Glu Ser Val Leu Arg Ile
145                 150                 155                 160

His Glu Phe Arg Phe Thr Thr Ile Phe Gln Arg Leu Lys Val Arg Ser
                165                 170                 175

Phe Phe Leu Val Pro Arg Tyr Leu Leu Gly Thr Gly Phe Ser Arg Leu
            180                 185                 190

Met Ser Gln Gly Ala Glu Gln Ile Gly Phe Ser Ser Phe Gly Asp Met
        195                 200                 205

Ile Glu Lys Thr Leu Glu Ile Leu Ala Asn Gln Glu Thr Val Leu Val
210                 215                 220

Phe Ala Tyr Trp Pro Ser Leu Asp Ser Ile Ala His Lys Ser Gly Val
225                 230                 235                 240

Gly Arg Ala Tyr Phe Arg Glu Leu Lys Trp Leu Tyr Arg Ile Leu Lys
                245                 250                 255

Glu Glu Leu Ile Arg Arg Leu Lys Ser Asp Thr Leu Phe Phe Met Val
            260                 265                 270

Ser Asp His Gly Gln Ile Ser Thr Pro Pro Glu Arg Glu Val Trp Trp
        275                 280                 285

Asp Ser Phe Ser Glu Val Met Arg Phe Leu Asp Arg Pro Pro Ala Gly
290                 295                 300

Glu Gln Arg Met Met Tyr Leu Tyr Thr Lys Arg Lys Ala Leu Val
305                 310                 315                 320

Glu Tyr Leu Val Glu Lys Tyr Ala Asp Phe Ala Ile Phe Ile Asp Ala
                325                 330                 335

Arg Arg Ala Thr Arg Leu Phe Gly Ile Gly Lys Ser His Pro Glu Phe
            340                 345                 350

Phe His Arg Ile Gly Asp Leu Ile Leu Ile Thr Lys Glu Asn Phe Ser
        355                 360                 365

Phe Asn Tyr Arg Tyr Thr Gly Lys Glu Glu Ser Leu Ser Gly Arg His
```

```
                370                 375                 380
Gly Ser Leu Thr His Gln Glu Leu Val Val Pro Leu Val Val Tyr Arg
385                 390                 395                 400

Arg

<210> SEQ ID NO 208
<211> LENGTH: 229
<212> TYPE: PRT
<213> ORGANISM: Thermotoga neapolitana

<400> SEQUENCE: 208

Met Lys Ala Asp Leu His Val His Thr Cys Leu Ser Pro Cys Ala Asp
1               5                   10                  15

Leu Leu Met Ile Pro Pro Val Ile Glu Lys Ala Glu Val Asp Ile Leu
            20                  25                  30

Gly Ile Val Asp His Asn Ser Ala Arg Asn Ala Leu Ala Phe Ser Lys
        35                  40                  45

Met Lys Lys Leu Val Ile Pro Gly Val Glu Ile Gln Thr Val Glu Asp
50                  55                  60

Val His Leu Leu Gly Phe Phe Val Asn Phe Glu Asp Ala Leu Lys Leu
65                  70                  75                  80

Thr Glu Val Leu Tyr Glu His Leu Pro Arg Leu Lys His Asp His Glu
                85                  90                  95

Lys Met Gly Tyr Gln Leu Leu Val Asn Glu Asp Gly Asp Tyr Ile Gly
            100                 105                 110

Tyr Glu Asn Met Pro Leu Gly Phe Pro Ala Asn Leu Thr Ile Ser Gln
        115                 120                 125

Ala Val Asp Leu Val Leu Ser Phe Arg Gly Val Pro Ala Tyr Ala His
130                 135                 140

Val Glu Arg Arg Phe Gly Val Leu Tyr Gln Leu Gly Phe Phe Pro Asn
145                 150                 155                 160

Leu Asp Val Pro Val Ala Glu Val Val Ser Glu Glu Gly Arg Ser Lys
                165                 170                 175

Ala Glu Gly Arg Phe Arg Val Ile Val Ser Ser Asp Ala His Phe Pro
            180                 185                 190

Asp Glu Val Gly Arg Arg Tyr Ile Glu Leu Lys Gly Lys Pro Asp Ser
        195                 200                 205

Pro Lys Lys Val Leu Asp Gln Ile Leu Ala Gly Glu Tyr Thr Leu Gly
210                 215                 220

Gly Val Leu Asp Trp
225

<210> SEQ ID NO 209
<211> LENGTH: 122
<212> TYPE: PRT
<213> ORGANISM: Thermotoga neapolitana

<400> SEQUENCE: 209

Met Leu Asp Val Trp Lys Ile Phe Arg Ser Thr Pro Phe Thr Thr Ala
1               5                   10                  15

Val Val Ser Phe Leu Val Ala Gln Phe Ile Lys Phe Leu Ile Lys Arg
            20                  25                  30

Asp Val Lys Met Leu Lys Ser Tyr Gly Gly Met Pro Ser Gly His Val
        35                  40                  45

Ala Thr Val Ser Gly Leu Ala Trp Ser Leu Ala Arg Ser Thr Gly Phe
50                  55                  60
```

Asp Ser Pro Tyr Thr Ser Ile Ala Ser Ile Phe Leu Val Ile Ile Phe
65                  70                  75                  80

Met Asp Ala Ile Val Leu Arg Pro Ala Val Lys Lys Asp Leu Gly His
                85                  90                  95

Ser Phe Leu Glu Ala Leu Ala Gly Phe Gly Leu Gly Met Leu Ile Ala
            100                 105                 110

His Leu Phe Pro Ala Arg Leu His Leu Trp
        115                 120

<210> SEQ ID NO 210
<211> LENGTH: 181
<212> TYPE: PRT
<213> ORGANISM: Thermotoga neapolitana

<400> SEQUENCE: 210

Met Thr Val Lys Phe Tyr Glu Gln Lys Ile Glu Ser Lys Arg Val Phe
1               5                   10                  15

Glu Gly Lys Met Ile Ser Val Arg Val Asp Arg Val Arg Leu Pro Asn
            20                  25                  30

Gly Glu Glu Ser Thr Arg Glu Val Val Asp His Pro Gly Ala Val Val
        35                  40                  45

Ile Val Pro Val Leu Gly Glu Ile Ile Phe Val Glu Gln Tyr Arg
    50                  55                  60

Tyr Pro Ile Glu Gln Met Leu Leu Glu Leu Pro Ala Gly Lys Met Asp
65                  70                  75                  80

Pro Gly Glu Ser Pro Glu Glu Cys Ala Lys Arg Glu Leu Glu Glu Glu
                85                  90                  95

Thr Gly Tyr Arg Ala Lys Arg Phe Ser Tyr Leu Gly Lys Ile Phe Thr
            100                 105                 110

Thr Pro Gly Phe Thr Thr Glu Val Ile His Ile Phe Ala Ala Glu Glu
        115                 120                 125

Leu Glu Lys Thr Thr Gln Asn Thr Asp Pro Asp Glu Phe Ile Glu Val
    130                 135                 140

Lys Lys Ile Pro Val Glu Lys Val Leu Ser Leu Leu Arg Asn Ala Glu
145                 150                 155                 160

Ile Glu Asp Ser Lys Thr Ile Cys Ala Leu Thr Arg Tyr Phe Leu Ser
                165                 170                 175

Lys Gly Val Ile Gly
            180

<210> SEQ ID NO 211
<211> LENGTH: 224
<212> TYPE: PRT
<213> ORGANISM: Thermotoga neapolitana

<400> SEQUENCE: 211

Met Lys Lys Ala Val Leu Phe Asp Leu Asp Gly Thr Ile Leu Asp Phe
1               5                   10                  15

Glu Lys Ser Glu Glu Thr Ala Leu Lys Lys Thr Phe Leu Arg His Gly
            20                  25                  30

Ile Pro Leu Thr Glu Glu Gln Val Leu Leu Tyr Lys Ser Ile Asn Arg
        35                  40                  45

Lys Trp Trp Lys Met Leu Ala Glu Lys Val Ser Lys Glu Glu Val
    50                  55                  60

Val Val Ala Arg Phe Glu Glu Phe Leu Gly Ile Gly Ser Leu Leu
65                  70                  75                  80

```
Asp Pro Glu Glu Val Ala Lys Glu Tyr Leu Glu Phe Leu Ser Glu Glu
                85                  90                  95

Ala Tyr Phe Leu Pro Gly Ala Glu Asp Phe Leu Lys Glu Leu Lys Arg
            100                 105                 110

Asn Gly Phe Arg Met Ala Ala Val Thr Asn Gly Val Arg Phe Val Gln
        115                 120                 125

Glu Arg Arg Ser Lys Lys Leu Gly Leu Glu Arg Phe Phe Glu Phe Val
    130                 135                 140

Leu Thr Ser Glu Glu Val Gly Val Glu Lys Pro Asp Pro Arg Ile Phe
145                 150                 155                 160

Trp Ile Ala Leu Glu Arg Met Gly Leu Lys Lys Glu Asp Ala Leu Tyr
                165                 170                 175

Val Gly Asp Asp Pro Ala Ser Asp Leu Glu Gly Ala Arg Asn Ala Gly
            180                 185                 190

Ile Asp Phe Val Leu Phe Ser Pro Ser Gly Asp Val Ser Arg Glu Phe
        195                 200                 205

Pro Val Val Arg Asn Phe Glu Glu Leu Arg Glu Ile Leu Arg Ile Leu
    210                 215                 220

<210> SEQ ID NO 212
<211> LENGTH: 204
<212> TYPE: PRT
<213> ORGANISM: Thermotoga neapolitana

<400> SEQUENCE: 212

Met Asn Ile Ser Glu Arg Gln Lys Asp Leu Leu Lys Glu Ile Gly Asn
1               5                   10                  15

Ile Gly Ala Gly Asn Ala Ala Thr Ala Ile Ser Tyr Met Val Asn Lys
            20                  25                  30

Lys Val Glu Ile Ser Val Pro Thr Val Glu Ile Ile Pro Leu Ser Asp
        35                  40                  45

Val Ile Phe Val Ala Lys Asp Pro Glu Glu Ile Val Gly Val Lys
    50                  55                  60

Met Pro Val Thr Gly Glu Ile Glu Gly Asn Val Leu Leu Ile Met Gly
65                  70                  75                  80

Thr Gln Val Val Lys Lys Ile Leu Glu Ile Leu Ile Gly His Ala Pro
                85                  90                  95

Glu Asn Leu Leu Gln Leu Asp Glu Phe Ala Ala Ser Ala Leu Gln Glu
            100                 105                 110

Val Gly Asn Ile Met Cys Gly Thr Tyr Val Ser Ala Leu Ala Asp Phe
        115                 120                 125

Leu Gly Phe Lys Ile Asp Thr Leu Pro Pro Gln Leu Val Val Asp Met
    130                 135                 140

Ile Ser Ala Ile Phe Ala Glu Val Ser Ile Glu Glu Leu Gly Glu Ser
145                 150                 155                 160

Val Asp Asp Gln Val Val Phe Glu Thr Ser Leu Thr Val Glu Glu
                165                 170                 175

Glu Glu Pro Leu Thr Ser Tyr Leu Met Leu Val Pro Lys Pro Gly Tyr
            180                 185                 190

Leu Lys Lys Ile Phe Glu Arg Met Gly Val Gln Glu
        195                 200

<210> SEQ ID NO 213
<211> LENGTH: 236
<212> TYPE: PRT
```

<213> ORGANISM: Thermotoga neapolitana

<400> SEQUENCE: 213

| Met | Glu | Met | Leu | Leu | Gly | Ile | Val | Gln | Gly | Leu | Thr | Glu | Phe | Leu | Pro |
|---|---|---|---|---|---|---|---|---|---|---|---|---|---|---|---|
| 1 | | | | 5 | | | | | 10 | | | | | 15 | |

Val Ser Ser Ser Gly His Leu Val Leu Phe Ser His Val Phe Lys Met
20              25                  30

Asp Leu Asn Ala Tyr Gln Thr Ala Ile Leu His Leu Gly Thr Leu Ala
    35                  40                  45

Ala Val Val Val Phe Ala Leu Glu Gly Ile Arg Arg Ser Leu Arg Asn
50                  55                  60

Trp Arg Val Ile Leu Asn Leu Val Ile Ser Thr Ile Pro Ala Gly Val
65                  70                  75                  80

Phe Gly Val Leu Phe Glu Ser Arg Val Asp Glu Ala Phe Ser Ser Pro
                85                  90                  95

Val Val Leu Pro Leu Phe Phe Ser Phe Thr Ala Leu Val Leu Leu Phe
                100                 105                 110

Thr Ser Ser Phe Ser Gly Glu Lys Arg Met Glu Glu Met Thr Ile Leu
            115                 120                 125

Asp Ala Thr Leu Val Gly Leu Ala Gln Val Leu Ala Leu Phe Pro Gly
    130                 135                 140

Val Ser Arg Ser Gly Ile Thr Ile Ala Thr Leu Leu Phe Leu Lys Tyr
145                 150                 155                 160

Arg Arg Glu Asp Ala Leu Gln Tyr Ser Phe Leu Met Ser Ile Pro Val
                165                 170                 175

Val Leu Gly Ala Gly Ile Leu Gly Met Glu Lys Gly Asn Ile Ser Leu
                180                 185                 190

Thr Ala Pro Phe Phe Ala Phe Leu Ser Gly Ile Leu Ala Leu Tyr Ile
            195                 200                 205

Leu Ser Arg Ser Val Arg Ser Gly Lys Met Trp Gln Phe Ala Tyr Tyr
    210                 215                 220

Cys Leu Phe Val Ala Ile Val Ser Tyr Phe Val Gly
225                 230                 235

<210> SEQ ID NO 214
<211> LENGTH: 233
<212> TYPE: PRT
<213> ORGANISM: Thermotoga neapolitana

<400> SEQUENCE: 214

Met Ile Asp Met His Leu His Ser Thr Phe Ser Tyr Asp Gly Lys Ala
1               5                   10                  15

Glu Val Glu Asp Ile Ile Ala Gln Val Gln Lys Leu Gly Ile Asn His
                20                  25                  30

Phe Cys Ile Thr Asp His Tyr Glu Tyr Glu Asn Gly Lys Leu Val His
            35                  40                  45

Asp Phe Asn Val Glu Glu Tyr Phe Leu Thr Met Asp Lys Phe Asp Leu
    50                  55                  60

Pro Arg Gly Ala Glu Ile Ser Trp Asp Gly Val Lys Glu Ala Ile Phe
65                  70                  75                  80

Pro Glu Gly Phe Asp Tyr Leu Leu Leu Gly Val His Arg Tyr Asp Glu
                85                  90                  95

Asn Leu Pro Pro Asp Glu Leu Ala Arg Asp Tyr Leu Glu Arg Thr Leu
                100                 105                 110

Tyr Val Met Glu Arg Val Glu Phe His Thr Leu Ala His Leu Asp Tyr

```
               115                 120                 125
Pro Ala Arg Tyr Ala Asn Ala Asp Phe Lys Ala Asn Arg Asp Leu Ile
        130                 135                 140

Glu Lys Ile Leu Arg Phe Leu Val Ala Arg Glu Lys Ile Leu Glu Val
145                 150                 155                 160

Asn Thr Ala Gly Leu Phe Lys His Gly Lys Pro Asn Pro Asp Tyr Trp
                165                 170                 175

Ile Leu Glu Met Tyr Trp Asp Leu Gly Gly Arg Phe Ile Thr Ile Gly
                180                 185                 190

Ser Asp Ala His Glu Val Gln His Ile Gly Arg Gly Ile Glu Glu Val
                195                 200                 205

Met Ser Lys Leu Arg Arg Phe Asn Phe Glu Tyr Val Val Glu Gly
        210                 215                 220

Lys Lys Leu Phe Thr Lys Lys Leu Arg
225                 230

<210> SEQ ID NO 215
<211> LENGTH: 227
<212> TYPE: PRT
<213> ORGANISM: Thermotoga neapolitana

<400> SEQUENCE: 215

Met Val Asn Val Met Val Pro Cys Ser Val Val Lys Asp Glu Thr
1               5                   10                  15

Val Val Val Asp Val Leu Arg Ala Thr Ser Thr Ile Val Thr Ala
                20                  25                  30

Leu Ala Asn Gly Ala Lys Glu Val Ile Pro Val Lys Thr Val Glu Glu
                35                  40                  45

Ala Leu Lys Arg Lys Glu Arg Asp Val Leu Val Cys Gly Glu Arg Asn
50                  55                  60

Ala Lys Lys Ile Glu Gly Phe Asp Leu Gly Asn Ser Pro Leu Glu Tyr
65                  70                  75                  80

Lys Ser Glu Leu Val Leu Gly Lys Thr Ile Val Leu Thr Thr Thr Asn
                85                  90                  95

Gly Thr Gln Val Ile Glu Arg Val Glu Gly Asp Ser Val Ile Ala Ala
                100                 105                 110

Ser Phe Leu Asn Val Ser Ala Val Val Glu Tyr Leu Lys Glu Lys Glu
                115                 120                 125

Asn Ile Thr Ile Val Cys Ala Gly Thr Ser Gly Asp Phe Ser Leu Glu
        130                 135                 140

Asp Phe Leu Leu Ala Gly Met Ile Val Lys Arg Met Lys Arg Glu Asp
145                 150                 155                 160

Leu Leu Asp Gly Ala Leu Val Val Met Arg Tyr Phe Glu Ser Val Gln
                165                 170                 175

Asn Ile Arg Glu Glu Ile Lys Arg Phe Ser Ser His Ala Lys Arg Leu
                180                 185                 190

Ile Ser Leu Gly Phe Glu Lys Asp Val Asp Phe Cys Thr Thr Glu Asp
        195                 200                 205

Leu Phe His Glu Val Pro Val Leu Val Asn Gly Ala Phe Thr Leu Lys
        210                 215                 220

Glu Ala Arg
225

<210> SEQ ID NO 216
<211> LENGTH: 209
```

<212> TYPE: PRT
<213> ORGANISM: Thermotoga neapolitana

<400> SEQUENCE: 216

```
Met Thr Tyr Ala Val Gly Asp Ile His Gly Cys Phe Phe Ala Leu Lys
1               5                   10                  15

Ala Leu Leu Glu Lys Leu Pro Leu Gly Lys Glu Asp Glu Leu Val Phe
            20                  25                  30

Leu Gly Asp Tyr Val Asp Arg Gly Pro Asn Ser Lys Glu Val Val Glu
        35                  40                  45

Phe Leu Met Glu Leu Ser Lys His His Arg Cys Ile Phe Leu Arg Gly
    50                  55                  60

Asn His Glu Glu Met Leu Leu Asn Cys Val Lys Asn His Ser Gly Cys
65                  70                  75                  80

Asp Leu Trp Tyr Phe Asn Gly Ala Arg Ser Thr Val Glu Ser Phe Gly
                85                  90                  95

Gly Ile Asp Glu Ile Arg Lys Tyr Leu Asp Phe Phe Glu Ser Thr Val
            100                 105                 110

Tyr Tyr Tyr Glu Lys Gly Asn Phe Val Phe Val His Gly Gly Val Lys
        115                 120                 125

Pro Gly Ile Pro Leu Glu Glu Gln Asp Pro Phe Asp Leu Val Trp Ile
    130                 135                 140

Arg Glu Glu Phe Ile Tyr Ser Glu Asn Pro Leu Pro Gly Lys Thr Val
145                 150                 155                 160

Val Phe Gly His Thr Pro Leu Glu Lys Pro Tyr Val Ser Ser Asp Lys
                165                 170                 175

Ile Gly Ile Asp Thr Gly Cys Val Tyr Gly Gly Lys Leu Thr Ala Phe
            180                 185                 190

Arg Val Glu Asp Arg Thr Phe Phe Gln Val Glu Cys Ile Gly Arg Arg
        195                 200                 205

Trp
```

<210> SEQ ID NO 217
<211> LENGTH: 264
<212> TYPE: PRT
<213> ORGANISM: Thermotoga petrophilia

<400> SEQUENCE: 217

```
Met Phe Val Phe Asp Leu Asp Gly Thr Leu Leu Asn Asp Ser Leu Glu
1               5                   10                  15

Ile Ser Glu Lys Asp Arg Arg Ala Ile Glu Arg Leu Ser Arg Lys Cys
            20                  25                  30

Arg Val Val Phe Ala Ser Gly Arg Met Leu Val Ser Thr Leu Asn Val
        35                  40                  45

Glu Lys Lys Tyr Phe Gly Arg Thr Phe Pro Thr Ile Ala Tyr Asn Gly
    50                  55                  60

Ala Met Val Tyr Ile Pro Glu Glu Gly Val Ile Leu Asn Glu Lys Ile
65                  70                  75                  80

Pro Pro Glu Val Ala Lys Asp Ile Val Glu Tyr Val Lys Gln Phe Asn
                85                  90                  95

Val His Trp Gln Ala Tyr Ile Asp Asp Val Leu Tyr Ser Glu Lys Asp
            100                 105                 110

Asn Glu Glu Ile Arg Gly Tyr Ala Lys His Ser Ser Val Glu Tyr Arg
        115                 120                 125

Val Glu Pro Lys Leu Leu Glu Leu Val Ser Lys Val Gly Thr Thr Lys
```

```
                130              135              140
Ile Leu Leu Ile Asp Thr Pro Glu Lys Leu Asp Glu Leu Lys Lys Ile
145                 150                 155                 160

Leu Leu Glu Lys Phe Asn Asn Val Val Lys Val Phe Lys Ser Phe Pro
                165                 170                 175

Thr Tyr Leu Glu Ile Val Pro Glu Asn Val Asp Lys Gly Lys Ala Leu
            180                 185                 190

Arg Phe Leu Arg Glu Arg Met Gly Trp Lys Lys Glu Ile Val Val
            195                 200                 205

Phe Gly Asp Asn Glu Asn Asp Leu Phe Met Phe Glu Glu Ala Gly Leu
            210                 215                 220

Arg Val Ala Met Gly Asn Ala Ile Asp Lys Val Lys Glu Ala Ala Asp
225                 230                 235                 240

Val Val Thr Leu Thr Asn Asn Asp Ser Gly Val Ser His Val Leu Glu
                245                 250                 255

Leu Ile Ser Thr Asp Cys Leu Asp
            260

<210> SEQ ID NO 218
<211> LENGTH: 208
<212> TYPE: PRT
<213> ORGANISM: Thermus amyloliquefaciens

<400> SEQUENCE: 218

Met Leu Lys Ala Leu Leu Phe Asp Leu Asp Gly Thr Leu Ala Asp Thr
1               5                   10                  15

Asp Pro Leu His Leu Gln Ala Trp Arg Glu Ala Leu Ala Pro Trp Gly
                20                  25                  30

Leu Gln Val Asp Glu Ala Phe Tyr Arg Lys Arg Ile Ser Gly Arg Leu
            35                  40                  45

Asn Pro Asp Ile Val Gln Asp Leu Leu Gly Leu Glu Gly Glu Ala Ala
        50                  55                  60

Gln Arg Leu Ile Glu Ala Lys Glu Ala Arg Phe Arg Glu Leu Ala Gln
65              70                  75                  80

Asp Leu Lys Pro Thr Pro Gly Leu His Gly Leu Ala Lys Ala Glu
                85                  90                  95

Ala Gln Gly Leu Thr Trp Gly Val Val Thr Asn Ala Pro Arg Glu Asn
            100                 105                 110

Ala Leu His Val Leu Arg Ala Leu Gly Leu Asn Pro Pro Leu Leu Val
        115                 120                 125

Leu Ala Glu Glu Val Gly Arg Gly Lys Pro Asp Pro Leu Pro Tyr Arg
    130                 135                 140

Val Ala Leu Glu Arg Leu Gly Ile Glu Pro Gly Glu Ala Leu Ala Phe
145                 150                 155                 160

Glu Asp Ser Pro Ser Gly Val Arg Ser Ala Val Gly Ala Gly Ile Pro
                165                 170                 175

Thr Tyr Ala Leu Leu Thr Gly His Gly Lys Glu Ala Leu Leu Glu Ala
            180                 185                 190

Gly Ala Leu Glu Ala Leu Arg Asp Phe Gln Gln Ile Val Asp Leu Leu
        195                 200                 205

<210> SEQ ID NO 219
<211> LENGTH: 260
<212> TYPE: PRT
<213> ORGANISM: Thermus filiformis
```

<400> SEQUENCE: 219

Met Lys Val Ser Gln Ala His Leu Glu Ala Ala Ile Asp Ala Ala Phe
1               5                   10                  15

Leu Ala Gln Gly Ile His Thr Tyr Tyr Leu Glu Arg Gly Phe Thr Gln
            20                  25                  30

Lys Thr Lys Ser Gly Pro Thr Asp Leu Val Thr Gln Ala Asp Lys Glu
        35                  40                  45

Ser Glu Glu Ala Ile Lys Asp Leu Leu Leu Ser Arg Phe Pro Asp His
    50                  55                  60

Gly Phe Leu Gly Glu Glu Gly Gly Asp Ala Gly Gly Val Arg
65                  70                  75                  80

Trp Val Val Asp Pro Leu Asp Gly Thr Val Asn Tyr Ala His Gly Phe
                85                  90                  95

Pro Phe Tyr Gly Val Ser Ile Ala Leu Glu Val Glu Gly Arg Val Glu
            100                 105                 110

Leu Gly Val Val Leu Asp Thr Ala Arg Gly Glu Leu Phe Thr Ala Leu
            115                 120                 125

Arg Gly Gln Gly Ala Tyr Leu Asn Gly Arg Pro Ile Arg Val Thr Glu
130                 135                 140

Arg Thr Glu Leu Leu Gly Ser Leu Leu Ala Thr Gly Phe Pro Tyr Asp
145                 150                 155                 160

Val Ala Arg Asp Pro Glu Asn Leu Thr Tyr Phe Glu Arg Ala Leu Arg
                165                 170                 175

Arg Gly Leu Leu Val Arg Arg Pro Gly Ala Ala Ala Leu Asp Leu Ala
            180                 185                 190

Tyr Val Ala Ala Gly Arg Leu Asp Gly Phe Trp Glu Val Lys Leu Asn
        195                 200                 205

Pro Trp Asp Val Ala Ala Gly Trp Leu Leu Val Glu Glu Ala Gly Gly
    210                 215                 220

Arg Val Thr Asp Leu Glu Gly Glu Ala Tyr Arg Leu Gly His Arg Tyr
225                 230                 235                 240

Ile Val Ala Thr Asn Gly Arg Ile His Gln Ala Leu Leu Ala Val Leu
                245                 250                 255

Arg Gly Thr Met
            260

<210> SEQ ID NO 220
<211> LENGTH: 208
<212> TYPE: PRT
<213> ORGANISM: Thermus thermophilus

<400> SEQUENCE: 220

Met Leu Lys Ala Val Leu Phe Asp Leu Asp Gly Thr Leu Ala Asp Thr
1               5                   10                  15

Asp Pro Leu His Leu Leu Ala Trp Arg Glu Ala Leu Ala Pro Tyr Gly
            20                  25                  30

Leu Glu Val Asp Pro Ile Phe Tyr Arg Lys Arg Ile Ser Gly Arg Leu
        35                  40                  45

Asn Pro Glu Ile Val Arg Asp Leu Leu Gly Leu Glu Gly Glu Glu Ala
    50                  55                  60

Glu Arg Leu Ile Ala Ala Lys Glu Ala Arg Phe Arg Ala Leu Ala Gln
65                  70                  75                  80

Gly Leu Arg Pro Thr Pro Gly Leu Ala Glu Phe Leu Glu His Ile Arg
                85                  90                  95

```
Glu Lys Gly Leu Leu Trp Gly Val Val Thr Asn Ala Pro Lys Glu Asn
            100                 105                 110

Ala Arg His Val Leu Glu Ala Leu Gly Leu Arg Pro Pro Leu Leu Val
        115                 120                 125

Leu Ala Glu Glu Val Gly Arg Gly Lys Pro Asp Pro Leu Pro Tyr Arg
    130                 135                 140

Val Ala Leu Arg Arg Leu Gly Val Ala Pro Glu Glu Ala Leu Ala Phe
145                 150                 155                 160

Glu Asp Ser Pro Ser Gly Val Arg Ser Val Gly Ala Gly Ile Pro
                165                 170                 175

Thr Tyr Gly Leu Leu Thr Gly His Glu Ala Glu Ala Leu Arg Glu Ala
            180                 185                 190

Gly Ala Arg Gly Val Phe Arg Asp Phe Arg Glu Ala Leu Gly Leu Leu
        195                 200                 205

<210> SEQ ID NO 221
<211> LENGTH: 264
<212> TYPE: PRT
<213> ORGANISM: Thermus thermophilus

<400> SEQUENCE: 221

Met Ile Gly Arg Arg His Pro Tyr Tyr Pro Tyr Leu Glu Ala Ala Leu
1               5                   10                  15

Glu Ala Ala Ser Leu Ala Arg Gly Ile His Leu Tyr Tyr Leu Glu Lys
            20                  25                  30

Gly Phe Thr Glu Gly Thr Lys Ser Gly Pro Thr Asp Leu Val Thr Gln
        35                  40                  45

Ala Asp Arg Glu Ala Glu Ala Val Lys Gly Leu Leu Leu Ser Arg
50                  55                  60

Phe Pro Glu Ala Gly Phe Leu Gly Glu Glu Gly Ser Glu Gly Gly
65                  70                  75                  80

Lys Ala Leu Arg Phe Ile Val Asp Pro Leu Asp Gly Thr Val Asn Tyr
                85                  90                  95

Ala His Gly Phe Pro Phe Ala Val Ser Ile Ala Leu Glu Ala Glu
            100                 105                 110

Gly Ala Ile Gln Met Gly Val Val Met Asp Thr Ala Arg Gly Glu Val
        115                 120                 125

Phe Tyr Ala Leu Arg Gly Glu Gly Ala Tyr Leu Asn Gly Arg Pro Ile
    130                 135                 140

Arg Val Thr Gly Arg Glu Ser Leu Val Gly Ser Leu Leu Ala Thr Gly
145                 150                 155                 160

Phe Pro Tyr Asp Val Ala Lys Asp Pro Glu Asn Leu Thr Tyr Phe Glu
                165                 170                 175

Arg Ala Leu Gly Lys Gly Leu Leu Val Arg Arg Pro Gly Ala Ala Ala
            180                 185                 190

Leu Asp Leu Ala Tyr Val Ala Ala Gly Arg Leu Glu Gly Phe Trp Glu
        195                 200                 205

Val Lys Leu Asn Pro Trp Asp Val Ala Ala Gly Trp Leu Leu Val Glu
    210                 215                 220

Glu Ala Gly Gly Arg Val Thr Asp Leu Glu Gly Asn Pro Tyr Arg Leu
225                 230                 235                 240

Gly Ser Arg Tyr Ile Leu Ala Thr Asn Gly Arg Val His Glu Ala Leu
                245                 250                 255

Arg Arg Thr Leu Leu Gly Leu Asp
            260
```

```
<210> SEQ ID NO 222
<211> LENGTH: 229
<212> TYPE: PRT
<213> ORGANISM: Truepera radiovictrix

<400> SEQUENCE: 222

Met Gly His Pro Lys Ala Val Leu Leu Asp Val Asp Gly Thr Leu Val
1               5                   10                  15

Asp Ser Asn Asp Ala His Ala Arg Ala Tyr Val Asp Ala Leu Lys Ala
            20                  25                  30

Tyr Gly Tyr Asp Val Pro Phe Glu Lys Val Arg Pro Leu Ile Gly Met
        35                  40                  45

Gly Gly Asp Lys Leu Leu Pro Gln Val Ile Asp Val Glu Ser Asp Ala
    50                  55                  60

Pro Leu Arg Glu Glu Ile Asp Ala Arg Arg Gly Glu Ile Phe Lys Ser
65                  70                  75                  80

Arg Tyr Leu Pro Asp Ile Lys Pro Phe Pro Gly Val Arg Glu Leu Leu
                85                  90                  95

Glu Arg Leu Arg Arg Asp Gly Leu Thr Leu Val Ala Ala Ser Ser Ala
            100                 105                 110

Lys Glu Asp Glu Ala Asp Ala Leu Leu Glu Arg Ala Gly Val Ala Asp
            115                 120                 125

Leu Ile Asp Ala Arg Thr Ser Ser Asp Asp Ala Glu Asn Ser Lys Pro
    130                 135                 140

Asp Pro Asp Ile Leu Gln Ala Ala Leu Glu Arg Ala Gly Val Ser Ala
145                 150                 155                 160

Gln Glu Ala Leu Leu Leu Gly Asp Thr Pro Tyr Asp Leu Gln Ala Ala
                165                 170                 175

Ala Pro Leu Gly Leu Gly Val Val Ala Leu Arg Cys Gly Gly Trp Arg
            180                 185                 190

Asp Glu Asp Leu Leu Gly Ala Leu Ala Val Tyr Asp Asp Pro Gln Ala
            195                 200                 205

Leu Leu Ala Gly Tyr Asp Ala Ser Pro Leu Ala Pro Glu Pro Ala Ser
    210                 215                 220

Ala Pro Gly Asp Val
225
```

PSICOSE-6-PHOSPHATE PHOSPHATASE, COMPOSITION FOR PRODUCING PSICOSE COMPRISING THE SAME, AND METHOD FOR PRODUCING PSICOSE USING THE SAME

TECHNICAL FIELD

The present application relates to a novel enzyme for dephosphorylating psicose-6-phosphate for the production of psicose, a composition for producing psicose including the same, and a method for producing psicose using the same.

BACKGROUND ART

D-Psicose-3-epimerase (EC 5.1.3.30) and D-tagatose-3-epimerase (EC 5.1.3.31) are known as enzymes that catalyze the 3-epimerization of D-fructose to produce D-psicose. When D-psicose is produced through a single enzymatic reaction using the enzyme, reaction equilibrium between the substrate (i.e., D-fructose) and the product (i.e., D-psicose) exists at a constant level (product/substrate=appropriately 20-35%). Thus, the production of high-purity D-psicose requires an additional process for separating and removing a relatively high concentration of D-fructose from the enzymatic reaction product. Additionally, fructose is a relatively expensive raw material compared to starch or glucose, and when fructose is used as a raw material, the cost ratio of psicose and tagatose increases. Accordingly, various studies on the production of allulose and tagatose through a reaction using starch or glucose, which is relatively economical raw material, have been reported (KR 10-2018-0004023, WO 2018-112139, WO 2017-059278, WO 2018-129275).

Meanwhile, Chan et al. (2008. *Biochemistry.* 47:9608-9617) reported D-ribulose-5-phosphate-3-epimerase (EC 5.1.3.1) derived from *Streptococcus pyogenes* and D-psicose-6-phosphate-3-epimerase (EC 5.1.3.-) derived from *E. coli* capable of catalyzing the 3-epimerization of D-fructose-6-phosphate and D-psicose-6-phosphate. However, these enzymes are not industrially applicable due to poor thermal resistance.

DISCLOSURE

Technical Problem

Under such circumstances, the present inventors have earnestly conducted research to develop a method for increasing the conversion rate of allulose on an industrial scale in an economical manner. As a result, the present inventors have found that after sucrose or starch (e.g., maltodextrin) as an inexpensive raw material is converted to psicose-6-phosphate, the use of the psicose-6-phosphate phosphatase of the present application, which is specific to psicose-6-phosphate and participates in an irreversible reaction pathway, enables the production of psicose through one-pot enzymatic conversions using a plurality of enzymes involved in the psicose production pathways and can significantly increase the rate of conversion to psicose.

Accordingly, the present application has been accomplished based on this finding. The enzyme of the present application has better advantages in the production of psicose compared to the conventionally known psicose-6-phosphate phosphatase (Panoramic view of a superfamily of phosphatases through substrate profiling, *PNAS*, 06.04.2015, Huang, etc.).

Technical Solution

It is one object of the present application to provide a psicose-6-phosphate phosphatase.

It is another object of the present application to provide a nucleic acid encoding the psicose-6-phosphate phosphatase.

It is still another object of the present application to provide a transformant including the nucleic acid encoding the psicose-6-phosphate phosphatase.

It is yet another object of the present application to provide a composition for producing psicose, including the psicose-6-phosphate phosphatase, a microorganism expressing the same, or a culture of the microorganism.

It is even another object of the present application to provide a method for producing psicose, including converting psicose-6-phosphate into psicose by bringing psicose-6-phosphate into contact with the psicose-6-phosphate phosphatase, a microorganism expressing the same, or a culture of the microorganism.

Advantageous Effects

The novel enzymes and combination thereof of the present application are thermoresistant, and accordingly, the enzyme of the present application can participate in the pathway for the conversion of psicose-6-phosphate to psicose in an industrial manner, allows the progression of the pathway for the synthesis of psicose from glucose or starch (e.g., maltodextrin) as an inexpensive raw material, and enables the production of psicose through the dephosphorylation of psicose-6-phosphate, an irreversible reaction pathway, thereby significantly increasing the rate of conversion to psicose. Thermoresistant enzymes can commercially prevent microorganisms and easily react with high-concentration substrates, and thus their effects are prominent. In addition, the production method of the present application can simplify or eliminate the separation and purification process, including the high concentration of the reaction product (i.e., psicose) by the increase in the conversion rate of psicose, and thus there is an economic advantage, while allowing a simple production method. In particular, separation using SMB can be minimized or eliminated, thus maximizing separation efficiency and yield.

DETAILED DESCRIPTION OF EMBODIMENTS

Hereinafter, the present application will be described in detail. Meanwhile, the description of one aspect and embodiment disclosed in the present application may also be applied to other aspects and embodiments with respect to common elements. Moreover, all combinations of various elements disclosed in the present application fall within the scope of the present application. In addition, it does not appear that the scope of the present application is limited by the following detailed description.

In order to achieve the objects above, one aspect of the present application provides a psicose-6-phosphate phosphatase.

Specifically, the psicose-6-phosphate phosphatase of the present application may be a psicose-6-phosphate phosphatase derived from the genus of *Alicyclobacillus, Amycolatopsis, Anaerolinea, Archaeoglobus, Bacillus, Caldicellulosiruptor, Caldilinea, Caldithrix, Carboxydocella, Carboxydothermus, Chloroflexi, Defluviitoga, Deinococcus, Desulfurococcus, Dictyoglomus, Effusibacillus, Fervidobacterium, Geobacillus, Halococcus, Hydrogenivirga, Hydrogenobacter, Hyperthermus, Kosmotoga, Marinitoga, Meio-*

*thermus, Mesotoga, Metallosphaera, Methanocella, Methanococcoides, Methanohalobium, Methanolobus, Methanosarcina, Methanothermus, Petrotoga, Picrophilus, Pseudonocardia, Pyrococcus, Pyrodictium, Rhodothermus, Slackia, Staphylothermus, Sulfolobus, Thermanaerothrix, Thermoanaerobacter, Thermoanaerobacterium, Thermobifida, Thermococcus, Thermocrinis, Thermoflexus, Thermotoga, Thermus*, and *Truepera*, and more specifically derived from *Alicyclobacillus acidocaldarius, Alicyclobacillus tengchongensis, Amycolatopsis thermoflava, Anaerolinea thermolimosa, Anaerolinea thermophila, Archaeoglobus fugidus, Archaeoglobus profundus, Archaeoglobus veneficus, Bacillus lichenformis, Caldicellulosiruptor bescii, Caldilinea aerophila, Caldithrix abyssi, Carboxydocella sp.* ULO1, *Carboxydothermus ferrireducens, Chloroflexi bacterium* 54-19, *Defluviitoga tunisiensis, Deinococcus aerius, Deinococcus apachensis, Deinococcus aquatilis, Deinococcus geothermalis, Deinococcus hopiensis, Deinococcus maricopensis, Deinococcus murrayi, Deinococcus reticulitermitis, Deinococcus wulumuqiensis, Deinococcus* sp. Leaf326, *Deinococcus phoenicis, Deinococcus proteolyticus, Deinococcus* sp. 17bor-2, *Deinococcus* sp. NW-56, *Deinococcus* sp. RL, *Deinococcus* sp. YIM 77859, *Desulfurococcus mucosus, Dictyoglomus turgidum, Effusibacillus pohliae, Fervidobacterium* gondwanense, *Fervidobacterium islandicum, Fervidobacterium nodosum, Fervidobacterium pennivorans, Geobacillus* sp., *Geobacillus stearothermophilus, Halococcus salifodinae, Hydrogenivirga* sp. 128-5-R1-1, *Hydrogenobacter hydrogenophilus, Hydrogenobacter thermophilus, Hyperthermus butylicus, Kosmotoga arenicorallina, Kosmotoga olearia, Marinitoga piezophila, Meiothermus cerbereus, Meiothermus chliarophilus, Meiothermus ruber, Meiothermus Silvanus, Meiothermus taiwanensis, Meiothermus timidus, Meiothermus rufus, Mesotoga infera, Metallosphaera sedula, Methanocella conradii, Methanococcoides methylutens, Methanohalobium evestigatum, Methanolobus tindarius, Methanosarcina sicilia, Methanothermus fervidus, Petrotoga mobilis, Picrophilus torridus, Pseudonocardia thermophila, Pyrococcus furiosus, Pyrodictium occultum, Rhodothermus marinus, Slackia heliotrinireducens, Staphylothermus marinus, Sulfolobus acidocaldarius, Thermanaerothrix daxensis, Thermoanaerobacter* sp., *Thermoanaerobacter thermohydrosulfuricus, Thermoanaerobacter wiegelii, Thermoanaerobacterium xylanolyticum, Thermobifida halotolerans, Thermococcus celer, Thermococcus litoralis, Thermococcus profundus, Thermocrinis minervae, Thermocrinis ruber, Thermoflexus hugenholtzii, Thermotoga lettingae, Thermotoga neapolitana, Thermotoga petrophilia, Thermus amyloliquefaciens, Thermus filformis, Thermus thermophilus*, or *Truepera radiovictrix*, but is not limited thereto.

As used herein, the "psicose-6-phosphate" is known as allulose-6-phosphate, and the "psicose-6-phosphate phosphatase" is an enzyme that catalyzes the production of psicose by dephosphorylating the phosphate group of psicose-6-phosphate.

The psicose-6-phosphate phosphatase of the present application can be used to produce psicose with high efficiency in combination with starch-processing enzymes and sugar phosphate-converting enzymes, in the preparation of psicose by decomposing high-concentration starch.

The psicose-6-phosphate phosphatase of the present application may have an amino acid sequence of any one of SEQ ID NOS: 1 to 222 or may include an amino acid sequence having a homology of at least 70% to the amino acid sequence.

Additionally, it may have an amino acid sequence of any one of SEQ ID NOS: 1, 6, 9, 12, 26, 29, 38 to 43, 45 to 53, 56, 57, 59, 60, 64 to 66, 69, 70, 72, 76, 80, 81, 91 to 93, 95, 99 to 103, 113, 114, 116, 117, 131, 134, 136, 142, 145, 146, 148, 164, 167, 169, 172, 177, 184 to 187, 189, 191, 192, 211, 217, and 221, or may include an amino acid sequence having a homology of at least 70% to the amino acid sequence.

More specifically, it may have an amino acid sequence of any one of SEQ ID NOS: 26, 29, 53, 56, 60, 70, 76, 80, 81, 116, 117, 131, 134, 145, 167, 185, 186, and 191, or may include an amino acid sequence having a homology of at least 70% to the amino acid sequence, but is not limited thereto.

Further, any sequences having the same activity as the amino acid sequence may be included without limitation. In addition, it may include an amino acid sequence of any one of SEQ ID NOS: 1 to 222 or an amino acid sequence having at least 80% homology or identity thereto, but is not limited thereto. Specifically, the amino acid may include an amino acid having at least 70%, 75%, 80%, 85%, 90%, 95%, 96%, 97%, 98%, or 99% homology or identity thereto. Furthermore, it is apparent that any protein having an amino acid sequence, in which part of the amino acid sequence is deleted, modified, substituted, or added, may also fall within the scope of the present application as long as it includes an amino acid sequence having such a homology or identity and exhibiting an effect corresponding to that of the above protein.

That is, in the present application, although it is described as "a protein having an amino acid sequence of a particular SEQ ID NO", it is apparent that any protein, in which part of the amino acid sequence is deleted, modified, substituted, conservatively substituted, or added, may also be used in the present application as long as the protein has the same or corresponding activity to the protein composed of the amino acid sequence of the corresponding SEQ ID NO. For example, as long as a protein has activity identical or corresponding to that of the enzyme, addition of a sequence that does not alter the function of the protein upstream and downstream of the amino acid sequence, naturally occurring mutations, silent mutations, or conservative substitutions thereof are not excluded. It is apparent that even though the protein has such a sequence addition or mutation, it falls within the scope of the present application.

As used herein, the term "homology" or "identity" refers to a degree of relatedness between two given amino acid sequences or nucleotide sequences, and may be expressed as a percentage.

The terms homology and identity may often be used interchangeably with each other.

The sequence homology or identity of the conserved polynucleotide or polypeptide may be determined using standard alignment algorithms, and may be used with default gap penalties established by the program being used. Substantially, homologous or identical sequences may hybridize under moderately or highly stringent conditions such that the full length of the sequence or at least about 50%, 60%, 70%, 80%, or 90% or more of the full length may hybridize. Polynucleotides that contain degenerate codons instead of codons in hybridizing polynucleotides are also considered.

Whether any two polynucleotide sequences have homology, similarity, or identity may be, for example, determined by a known computer algorithm such as the "FASTA" program (Pearson et al, (1988) *Proc. Natl. Acad. Sci. USA* 85: 2444) using default parameters. Alternatively, it may be determined by the Needleman-Wunsch algorithm (Needleman and Wunsch, 1970, *J. Mol. Biol.* 48: 443-453), which is performed using the Needleman program of the EMBOSS package (EMBOSS: The European Molecular Biology Open Software Suite, Rice et al., 2000, *Trends Genet.* 16:276-277) (preferably, version 5.0.0 or versions thereafter) (GCG program package (Devereux, J. et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994; and CARILLO et al. (1988) *SIAM J Applied Math* 48:1073). For example, the homology, similarity, or identity may be determined using BLAST or ClustalW of the National Center for Biotechnology Information (NCBI).

The homology, similarity, or identity of polynucleotides or polypeptides may be determined by comparing sequence information using, for example, the GAP computer program, such as Needleman et al. (1970), *J Mol Biol.* 48:443 as disclosed in Smith and Waterman, *Adv. Appl. Math* (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps. Therefore, as used herein, the term "homology" or "identity" represents relatedness between sequences.

The psicose-6-phosphate phosphatase of the present application may be an enzyme that selectively catalyzes the dephosphorylation of psicose-6-phosphate. Specifically, the psicose-6-phosphate phosphatase may be an enzyme that catalyzes the dephosphorylation of psicose-6-phosphate when it is mixed with glucose-1-phosphate, glucose-6-phosphate, or fructose-6-phosphate. For example, when the psicose-6-phosphate phosphatase is mixed with the same amount of psicose-6-phosphate, glucose-1-phosphate, glucose-6-phosphate, and fructose-6-phosphate, the dephosphorylation rate of psicose-6-phosphate is 1% or more, 10% or more, or 30% or more. Due to the selective activity of the psicose-6-phosphate phosphatase of the present application, a high rate of psicose conversion can be exhibited in one-pot enzymatic conversion using a plurality of enzymes and substrates at the same time.

The psicose-6-phosphate phosphatase of the present application may be produced by transforming a strain with the enzyme itself or DNA expressing the enzyme, culturing the transformed strain to obtain a culture, and disrupting the culture, followed by purification via column chromatography. The strain for transformation may be *Escherichia coli, Corynebacterum glutamicum, Aspergillus oryzae, Saccharomyces cerevisiae, Yarrowia lipolytica, Pichia pastoris*, or *Bacillus subtilis*, but is not limited thereto, and it may have potential to be transformed into GRAS (Generally Recognized as Safe) strains thereafter.

Another aspect of the present application provides a nucleic acid encoding the psicose-6-phosphate phosphatase, or a vector including the nucleic acid.

As used herein, the term "nucleic acid" has a meaning which collectively includes DNA or RNA molecules. Nucleotides, which are the basic structural units of the nucleic acids, include not only natural nucleotides but also modified analogs thereof in which sugar or base sites are modified (see Scheit, *Nucleotide Analogs*, John Wiley, New York (1980); Uhlman and Peyman, *Chemical Reviews*, 90:543-584 (1990)).

The nucleic acid encoding the enzyme of the present application may be a DNA or RNA sequence in which nucleotides as a unit are covalently linked, and specifically, it may be any one nucleotide sequence among all possible numbers at the time of DNA conversion of the amino acid sequence of SEQ ID NOS: 1 to 222 (modification of amino acids into 61 codons), and more specifically it may include a nucleic acid capable of being translated to exhibit a desired enzymatic activity while having at least 90% or more, 95% or more, 97% or more, 99% or more, or 100% homology, similarity, or identity to each nucleotide that can be translated into any one of the amino acid sequences of SEQ ID NOS: 1 to 222 of the present application. It is apparent that proteins having the same activity due to codon degeneracy, proteins having the same amino acid sequences after being transcribed, specifically, proteins consisting of any one of the amino acid sequences of SEQ ID NOS: 1 to 222, or polynucleotides that can be translated into proteins having a homology, similarity, or identity thereto are also within the scope of the present application. More specifically, the nucleic acid sequence of the present application is not separately shown, and may be composed of all number of DNA codon that can be translated into the amino acid sequences of SEQ ID NOS: 1 to 222, but is not limited thereto.

Additionally, a probe that may be prepared from a known gene sequence, for example, any sequence which can hybridize with a sequence complementary to all or part of the nucleotide sequence under stringent conditions to encode the enzyme of the present application, may be included without limitation.

The "stringent conditions" refer to conditions under which specific hybridization between polynucleotides is allowed. Such conditions are specifically described in the literature (see J. Sambrook et al., *supra* 9.50-9.51, 11.7-11.8). For example, the stringent conditions may include conditions under which genes having a high homology or identity of 80% or higher, 85% or higher, specifically 90% or higher, more specifically 95% or higher, much more specifically 97% or higher, still much more specifically 99% or higher are hybridized with each other, and genes having a homology or identity lower than the above homologies or identities are not hybridized with each other, or washing conditions of Southern hybridization, that is, washing once, specifically twice or three times at a salt concentration and a temperature corresponding to 60° C., 1×SSC, 0.1% SDS, specifically 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the present application may include isolated nucleotide fragments complementary to the entire sequence as well as nucleic acid sequences substantially similar thereto.

Specifically, the polynucleotides having a homology or identity may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing polynucleotides depends on the length of the polynucleotides and the degree of complementation, and these variables are well known in the art (see Sambrook et al., *supra,* 9.50-9.51, 11.7-11.8).

As used herein, the term "vector" may refer to a DNA construct containing the nucleotide sequence of a nucleic acid encoding the enzyme of the present application, which is operably linked to a suitable regulatory sequence such that the target modified protein can be expressed in an appropriate host. The regulatory sequence may include a promoter capable of initiating transcription, any operator sequence for regulating the transcription, a sequence encoding an appropriate mRNA ribosome binding domain, and a sequence regulating the termination of transcription and translation. After being transformed into a suitable host cell, the vector may be replicated or function irrespective of the host genome, and may be integrated into the host genome itself.

The vector used in the present application is not particularly limited as long as it is able to replicate in the host cell, and any vector known in the art may be used. Examples of the vector conventionally used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used; and as a plasmid vector, those based on pBR, pUC, pBluescriptII, pGEM, pTZ, pCL, pET, etc. and may be used. Specifically, pDZ, pACYC177, pACYC184, pCL, pECCG117, pUC19, pBR322, pMW118, and pCC1BAC vectors may be used.

Still another aspect of the present application provides a transformant including a vector including a nucleic acid encoding the enzyme of the present application.

As used herein, the "transformant including the nucleic acid encoding the enzyme" or "transformant including the vector including the nucleic acid encoding the enzyme" may refer to a microorganism that has been recombined so that the psicose-6-phosphate phosphatase of the present application is expressed. For example, it may refer to a host cell or a microorganism containing a nucleic acid encoding the psicose-6-phosphate phosphatase, or which is transformed with a vector containing a nucleic acid encoding psicose-6-phosphate phosphatase so that the psicose-6-phosphate phosphatase is expressed. For the purpose of the present application, the psicose-6-phosphate phosphatase expressed by the transformant may be composed of any one amino acid sequence of SEQ ID NOS: 1 to 222, but is not limited thereto.

As used herein, the term "transformation" refers to the introduction of a vector including a nucleic acid encoding the psicose-6-phosphate phosphatase into a host cell so that the protein encoded by the nucleic acid can be expressed in the host cell. As long as the transformed nucleic acid can be expressed in a host cell, it does not matter whether it is integrated into the chromosome of the host cell and located therein or located extrachromosomally, and both cases can be included. Further, the nucleic acid may include DNA and RNA encoding the nucleic acid encoding the psicose-6-phosphate phosphatase of the present application. The nucleic acid may be introduced in any form, as long as it can be introduced into the host cell and expressed therein. For example, the nucleic acid may be introduced into the host cell in the form of an expression cassette, which is a gene construct including all elements required for its autonomous expression. The expression cassette may commonly include a promoter operably linked to the nucleic acid, a transcription terminator, a ribosome binding domain, or a translation terminator. The expression cassette may be in the form of a self-replicable expression vector. Additionally, the nucleic acid may be introduced into the host cell as it is and operably linked to sequences required for expression in the host cell, but is not limited thereto.

In addition, as used herein, the term "operably linked" means that the gene sequence is functionally linked to a promoter sequence that initiates and mediates transcription of the nucleic acid encoding the psicose-6-phosphate phosphatase of the present application.

The insertion of the nucleic acid or the vector into the chromosome may be performed by any method known in the art, for example, by homologous recombination, but the method is not limited thereto. Additionally, the vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell-toxic agents, or expression of surface modified proteins, may be used. When treated with a selective agent, only the cells expressing the selection marker can survive or express other phenotypic traits, and thus the transformed cells can be selected.

The method of transforming the vector of the present application includes any method of introducing a nucleic acid into a cell, and may be performed by selecting a suitable standard technique known in the art, depending on the host cell. For example, the method may include electroporation, calcium phosphate ($CaPO_4$) precipitation, calcium chloride ($CaCl_2$)) precipitation, retroviral infection, microinjection, a polyethyleneglycol (PEG) method, a DEAE-dextran method, a cationic liposome method, and a lithium acetate-DMSO method, but is not limited thereto.

As the host cell, it is preferable to use a host having a high efficiency of introducing DNA and a high efficiency of expressing the introduced DNA. For example, it may be a microorganism of the genus *Corynebacterium*, a microorganism of the genus *Escherichia*, a microorganism of the genus *Serratia*, a microorganism of the genus *Bacillus*, a microorganism of the genus *Saccharomyces*, or a microorganism of the genus *Pichia*, and specifically, it may be *E. coli*, but is not limited thereto, and may be applied to all GRAS strains.

More specifically, the transformant of the present application may be 222 in total, from *E. coli* BL21(DE3)/pET-CJ-ap1 to *E. coli* BL21(DE3)/pET-CJ-ap222.

Yet another aspect of the present application provides a composition for producing psicose including the psicose-6-phosphate phosphatase, a microorganism expressing the same, or a culture of the microorganism. Specifically, the composition may further include a sugar phosphate, and more specifically, it may further include psicose-6-phosphate as a substrate, but is not limited thereto.

The composition for producing psicose of the present application may produce psicose through the dephosphorylation of psicose-6-phosphate by including the psicose-6-phosphate phosphatase which acts to produce psicose by dephosphorylating psicose-6-phosphate, a microorganism expressing the same, or a culture of the microorganism.

Additionally, the composition for producing psicose of the present application may further include an enzyme and/or a substrate involved in the psicose production pathway of the present application [(i) starch, maltodextrin, sucrose, or a combination thereof, (ii) a phosphate or polyphosphate or other phosphorylating compounds; (iii) a fructose-6-phosphate-3-epimerase; (iv) a glucose-6-phosphate-isomerase; (v) a phosphoglucomutase or a glucokinase; and/or (vi) an α-glucan phosphorylase, a starch phosphorylase, a maltodextrin phosphorylase, a sucrose phosphorylase, an α-amylase, a pullulanase, an isoamylase, a glucoamylase, an α-glucanotransferase, a polyphosphate glucokinase, or a sucrase]; a microorganism expressing the enzymes involved in the psicose production pathway; or a culture of the microorganism expressing the enzymes involved in the psicose production pathway. However, the enzymes that are included in the composition for producing psicose of the present application and the substrates used in the production of psicose are merely illustrative and are not limited as long as psicose can be produced using the psicose-6-phosphate phosphatase of the present application.

Specifically, the fructose-6-phosphate-3-epimerase may include any protein that is active in converting fructose-6-phosphate to psicose-6-phosphate. The glucose-6-phosphate-isomerase may include any protein that is active in converting glucose-6-phosphate to fructose-6-phosphate. The phosphoglucomutase (EC 5.4.2.2) may include any protein that is active in converting glucose-1-phosphate to glucose-6-phosphate. The starch/maltodextrin phosphorylase (EC 2.4.1.1) and α-glucan phosphorylase may include any protein that is active in phosphoryl transfer to glucose to produce glucose-1-phosphate from starch or maltodextrin. The sucrose phosphorylase (EC 2.4.1.7) may include any protein that is active in phosphoryl transfer to glucose to produce glucose-1-phosphate from sucrose. The α-amylase (EC 3.2.1.1), pullulanase (EC 3.2.1.41), isoamylase (EC 3.2.1.68), 4-α-glucanotransferase (EC 2.4.1.25), and glucoamylase (EC 3.2.1.3), which are starch-liquefying enzymes, may include any protein that is active in converting starch or maltodextrin to debranched maltooligosaccharide or glucose. The sucrase (EC 3.2.1.26) may include any protein that is active in converting sucrose to glucose. The polyphosphate glucokinase (EC 2.7.1.63) may include any protein that is active in phosphoryl transfer to glucose to convert glucose to glucose-6-phosphate.

The psicose-6-phosphate phosphatase, α-glucan phosphorylase, phosphoglucomutase (or phosphomannomutase), glucose-6-phosphate isomerase, psicose-6-phosphate-3-epimerase (or ribulose-5-phosphate-3-epimerase), pullulanase (or isoamylase), 4-α-glucanotransferase, and polyphosphate glucokinase that are included in the composition for producing psicose of the present application may have little or no side reactions with psicose, which is the final product.

The composition for producing psicose of the present application may properly contain not only the psicose-6-phosphate phosphatase, but also a plurality of enzymes and substrates thereof for preparing psicose. The psicose-6-phosphate phosphatase has the effect of being able to selectively and irreversibly produce psicose from psicose-6-phosphate even in an environment in which several enzymes are present.

The composition for producing psicose of the present application may further include any suitable conventionally used excipients. Examples of such excipients include, for example, preservatives, wetting agents, dispersants, suspending agents, buffers, stabilizers, and isotonic agents, but are not limited thereto.

The composition for producing psicose of the present application may further include a metal ion or a metal salt. In one embodiment, the metal ion may be a divalent metal cation. Specifically, the metal ion may be at least one selected from the group consisting of Ni, Mg, Co, Mn, Fe, and Zn ions. More specifically, the composition for producing psicose of the present application may further include a metal salt. Even more specifically, the metal salt may be at least one selected from the group consisting of $NiSO_4$, $MgSO_4$, $MgCl_2$, $NiCl_2$, $CoSO_4$, $CoCl_2$, $MnCl_2$, $MnSO_4$, $FeSO_4$, and $ZnSO_4$.

Even another aspect of the present application provides a method for producing psicose, including converting psicose-6-phosphate into psicose by bringing psicose-6-phosphate into contact with the psicose-6-phosphate phosphatase, a microorganism expressing the same, or a culture of the microorganism.

Specifically, in the method for producing psicose, psicose may be produced by bringing psicose-6-phosphate into contact with the psicose-6-phosphate phosphatase, a microorganism expressing the same, or a culture of the microorganism, but is not limited thereto.

The method of the present application may further include converting fructose-6-phosphate into psicose-6-phosphate by bringing fructose-6-phosphate into contact with fructose-6-phosphate-3-epimerase, a microorganism expressing the fructose-6-phosphate-3-epimerase, or a culture of the microorganism expressing the fructose-6-phosphate-3-epimerase, prior to the step of converting psicose-6-phosphate to psicose.

The method of the present application may further include converting glucose-6-phosphate into fructose-6-phosphate by bringing glucose-6-phosphate into contact with glucose-6-phosphate-isomerase, a microorganism expressing the glucose-6-phosphate-isomerase, or a culture of the microorganism expressing the glucose-6-phosphate-isomerase, prior to the step of converting fructose-6-phosphate to psicose-6-phosphate.

The method of the present application may further include converting glucose-1-phosphate into glucose-6-phosphate by bringing glucose-1-phosphate into contact with phosphoglucomutase, a microorganism expressing the phosphoglucomutase, or a culture of the microorganism expressing the phosphoglucomutase, prior to the step of converting glucose-6-phosphate into fructose-6-phosphate.

The method of the present application may further include converting glucose into glucose-6-phosphate by bringing glucose into contact with polyphosphate glucokinase, a microorganism expressing the polyphosphate glucokinase, or a culture of the microorganism expressing the polyphosphate glucokinase, and polyphosphate, prior to the step of converting glucose-6-phosphate into fructose-6-phosphate.

The method of the present application may further include converting starch, maltodextrin, sucrose, or a combination thereof into glucose-1-phosphate by bringing starch, maltodextrin, sucrose, or a combination thereof into contact with α-glucan phosphorylase, starch phosphorylase, maltodextrin phosphorylase, or sucrose phosphorylase; a microorganism expressing the phosphorylase; or a culture of the microorganism expressing the phosphorylase, and phosphate, prior to the step of converting glucose-1-phosphate into glucose-6-phosphate.

The method of the present application may further include converting starch, maltodextrin, sucrose, or a combination thereof into glucose by bringing starch, maltodextrin, sucrose, or a combination thereof into contact with α-amylase, pullulanase, isoamylase, glucoamylase, or sucrase; a microorganism expressing the α-amylase, pullulanase, glucoamylase, sucrase, or isoamylase; or a culture of the microorganism expressing the α-amylase, pullulanase, glucoamylase, sucrase, or isoamylase, prior to converting starch, maltodextrin, sucrose, or a combination thereof into glucose-1-phosphate.

The psicose-6-phosphate phosphatase, α-glucan phosphorylase, phosphoglucomutase (or phosphomannomutase), glucose-6-phosphate isomerase, psicose-6-phosphate-3-epimerase (or ribulose-5-phosphate-3-epimerase), pullulanase (or isoamylase), 4-α-glucanotransferase, and polyphosphate glucokinase that are used in the method for producing psicose of the present application may have little or no side reactions with psicose, which is the final product.

In the method for producing psicose of the present application, the optimal/maximum psicose may be produced in a complex combination with sugar phosphate-converting enzymes by decomposing a high concentration of starch, and a maximum of 8 kinds of enzymes may be used in combination to secure the maximum productivity of psicose.

First, glucan phosphorylase (glycogen phosphorylase, EC 2.4.1.1), an enzyme that degrades starch and produces glucose-1-phosphate, specifically produces glucose-1-phosphate on α-1,4-bound starch. Secondly, phosphoglucomutase (EC 2.7.5.1) or phosphomannomutase (EC 5.4.2.8), which converts the thus-produced glucose-1-phosphate into glucose-6-phosphate, is used in the intermediate complex enzyme reaction. As the third enzyme used, glucose-6-phosphate isomerase (EC 5.3.1.9), which converts glucose-6-phosphate to fructose-6-phosphate, is used. Fourth, ribulose-5-phosphate-3-epimerase or psicose-6-phosphate-3-epimerase, which is the enzyme that converts fructose-6-phosphate to psicose-6-phosphate as described above, is used to produce psicose-6-phosphate in a reversible reaction. In the reaction of starch to psicose-6-phosphate, although it is impossible to produce more than a certain amount in the reversible reaction, the use of the selective psicose-6-phosphate phosphatase included in the present invention enables the production of psicose in high yield.

In order to further increase the starch utilization rate, pullulanase (EC 3.2.1.41) or isoamylase (EC 3.2.1.68) is used together to degrade branched α-1,6 bonds in addition to the α-1,4 bonds of amylopectin. Additionally, in order to increase the starch utilization of glucan phosphorylase, 4-α-glucanotransferase (EC 2.4.1.25) is used. The utilization of the segmented starch substrate can be increased by binding oligosaccharides in the form of α-1,4 bonds to maltose or other oligosaccharides, which are substrates with relatively low activity. In addition, polyphosphate-glucose phosphotransferase (EC 2.7.1.63) can be used to produce additional psicose through complex enzymatic reactions from glucose degraded after the use of starch, thereby securing the maximum psicose conversion rate.

Further, in the method of the present application, the contact may be carried out at a pH of 5.0 to 9.0, specifically at a pH of 6.0 to 8.0.

In the method of the present application, the contact may be carried out at a temperature of 40° C. to 80° C., specifically at a temperature of 40° C. to 60° C. or 50° C. to 60° C.

In the method of the present application, the contact may be carried out for 2 hours to 24 hours, specifically for 6 to 24 hours or 120 hours.

In the method of the present application, the contact may be carried out at a pH of 5.0 to 9.0, at a temperature of 40° C. to 80° C., and/or for 2 hours to 24 hours. Specifically, the contact may be carried out at a pH of 6.0 to 8.0, at a temperature of 40° C. to 60° C. or 50° C. to 60° C., and/or for 6 hours to 24 hours or 120 hours.

The method of the present application may further include purifying psicose. There is no particular limitation on the method for purifying psicose, and any suitable method known in the art may be used. Non-limiting examples of such purification methods include chromatography, fractional crystallization, and ion purification, which may be carried out alone or in a combination of two or more thereof. For example, the reaction product of psicose may be purified by chromatography. In this case, the purification of saccharides by chromatography may be performed based on small differences in binding force between saccharides to be purified and metal ions attached to an ionic resin.

The method of the present application may further include bleaching, demineralizing, or both before or after the purification step. The bleaching and/or demineralizing enables production of purer psicose without impurities.

MODE FOR CARRYING OUT THE INVENTION

Hereinafter, the present application will be described in more detail by way of Examples. However, these Examples are provided for illustrative purposes only to aid in the understanding of the present application, and the scope of the present application is not intended to be limited to or by these Examples.

In the present application, amino acids may be represented by the following abbreviations or amino acid names.

TABLE 1

| Type of amino acids | Abbreviation | DNA codon encoded by corresponding amino acid | RNA codon encoded by corresponding amino acid |
|---|---|---|---|
| alanine | A | GCT, GCC, GCA, GCG | GCU, GCC, GCA, GCG |
| arginine | R | AGA, AGG | AGA, AGG |
| asparagine | N | AAT, AAC | AAU, AAC |
| aspartic acid | D | GAT, GAC | GAU, GAC |
| cystein | C | TGT, TGC | UGU, UGC |
| glutamic acid | R | GAA, GAG | GAA, GAG |
| glutamine | Q | CAA, CAG | CAA, CAG |
| glycine | G | GGT, GGC, GGA, GGG | GGU, GGC, GGA, GGG |
| histidine | H | CAC, CAT | CAC, CAU |
| isoleucine | I | ATT, ATC, ATA | AUU, AUC, AUA |
| leucine | L | TTA, TTG, CTT, CTC, CTA, CTG | UVA, UUG, CUU, CUC, CUA, CUG |
| lysine | K | AAA, AAG | AAA, AAG |
| methionine | M | ATG | AUG |
| phenylalanine | F | ITT, TTC | UUU, UUC |
| proline | P | CCT, CCC, CCA, CCG | CCU, CCC, CCA, CCG |
| serine | S | TCT, TCC, TCA, TCG | UCU, UCC, UCA, UCG |

TABLE 1-continued

| Type of amino acids | Abbreviation | DNA codon encoded by corresponding amino acid | RNA codon encoded by corresponding amino acid |
|---|---|---|---|
| threonine | T | ACT, ACC, ACA, ACG | ACU, ACC, ACA, ACG |
| tryptophan | V | TGG | UGG |
| tyrosine | Y | TAT, TAC | UAU, UAC |
| valine | V | GTT, GTC, GTA, GTG | GUU, GUC, GUA, GUG |

Example 1: Preparation of Recombinant Expression Vector of Each Enzyme and Transformed Microorganism In order to provide the enzymes necessary for the psicose production pathway, thermoresistant genes were selected, which are summarized in Table 2 below.

TABLE 2

| SEQ ID NO | Species and Genus | NCBI No. |
|---|---|---|
| 1 | *Alicyclobacillus acidocaldarius* | ACV59297.1 |
| 2 | *Alicyclobacillus teagchongensis* | KRW92667.1 |
| 3 | | WP_058093972.1 |
| 4 | *Amycolstopsis thermoflava* | WP_017986193.1 |
| 5 | | WP_037323890.1 |
| 6 | *Anaerolines thermolimosa* | WP_084001059.1 |
| 7 | | WP_062189018.1 |
| 8 | | GAP08215.1 |
| 9 | *Anaerolinea thermophila* | BAJ62794.1 |
| 10 | | KUK46216.1 |
| 11 | | BAJ63987.1 |
| 12 | *Archaeoglobus fugidus* | AAB91288.1 |
| 13 | | AAB89113.1 |
| 14 | | AAB89416.1 |
| 15 | *Archaeoglobus profundus* | WP_012940213.1 |
| 16 | *Archaeoglobus veseficus* | WP_013683862.1 |
| 17 | *Bacillus licheniformis* | AAU41557.1 |
| 18 | | AAU39603.1 |
| 19 | | AAU43073.1 |
| 20 | *Caldicellulosiruptor bescii* | ACM59531.1 |
| 21 | | ACM59457.1 |
| 22 | | ACM61198.1 |
| 23 | | ACM61211.1 |
| 24 | | ACM60182.1 |
| 25 | *Caldilinea aerophila* | BAL98676.1 |
| 26 | | BAM00874.1 |
| 27 | | WP_014433277.1 |
| 28 | *Caldithrix abyssi* | APF18124.1 |
| 29 | | APF18744.1 |
| 30 | | APF16831.1 |
| 31 | | WP_006929206.1 |
| 32 | *Carboxydocella* sp. ULO1 | WP_079933669.1 |
| 33 | *Carboxydothermus ferrireducens* | WP_028051691.1 |
| 34 | | WP_028051711.1 |
| 35 | | WP_028053062.1 |
| 36 | *Chloroflexi bacterium* 54-19 | OJW02856.1 |
| 37 | *Defluviitoga tunisiensis* | WP_045087739.1 |
| 38 | *Deinococcus aerius* | WP_103127908.1 |
| 39 | *Deinococcus apacheasis* | WP_019584763.1 |
| 40 | *Deinococcus aquatilis* | WP_019011981.1 |
| 41 | *Deinococcus geothermalis* | WP_011529832.1 |
| 42 | *Deinococcus hopiensis* | WP_084049191.1 |
| 43 | *Deinococcus maricopensis* | WP_013556873.1 |
| 44 | *Deinococcus murrayi* | WP_084542862.1 |
| 45 | | WP_051363537.1 |
| 46 | *Deinococcus reticulitermitis* | WP_092263046.1 |
| 47 | *Deinococcus wulumuqiensis* | WP_017870657.1 |
| 48 | *Deinococcus* sp. Leaf326 | WP_056297006.1 |
| 49 | *Deinococcus phoenicis* | WP_034353069.1 |
| 50 | *Deinococcus proteolyticus* | WP_013614672.1 |
| 51 | *Deinococcus* sp. 17bor-2 | WP_109826642.1 |
| 52 | *Deinococcus* sp. NW-56 | WP_104990527.1 |
| 53 | *Deinococcus* sp. RL | KEF35131.1 |
| 54 | | WP_081851636.1 |

TABLE 2-continued

| SEQ ID NO | Species and Genus | NCBI No. |
|---|---|---|
| 55 | *Deinococcus* sp. YIM 77859 | WP_034384462.1 |
| 56 | *Desulfurococcus mucosus* | ADV64381.1 |
| 57 | | ADV64382.1 |
| 58 | | ADV64566.1 |
| 59 | *Dictyoglomus turgidum* | YP_002352793.1 |
| 60 | | YP_002353123.1 |
| 61 | | YP_002352154.1 |
| 62 | *Effusibacillus pohliae* | WP_018132070.1 |
| 63 | *Fervidobacterium goudwanense* | WP_072759218.1 |
| 64 | *Fervidobacterium islandicum* | AMW32328.1 |
| 65 | | AMW33413.1 |
| 66 | *Fervidobacterium nodosum* | ABS60322.1 |
| 67 | | ABS61294.1 |
| 68 | *Fervidobacterium pennivorans* | AFG34634.1 |
| 69 | | AFG35917.1 |
| 70 | | WP_064011782.1 |
| 71 | *Geobacillus* sp. | WP_011232549.1 |
| 72 | *Geobacillus stearothermophilus* | ALA69320.1 |
| 73 | | ALA71677.1 |
| 74 | | ALA71036.1 |
| 75 | | ALA70927.1 |
| 76 | | ALA69332.1 |
| 77 | *Halococcus salifodinae* | WP_005045395.1 |
| 78 | | EMA49396.1 |
| 79 | | EMA52756.1 |
| 80 | *Hydrogenivirga* sp. 128-5-R1-1 | WP_008285887.1 |
| 81 | *Hydrogenobacter hydrogenophilus* | WP_096602199.1 |
| 82 | | WP_096601840.1 |
| 83 | *Hydrogenobacter thermophilus* | WP_012963417.1 |
| 84 | *Hyperthermus butylicus* | ABM80367.1 |
| 85 | *Kosmotoga aresicorallina* | WP_084251417.1 |
| 86 | *Kosmotoga olearia* | ACR80305.1 |
| 87 | | ACR80819.1 |
| 88 | *Narinitoga piezophila* | AEX84499.1 |
| 89 | | AEX85453.1 |
| 90 | | AEX85799.1 |
| 91 | *Neiothermus cerbereus* | WP_027877060.1 |
| 92 | | WP_027878515.1 |
| 93 | *Neiothermus chliarophilus* | WP_027892542.1 |
| 94 | | WP_051304156.1 |
| 95 | *Neiothermus ruber* | ADD26908.1 |
| 96 | | WP_013013826.1 |
| 97 | | WP_013013825.1 |
| 98 | | WP_013012548.1 |
| 99 | | WP_027883570.1 |
| 100 | *Neiothermus silvanus* | ADH63424.1 |
| 101 | | WP_013157023.1 |
| 102 | *Neiothermus taiwanensis* | WP_027888084.1 |
| 103 | | WP_027888305.1 |
| 104 | *Neiothermus timidus* | WP_018466213.1 |
| 105 | | WP_018465080.1 |
| 106 | | WP_018467688.1 |
| 107 | | WP_018467518.1 |
| 108 | | WP_018465603.1 |
| 109 | | WP_018466116.1 |
| 110 | | WP_018467797.1 |
| 111 | | WP_018467420.1 |
| 112 | | WP_018466214.1 |
| 113 | | WP_018465420.1 |
| 114 | *Neiothermus rufus* | WP_036271046.1 |
| 115 | *Nesotoga infera* | KUI90417.1 |
| 116 | *Netallosphaera sedula* | ABP94905.1 |
| 117 | *Nethanocella conradii* | AFC99407.1 |
| 118 | | WP_014405429.1 |
| 119 | | AFD00405.1 |

TABLE 2-continued

| SEQ ID NO | Species and Genus | NCBI No. |
|---|---|---|
| 120 | Nethanococcoides methylutens | WP_048194361.1 |
| 121 | | AKB84306.1 |
| 122 | Nethanohalobium evestigatum | ADI75005.1 |
| 123 | | WP_013193898.1 |
| 124 | Nethanolobus tindarius | WP_048135864.1 |
| 125 | | WP_048135649.1 |
| 126 | | ETA67773.1 |
| 127 | Nethanosarcina siciliae | WP_048179383.1 |
| 128 | | AIB37722.1 |
| 129 | | AKB35909.1 |
| 130 | Nethanothermus fervidus | ADP76907.1 |
| 131 | Petrotoga mobilis | ABX30802.1 |
| 132 | | KUI15285.1 |
| 133 | Picrophilus torridus | AAT44010.1 |
| 134 | | MAT43693.1 |
| 135 | Psendonocardia thermophila | WP_073456926.1 |
| 136 | Pyrococcus furiosus | AAL80556.1 |
| 137 | | AAL81109.1 |
| 138 | | WP_014835302.1 |
| 139 | | AAL82045.1 |
| 140 | | AAL82122.1 |
| 141 | | AAL81285.1 |
| 142 | | AAL81790.1 |
| 143 | | AAL80346.1 |
| 144 | | AAL80703.1 |
| 145 | | AAL81901.1 |
| 146 | | AAL81913.1 |
| 147 | | KAL80587.1 |
| 148 | | AFN04628.1 |
| 149 | Pyrodictium occultum | WP_083494490.1 |
| 150 | Rhodothermus marinus | WP_041806336.1 |
| 151 | | WP_012844425.1 |
| 152 | | ACY47561.1 |
| 153 | | ACY48134.1 |
| 154 | | ACY47672.1 |
| 155 | | ACY48911.1 |
| 156 | | WP_012843092.1 |
| 157 | | WP_012843709.1 |
| 158 | | WP_012844300.1 |
| 159 | | ACY48106.1 |
| 160 | | WP_012844667.1 |
| 161 | | WP_012845116.1 |
| 162 | | WP_012844208.1 |
| 163 | | WP_012843855.1 |
| 164 | | ACY47289.1 |
| 165 | Slackia heliotrinireducens | WP_012798605.1 |
| 166 | | ACY22623.1 |
| 167 | Staphylothermus marinus | ABN70247.1 |
| 168 | | ABN69637.1 |
| 169 | | ABN69899.1 |
| 170 | Sulfolobus acidocaldarius | MAY79446.1 |
| 171 | | WP_015385352.1 |
| 172 | | MAY80292.1 |
| 173 | Thermanaerothrix daxensis | KPI83857.1 |
| 174 | Thermoanaerobacter sp. | WP_004400108.1 |
| 179 | Thermoanaerobacterium xylanolyticun | WP_013788008.1 |
| 180 | Thermobifida halotolerans | WP_068689397.1 |
| 181 | | WP_068692137.1 |
| 182 | Thermococcus celer | WP_088862065.1 |
| 183 | | ASI98087.1 |
| 184 | Thermococcus litoralis | EHR78031.1 |
| 185 | Thermococcus profundus | WP_088857759.1 |
| 186 | Thermocrinis minervae | WP_079653666.1 |
| 187 | Thermocrinis ruber | AHE95294.1 |
| 188 | Thermoflexus hugenboltzii | WP_088571736.1 |
| 189 | Thermotoga lettingae | ABV34293.1 |
| 190 | Thermotoga neapolitana | WP_015919708.1 |
| 191 | | ACM22182.1 |
| 192 | | ACM22192.1 |
| 193 | | ACM22252.1 |
| 194 | | ACM22284.1 |
| 195 | | ACM22382.1 |
| 196 | | ACM22666.1 |
| 197 | | ACM22704.1 |
| 198 | | ACM22708.1 |
| 199 | | ACM22832.1 |
| 200 | | ACM22990.1 |
| 201 | | ACM23016.1 |
| 202 | | ACM23040.1 |
| 203 | | ACM23081.1 |
| 204 | | ACM23138.1 |
| 205 | | ACM23254.1 |
| 206 | | ACM23323.1 |
| 207 | | ACM23341.1 |
| 208 | | ACM23415.1 |
| 209 | | ACM23510.1 |
| 210 | | ACM23571.1 |
| 211 | | ACM23575.1 |
| 212 | | ACM23847.1 |
| 213 | | ACM23859.1 |
| 214 | | ACM23950.1 |
| 215 | | ACM23957.1 |
| 216 | | ACM24018.1 |
| 217 | Thermotoga petrophilia | ABQ46309.1 |
| 218 | Thermus amyloliquefaciens | WP_038055695.1 |
| 219 | Thermus filiformis | WP_038062097.1 |
| 220 | Thermus thermophilus | WP_096411270.1 |
| 221 | | AAS82270.1 |
| 222 | Truepera radiovictrix | WP_013176662.1 |

The genes of the selected amino acids were amplified by way of polymerase chain reaction (PCR) using gene synthesis or chromosomal DNA (genomic DNA) of each cultured strain, and the amplified DNA was inserted into plasmid vector pET21a (Novagen) for *E. coli* expression using restriction enzymes NdeI and XhoI or SalI to construct recombinant expression vectors. The expression vectors were transformed into strain *E. coli* BL21(DE3) using a general transformation technique (see Sambrook et al. 1989) to produce transformed microorganisms.

Specifically, the psicose-6-phosphate phosphatase of SEQ ID NOS: 26, 29, 53, 56, 60, 70, 76, 80, 81, 116, 117, 131, 134, 145, 167, 185, 186, and 191 was transformed into the *E. coli* BL21(DE3) strain to prepare transformed microorganisms, which were named *E. coli* BL21(DE3)/pET-CJ-ap26, *E. coli* BL21(DE3)/pET-CJ-ap29, *E. coli* BL21(DE3)/pET-CJ-ap53, *E. coli* BL21(DE3)/pET-CJ-ap56, *E. coli* BL21(DE3)/pET-CJ-ap60, *E. coli* BL21(DE3)/pET-CJ-ap70, *E. coli* BL21(DE3)/pET-CJ-ap76, *E. coli* BL21(DE3)/pET-CJ-ap80, *E. coli* BL21(DE3)/pET-CJ-ap81, *E. coli* BL21(DE3)/pET-CJ-ap116, *E. coli* BL21(DE3)/pET-CJ-ap117, *E. coli* BL21 (DE3)/pET-CJ-ap131, *E. coli* BL21 (DE3)/pET-CJ-ap134, *E. coli* BL21(DE3)/pET-CJ-ap145, *E. coli* BL21(DE3)/pET-CJ-ap167, *E. coli* BL21(DE3)/pET-CJ-ap185, *E. coli* BL21(DE3)/pET-CJ-ap186, and *E. coli* BL21(DE3)/pET-CJ-ap191.

The thus-prepared transformed microorganisms were deposited at the Korean Culture Center of Microorganisms (KCCM), an International Depositary Authority, on Nov. 14, 2018 with Accession Nos. KCCM12390P (*E. coli* BL21 (DE3)/pET-CJ-ap26), KCCM12391P (*E. coli* BL21(DE3)/pET-CJ-ap29), KCCM12392P (*E. coli* BL21(DE3)/pET-CJ-ap53), KCCM12393P (*E. coli* BL21(DE3)/pET-CJ-ap56), KCCM12394P (*E. coli* BL21(DE3)/pET-CJ-ap60), KCCM12395P (*E. coli* BL21(DE3)/pET-CJ-ap70), KCCM12396P (*E. coli* BL21(DE3)/pET-CJ-ap76), KCCM12397P (*E. coli* BL21(DE3)/pET-CJ-ap80), KCCM12398P (*E. coli* BL21(DE3)/pET-CJ-ap81), KCCM12399P (*E. coli* BL21(DE3)/pET-CJ-ap116), KCCM12400P (*E. coli* BL21(DE3)/pET-CJ-ap117), KCCM12401P (*E. coli* BL21(DE3)/pET-CJ-ap131), KCCM12402P (*E. coli* BL21(DE3)/pET-CJ-ap134), KCCM12403P (*E. coli* BL21(DE3)/pET-CJ-ap145), KCCM12404P (*E. coli* BL21(DE3)/pET-CJ-ap167), KCCM12405P (*E. coli* BL21(DE3)/pET-CJ-ap185), KCCM12406P (*E. coli* BL21(DE3)/pET-CJ-ap186), and KCCM12407P (*E. coli* BL21(DE3)/pET-CJ-ap191).

Example 2: Preparation of Recombinant Enzymes

In order to prepare recombinant enzymes, a culture tube containing 5 mL of an LB liquid medium was inoculated with each of the transformed microorganisms prepared in Example 1. The seed culture was performed in a shaking incubator at 37° C. until an absorbance of 2.0 at 600 nm was reached. The culture broth obtained by way of the seed culture was inoculated to a culture flask containing the LB liquid medium, followed by main culture. When the absorbance of the culture at 600 nm reached 2.0, 1 mM IPTG was added to induce the expression and production of a recombinant enzyme. The culture was performed at a stirring speed of 180 rpm, and the culture temperature was maintained at 37° C. The culture broth was centrifuged at 8,000×g and at 4° C. for 20 minutes to recover cells. The recovered cells were washed with 50 mM Tris-HCl (pH 8.0) buffer twice and re-suspended in the same buffer, and the cells were disrupted using an ultrasonic homogenizer. The cell lysates were centrifuged at 13,000×g and 4° C. for 20 minutes to obtain only supernatant. The recombinant enzyme was purified from the supernatant by His-tag affinity chromatography, and the purified recombinant enzyme was dialyzed against 50 mM Tris-HCl buffer (pH 8.0) and was then used for subsequent reaction.

Example 3: Analysis of Dephosphorylation Activity of Sugar Phosphate and Psicose-6-Phosphate After preparing psicose-6-phosphate from fructose-6-phosphate, the activity of psicose production by psicose-6-phosphate phosphatase was confirmed, or the activity was measured by detecting psicose by further adding three enzymes using glucose-1-phosphate as the first substrate. In particular, glucose, fructose, and psicose, which are common sugars produced by mixing each of the 222 phosphatases of the present application with the three enzymes (i.e., phosphoglucomutase (EC 2.7.5.1) or phosphomannomutase (EC 5.4.2.8), which converts glucose-1-phosphate to glucose-6-phosphate; glucose-6-phosphate isomerase (EC 5.3.1.9), which converts glucose-6-phosphate to fructose-6-phosphate; and ribulose-5-phosphate-3-epimerase or psicose-6-phosphate-3-epimerase, which is an enzyme that converts fructose-6-phosphate to psicose-6-phosphate) were qualitatively and quantitatively evaluated.

Specifically, 50 mM fructose-6-phosphate or 20 mM glucose-1-phosphate was suspended in 50 mM Tris-HCl (pH 7.0), 50 mM sodium phosphate (pH 6 to 7), or 50 mM potassium phosphate (pH 6 to 7), and then 0.1 unit/mL of phosphoglucomutase; phosphomannomutase, glucose-6-phosphate isomerase, and ribulose-5-phosphate-3-epimerase; or psicose-6-phosphate-3-epimerase and each of the 222 recombinant psicose-6-phosphate phosphatases prepared in Example 2 were added thereto, and the mixture was allowed to react at 45° C. to 70° C. for 1 to 24 hours. The production of glucose, fructose, and psicose was confirmed by HPLC, which was performed using an SP 0810 column (Shodex) and an Aminex HPX-87C column (Bio-RAD) at 80° C. with a mobile phase flow rate of 0.6 mL/min, and detected using a refractive index detector (RID).

Thereafter, in the prepared mixed solution of glucose-1-phosphate, glucose-6-phosphate, fructose-6-phosphate, and psicose-6-phosphate, the dephosphorylation activity of the psicose-6-phosphate phosphatase of the present application and the psicose-6-phosphate-specific (selective) dephosphorylation rate were measured.

Specifically, 0.1 unit/mL of each of the psicose-6-phosphate phosphatase and 5 mM $MgCl_2$ (or $MgSO_4$) were added to the mixed solution of 1% (w/v) glucose-6-phosphate, glucose-1-phosphate, fructose-6-phosphate, and psicose-6-phosphate, and the mixture was allowed to react at 50° C. for 12 hours. The reaction products were analyzed by HPLC using an Aminex HPX-87C column (Bio-RAD), at 80° C. with a mobile phase flow rate of 0.6 mL/min. A refractive index detector was used to detect the production of psicose and other saccharides (fructose and glucose).

As a result, among all 222 enzymes, 69 enzymes showed high selective dephosphorylation activity for psicose-6-phosphate, and 45 enzymes showed weak selective dephosphorylation activity for psicose-6-phosphate. Additionally, in 108 enzymes, the dephosphorylation titer for selective psicose-6-phosphate could not be confirmed. However, dephosphorylation activity was confirmed in 221 enzymes excluding one of the 222 enzymes, of which 113 enzymes showed high dephosphorylation activity, and 108 enzymes showed low dephosphorylation activity. Meanwhile, the enzyme of SEQ ID NO: 54, which was confirmed to have no dephosphorylation titer, is known as a dephosphorylation enzyme, but it was confirmed that it has no substantial dephosphorylation activity. The results are summarized in Table 3 below.

A=Low Activity (Dephosphorylation conversion rate from sugar phosphate to simple sugar is 1-30%)
B=High Activity (Dephosphorylation conversion rate from sugar phosphate to simple sugar is 30% or more)
C=No Activity (Dephosphorylation conversion rate from sugar phosphate to simple sugar is less than 1%)

TABLE 3

| SEQ ID NO | Species and Genus | NCBI No. | G1P/G6P/F6P/ P6P Dephosphorylation activity | P6P (Selective)/ G1P + G6P + F6P + P6P Dephosphorylation activity |
|---|---|---|---|---|
| 1 | Alicyclobacillus acidocaldarius | ACV59297.1 | B | B |
| 2 | Alicyclobacillus | KRW92667.1 | A | C |
| 3 | tengchongensis | WP_058093972.1 | A | C |
| 4 | Amycolatopsis thermoflava | WP_017986193.1 | A | C |
| 5 | | WP_037323890.1 | A | C |
| 6 | Anaerolinea thermolimosa | WP_084001059.1 | B | B |
| 7 | | WP_062189018.1 | A | C |
| 8 | | GAP08215.1 | A | C |

TABLE 3-continued

| SEQ ID NO | Species and Genus | NCBI No. | G1P/G6P/F6P/P6P Dephosphorylation activity | P6P (Selective)/G1P + G6P + F6P + P6P Dephosphorylation activity |
|---|---|---|---|---|
| 9 | *Anaerolinea thermophila* | BAJ62794.1 | B | B |
| 10 | | KUK46216.1 | A | C |
| 11 | | BAJ63987.1 | A | C |
| 12 | *Archaeoglobus fugidus* | AAB91288.1 | B | B |
| 13 | | AAB89113.1 | B | A |
| 14 | | AAB89416.1 | B | A |
| 15 | *Archacoglobus profundus* | WP_012940218.1 | A | C |
| 16 | *Archacoglobus veneficus* | WP_013683862.1 | A | C |
| 17 | *Bacillus licheniformis* | AAU41557.1 | B | A |
| 18 | | AAU39603.1 | B | A |
| 19 | | AAU43073.1 | A | C |
| 20 | *Caldicellosiruptor bescii* | ACM59581.1 | B | A |
| 21 | | ACM59457.1 | B | A |
| 22 | | ACM61198.1 | B | A |
| 23 | | ACM61211.1 | B | A |
| 24 | | ACM60182.1 | A | C |
| 25 | *Caldilinea aerophila* | BAL98676.1 | B | A |
| 26 | | BAM0087.1 | B | B |
| 27 | | WP_014433277.1 | A | C |
| 28 | *Caldithrix abyssi* | APF18124.1 | B | A |
| 29 | | APF18744.1 | B | B |
| 80 | | APF16831.1 | A | C |
| 31 | | WP_006929206.1 | A | C |
| 32 | *Carboxydocella* sp. ULO1 | WP_079933669.1 | A | C |
| 33 | *Carboxydothermus ferrireducens* | WP_028051691.1 | A | C |
| 34 | | WP_028051711.1 | A | C |
| 35 | | WP_028053062.1 | A | C |
| 36 | *Chloroflexi bacterium* 54-19 | OJW02856.1 | A | C |
| 37 | *Defluviitoga tunisiensis* | WP_045087739.1 | B | A |
| 38 | *Deinococcus aerius* | WP_103127908.1 | B | B |
| 39 | *Deinococcus apachensis* | WP_019584763.1 | B | B |
| 40 | *Deinococcus aquatilis* | WP_019011981.1 | B | B |
| 41 | *Deinococcus geothermalis* | WP_011529832.1 | B | B |
| 42 | *Deinococcus hopiensis* | WP_084049191.1 | B | B |
| 43 | *Deinococcus maricopensis* | WP_013556873.1 | B | B |
| 44 | *Deinococcus murrayi* | WP_084542862.1 | B | A |
| 45 | | WP_051363537.1 | B | B |
| 46 | *Deinococcus reticulitermitis* | WP_092263046.1 | B | B |
| 47 | *Deinococcus wulumugiensis* | WP_017870657.1 | B | B |
| 48 | *Deinococcus* sp. Leaf326 | WP_056297006.1 | B | B |
| 49 | *Deinococcus phoenicis* | WP_034358069.1 | B | B |
| 50 | *Deinococcus proteolyticus* | WP_013614672.1 | B | B |
| 51 | Deinococcus sp. 17bor-2 | WP_109826642.1 | B | B |
| 52 | *Deinococcus* sp. NW-56 | WP_104990527.1 | B | B |
| 53 | *Deinococcus* sp. RL | KEF35131.1 | B | B |
| 54 | | WP_081851636.1 | C | C |
| 55 | *Deinococcus* sp. YIM 77859 | WP_034384462.1 | B | A |
| 56 | *Desulfurococcus mucosus* | ADV64381.1 | B | B |
| 57 | | ADV64382.1 | B | B |
| 58 | | ADV64566.1 | A | C |
| 59 | *Dictyoglomus turgidum* | YP_002352793.1 | B | B |
| 60 | | YP_002353123.1 | B | B |
| 61 | | YP_002352154.1 | B | A |
| 62 | *Effusibacillus pohliae* | WP_018182070.1 | A | C |
| 63 | *Fervidobacterium gondwanense* | WP_072759218.1 | A | C |
| 64 | *Fervidobacterium islandicum* | ANW32328.1 | B | B |
| 65 | | ANW33413.1 | B | B |
| 66 | *Fervidobacterium nodosum* | ABS60322.1 | B | B |
| 67 | | ABS61294.1 | A | C |
| 68 | *Fervidobacterium pennivorans* | AFG34634.1 | A | C |
| 69 | | AFG35917.1 | B | B |
| 70 | | WP_064011782.1 | B | B |
| 71 | *Geobacillus* sp. | WP_011232549.1 | A | C |
| 72 | *Geobacillus stearothermophilus* | ALA69320.1 | B | B |
| 73 | | ALA71677.1 | B | A |
| 74 | | ALA71036.1 | A | C |
| 75 | | ALA70927.1 | A | C |
| 76 | | ALA69332.1 | B | B |
| 77 | *Halococcus salifodinae* | WP_005045895.1 | B | A |
| 78 | | EMA49896.1 | A | C |
| 79 | | EMA52756.1 | A | C |
| 80 | *Hydrogenivirga* sp. 128-5-R1-1 | WP_008285887.1 | B | B |
| 81 | *Hydrogenobacter* | WP_096602199.1 | B | B |
| 82 | *hydrogenophilus* | WP_096601840.1 | A | C |

TABLE 3-continued

| SEQ ID NO | Species and Genus | NCBI No. | G1P/G6P/F6P/P6P Dephosphorylation activity | P6P (Selective)/ G1P + G6P + F6P + P6P Dephosphorylation activity |
|---|---|---|---|---|
| 83 | Hydrogenobacter thermophilus | WP_012963417.1 | A | C |
| 84 | Hyperthermus butylicus | ABM80367.1 | A | C |
| 85 | Kosmotoga arenicorallina | WP_084251417.1 | B | A |
| 86 | Kosmotoga olearia | ACR80305.1 | A | C |
| 87 | | ACR80819.1 | A | C |
| 88 | Marinitoga piezophila | AEX84499.1 | B | A |
| 89 | | AEX85453.1 | A | C |
| 90 | | AEX85799.1 | A | C |
| 91 | Meiothermus cerberus | WP_027877060.1 | B | B |
| 92 | | WP_027878515.1 | B | B |
| 93 | Meiothermus chliarophilus | WP_027892542.1 | B | B |
| 94 | | WP_051304156.1 | A | C |
| 95 | Meiothermus ruber | ADD26908.1 | B | B |
| 96 | | WP_013013826.1 | A | C |
| 97 | | WP_013018825.1 | A | C |
| 98 | | WP_013012548.1 | A | C |
| 99 | | WP_027883570.1 | B | B |
| 100 | Meiothermus silvanus | ADH63424.1 | B | B |
| 101 | | WP_013157023.1 | B | B |
| 102 | Meiothermus taiwanensis | WP_027888084.1 | B | B |
| 103 | | WP_027888305.1 | B | B |
| 104 | Meiothermus timidus | WP_018466213.1 | B | A |
| 105 | | WP_018465080.1 | B | A |
| 106 | | WP_018467688.1 | A | C |
| 107 | | WP_018467518.1 | A | C |
| 108 | | WP_018465603.1 | B | A |
| 109 | | WP_018466116.1 | A | C |
| 110 | | WP_018467797.1 | A | C |
| 111 | | WP_018467420.1 | A | C |
| 112 | | WP_018466214.1 | A | C |
| 113 | | WP_018465420.1 | B | B |
| 114 | Meiothermus rufus | WP_036271046.1 | B | B |
| 115 | Mesotoga infera | KUK90417.1 | A | C |
| 116 | Metallosphaera sedula | ABP94905.1 | B | B |
| 117 | Methanocella conradii | AFC99407.1 | R | B |
| 118 | | WP_014405429.1 | A | C |
| 119 | | AFD00405.1 | A | C |
| 120 | Methanococcoides methylutens | WP_048194361.1 | A | C |
| 121 | | AKB84306.1 | A | C |
| 122 | Methanohaloblum evestigatum | ADI75005.1 | B | A |
| 123 | | WP_013193898.1 | A | C |
| 124 | Methanolobus tindarius | WP_048135864.1 | A | C |
| 125 | | WP_048135649.1 | A | C |
| 126 | | ETA67773.1 | A | C |
| 127 | Methanosarcina siciliae | WP_048179383.1 | A | C |
| 128 | | AKB37722.1 | A | C |
| 129 | | AKB35909.1 | A | C |
| 130 | Methanothermus fervidus | ADP76907.1 | A | C |
| 131 | Petrotoga mobilis | ABX30802.1 | B | B |
| 132 | | KUK15285.1 | A | C |
| 133 | Picrophilus torridus | AAT44010.1 | B | A |
| 134 | | AAT43693.1 | B | B |
| 135 | Pseudonocardia thermophila | WP_073456926.1 | A | C |
| 136 | Pyrococcus furiosus | AAL80556.1 | B | B |
| 137 | | AAL81109.1 | A | C |
| 188 | | WP_014835802.1 | A | C |
| 139 | | AAL82045.1 | A | C |
| 140 | | AAL82122.1 | A | C |
| 141 | | AAL81285.1 | A | C |
| 142 | | AAL81790.1 | B | B |
| 143 | | AAL80346.1 | B | A |
| 144 | | AAL80703.1 | B | A |
| 145 | | AAL81901.1 | B | B |
| 146 | | AAL81913.1 | B | B |
| 147 | | AAL80587.1 | B | A |
| 148 | | AFN04628.1 | B | B |
| 149 | Pyrodictium occultum | WP_083494490.1 | A | C |
| 150 | Rhodothermus marinus | WP_041806336.1 | B | A |
| 151 | | WP_012844425.1 | B | A |
| 152 | | ACY47561.1 | B | A |
| 153 | | ACY48134.1 | A | C |
| 154 | | ACY47672.1 | B | A |
| 155 | | ACY48911.1 | B | A |
| 156 | | WP_012843092.1 | B | A |

TABLE 3-continued

| SEQ ID NO | Species and Genus | NCBI No. | G1P/G6P/F6P/P6P Dephosphorylation activity | P6P (Selective)/ G1P + G6P + F6P + P6P Dephosphorylation activity |
|---|---|---|---|---|
| 157 | | WP_012843709.1 | A | C |
| 158 | | WP_012844300.1 | A | C |
| 159 | | ACY48106.1 | B | A |
| 160 | | WP_012844667.1 | B | A |
| 161 | | WP_012845116.1 | B | A |
| 162 | | WP_012844208.1 | B | A |
| 163 | | WP_012848855.1 | B | A |
| 164 | | ACY47289.1 | B | B |
| 165 | *Slackia heliotrinireducens* | WP_012798605.1 | A | C |
| 166 | | ACV22623.1 | A | C |
| 167 | *Staphylothermus marinus* | ABN70247.1 | B | B |
| 168 | | ABN69637.1 | A | C |
| 169 | | ABN69899.1 | B | B |
| 170 | *Sulfolobus acidocaldarius* | AAY79446.1 | A | C |
| 171 | | WP_015385352.1 | A | C |
| 172 | | AAY80292.1 | B | B |
| 173 | *Thermanaerothrix daxensis* | KPL83857.1 | B | A |
| 174 | *Thermoanaerobacter* sp. | WP_004400108.1 | A | C |
| 175 | *Thermoanaerobacter thermohydrosulfuricus* | WP_074592559.1 | B | A |
| 176 | | WP_074665888.1 | A | C |
| 177 | *Thermoanaerobacter wiegelii* | AEM79256.1 | B | B |
| 178 | | AEM79180.1 | A | C |
| 179 | *Thermoanaerobacterium xylanolyticum* | WP_013788008.1 | A | C |
| 180 | *Thermobifida halotolerans* | WP_068689397.1 | A | C |
| 181 | | WP_068692137.1 | A | C |
| 182 | *Thermococcus celer* | WP_088862065.1 | A | C |
| 183 | | ASI98087.1 | A | C |
| 184 | *Thermococcus litoralis* | EHR78081.1 | B | B |
| 185 | *Thermococcus profundus* | WP_088857759.1 | B | B |
| 186 | *Thermocrinis minervae* | WP_079653666.1 | B | B |
| 187 | *Thermocrinis ruber* | AHE95294.1 | B | B |
| 188 | *Thermoflexus hugenholtzii* | WP_088571736.1 | A | C |
| 189 | *Thermotoga lettingae* | ABV34293.1 | B | B |
| 190 | *Thermotoga neapolitana* | WP_015919708.1 | A | C |
| 191 | | ACM22182.1 | B | B |
| 192 | | ACM22192.1 | B | B |
| 193 | | ACM22252.1 | A | C |
| 194 | | ACM22284.1 | A | C |
| 195 | | ACM22382.1 | B | A |
| 196 | | ACM22666.1 | A | C |
| 197 | | ACM22704.1 | A | C |
| 198 | | ACM22708.1 | B | A |
| 199 | | ACM22832.1 | A | C |
| 200 | | ACM22990.1 | A | C |
| 201 | | ACM23016.1 | A | C |
| 202 | | ACM23040.1 | A | C |
| 203 | | ACM23081.1 | A | C |
| 204 | | ACM23138.1 | A | C |
| 205 | | ACM23254.1 | A | A |
| 206 | | ACM23323.1 | A | C |
| 207 | | ACM23341.1 | A | C |
| 208 | | ACM23415.1 | A | C |
| 209 | | ACM23510.1 | A | C |
| 210 | | ACM23571.1 | B | A |
| 211 | | ACM23575.1 | B | B |
| 212 | | ACM23847.1 | A | C |
| 213 | | ACM23859.1 | A | C |
| 214 | | ACM23950.1 | B | A |
| 215 | | ACM23957.1 | A | C |
| 216 | | ACM24018.1 | B | A |
| 217 | *Thermotoga petrophilia* | ABQ46309.1 | B | B |
| 218 | *Thermus amyloliquefaciens* | WP_038055695.1 | A | C |
| 219 | *Thermus filiformis* | WP_038062097.1 | A | C |
| 220 | *Thermus thermophilus* | WP_096411270.1 | A | C |
| 221 | | AAS82270.1 | B | B |
| 222 | *Truepera radiovictrix* | WP_013176662.1 | A | C |

Example 4: Analysis of Psicose Production Activity Through Multiple Enzymatic Reactions (Multiple Enzymes)

For the production of psicose from maltodextrin, seven enzymes were selected and reacted simultaneously (one-pot). As the seven enzymes, glucan phosphorylase, which degrades starch and converts it into glucose-1-phosphate, pullulanase, which debranches starch, 4-α-glucanotransferase, which increases the utilization of starch substrate, phosphoglucomutase, which converts glucose-1-phosphate into glucose-6-phosphate, glucose-6-phosphate isomerase, which converts glucose-6-phosphate into fructose-6-phosphate, psicose-6-phosphate-3-epimerase, which converts fructose-6-phosphate into psicose-6-phosphate, and enzymes of SEQ ID NOS: 1 to 222 capable of producing psicose from psicose-6-phosphate were prepared and used in an amount of 0.1 unit/mL. 5% (w/v) maltodextrin was added to 1 mM to 5 mM $MgCl_2$ and 10 mM to 50 mM sodium phosphate (pH 7.0), and the mixture was allowed to react at a temperature of 50° C. for 12 hours. The reaction products were analyzed by HPLC using an Aminex HPX-87C column (Bio-RAD) at 80° C. at a mobile phase flow rate of 0.6 mL/min and detected using a refractive index detector.

As a result, it was confirmed that psicose was produced from maltodextrin through the multiple enzymatic reactions.

While the present application has been described with reference to the particular illustrative embodiments, it will be understood by those skilled in the art to which the present application pertains that the present application may be embodied in other specific forms without departing from the technical spirit or essential characteristics of the present application. Therefore, the embodiments described above are considered to be illustrative in all respects and not restrictive. Furthermore, the scope of the present application is defined by the appended claims rather than the detailed description, and it should be understood that all modifications or variations derived from the meanings and scope of the present application and equivalents thereof are included in the scope of the appended claims.

[Deposition No.]
Depository Institution: Korean Culture Center of Microorganisms (KCCM)
  Accession No.: KCCM12390P
  Deposition Date: 20181114
Depository Institution: Korean Culture Center of Microorganisms (KCCM)
  Accession No.: KCCM12391P
  Deposition Date: 20181114
Depository Institution: Korean Culture Center of Microorganisms (KCCM)
  Accession No.: KCCM12392P
  Deposition Date: 20181114
Depository Institution: Korean Culture Center of Microorganisms (KCCM)
  Accession No.: KCCM12393P
  Deposition Date: 20181114
Depository Institution: Korean Culture Center of Microorganisms (KCCM)
  Accession No.: KCCM12394P
  Deposition Date: 20181114
Depository Institution: Korean Culture Center of Microorganisms (KCCM)
  Accession No.: KCCM12395P
  Deposition Date: 20181114
Depository Institution: Korean Culture Center of Microorganisms (KCCM)
  Accession No.: KCCM12396P
  Deposition Date: 20181114
Depository Institution: Korean Culture Center of Microorganisms (KCCM)
  Accession No.: KCCM12397P
  Deposition Date: 20181114
Depository Institution: Korean Culture Center of Microorganisms (KCCM)
  Accession No.: KCCM12398P
  Deposition Date: 20181114
Depository Institution: Korean Culture Center of Microorganisms (KCCM)
  Accession No.: KCCM12399P
  Deposition Date: 20181114
Depository Institution: Korean Culture Center of Microorganisms (KCCM)
  Accession No.: KCCM12400P
  Deposition Date: 20181114
Depository Institution: Korean Culture Center of Microorganisms (KCCM)
  Accession No.: KCCM12401P
  Deposition Date: 20181114
Depository Institution: Korean Culture Center of Microorganisms (KCCM)
  Accession No.: KCCM12402P
  Deposition Date: 20181114
Depository Institution: Korean Culture Center of Microorganisms (KCCM)
  Accession No.: KCCM12403P
  Deposition Date: 20181114
Depository Institution: Korean Culture Center of Microorganisms (KCCM)
  Accession No.: KCCM12404P
  Deposition Date: 20181114
Depository Institution: Korean Culture Center of Microorganisms (KCCM)
  Accession No.: KCCM12405P
  Deposition Date: 20181114
Depository Institution: Korean Culture Center of Microorganisms (KCCM)
  Accession No.: KCCM12406P
  Deposition Date: 20181114
Depository Institution: Korean Culture Center of Microorganisms (KCCM)
  Accession No.: KCCM12407P
  Deposition Date: 20181114

The invention claimed is:

1. A method for producing psicose, comprising converting psicose-6-phosphate into psicose by bringing psicose-6-phosphate into contact with a psicose-6-phosphate phosphatase, a microorganism expressing the same, or a culture of the microorganism, wherein the psicose-6-phosphate phosphatase is derived from any one selected from the group consisting of the genus *Alicyclobacillus, Amycolatopsis, Anaerolinea, Archaeoglobus, Bacillus, Caldicellulosiruptor, Caldilinea, Caldithrix, Carboxydocella, Carboxydothermus, Chloroflexi, Defluviitoga, Deinococcus, Desulfurococcus, Dictyoglomus, Effusibacillus, Fervidobacterium, Geobacillus, Halococcus, Hydrogenivirga, Hydrogenobacter, Hyperthermus, Kosmotoga, Marinitoga, Meiothermus, Mesotoga, Metallosphaera, Methanocella, Methanococcoides, Methanohalobium, Methanolobus, Methanosarcina, Methanothermus, Petrotoga, Picrophilus, Pseudonocardia, Pyrococcus, Pyrodictium, Rhodothermus, Slackia, Staphylothermus, Sulfolobus, Thermanaerothrix, Thermoanaerobacter, Thermoanaerobacterium, Thermobifida, Thermococcus, Thermocrinis, Thermoflexus, Thermotoga, Thermus*, and *Truepera*.

2. The method of claim 1, wherein the method further comprises converting fructose-6-phosphate into psicose-6-phosphate by bringing fructose-6-phosphate into contact with fructose-6-phosphate-3-epimerase, a microorganism expressing the same, or a culture of the microorganism, prior to the converting psicose-6-phosphate into psicose.

3. The method of claim 2, wherein the method further comprises converting glucose-6-phosphate into fructose-6-phosphate by bringing glucose-6-phosphate into contact with glucose-6-phosphate-isomerase, a microorganism expressing the same, or a culture of the microorganism, prior to the converting fructose-6-phosphate into psicose-6-phosphate.

4. The method of claim 3, wherein the method further comprises converting glucose-1-phosphate into glucose-6-phosphate by bringing glucose-1-phosphate into contact with phosphoglucomutase, a microorganism expressing the same, or a culture of the microorganism, prior to the converting glucose-6-phosphate into fructose-6-phosphate.

5. The method of claim 3, wherein the method further comprises converting glucose into glucose-6-phosphate by bringing glucose into contact with polyphosphate glucokinase, a microorganism expressing the same, or a culture of the microorganism, and polyphosphate, prior to the converting glucose-6-phosphate into fructose-6-phosphate.

6. The method of claim 4, wherein the method further comprises converting starch, maltodextrin, sucrose, or a combination thereof into glucose-1-phosphate by bringing starch, maltodextrin, sucrose, or a combination thereof into contact with α-glucan phosphorylase, starch phosphorylase, maltodextrin phosphorylase, or sucrose phosphorylase; a microorganism expressing the same; or a culture of the microorganism, and phosphate, prior to the converting glucose-1-phosphate into glucose-6-phosphate.

7. The method of claim 6, wherein the converting starch, maltodextrin, sucrose, or a combination thereof into glucose-1-phosphate further comprises converting starch, maltodextrin, sucrose, or a combination thereof into a maltooligosaccharide or glucose by further comprising α-amylase, pullulanase, isoamylase, α-glucanotransferase, glucoamylase, or sucrase; a microorganism expressing the same; or a culture of the microorganism.

8. A method for producing psicose, comprising bringing starch, maltodextrin, sucrose, or a combination thereof into contact with (a) a psicose-6-phosphate phosphatase; fructose-6-phosphate-3-epimerase; glucose-6-phosphate-isomerase; phosphoglucomutase or glucokinase; and α-glucan phosphorylase, starch phosphorylase, maltodextrin phosphorylase, sucrose phosphorylase, α-amylase, pullulanase, isoamylase, glucoamylase, α-glucanotransferase, polyphosphate glucokinase, or sucrase; or (b) a microorganism expressing the enzymes of item (a) or a culture of the microorganism, wherein the psicose-6-phosphate phosphatase is derived from any one selected from the group consisting of the genus *Alicyclobacillus, Amycolatopsis, Anaerolinea, Archaeoglobus, Bacillus, Caldicellulosiruptor, Caldilinea, Caldithrix, Carboxydocella, Carboxydothermus, Chloroflexi, Defluviitoga, Deinococcus, Desulfurococcus, Dictyoglomus, Effusibacillus, Fervidobacterium, Geobacillus, Halococcus, Hydrogenivirga, Hydrogenobacter, Hyperthermus, Kosmotoga, Marinitoga, Meiothermus, Mesotoga, Metallosphaera, Methanocella, Methanococcoides, Methanohalobium, Methanolobus, Methanosarcina, Methanothermus, Petrotoga, Picrophilus, Pseudonocardia, Pyrococcus, Pyrodictium, Rhodothermus, Slackia, Staphylothermus, Sulfolobus, Thermanaerothrix, Thermoanaerobacter, Thermoanaerobacterium, Thermobifida, Thermococcus, Thermocrinis, Thermoflexus, Thermotoga, Thermus,* and *Truepera.*

9. The method of claim 2, the contact is performed at a pH of 5.0 to 9.0, at a temperature of 40° C. to 80° C., and/or for 2 hours to 24 hours or 120 hours.

10. The method of claim 1, wherein the psicose-6-phosphate phosphatase is derived from any one selected from the group consisting of *Alicyclobacillus acidocaldarius, Alicyclobacillus tengchongensis, Amycolatopsis thermoflava, Anaerolinea thermolimosa, Anaerolinea thermophila, Archaeoglobus fugidus, Archaeoglobus profundus, Archaeoglobus veneficus, Bacillus licheniformis, Caldicellulosiruptor bescii, Caldilinea aerophila, Caldithrix abyssi, Carboxydocella* sp. ULO1, *Carboxydothermus ferrireducens, Chloroflexi bacterium* 54-19, *Defluviitoga tunisiensis, Deinococcus aerius, Deinococcus apachensis, Deinococcus aquatilis, Deinococcus geothermalis, Deinococcus hopiensis, Deinococcus maricopensis, Deinococcus murrayi, Deinococcus reticulitermitis, Deinococcus wulumuqiensis, Deinococcus* sp. Leaf326, *Deinococcus phoenicis, Deinococcus proteolyticus, Deinococcus* sp. 17bor-2, *Deinococcus* sp. NW-56, *Deinococcus* sp. RL, *Deinococcus* sp. YIM 77859, *Desulfurococcus mucosus, Dictyoglomus turgidum, Effusibacillus pohliae, Fervidobacterium gondwanense, Fervidobacterium islandicum, Fervidobacterium nodosum, Fervidobacterium pennivorans, Geobacillus* sp., *Geobacillus stearothermophilus, Halococcus salifodinae, Hydrogenivirga* sp. 128-5-R1-1, *Hydrogenobacter hydrogenophilus, Hydrogenobacter thermophilus, Hyperthermus butylicus, Kosmotoga arenicorallina, Kosmotoga olearia, Marinitoga piezophila, Meiothermus cerbereus, Meiothermus chliarophilus, Meiothermus ruber, Meiothermus silvanus, Meiothermus taiwanensis, Meiothermus timidus, Meiothermus rufus, Mesotoga infera, Metallosphaera sedula, Methanocella conradii, Methanococcoides methylutens, Methanohalobium evestigatum, Methanolobus tindarius, Methanosarcina sicilia, Methanothermus fervidus, Petrotoga mobilis, Picrophilus torridus, Pseudonocardia thermophila, Pyrococcus furiosus, Pyrodictium occultum, Rhodothermus marinus, Slackia heliotrinireducens, Staphylothermus marinus, Sulfolobus acidocaldarius, Thermanaerothrix daxensis, Thermoanaerobacter* sp., *Thermoanaerobacter thermohydrosulfuricus, Thermoanaerobacter wiegelii, Thermoanaerobacterium xylanolyticum, Thermobifida halotolerans, Thermococcus celer, Thermococcus litoralis, Thermococcus profundus, Thermocrinis minervae, Thermocrinis ruber, Thermoflexus hugenholtzii, Thermotoga lettingae, Thermotoga neapolitana, Thermotoga petrophilia, Thermus amyloliquefaciens, Thermus filiformis, Thermus thermophilus,* and *Truepera radiovictrix.*

11. The method of claim 1, wherein the psicose-6-phosphate phosphatase comprises an amino acid sequence having a homology of at least 70% to any one of amino acid sequences of SEQ ID NOS: 1 to 222.

12. The method of claim 1, wherein the psicose-6-phosphate phosphatase comprises an amino acid sequence having a sequence identity of at least 70% to any one of amino acid sequences of SEQ ID NOS: 1, 6, 9, 12, 26, 29, 38 to 43, 45 to 53, 56, 57, 59, 60, 64 to 66, 69, 70, 72, 76, 80, 81, 91 to 93, 95, 99 to 103, 113, 114, 116, 117, 131, 134, 136, 142, 145, 146, 148, 164, 167, 169, 172, 177, 184 to 187, 189, 191, 192, 211, 217, and 221.

13. The method of claim 1, wherein the psicose-6-phosphate phosphatase exhibits an activity selective to psicose-6-phosphate.

14. The method of claim 1, wherein the psicose-6-phosphate phosphatase comprises an amino acid sequence of any one of amino acid sequences of SEQ ID NOS: 1, 6, 9, 12, 26, 29, 38 to 43, 45 to 53, 56, 57, 59, 60, 64 to 66, 69, 70, 72, 76, 80, 81, 91 to 93, 95, 99 to 103, 113, 114, 116, 117, 131, 134, 136, 142, 145, 146, 148, 164, 167, 169, 172, 177, 184 to 187, 189, 191, 192, 211, 217, and 221.

15. The method of claim 8, wherein the psicose-6-phosphate phosphatase comprises an amino acid sequence having a homology of at least 70% to any one of amino acid sequences of SEQ ID NOS: 1, 6, 9, 12 to 14, 17, 18, 20 to 23, 25, 26, 28, 29, 37 to 53, 55 to 57, 59 to 61, 64 to 66, 69, 70, 72, 73, 76, 77, 80, 81, 85, 88, 91 to 93, 95, 99 to 105, 108, 113, 114, 116, 117, 122, 131, 133, 134, 136, 142 to 148, 150 to 152, 154 to 156, 159 to 164, 167, 169, 172, 173, 175, 177, 184 to 187, 189, 191, 192, 195, 198, 205, 210, 211, 214, 216, 217, and 221.

16. The method of claim 8, wherein the psicose-6-phosphate phosphatase comprises an amino acid sequence of any one of SEQ ID NOS: 1, 6, 9, 12 to 14, 17, 18, 20 to 23, 25, 28, 29, 37 to 53, 55 to 57, 59 to 61, 64 to 66, 69, 70, 72, 73, 76, 77, 80, 81, 85, 88, 91 to 93, 95, 99 to 105, 108, 113, 114, 116, 117, 122, 131, 133, 134, 136, 142 to 148, 150 to 152, 154 to 156, 159 to 164, 167, 169, 172, 173, 175, 177, 184 to 187, 189, 191, 192, 195, 198, 205, 210, 211, 214, 216, 217, and 221.

17. The method of claim 8, wherein the psicose-6-phosphate phosphatase comprises an amino acid sequence of any one of SEQ ID NOS: 1, 6, 9, 12, 29, 38 to 43, 45 to 53, 56, 57, 59, 60, 64 to 66, 69, 70, 72, 76, 80, 81, 91 to 93, 95, 99 to 103, 113, 114, 116, 117, 131, 134, 136, 142, 145, 146, 148, 164, 167, 169, 172, 177, 184 to 187, 189, 191, 192, 211, 217, and 221.

18. A method for producing psicose, comprising converting psicose-6-phosphate into psicose by bringing psicose-6-phosphate into contact with a psicose-6-phosphate phosphatase, a microorganism expressing the same, or a culture of the microorganism, wherein the psicose-6-phosphate phosphatase comprises an amino acid sequence having a sequence identity of at least 70% to any one of amino acid sequences of SEQ ID NOS: 1, 6, 9, 12 to 14, 17, 18, 20 to 23, 25, 26, 28, 29, 37 to 53, 55 to 57, 59 to 61, 64 to 66, 69, 70, 72, 73, 76, 77, 80, 81, 85, 88, 91 to 93, 95, 99 to 105, 108, 113, 114, 116, 117, 122, 131, 133, 134, 136, 142 to 148, 150 to 152, 154 to 156, 159 to 164, 167, 169, 172, 173, 175, 177, 184 to 187, 189, 191, 192, 195, 198, 205, 210, 211, 214, 216, 217, and 221.

19. The method of claim 15, wherein the psicose-6-phosphate phosphatase comprises an amino acid sequence of any one of SEQ ID NOS: 1, 6, 9, 12 to 14, 17, 18, 20 to 23, 25, 28, 29, 37 to 53, 55 to 57, 59 to 61, 64 to 66, 69, 70, 72, 73, 76, 77, 80, 81, 85, 88, 91 to 93, 95, 99 to 105, 108, 113, 114, 116, 117, 122, 131, 133, 134, 136, 142 to 148, 150 to 152, 154 to 156, 159 to 164, 167, 169, 172, 173, 175, 177, 184 to 187, 189, 191, 192, 195, 198, 205, 210, 211, 214, 216, 217, and 221.

20. The method of claim 15, wherein the psicose-6-phosphate phosphatase comprises an amino acid sequence of any one of SEQ ID NOS: 1, 6, 9, 12, 29, 38 to 43, 45 to 53, 56, 57, 59, 60, 64 to 66, 69, 70, 72, 76, 80, 81, 91 to 93, 95, 99 to 103, 113, 114, 116, 117, 131, 134, 136, 142, 145, 146, 148, 164, 167, 169, 172, 177, 184 to 187, 189, 191, 192, 211, 217, and 221.

* * * * *